(12) United States Patent
Frejd et al.

(10) Patent No.: US 10,208,128 B2
(45) Date of Patent: Feb. 19, 2019

(54) HER3 BINDING POLYPEPTIDES

(75) Inventors: Fredrik Frejd, Stockholm (SE); Elin Gunneriusson, Saltsjöbaden (SE); Nina Kronqvist, Täby (SE); John Löfblom, Huddinge (SE); Stefan Ståhl, Stockholm (SE)

(73) Assignee: AFFIBODY AB, Solna (SE)

( * ) Notice: Subject to any disclaimer, the term of this patent is extended or adjusted under 35 U.S.C. 154(b) by 0 days.

(21) Appl. No.: 13/505,493

(22) PCT Filed: Oct. 27, 2010

(86) PCT No.: PCT/SE2010/051164
§ 371 (c)(1),
(2), (4) Date: Jun. 14, 2012

(87) PCT Pub. No.: WO2011/056124
PCT Pub. Date: May 12, 2011

(65) Prior Publication Data
US 2012/0270801 A1 Oct. 25, 2012

(30) Foreign Application Priority Data
Nov. 4, 2009 (EP) .................... 09175025

(51) Int. Cl.
C07K 14/31 (2006.01)
C07K 14/00 (2006.01)
C07K 16/32 (2006.01)
C07K 14/705 (2006.01)
C07K 16/28 (2006.01)

(52) U.S. Cl.
CPC .............. *C07K 16/32* (2013.01); *C07K 14/31* (2013.01); *C07K 14/705* (2013.01); *C07K 16/2863* (2013.01); *C07K 2318/20* (2013.01); *C07K 2319/21* (2013.01); *C07K 2319/31* (2013.01)

(58) Field of Classification Search
None
See application file for complete search history.

(56) References Cited

U.S. PATENT DOCUMENTS

| 8,329,873 | B2 * | 12/2012 | Adams | A61K 51/109 424/130.1 |
| 2004/0071696 | A1 * | 4/2004 | Adams | C07K 16/2863 424/143.1 |
| 2007/0269369 | A1 * | 11/2007 | Gegg | A61K 47/48215 424/1.41 |
| 2015/0252079 | A1 | 9/2015 | Malm et al. | |

FOREIGN PATENT DOCUMENTS

| EP | 2072525 A1 | 6/2009 |
| WO | WO2005003156 | 1/2005 |
| WO | WO2007065635 | 6/2007 |
| WO | WO2008100624 | 8/2008 |
| WO | WO2009019117 | 2/2009 |
| WO | WO2016/054603 | * 4/2016 |

OTHER PUBLICATIONS

Horan et Al., The Journal of Biological Chemistry, vol. 270, No. 41, p. 24604-24608.*
Mendoza, Arch. Immunol. Ther. Exp., vol. 53, p. 47-60, 2005.*
Ju, Proceedings of the National Academy of Sciences, U.S.A., vol. 88, p. 2658-2662.*
Huang, Journal of Biological Chemistry, vol. 272, No. 43, p. 27155-27159, 1997.*
Montrose-Rafizadeh, Journal of Biological Chemistry, vol. 272, p. 21201-21206, 1997.*
Burgess et al., J of Cell Bio. 111:2129-2138, 1990.*
Huang, J. Biol. Chem. vol. 272, p. 27155-27159, 1997.*
Baker, Immunity, vol. 13, p. 475-484, 2000.*
Ju, Proc. Natl. Acad. Sci. USA., vol. 88, p. 2658-2662, 1991.*
Lazar, Mol. Cell. Biol., vol. 8, No. 3, p. 1247-1252, 1988.*
Kronqvist (Protein Engineering, Design and Selection, vol. 24, No. 4, p. 385-396, 2010).*
Mikaela Friedman, et al., "Directed Evolution to Low Nanomolar Affinity of a Tumor-Targeting Epidermal Growth Factor Receptor-Binding Affibody Molecule", Journal of Molecular Biology (2008), pp. 1388-1402, vol. 376.
Caroline Gronwall et al, "Engineered affinity proteins—Generation and applications", Journal of Biotechnology (2009), pp. 254-269, vol. 140.
Karin Nord et al., "A combinatorial library of an α-helical bacterial receptor domain", Protein Engineering (1995), pp. 601-608, vol. 8 No. 6.
Anna Orlova et al., "Affibody Molecules for Molecular Imaging and Therapy for Cancer", Cancer Biotherapy & Radiopharmaceuticals (2007), pp. 573-584, vol. 22, No. 5
Ekerljung et al., "Effects of HER2-Binding Affibody Molecules on Intracellular Signaling Pathways" TurmorBiology, 2006, 27, pp. 201-210.
Friedman et al., "Engineering and Characterization of a Bispecific HER x EGFR-binding Affibody Molecule", Biotechnol. Appl. Biochem. (2009) 54, pp. 121-131.

(Continued)

Primary Examiner — Michael Allen
(74) Attorney, Agent, or Firm — Cantor Colburn LLP

(57) ABSTRACT

The disclosure provides a HER3 binding polypeptide, comprising a HER3 binding motif, BM, which motif consists of the amino acid sequence selected from i) $EX_2X_3X_4A\ X_6X_7EIW\ X_{11}LPNL\ X_{16}X_{17}X_{18}QX_{20}\ X_{21}AFIX_{25}\ X_{26}LX_{28}D$, and ii) an amino acid sequence which has at least 90% identity to the sequence defined in i), wherein the polypeptide binds to the extra-cellular domain of HER3. Also provided is a bispecific ligand having binding affinity for HER3 and for HER2, or for HER3 and for EGFR, and comprising a HER3. binding polypeptide as defined herein and a HER2 binding polypeptide or a EGFR binding polypeptide.

39 Claims, 44 Drawing Sheets

Specification includes a Sequence Listing.

(56) References Cited

OTHER PUBLICATIONS

Kontermann, "Strategies to Extend Plasma Half-Lives of Recombinant Antibodies" Biodrugs, 2009, 23 (2); pp. 93-109.
Orlova et al., "Tumor Imaging Using a Picomolar Affinity HER2 Binding Affibody Molecule" Cancer Res 2006; 66: (8). Apr. 15, 2006.
Ronnmark et al., "Construction and Characterization of Affibody-Fc Chimeras Produced in *Escherichia coli*" Journal of Immunological Methods 261 (2002), pp. 199-211.
Tolmachev, "Imaging of HER-2 Overexpressioni n Tumors for Guiding Therapy" Current Pharmaceutical Design, 2008, 14, pp. 2999-3019.
Wikman et al., "Selection and Characterization of HER2/neu-binding Affibody Ligands" Protein Engineering, Design & Selection vol. 17 No. 5 (2004), pp. 455-462.
Nord et al., "Binding Proteins Selected from Combinatorial Libaries of an Alpha-Helical Bacterial Receptor Domain"; Nature Biotechnology, Nature Publishing Group. vol. 15, No. 8, pp. 772-777, (1997).

* cited by examiner

| Polypeptide | Amino acid sequence | SEQ ID NO |
|---|---|---|
| BM01748 | EKVAATGEIWDLPNLNTRQKNAFIGSLWD | SEQ ID NO:1 |
| BM01749 | EWRWAAHEIWDLPNLNVYQRAAFIRSLED | SEQ ID NO:2 |
| BM01750 | ERRLASVEIWELPNLNAVQKSAFISSLFD | SEQ ID NO:3 |
| BM01751 | EVKEARFEIWDLPNLNRTQKHAFIVSLED | SEQ ID NO:4 |
| BM01753 | EWKGAAGEIWNLPNLNVSQRVAFIGSLAD | SEQ ID NO:5 |
| BM01754 | EKYKAAHEIWELPNLNRDQRAAFITSLTD | SEQ ID NO:6 |
| BM01813 | ERSLASFEIWELPNLNPKQKAAFIVSLFD | SEQ ID NO:7 |
| BM01814 | EWKRASWEIWELPNLNNAQKRAFISSLSD | SEQ ID NO:8 |
| BM01815 | EKYKAMTEIWILPNLNQRQKVAFIGSLDD | SEQ ID NO:9 |
| BM01817 | EWRGAAGEIWALPNLNNRQKGAFIESLPD | SEQ ID NO:10 |
| BM01818 | ERWEATVEIWDLPNLNRNQKAAFIASLQD | SEQ ID NO:11 |
| BM01820 | EKYNAYAEIWLLPNLNRYQKAFIGSLSD | SEQ ID NO:12 |
| BM01821 | ERSVAQKEIWELPNLNRWQAGAFIASLYD | SEQ ID NO:13 |
| BM01824 | EKMDAMGEIWDLPNLNRGQASAFIASLQD | SEQ ID NO:14 |
| BM01825 | EKRNAQVEIWTLPNLNSKQRAFIKSLYD | SEQ ID NO:15 |
| BM01826 | ERRDARFEIWELPNLNKYQRAAFISSLDD | SEQ ID NO:16 |
| BM01828 | ERSMARFEIWELPNLNRGQKSAFIASLED | SEQ ID NO:17 |
| BM01830 | EWHGAASEIWELPNLNKSQKSAFIKSLPD | SEQ ID NO:18 |
| BM02009 | EWKQAAEEIWDLPNLNRRQAGAFITSLQD | SEQ ID NO:19 |
| BM02010 | EKVQASEEIWNLPNLNRRQRAAFIGSLYD | SEQ ID NO:20 |
| BM02011 | ERYSATVEIWDLPNLNTLQKSAFIGSLQD | SEQ ID NO:21 |
| BM05403 | ERYSAYYEIWQLPNLNRIQKAAFISSLQD | SEQ ID NO:22 |
| BM05404 | ERYRAYFEIWQLPNLNRLQKAAFISSLED | SEQ ID NO:23 |
| BM05405 | EKYKAYGEIWQLPNLNRVQKAAFIASLSD | SEQ ID NO:24 |

Figure 1A

| | | |
|---|---|---|
| HM00419 | KEWRGAAFEIWQLPNLNQRQKAAFIASLYDDPSQSANLLAEAKKLNDAQ | SEQ ID NO:650 |
| HM00420 | KEWKVASWEIWQLPNLNRQQKAAFIGSLSDDPSQSANLLAEAKKLNDAQ | SEQ ID NO:651 |
| HM00421 | KEWKLASWEIWQLPNLNRWQKAAFIGSLSDDPSQSANLLAEAKKLNDAQ | SEQ ID NO:652 |
| HM00422 | KEWKRASVEIWELPNLNRQQKAAFIGSLSDDPSQSANLLAEAKKLNDAQ | SEQ ID NO:653 |
| HM00425 | KEWKRASFEIWQLPNLNRLQKAAFIASLADDPSQSANLLAEAKKLNDAQ | SEQ ID NO:654 |
| HM00428 | KEWKRAAGEIWQLPNLNRRQKAAFISSLYDDPSQSANLLAEAKKLNDAQ | SEQ ID NO:655 |
| HM00429 | KEWKVAAFEIWQLPNLNRAQKAAFISSLADDPSQSANLLAEAKKLNDAQ | SEQ ID NO:656 |
| HM00430 | KEWKHAAGEIWQLPNLNRAQKAAFISSLADDPSQSANLLAEAKKLNDAQ | SEQ ID NO:657 |
| HM00431 | KEWKKAAYEIWQLPNLNRAQKAAFISSLYDDPSQSANLLAEAKKLNDAQ | SEQ ID NO:658 |
| HM00432 | KEWKLAAYEIWQLPNLNRHQKAAFISSLSDDPSQSANLLAEAKKLNDAQ | SEQ ID NO:659 |
| HM00433 | KEWKRAAFEIWQLPNLNRSQKAAFISSLADDPSQSANLLAEAKKLNDAQ | SEQ ID NO:660 |
| HM00435 | KEWKTAAFEIWQLPNLNRSQKAAFIASLADDPSQSANLLAEAKKLNDAQ | SEQ ID NO:661 |
| HM00437 | KEWKIAAFEIWQLPNLNRIQKAAFIGSLADDPSQSANLLAEAKKLNDAQ | SEQ ID NO:662 |
| HM00438 | KEWKQAAFEIWQLPNLNRIQKAAFITSLSDDPSQSANLLAEAKKLNDAQ | SEQ ID NO:663 |
| HM00439 | KEWKQAAFEIWQLPNLNRVQKAAFIVSLQDDPSQSANLLAEAKKLNDAQ | SEQ ID NO:664 |
| HM00440 | KEWKVAAGEIWQLPNLNRIQKAAFISSLSDDPSQSANLLAEAKKLNDAQ | SEQ ID NO:665 |
| HM00441 | KEWKIAAFEIWQLPNLNRWQKAAFISSLQDDPSQSANLLAEAKKLNDAQ | SEQ ID NO:666 |
| HM00442 | KEWKEAAGEIWQLPNLNRYQKAAFIASLQDDPSQSANLLAEAKKLNDAQ | SEQ ID NO:667 |
| HM00443 | KEWKTASFEIWQLPNLNRYQKAAFISSLQDDPSQSANLLAEAKKLNDAQ | SEQ ID NO:668 |
| Z01748 | VDNKFNKEKVAATGEIWDLPNLNTRQKNAFIGSLMDDPSQSANLLAEAKKLNDAQAPK | SEQ ID NO:669 |
| Z01749 | VDNKFNKEWRWAAHEIWDLPNLNVYQRAAFIRSLEDDPSQSANLLAEAKKLNDAQAPK | SEQ ID NO:670 |
| Z01750 | VDNKFNKERRLASVEIWELPNLNAVQKSAFISSLFDDPSQSANLLAEAKKLNDAQAPK | SEQ ID NO:671 |
| Z01751 | VDNKFNKEVKEARFEIWDLPNLNRTQKHAFIVSLEDDPSQSANLLAEAKKLNDAQAPK | SEQ ID NO:672 |
| Z01753 | VDNKFNKEWKGAAGEIWNLPNLNVSQRVAFIGSLADDPSQSANLLAEAKKLNDAQAPK | SEQ ID NO:673 |
| Z01754 | VDNKFNKEKYKAAHEIWELPNLNRDQRAFITSLTDDPSQSANLLAEAKKLNDAQAPK | SEQ ID NO:674 |

Figure 1AA

| | | |
|---|---|---|
| BM05406 | ERKQATFEIWELPNLNQRQKAAFIKSLWD | SEQ ID NO:25 |
| BM05407 | EWKIAAGEIWQLPNLNRHQKGAFISSLYD | SEQ ID NO:26 |
| BM05408 | EKYKAYVEIWQLPNLNRYQRAAFIGSLQD | SEQ ID NO:27 |
| BM05409 | ERKAATFEIWELPNLNRIQKAAFIASLFD | SEQ ID NO:28 |
| BM05410 | EKYKAYGEIWQLPNLNRIQKAAFISSLQD | SEQ ID NO:29 |
| BM05411 | EKRIATWEIWQLPNLNQHQKAAFISSLWD | SEQ ID NO:30 |
| BM05412 | EKYKAYVEIWQLPNLNRGQKAAFISSLQD | SEQ ID NO:31 |
| BM05413 | ERYLAYYEIWQLPNLNRTQKAAFIGSLQD | SEQ ID NO:32 |
| BM05414 | ERYIAYWEIWQLPNLNRRQKAAFISSLWD | SEQ ID NO:33 |
| BM05415 | EKYRAYGEIWQLPNLNRGQKAAFIASLQD | SEQ ID NO:34 |
| BM05416 | EKYTAYFEIWQLPNLNVRQKAAFISSLQD | SEQ ID NO:35 |
| BM05417 | ERYSAYYEIWQLPNLNVRQKAAFIGSLQD | SEQ ID NO:36 |
| BM05418 | EKYAAYGEIWQLPNLNRSQKAAFIGSLSD | SEQ ID NO:37 |
| BM05419 | ERKRATVEIWELPNLNRLQRGAFIASLWD | SEQ ID NO:38 |
| BM05420 | EWKQASFEIWELPNLNRLQKAAFIGSLAD | SEQ ID NO:39 |
| BM05421 | ERKHATVEIWELPNLNRVQKAAFISSLWD | SEQ ID NO:40 |
| BM05422 | EKYKAYVEIWQLPNLNQRQKAAFIGSLAD | SEQ ID NO:41 |
| BM05423 | EKYVAYGEIWQLPNLNRTQKAAFISSLSD | SEQ ID NO:42 |
| BM05424 | ERYIAYYEIWQLPNLNRYQKAAFIASLSD | SEQ ID NO:43 |
| BM05425 | EKYNAYGEIWQLPNLNVRQKAAFISSLAD | SEQ ID NO:44 |
| BM05426 | ERKAATVEIWELPNLNRVQKAAFIKSLFD | SEQ ID NO:45 |
| BM05427 | ERYVAYYEIWELPNLNQRQKAAFIGSLQD | SEQ ID NO:46 |
| BM05428 | ERYRAYYEIWQLPNLNQRQKAAFIGSLSD | SEQ ID NO:47 |
| BM05429 | EWKSAAFEIWELPNLNRLQKAAFIRSLSD | SEQ ID NO:48 |
| BM05430 | ERKQATFEIWELPNLNRHQKGAFIASLWD | SEQ ID NO:49 |

Figure 1B

| | | |
|---|---|---|
| Z01813 | VDNKFNKERSLASFEIWELPNLNPKQKAAFTVSLFDDPSQSANLLAEAKKLNDAQAPK | SEQ ID NO:675 |
| Z01814 | VDNKFNKEWKRASWEIWELPNLNNAQKRAFTSSLSDDPSQSANLLAEAKKLNDAQAPK | SEQ ID NO:676 |
| Z01815 | VDNKFNKEKYKAMTEIWILPNLNQRQKVAFIGSLDDDPSQSANLLAEAKKLNDAQAPK | SEQ ID NO:677 |
| Z01817 | VDNKFNKEWRGAAGEIWALPNLNNRQKGAFIESLPDDPSQSANLLAEAKKLNDAQAPK | SEQ ID NO:678 |
| Z01818 | VDNKFNKERWEATVEIWDLPNLNRNQKAAFIASLQDDPSQSANLLAEAKKLNDAQAPK | SEQ ID NO:679 |
| Z01820 | VDNKFNKEKYNAYAEIWLLPNLNRYQKAAFIGSLSDDPSQSANLLAEAKKLNDAQAPK | SEQ ID NO:680 |
| Z01821 | VDNKFNKERSVAQKEIWELPNLNRWQAGAFIKSLYDDPSQSANLLAEAKKLNDAQAPK | SEQ ID NO:681 |
| Z01824 | VDNKFNKEKMDAMGEIWDLPNLNRGQASAFIASLQDDPSQSANLLAEAKKLNDAQAPK | SEQ ID NO:682 |
| Z01825 | VDNKFNKEKRNAQVEIWTLPNLNSKQRAAFIKSLYDDPSQSANLLAEAKKLNDAQAPK | SEQ ID NO:683 |
| Z01826 | VDNKFNKERRDARFEIWELPNLNKYQRAAFISSLDDDPSQSANLLAEAKKLNDAQAPK | SEQ ID NO:684 |
| Z01828 | VDNKFNKERSMARFEIWELPNLNRGQKSAFIASLEDDPSQSANLLAEAKKLNDAQAPK | SEQ ID NO:685 |
| Z01830 | VDNKFNKEWHGAASEIWELPNLNKSQKSAFIKSLPDDPSQSANLLAEAKKLNDAQAPK | SEQ ID NO:686 |
| Z02009 | VDNKFNKEWKQAAEEIWDLPNLNRRQAGAFTTSLQDDPSQSANLLAEAKKLNDAQAPK | SEQ ID NO:687 |
| Z02010 | VDNKFNKEKVQASEEIWNLPNLNRRQRAAFIGSLYDDPSQSANLLAEAKKLNDAQAPK | SEQ ID NO:688 |
| Z02011 | VDNKFNKERYSATVEIWDLPNLNTLQKSAFIGSLQDDPSQSANLLAEAKKLNDAQAPK | SEQ ID NO:689 |
| Z05403 | VDNKFNKERYSAYYEIWQLPNLNRIQKAAFISSLQDDPSQSANLLAEAKKLNDAQAPK | SEQ ID NO:690 |
| Z05404 | VDNKFNKERYRAYFEIWQLPNLNRLQKAAFTSSLEDDPSQSANLLAEAKKLNDAQAPK | SEQ ID NO:691 |
| Z05405 | VDNKFNKERYKAYGEIWQLPNLNRVQKAAFIASLSDDPSQSANLLAEAKKLNDAQAPK | SEQ ID NO:692 |
| Z05406 | VDNKFNKERKQATFEIWELPNLNMRQRQKAAFIKSLWDDPSQSANLLAEAKKLNDAQAPK | SEQ ID NO:693 |
| Z05407 | VDNKFNKEWKIAAGEIWQLPNLNRHQKGAFISSLYDDPSQSANLLAEAKKLNDAQAPK | SEQ ID NO:694 |
| Z05408 | VDNKFNKEKYKAYVEIWQLPNLNRYQRAAFIGSLQDDPSQSANLLAEAKKLNDAQAPK | SEQ ID NO:695 |
| Z05409 | VDNKFNKERKAATFEIWELPNLNRIQKAAFIASLFDDPSQSANLLAEAKKLNDAQAPK | SEQ ID NO:696 |
| Z05410 | VDNKFNKEKYKAYGEIWQLPNLNRIQKAAFISSLQDDPSQSANLLAEAKKLNDAQAPK | SEQ ID NO:697 |
| Z05411 | VDNKFNKEKRIATWEIWQLPNLNQHQKAAFISSLWDDPSQSANLLAEAKKLNDAQAPK | SEQ ID NO:698 |
| Z05412 | VDNKFNKEKYKAYVEIWQLPNLNRGQKAAFISSLQDDPSQSANLLAEAKKLNDAQAPK | SEQ ID NO:699 |

Figure 1BB

| | | |
|---|---|---|
| BM05431 | EWKIAAGEIWQLPNLNRRQKAAFIASLSD | SEQ ID NO:50 |
| BM05432 | ERYLAYYEIWQLPNLNRRQKAAFIGSLQD | SEQ ID NO:51 |
| BM05433 | ERYHAYYEIWELPNLNRLQKAAFISSLSD | SEQ ID NO:52 |
| BM05434 | EKYKAYAEIWQLPNLNRTQKAAFISSLQD | SEQ ID NO:53 |
| BM05435 | ERYKAYYEIWQLPNLNRQQKGAFISSLQD | SEQ ID NO:54 |
| BM05436 | ERKLATFEIWELPNLNTSQKGAFISSLWD | SEQ ID NO:55 |
| BM05437 | ERYVAYYEIWQLPNLNVQQKAAFIASLQD | SEQ ID NO:56 |
| BM05438 | ERSIASVEIWELPNLNQRQKGAFIASLWD | SEQ ID NO:57 |
| BM05439 | ERKQAAVEIWELPNLNVRQKAAFIRSLFD | SEQ ID NO:58 |
| BM05440 | EKKIAAFEIWELPNLNQWQKAAFIASLFD | SEQ ID NO:59 |
| BM05441 | ERKIATVEIWELPNLNRIQKGAFIASLWD | SEQ ID NO:60 |
| BM05442 | EKYRAAGEIWELPNLNVLQKAAFIKSLWD | SEQ ID NO:61 |
| BM05443 | ERKIAAVEIWELPNLNRYQKAAFIKSLFD | SEQ ID NO:62 |
| BM05444 | EKRTATWEIWQLPNLNQRQRAAFIGSLWD | SEQ ID NO:63 |
| BM05445 | ERKTATVEIWELPNLNRRQKAAFIASLWD | SEQ ID NO:64 |
| BM05446 | ERKQAAVEIWELPNLNRIQKGAFIKSLWD | SEQ ID NO:65 |
| BM05447 | ERYIAYGEIWQLPNLNRRQKAAFIGSLSD | SEQ ID NO:66 |
| BM00014 | ERYRAYYEIWQLPNLNRTQKVAFIGSLQD | SEQ ID NO:67 |
| BM00015 | ERRLAYWEIWQLPNLNTTQKAAFIGSLQD | SEQ ID NO:68 |
| BM00016 | ERRRAYYEIWELPNLNRIQKAAFIGSLQD | SEQ ID NO:69 |
| BM00017 | ERRLAYYEIWELPNLNVAQKAAFIGSLQD | SEQ ID NO:70 |
| BM00018 | ERYLAYYEIWELPNLNVRQKAAFIGSLQD | SEQ ID NO:71 |
| BM00029 | ERYAAYYEIWQLPNLNSRQKAAFIGSLSD | SEQ ID NO:72 |
| BM00030 | ERYLAYYEIWQLPNLNQLQKAAFIGSLAD | SEQ ID NO:73 |
| BM00031 | ERYHAYYEIWQLPNLNSWQKAAFIGSLQD | SEQ ID NO:74 |

Figure 1C

| | | |
|---|---|---|
| Z05413 | VDNKFNKERYLAYYEIWQLPNLNRTQKAAFIGSLQDDPSQSANLLAEAKKLNDAQAPK | SEQ ID NO:700 |
| Z05414 | VDNKFNKERYIAYWEIWQLPNLNRRQKAAFISSLQDDPSQSANLLAEAKKLNDAQAPK | SEQ ID NO:701 |
| Z05415 | VDNKFNKERYRAYGEIWQLPNLNRGQKAAFIASLQDDPSQSANLLAEAKKLNDAQAPK | SEQ ID NO:702 |
| Z05416 | VDNKFNKEKYTAYFEIWQLPNLNVRQKAAFISSLQDDPSQSANLLAEAKKLNDAQAPK | SEQ ID NO:703 |
| Z05417 | VDNKFNKERYSAYYEIWQLPNLNVRQKAAFISSLQDDPSQSANLLAEAKKLNDAQAPK | SEQ ID NO:704 |
| Z05418 | VDNKFNKEKYAAYGEIWQLPNLNRSQKAAFIGSLSDDPSQSANLLAEAKKLNDAQAPK | SEQ ID NO:705 |
| Z05419 | VDNKFNKERKRATVEIWELPNLNRLQRGAFIASLWDDPSQSANLLAEAKKLNDAQAPK | SEQ ID NO:706 |
| Z05420 | VDNKFNKEWKQASFEIWELPNLNRLQKAAFISSLWDDPSQSANLLAEAKKLNDAQAPK | SEQ ID NO:707 |
| Z05421 | VDNKFNKERKHATVEIWELPNLNRVQKAAFIGSLADDPSQSANLLAEAKKLNDAQAPK | SEQ ID NO:708 |
| Z05422 | VDNKFNKEKYKAYVEIWQLPNLNQRQKAAFIGSLADDPSQSANLLAEAKKLNDAQAPK | SEQ ID NO:709 |
| Z05423 | VDNKFNKEKYVAYGEIWQLPNLNRTQKAAFISSLSDDPSQSANLLAEAKKLNDAQAPK | SEQ ID NO:710 |
| Z05424 | VDNKFNKERYIAYYEIWQLPNLNRYQKAAFIASLSDDPSQSANLLAEAKKLNDAQAPK | SEQ ID NO:711 |
| Z05425 | VDNKFNKEWKSAAFEIWQLPNLNVRQKAAFISSLADDPSQSANLLAEAKKLNDAQAPK | SEQ ID NO:712 |
| Z05426 | VDNKFNKERKAATVEIWELPNLNRVQKAAFIKSLFDDPSQSANLLAEAKKLNDAQAPK | SEQ ID NO:713 |
| Z05427 | VDNKFNKERYVAYYEIWQLPNLNQRQKAAFIGSLQDDPSQSANLLAEAKKLNDAQAPK | SEQ ID NO:714 |
| Z05428 | VDNKFNKERTRAYYEIWQLPNLNQRQKAAFIGSLSDDPSQSANLLAEAKKLNDAQAPK | SEQ ID NO:715 |
| Z05429 | VDNKFNKEWKSAAFEIWELPNLNRLQKAAFIRSLSDDPSQSANLLAEAKKLNDAQAPK | SEQ ID NO:716 |
| Z05430 | VDNKFNKERKQATFEIWELPNLNRHQKGAFIASLWDDPSQSANLLAEAKKLNDAQAPK | SEQ ID NO:717 |
| Z05431 | VDNKFNKEWKIAAGEIWQLPNLNRROKAAFIASLSDDPSQSANLLAEAKKLNDAQAPK | SEQ ID NO:718 |
| Z05432 | VDNKFNKERYLAYYEIWQLPNLNRRQKAAFIGSLQDDPSQSANLLAEAKKLNDAQAPK | SEQ ID NO:719 |
| Z05433 | VDNKFNKERYHAYYEIWELPNLNRLQKAAFISSLSDDPSQSANLLAEAKKLNDAQAPK | SEQ ID NO:720 |
| Z05434 | VDNKFNKERYLAEIWQLPNLNRTQKAAFISSLQDDPSQSANLLAEAKKLNDAQAPK | SEQ ID NO:721 |
| Z05435 | VDNKFNKEKYKAYYEIWQLPNLNRQQKAAFISSLQDDPSQSANLLAEAKKLNDAQAPK | SEQ ID NO:722 |
| Z05436 | VDNKFNKERKLATFEIWELPNLNTSQKGAFISSIWDDPSQSANLLAEAKKLNDAQAPK | SEQ ID NO:723 |
| Z05437 | VDNKFNKERYVAYYEIWQLPNLNVQKAAFIASLQDDPSQSANLLAEAKKLNDAQAPK | SEQ ID NO:724 |

Figure 1CC

| | | |
|---|---|---|
| BM00033 | ERYHAYYEIWQLPNLNSAQKAAFIGSLQD | SEQ ID NO:75 |
| BM00034 | ERYEAYYEIWQLPNLNSVQKAAFIGSLQD | SEQ ID NO:76 |
| BM00035 | ERYHAYYEIWQLPNLNRRQKAAFIGSLQD | SEQ ID NO:77 |
| BM00036 | ERYTAYYEIWQLPNLNRAQKAAFIGSLQD | SEQ ID NO:78 |
| BM00039 | ERYSAYYEIWQLPNLNRAQKAAFIGSLSD | SEQ ID NO:79 |
| BM00042 | ERYSAYYEIWELPNLNRAQKAAFIGSLSD | SEQ ID NO:80 |
| BM00043 | ERYHAYYEIWQLPNLNRAQKAAFIGSLYD | SEQ ID NO:81 |
| BM00044 | ERYSAYVEIWQLPNLNRGQKAAFIGSLYD | SEQ ID NO:82 |
| BM00045 | ERYSAYFEIWQLPNLNRLQKAAFIGSLQD | SEQ ID NO:83 |
| BM00046 | ERYNAYFEIWQLPNLNRYQKSAFIGSLQD | SEQ ID NO:84 |
| BM00047 | ERYAAYFEIWQLPNLNVAQKAAFIGSLQD | SEQ ID NO:85 |
| BM00048 | ERYQAYFEIWQLPNLNQWQKAAFIGSLQD | SEQ ID NO:86 |
| BM00049 | ERYKAYWEIWQLPNLNQGQKAAFIGSLQD | SEQ ID NO:87 |
| BM00050 | ERYIAYGEIWQLPNLNVGQKAAFIGSLQD | SEQ ID NO:88 |
| BM00051 | ERYRAYVEIWQLPNLNRVQKAAFIGSLQD | SEQ ID NO:89 |
| BM00052 | ERYKAYVEIWQLPNLNRTQKAAFIGSLQD | SEQ ID NO:90 |
| BM00053 | EKYEAYGEIWELPNLNRSQKAAFIGSLED | SEQ ID NO:91 |
| BM00054 | EKYQAYGEIWQLPNLNRSQKAAFITSLED | SEQ ID NO:92 |
| BM00058 | EKYAAYGEIWLLPNLNRIQKAAFIGSLQD | SEQ ID NO:93 |
| BM00060 | EKYKAYGEIWELPNLNRRQKVAFISSLSD | SEQ ID NO:94 |
| BM00061 | EKYKAYGEIWELPNLNRSQKAAFIASLSD | SEQ ID NO:95 |
| BM00072 | EKYKAYGEIWQLPNLNQRQKAAFIASLSD | SEQ ID NO:96 |
| BM00075 | EKYKAYGEIWQLPNLNRSQKAAFISSLQD | SEQ ID NO:97 |
| BM00076 | EKYKAYGEIWQLPNLNRRQKAAFISSLAD | SEQ ID NO:98 |
| BM00077 | EKYNAYGEIWQLPNLNRGQKAAFISSLSD | SEQ ID NO:99 |

Figure 1D

| | | |
|---|---|---|
| Z05438 | VDNKFNKERSIASVEIWELPNLNQRQKGAFTASLWDDPSQSANLLAEAKKLNDAQAPK | SEQ ID NO:725 |
| Z05439 | VDNKFNKERKQAAVEIWELPNLNVRQKAAFIRSLFDDPSQSANLLAEAKKLNDAQAPK | SEQ ID NO:726 |
| Z05440 | VDNKFNKEKIAAFEIWELPNLNQWQKAAFIASLFDDPSQSANLLAEAKKLNDAQAPK | SEQ ID NO:727 |
| Z05441 | VDNKFNKERKIATVEIWELPNLNRIQKGAFTASLWDDPSQSANLLAEAKKLNDAQAPK | SEQ ID NO:728 |
| Z05442 | VDNKFNKEKYRAAGEIWELPNLNVLQKAAFIKSLWDDPSQSANLLAEAKKLNDAQAPK | SEQ ID NO:729 |
| Z05443 | VDNKFNKERKIAAVEIWELPNLNRYQKAAFIKSLFDDPSQSANLLAEAKKLNDAQAPK | SEQ ID NO:730 |
| Z05444 | VDNKFNKERTATWEIWQLPNLNQRQRAAFIGSLWDDPSQSANLLAEAKKLNDAQAPK | SEQ ID NO:731 |
| Z05445 | VDNKFNKERKTATVEIWELPNLNRRQKAAFTASLWDDPSQSANLLAEAKKLNDAQAPK | SEQ ID NO:732 |
| Z05446 | VDNKFNKERKQAAVEIWELPNLNRIQKGAFTKSLWDDPSQSANLLAEAKKLNDAQAPK | SEQ ID NO:733 |
| Z05447 | VDNKFNKERYIAYGEIWQLPNLNRRQKAAFIGSLSDDPSQSANLLAEAKKLNDAQAPK | SEQ ID NO:734 |
| Z00014 | VDNKFNKERYRAYYEIWQLPNLNRTQKVAFIGSLQDDPSQSANLLAEAKKLNDAQAPK | SEQ ID NO:735 |
| Z00015 | VDNKFNKERLAYWEIWQLPNLNTTQKAAFIGSLQDDPSQSANLLAEAKKLNDAQAPK | SEQ ID NO:736 |
| Z00016 | VDNKFNKERRAYYEIWQLPNLNRIQKAAFIGSLQDDPSQSANLLAEAKKLNDAQAPK | SEQ ID NO:737 |
| Z00017 | VDNKFNKERLAYYEIWELPNLNVAQKAAFIGSLQDDPSQSANLLAEAKKLNDAQAPK | SEQ ID NO:738 |
| Z00018 | VDNKFNKERLAYYEIWELPNLNVRQKAAFIGSLQDDPSQSANLLAEAKKLNDAQAPK | SEQ ID NO:739 |
| Z00029 | VDNKFNKERYAAYYEIWQLPNLNSRQKAAFIGSLSDDPSQSANLLAEAKKLNDAQAPK | SEQ ID NO:740 |
| Z00030 | VDNKFNKERYLAYYEIWQLPNLNLQKAAFIGSLADDPSQSANLLAEAKKLNDAQAPK | SEQ ID NO:741 |
| Z00031 | VDNKFNKERYHAYYEIWQLPNLNSWQKAAFIGSLQDDPSQSANLLAEAKKLNDAQAPK | SEQ ID NO:742 |
| Z00033 | VDNKFNKERYHAYYEIWQLPNLNSAQKAAFIGSLQDDPSQSANLLAEAKKLNDAQAPK | SEQ ID NO:743 |
| Z00034 | VDNKFNKERYEAYYEIWQLPNLNSVQKAAFIGSLQDDPSQSANLLAEAKKLNDAQAPK | SEQ ID NO:744 |
| Z00035 | VDNKFNKERYHAYYEIWQLPNLNRRQKAAFIGSLQDDPSQSANLLAEAKKLNDAQAPK | SEQ ID NO:745 |
| Z00036 | VDNKFNKERYTAYYEIWQLPNLNRAQKAAFIGSLQDDPSQSANLLAEAKKLNDAQAPK | SEQ ID NO:746 |
| Z00039 | VDNKFNKERYSAYYEIWQLPNLNRAQKAAFIGSLSDDPSQSANLLAEAKKLNDAQAPK | SEQ ID NO:747 |
| Z00042 | VDNKFNKERYSAYYEIWELPNLNRAQKAAFTGSLSDDPSQSANLLAEAKKLNDAQAPK | SEQ ID NO:748 |
| Z00043 | VDNKFNKERYHAYYEIWQLPNLNRAQKAAFIGSLYDDPSQSANLLAEAKKLNDAQAPK | SEQ ID NO:749 |

Figure 1DD

| | | |
|---|---|---|
| BM00080 | EKYVAYAEIWQLPNLNRVQKAAFIGSLSD | SEQ ID NO:100 |
| BM00083 | EKYQAYGEIWQLPNLNRVQKAAFIGSLSD | SEQ ID NO:101 |
| BM00088 | EKYHAYGEIWQLPNLNRIQKAAFIASLQD | SEQ ID NO:102 |
| BM00092 | EKYTAYVEIWQLPNLNRYQRAAFIASLSD | SEQ ID NO:103 |
| BM00095 | EKYKAYVEIWQLPNLNRGQKAAFIGSLSD | SEQ ID NO:104 |
| BM00096 | EKYVAYVEIWQLPNLNRTQKAAFIASLED | SEQ ID NO:105 |
| BM00097 | EKYTAYVEIWQLPNLNRTQKAAFIASLSD | SEQ ID NO:106 |
| BM00100 | EKYKAYAEIWQLPNLNRAQKAAFIGSLYD | SEQ ID NO:107 |
| BM00113 | EKYTAYGEIWQLPNLNVRQKAAFISSLSD | SEQ ID NO:108 |
| BM00116 | EKYTAYGEIWQLPNLNQRQKAAFIGSLQD | SEQ ID NO:109 |
| BM00117 | EKYTAYFEIWQLPNLNQGQKAAFIGSLQD | SEQ ID NO:110 |
| BM00122 | EKYQAYVEIWQLPNLNQRQKAAFIGSLAD | SEQ ID NO:111 |
| BM00123 | EKYAAYVEIWQLPNLNQRQKAAFIGSLQD | SEQ ID NO:112 |
| BM00126 | EKYVAYVEIWQLPNLNTSQKAAFIGSLQD | SEQ ID NO:113 |
| BM00127 | EKYQAYAEIWQLPNLNVRQKSAFIGSLQD | SEQ ID NO:114 |
| BM00128 | EKYQAYYEIWELPNLNVQQKSAFITSLSD | SEQ ID NO:115 |
| BM00129 | EKYHAYYEIWQLPNLNVHQKAAFIRSLAD | SEQ ID NO:116 |
| BM00130 | EKYQAYYEIWQLPNLNVAQKAAFIRSLSD | SEQ ID NO:117 |
| BM00131 | EKYTAYYEIWQLPNLNRTQKAAFIGSLSD | SEQ ID NO:118 |
| BM00137 | ERYRAYYEIWQLPNLNRQQKAAFIGSLQD | SEQ ID NO:119 |
| BM00138 | EKYKAYYEIWQLPNLNRSQKGAFIGSLQD | SEQ ID NO:120 |
| BM00139 | EKYIAYYEIWQLPNLNRSQKGAFIGSLQD | SEQ ID NO:121 |
| BM00140 | ERYKAYYEIWQLPNLNRQQKAAFIGSLAD | SEQ ID NO:122 |
| BM00141 | ERYLAYYEIWQLPNLNQFQKAAFIASLQD | SEQ ID NO:123 |
| BM00142 | ERYLAYYEIWQLPNLNREQKAAFIASLQD | SEQ ID NO:124 |

Figure 1E

| | | |
|---|---|---|
| Z00044 | VDNKFNKERYSAYVEIWQLPNLNRGQKAAFIGSLYDDPSQSANLLAEAKKLNDAQAPK | SEQ ID NO:750 |
| Z00045 | VDNKFNKERYSAYFEIWQLPNLNRLQKAAFIGSLQDDPSQSANLLAEAKKLNDAQAPK | SEQ ID NO:751 |
| Z00046 | VDNKFNKERYNAYFEIWQLPNLNRYQKSAFIGSLQDDPSQSANLLAEAKKLNDAQAPK | SEQ ID NO:752 |
| Z00047 | VDNKFNKERYAAYFEIWQLPNLNVAQKAAFIGSLQDDPSQSANLLAEAKKLNDAQAPK | SEQ ID NO:753 |
| Z00048 | VDNKFNKERYQAYFEIWQLPNLNQMQKAAFIGSLQDDPSQSANLLAEAKKLNDAQAPK | SEQ ID NO:754 |
| Z00049 | VDNKFNKERYKAYWEIWQLPNLNQGQKAAFIGSLQDDPSQSANLLAEAKKLNDAQAPK | SEQ ID NO:755 |
| Z00050 | VDNKFNKERYIAYGEIWQLPNLNVGQKAAFIGSLQDDPSQSANLLAEAKKLNDAQAPK | SEQ ID NO:756 |
| Z00051 | VDNKFNKERYRAYVEIWQLPNLNRVQKAAFIGSLQDDPSQSANLLAEAKKLNDAQAPK | SEQ ID NO:757 |
| Z00052 | VDNKFNKERYKAYVEIWQLPNLNRTQKAAFIGSLQDDPSQSANLLAEAKKLNDAQAPK | SEQ ID NO:758 |
| Z00053 | VDNKFNKEKYEAYGEIWELPNLNRSQKAAFIGSLEDDPSQSANLLAEAKKLNDAQAPK | SEQ ID NO:759 |
| Z00054 | VDNKFNKEKYQAYGEIWQLPNLNRSQKAAFITSLEDDPSQSANLLAEAKKLNDAQAPK | SEQ ID NO:760 |
| Z00058 | VDNKFNKEKYAAYGEIWLLPNLNRIQKAAFIGSLQDDPSQSANLLAEAKKLNDAQAPK | SEQ ID NO:761 |
| Z00060 | VDNKFNKEKYKAYGEIWELPNLNRRQKVAFISSLSDDPSQSANLLAEAKKLNDAQAPK | SEQ ID NO:762 |
| Z00061 | VDNKFNKEKYKAYGEIWELPNLNRSQKAAFIASLSDDPSQSANLLAEAKKLNDAQAPK | SEQ ID NO:763 |
| Z00072 | VDNKFNKEKYKAYGEIWQLPNLNQROKAAFIASLSDDPSQSANLLAEAKKLNDAQAPK | SEQ ID NO:764 |
| Z00075 | VDNKFNKEKYKAYGEIWQLPNLNRSQKAAFISSLQDDPSQSANLLAEAKKLNDAQAPK | SEQ ID NO:765 |
| Z00076 | VDNKFNKEKYKAYGEIWQLPNLNRRQKAAFISSLADDPSQSANLLAEAKKLNDAQAPK | SEQ ID NO:766 |
| Z00077 | VDNKFNKEKYNAYGEIWQLPNLNRGQKAAFISSLSDDPSQSANLLAEAKKLNDAQAPK | SEQ ID NO:767 |
| Z00080 | VDNKFNKEKYVAYAEIWQLPNLNRVQKAAFIGSLSDDPSQSANLLAEAKKLNDAQAPK | SEQ ID NO:768 |
| Z00083 | VDNKFNKEKYQAYGEIWQLPNLNRVQKAAFIGSLSDDPSQSANLLAEAKKLNDAQAPK | SEQ ID NO:769 |
| Z00088 | VDNKFNKEKYHAYGEIWQLPNLNRIQKAAFIASLQDDPSQSANLLAEAKKLNDAQAPK | SEQ ID NO:770 |
| Z00092 | VDNKFNKEKYTAYVEIWQLPNLNRYQRAAFIASLSDDPSQSANLLAEAKKLNDAQAPK | SEQ ID NO:771 |
| Z00095 | VDNKFNKEKYKAYVEIWQLPNLNRGQKAAFIGSLSDDPSQSANLLAEAKKLNDAQAPK | SEQ ID NO:772 |
| Z00096 | VDNKFNKEKYVAYVEIWQLPNLNRTQKAAFIASLEDDPSQSANLLAEAKKLNDAQAPK | SEQ ID NO:773 |
| Z00097 | VDNKFNKEKYIAYVEIWQLPNLNRTQKAAFIASLSDDPSQSANLLAEAKKLNDAQAPK | SEQ ID NO:774 |

Figure 1EE

| | | |
|---|---|---|
| BM00146 | ERYVAYGEIWQLPNLNRYQKAAFIASLQD | SEQ ID NO:125 |
| BM00147 | ERYIAYYEIWQLPNLNRAQKAAFIASLQD | SEQ ID NO:126 |
| BM00152 | ERYQAYYEIWQLPNLNRIQKAAFIKSLQD | SEQ ID NO:127 |
| BM00153 | ERYTAYYEIWQLPNLNTQKAAFIRSLED | SEQ ID NO:128 |
| BM00154 | ERYQAYYEIWQLPNLNTIQKAAFIRSLQD | SEQ ID NO:129 |
| BM00155 | ERYAAYAEIWQLPNLNRWQKAAFISSLQD | SEQ ID NO:130 |
| BM00157 | ERYRAYAEIWQLPNLNRWQKAAFIASLQD | SEQ ID NO:131 |
| BM00158 | ERYRAYAEIWQLPNLNRIQKAAFIGSLED | SEQ ID NO:132 |
| BM00160 | ERYHAYAEIWQLPNLNRIQKAAFIGSLQD | SEQ ID NO:133 |
| BM00161 | ERYRAYYEIWQLPNLNRYQKAAFIASLSD | SEQ ID NO:134 |
| BM00168 | ERYTAYYEIWQLPNLNRVQKAAFIASLSD | SEQ ID NO:135 |
| BM00169 | ERYHAYYEIWQLPNLNRTQKAAFIASLSD | SEQ ID NO:136 |
| BM00170 | ERYVAYYEIWQLPNLNRRQKAAFISSLSD | SEQ ID NO:137 |
| BM00171 | ERYLAYFEIWQLPNLNRHQKGAFIASLED | SEQ ID NO:138 |
| BM00172 | ERYTAYFEIWQLPNLNRWQKGAFIASLED | SEQ ID NO:139 |
| BM00176 | ERYAAYFEIWQLPNLNRLQKAAFISSLED | SEQ ID NO:140 |
| BM00177 | ERYVAYFEIWQLPNLNRSQKAAFISSLED | SEQ ID NO:141 |
| BM00178 | ERYGAYFEIWQLPNLNRTQKAAFIASLAD | SEQ ID NO:142 |
| BM00182 | EKYIAYWEIWQLPNLNREQKAAFISSLQD | SEQ ID NO:143 |
| BM00184 | ERYIAYAEIWQLPNLNRRQKAAFIASLED | SEQ ID NO:144 |
| BM00185 | ERYIAYWEIWQLPNLNQRQKAAFIASLAD | SEQ ID NO:145 |
| BM00186 | ERYIAYWEIWQLPNLNRLQKSAFIASLQD | SEQ ID NO:146 |
| BM00187 | ERYHAYWEIWQLPNLNRAQKAAFIRSLQD | SEQ ID NO:147 |
| BM00188 | ERYNAYWEIWQLPNLNRLQKAAFIRSLQD | SEQ ID NO:148 |
| BM00189 | ERYTAYGEIWELPNLNRVQRAAFIASLAD | SEQ ID NO:149 |

Figure 1F

| | | |
|---|---|---|
| Z00100 | VDNKFNKEKYKAYAEIWQLPNLNRAQKAAFIGSLYDDPSQSANLLAEAKKLNDAQAPK | SEQ ID NO:775 |
| Z00113 | VDNKFNKEKYTAYGEIWQLPNLNVRQKAAFISSLSDDPSQSANLLAEAKKLNDAQAPK | SEQ ID NO:776 |
| Z00116 | VDNKFNKEKYTAYGEIWQLPNLNQRQKAAFISSLQDDPSQSANLLAEAKKLNDAQAPK | SEQ ID NO:777 |
| Z00117 | VDNKFNKEKYTAYFEIWQLPNLNQGKAAFIGSLQDDPSQSANLLAEAKKLNDAQAPK | SEQ ID NO:778 |
| Z00122 | VDNKFNKEKYQAYVEIWQLPNLNQRQKAAFIGSLADDPSQSANLLAEAKKLNDAQAPK | SEQ ID NO:779 |
| Z00123 | VDNKFNKEKYAAYVEIWQLPNLNQRQKAAFIGSLQDDPSQSANLLAEAKKLNDAQAPK | SEQ ID NO:780 |
| Z00126 | VDNKFNKEKYVAYVEIWQLPNLNTSQKAAFIGSLQDDPSQSANLLAEAKKLNDAQAPK | SEQ ID NO:781 |
| Z00127 | VDNKFNKEKYQAYAEIWQLPNLNVRQKSAFIGSLQDDPSQSANLLAEAKKLNDAQAPK | SEQ ID NO:782 |
| Z00128 | VDNKFNKEKYQAYYEIWELPNLNVQQKSAFITSLQDDPSQSANLLAEAKKLNDAQAPK | SEQ ID NO:783 |
| Z00129 | VDNKFNKEKYHAYYEIWQLPNLNVHQKAAFIRSLADDPSQSANLLAEAKKLNDAQAPK | SEQ ID NO:784 |
| Z00130 | VDNKFNKEKYQAYEIWQLPNLNVAQKAAFIRSLSDDPSQSANLLAEAKKLNDAQAPK | SEQ ID NO:785 |
| Z00131 | VDNKFNKEKYTAYYEIWQLPNLNRTQKAAFIGSLSDDPSQSANLLAEAKKLNDAQAPK | SEQ ID NO:786 |
| Z00137 | VDNKFNKERYRAYYEIWQLPNLNRQQKGAFIASLQDDPSQSANLLAEAKKLNDAQAPK | SEQ ID NO:787 |
| Z00138 | VDNKFNKEKYKAYYEIWQLPNLNRSQKGAFIGSLQDDPSQSANLLAEAKKLNDAQAPK | SEQ ID NO:788 |
| Z00139 | VDNKFNKEKYIAYYEIWQLPNLNRSQKGAFIGSLQDDPSQSANLLAEAKKLNDAQAPK | SEQ ID NO:789 |
| Z00140 | VDNKFNKERYKAYYEIWQLPNLNRQQKAAFIASLADDPSQSANLLAEAKKLNDAQAPK | SEQ ID NO:790 |
| Z00141 | VDNKFNKERYLAYYEIWQLPNLNREQKAAFIASLQDDPSQSANLLAEAKKLNDAQAPK | SEQ ID NO:791 |
| Z00142 | VDNKFNKERYVAYGEIWQLPNLNLNQFQKAAFIASLQDDPSQSANLLAEAKKLNDAQAPK | SEQ ID NO:792 |
| Z00146 | VDNKFNKERYIAYYEIWQLPNLNRYQKAAFIASLQDDPSQSANLLAEAKKLNDAQAPK | SEQ ID NO:793 |
| Z00147 | VDNKFNKERYIAYYEIWQLPNLNRAQKAAFIASLQDDPSQSANLLAEAKKLNDAQAPK | SEQ ID NO:794 |
| Z00152 | VDNKFNKERYQAYEIWQLPNLNRIQKAAFIKSLQDDPSQSANLLAEAKKLNDAQAPK | SEQ ID NO:795 |
| Z00153 | VDNKFNKERYTAYYEIWQLPNLNTQQKAAFIRSLEDDPSQSANLLAEAKKLNDAQAPK | SEQ ID NO:796 |
| Z00154 | VDNKFNKERYQAYYEIWQLPNLNTIQKAAFIRSLQDDPSQSANLLAEAKKLNDAQAPK | SEQ ID NO:797 |
| Z00155 | VDNKFNKERYAAYAEIWQLPNLNRWQKAAFISSLQDDPSQSANLLAEAKKLNDAQAPK | SEQ ID NO:798 |
| Z00157 | VDNKFNKERYRAYAEIWQLPNLNRWQKAAFIASLQDDPSQSANLLAEAKKLNDAQAPK | SEQ ID NO:799 |

Figure 1FF

| | | |
|---|---|---|
| BM00190 | ERYTAYGEIWELPNLNRLQKAAFIGSLAD | SEQ ID NO:150 |
| BM00191 | ERYHAYGEIWELPNLNRRQKAAFITSLAD | SEQ ID NO:151 |
| BM00192 | ERYKAYGEIWQLPNLNRLQKAAFIGSLAD | SEQ ID NO:152 |
| BM00193 | ERYQAYGEIWQLPNLNRLQKAAFIGSLAD | SEQ ID NO:153 |
| BM00194 | ERYVAYGEIWQLPNLNRLQKAAFISSLAD | SEQ ID NO:154 |
| BM00197 | ERYIAYGEIWELPNLNRLQKAAFIGSLSD | SEQ ID NO:155 |
| BM00198 | ERYQAYGEIWQLPNLNRRQKAAFISSLQD | SEQ ID NO:156 |
| BM00199 | ERRQAYGEIWQLPNLNRYQKAAFISSLQD | SEQ ID NO:157 |
| BM00200 | ERYRAYFEIWELPNLNRIQKVAFIASLQD | SEQ ID NO:158 |
| BM00201 | EKYTAYGEIWELPNLNRIQKVAFIASLQD | SEQ ID NO:159 |
| BM00202 | EKYAAYVEIWELPNLNRRQKAAFIASLQD | SEQ ID NO:160 |
| BM00203 | ERYRAYVEIWELPNLNRWQKAAFIRSLQD | SEQ ID NO:161 |
| BM00208 | ERYRAYFEIWELPNLNRAQKAAFISSLSD | SEQ ID NO:162 |
| BM00209 | ERYQAYFEIWQLPNLNRLQAGAFIASLSD | SEQ ID NO:163 |
| BM00210 | EKYQAYVEIWQLPNLNRLQKGAFIASLSD | SEQ ID NO:164 |
| BM00211 | EKYAAYYEIWELPNLNRSQKGAFIASLSD | SEQ ID NO:165 |
| BM00212 | EKYQAYYEIWELPNLNRGQKAAFIASLSD | SEQ ID NO:166 |
| BM00215 | EKYNAYFEIWQLPNLNRLQKAAFITSLSD | SEQ ID NO:167 |
| BM00217 | EKYSAYFEIWQLPNLNTSQKAAFIASLSD | SEQ ID NO:168 |
| BM00218 | ERYNAYFEIWELPNLNVRQKAAFIRSLSD | SEQ ID NO:169 |
| BM00219 | EKYEAYFEIWELPNLNSRQKAAFIGSLSD | SEQ ID NO:170 |
| BM00220 | ERYRAYWEIWELPNLNQQQKVAFIRSLYD | SEQ ID NO:171 |
| BM00222 | ERYNAYWEIWELPNLNQGQKVAFIRSLQD | SEQ ID NO:172 |
| BM00224 | ERRHAYGEIWQLPNLNQRQKVAFISSLQD | SEQ ID NO:173 |
| BM00225 | EKYVATWEIWELPNLNRAQKVAFIGSLWD | SEQ ID NO:174 |

Figure 1G

| | | |
|---|---|---|
| Z00158 | VDNKFNKERYRAYAEIWQLPNLNRIQKAAFIGSLEDDPSQSANLLAEAKKLNDAQAPK | SEQ ID NO:800 |
| Z00160 | VDNKFNKERYHAYAEIWQLPNLNRIQKAAFIGSLQDDPSQSANLLAEAKKLNDAQAPK | SEQ ID NO:801 |
| Z00161 | VDNKFNKERYRAYYEIWQLPNLNRYQKAAFIASLSDDPSQSANLLAEAKKLNDAQAPK | SEQ ID NO:802 |
| Z00168 | VDNKFNKERYTAYYEIWQLPNLNRVQKAAFIASLSDDPSQSANLLAEAKKLNDAQAPK | SEQ ID NO:803 |
| Z00169 | VDNKFNKERYHAYYEIWQLPNLNRTQKAAFIASLSDDPSQSANLLAEAKKLNDAQAPK | SEQ ID NO:804 |
| Z00170 | VDNKFNKERYVAYYEIWQLPNLNRRQKAAFISSLSDDPSQSANLLAEAKKLNDAQAPK | SEQ ID NO:805 |
| Z00171 | VDNKFNKERYLAYFEIWQLPNLNRHQKGAFIASLEDDPSQSANLLAEAKKLNDAQAPK | SEQ ID NO:806 |
| Z00172 | VDNKFNKERYTAYFEIWQLPNLNRWQKGAFIASLEDDPSQSANLLAEAKKLNDAQAPK | SEQ ID NO:807 |
| Z00176 | VDNKFNKERYAAYFEIWQLPNLNRLQKAAFISSLEDDPSQSANLLAEAKKLNDAQAPK | SEQ ID NO:808 |
| Z00177 | VDNKFNKERYVAYFEIWQLPNLNRSQKAAFIASLSDDPSQSANLLAEAKKLNDAQAPK | SEQ ID NO:809 |
| Z00178 | VDNKFNKERYGAYFEIWQLPNLNRTQKAAFIASLADDPSQSANLLAEAKKLNDAQAPK | SEQ ID NO:810 |
| Z00182 | VDNKFNKEKYIAYWEIWQLPNLNREQKAAFISSLQDDPSQSANLLAEAKKLNDAQAPK | SEQ ID NO:811 |
| Z00184 | VDNKFNKERYIAYAEIWQLPNLNRRQKAAFIASLEDDPSQSANLLAEAKKLNDAQAPK | SEQ ID NO:812 |
| Z00185 | VDNKFNKERYIAYWEIWQLPNLNQRQKAAFIASLADDPSQSANLLAEAKKLNDAQAPK | SEQ ID NO:813 |
| Z00186 | VDNKFNKERYIAYWEIWQLPNLNRLQKSAFIASLQDDPSQSANLLAEAKKLNDAQAPK | SEQ ID NO:814 |
| Z00187 | VDNKFNKERYHAYWEIWQLPNLNRAQKAAFIRSLQDDPSQSANLLAEAKKLNDAQAPK | SEQ ID NO:815 |
| Z00188 | VDNKFNKERYNAYWEIWQLPNLNRLQKAAFIRSLQDDPSQSANLLAEAKKLNDAQAPK | SEQ ID NO:816 |
| Z00189 | VDNKFNKERYTAYGEIWELPNLNRVQRAAFIASLADDPSQSANLLAEAKKLNDAQAPK | SEQ ID NO:817 |
| Z00190 | VDNKFNKERYTAYGEIWQLPNLNRLQKAAFIGSLADDPSQSANLLAEAKKLNDAQAPK | SEQ ID NO:818 |
| Z00191 | VDNKFNKERYHAYGEIWELPNLNRRQKAAFITSLADDPSQSANLLAEAKKLNDAQAPK | SEQ ID NO:819 |
| Z00192 | VDNKFNKERYKAYGEIWQLPNLNRLQKAAFIGSLADDPSQSANLLAEAKKLNDAQAPK | SEQ ID NO:820 |
| Z00193 | VDNKFNKERYQAYGEIWQLPNLNRLQKAAFIGSLADDPSQSANLLAEAKKLNDAQAPK | SEQ ID NO:821 |
| Z00194 | VDNKFNKERYVAYGEIWQLPNLNRLQKAAFISSLADDPSQSANLLAEAKKLNDAQAPK | SEQ ID NO:822 |
| Z00197 | VDNKFNKERYIAYGEIWELPNLNRLQKAAFIGSLSDDPSQSANLLAEAKKLNDAQAPK | SEQ ID NO:823 |
| Z00198 | VDNKFNKERYQAYGEIWQLPNLNRRQKAAFISSLQDDPSQSANLLAEAKKLNDAQAPK | SEQ ID NO:824 |

Figure 1GG

| | | |
|---|---|---|
| BM00226 | ERRIARWEIWELPNLNRLQKVAFIGSLED | SEQ ID NO:175 |
| BM00227 | EKYKAAGEIWQLPNLNRGQKVAFIGSLED | SEQ ID NO:176 |
| BM00228 | EKYLAYGEIWQLPNLNRHQKVAFIGSLSD | SEQ ID NO:177 |
| BM00229 | EKYQAYGEIWQLPNLNRQQKVAFISSLQD | SEQ ID NO:178 |
| BM00231 | EKYKAYGEIWQLPNLNRQQKVAFIISLQD | SEQ ID NO:179 |
| BM00232 | EKYAAAYEIWQLPNLNRQRQKGAFIASLFD | SEQ ID NO:180 |
| BM00233 | EKYAASYEIWELPNLNRQRQKAAFIKSLFD | SEQ ID NO:181 |
| BM00234 | EKYLASYEIWQLPNLNRRQKAAFIASLFD | SEQ ID NO:182 |
| BM00235 | EKYSATFEIWQLPNLNRQRQKAAFISSLWD | SEQ ID NO:183 |
| BM00237 | EKYAASFEIWQLPNLNTHQKAAFISSLWD | SEQ ID NO:184 |
| BM00238 | EKYKASGEIWQLPNLNRLQRAAFIKSLFD | SEQ ID NO:185 |
| BM00239 | EKYSASGEIWQLPNLNRTQKAAFIKSLWD | SEQ ID NO:186 |
| BM00243 | EKYHAAGEIWELPNLNRLQKAAFIRSLWD | SEQ ID NO:187 |
| BM00244 | EKYRAAGEIWELPNLNRQQKAAFIRSLFD | SEQ ID NO:188 |
| BM00245 | EKYQASGEIWELPNLNRLQKAAFIRSLFD | SEQ ID NO:189 |
| BM00246 | EKYKATGEIWELPNLNRIQKAAFIKSLWD | SEQ ID NO:190 |
| BM00247 | EKYQASFEIWELPNLNRSQKAAFIKSLWD | SEQ ID NO:191 |
| BM00248 | ERKVAAVEIWQLPNLNRWQRGAFISSLFD | SEQ ID NO:192 |
| BM00249 | ERKLAAVEIWELPNLNQYQRGAFISSLWD | SEQ ID NO:193 |
| BM00250 | ERKKASVEIWELPNLNRYQKGAFISSLFD | SEQ ID NO:194 |
| BM00253 | ERKHAAWEIWELPNLNRHQKGAFIKSLWD | SEQ ID NO:195 |
| BM00254 | ERKHAAVEIWELPNLNRWQKGAFISSLWD | SEQ ID NO:196 |
| BM00255 | EKRHAAVEIWELPNLNVFQRGAFIASLYD | SEQ ID NO:197 |
| BM00256 | ERKHAAVEIWELPNLNRLQRGAFIASLYD | SEQ ID NO:198 |
| BM00258 | EWKTAAVEIWELPNLNRRQKAAFIGSLYD | SEQ ID NO:199 |

Figure 1H

| | | |
|---|---|---|
| Z00199 | VDNKFNKERRQAYFEIWELPNLNRYQKAAFISSLQDDPSQSANLLAEAKKLNDAQAPK | SEQ ID NO:825 |
| Z00200 | VDNKFNKERYRAYVEIWELPNLNRIQKVAFIASLQDDPSQSANLLAEAKKLNDAQAPK | SEQ ID NO:826 |
| Z00201 | VDNKFNKEKYTAYGEIWELPNLNRIQKVAFIASLQDDPSQSANLLAEAKKLNDAQAPK | SEQ ID NO:827 |
| Z00202 | VDNKFNKEKYAAYVEIWELPNLNRRQKAAFIASLQDDPSQSANLLAEAKKLNDAQAPK | SEQ ID NO:828 |
| Z00203 | VDNKFNKERYRAYVEIWELPNLNRWQKAAFIRSLQDDPSQSANLLAEAKKLNDAQAPK | SEQ ID NO:829 |
| Z00208 | VDNKFNKERYRAYFEIWELPNLNRAQKAAFISSLDDPSQSANLLAEAKKLNDAQAPK | SEQ ID NO:830 |
| Z00209 | VDNKFNKERYQAYFEIWQLPNLNRLQAGAFIASLSDDPSQSANLLAEAKKLNDAQAPK | SEQ ID NO:831 |
| Z00210 | VDNKFNKERYQAYVEIWQLPNLNRLQKGAFIASLSDDPSQSANLLAEAKKLNDAQAPK | SEQ ID NO:832 |
| Z00211 | VDNKFNKEKYQAYVEIWQLPNLNRSQKGAFIASLSDDPSQSANLLAEAKKLNDAQAPK | SEQ ID NO:833 |
| Z00212 | VDNKFNKEKYQAYYEIWELPNLNRGQKAAFIASLSDDPSQSANLLAEAKKLNDAQAPK | SEQ ID NO:834 |
| Z00215 | VDNKFNKEKYNAYFEIWQLPNLNRLQKAAFITSLSDDPSQSANLLAEAKKLNDAQAPK | SEQ ID NO:835 |
| Z00217 | VDNKFNKEKYSAYFEIWQLPNLNTSQKAAFIASLSDDPSQSANLLAEAKKLNDAQAPK | SEQ ID NO:836 |
| Z00218 | VDNKFNKERYNAYFEIWEIWELPNLNVRQKAAFIRSLSDDPSQSANLLAEAKKLNDAQAPK | SEQ ID NO:837 |
| Z00219 | VDNKFNKEKYEAYFEIWELPNLNSRQKVAFIGSLSDDPSQSANLLAEAKKLNDAQAPK | SEQ ID NO:838 |
| Z00220 | VDNKFNKERYRAYWEIWELPNLNQQKVAFIRSLYDDPSQSANLLAEAKKLNDAQAPK | SEQ ID NO:839 |
| Z00222 | VDNKFNKERYNAYWEIWELPNLNQGQKVAFIRSLQDDPSQSANLLAEAKKLNDAQAPK | SEQ ID NO:840 |
| Z00224 | VDNKFNKERRHAYGEIWQLPNLNQRQKVAFISSLQDDPSQSANLLAEAKKLNDAQAPK | SEQ ID NO:841 |
| Z00225 | VDNKFNKEKYVATWEIWEIWELPNLNRAQKVAFIGSLWDDPSQSANLLAEAKKLNDAQAPK | SEQ ID NO:842 |
| Z00226 | VDNKFNKERRIARWEIWELPNLNRLQKVAFIGSLEDDPSQSANLLAEAKKLNDAQAPK | SEQ ID NO:843 |
| Z00227 | VDNKFNKEKYKAAGEIWQLPNLNRGQKVAFIGSLEDDPSQSANLLAEAKKLNDAQAPK | SEQ ID NO:844 |
| Z00228 | VDNKFNKEKYKAAGEIWQLPNLNRHQKVAFIGSLSDDPSQSANLLAEAKKLNDAQAPK | SEQ ID NO:845 |
| Z00229 | VDNKFNKEKYLAYGEIWQLPNLNRQQKVAFISSLQDDPSQSANLLAEAKKLNDAQAPK | SEQ ID NO:846 |
| Z00231 | VDNKFNKEKYKAYGEIWQLPNLNRQQKVAFITISLQDDPSQSANLLAEAKKLNDAQAPK | SEQ ID NO:847 |
| Z00232 | VDNKFNKEKYAAAYEIWQLPNLNQRQKGAFIASLFDDPSQSANLLAEAKKLNDAQAPK | SEQ ID NO:848 |
| Z00233 | VDNKFNKEKYAASYEIWELPNLNQRQKAAFIKSLFDDPSQSANLLAEAKKLNDAQAPK | SEQ ID NO:849 |

Figure 1HH

| | | |
|---|---|---|
| BM00261 | ERKVAAFEIWELPNLNRGQKAAFIGSLYD | SEQ ID NO:200 |
| BM00262 | EKRNAAVEIWELPNLNRRQRAAFISSLFD | SEQ ID NO:201 |
| BM00263 | ERRNAAVEIWELPNLNRHQRAAFISSLWD | SEQ ID NO:202 |
| BM00264 | EKRQASVEIWELPNLNRIQKAAFISSLFD | SEQ ID NO:203 |
| BM00265 | EKRRAAVEIWELPNLNRIQKSAFIASLWD | SEQ ID NO:204 |
| BM00266 | EKRHAAWEIWELPNLNRAQKSAFIKSLWD | SEQ ID NO:205 |
| BM00267 | EKRNATVEIWELPNLNRIQRAAFIASLWD | SEQ ID NO:206 |
| BM00268 | EKRAATVEIWELPNLNRLQKGAFIASLWD | SEQ ID NO:207 |
| BM00269 | ERRGAAVEIWELPNLNRQQKAAFIASLWD | SEQ ID NO:208 |
| BM00270 | ERRKATVEIWELPNLNRQQKSAFIASLFD | SEQ ID NO:209 |
| BM00271 | EKSTAAVEIWELPNLNRIQKAAFIKSLFD | SEQ ID NO:210 |
| BM00272 | EKSTAAVEIWELPNLNRYQKAAFIKSLFD | SEQ ID NO:211 |
| BM00273 | EKSHAAVEIWELPNLNRWQKAAFIKSLYD | SEQ ID NO:212 |
| BM00274 | ERSSAAVEIWELPNLNRFQKAAFIKSLFD | SEQ ID NO:213 |
| BM00275 | EKRIAAAEIWELPNLNRVQKAAFIKSLFD | SEQ ID NO:214 |
| BM00276 | EKRHAAGEIWELPNLNRIQKAAFIKSLFD | SEQ ID NO:215 |
| BM00277 | EKRIAAVEIWELPNLNRVQKAAFIASLYD | SEQ ID NO:216 |
| BM00278 | EKRIASYEIWELPNLNRRQRAAFIASLWD | SEQ ID NO:217 |
| BM00279 | EKRNATFEIWELPNLNRSQKGAFISSLYD | SEQ ID NO:218 |
| BM00282 | ERKVATFEIWELPNLNSRQKAAFIKSLFD | SEQ ID NO:219 |
| BM00283 | ERKNATFEIWELPNLNQRQKSAFIASLWD | SEQ ID NO:220 |
| BM00284 | ERSAATFEIWELPNLNQRQKSAFIASLWD | SEQ ID NO:221 |
| BM00285 | ERKHATFEIWELPNLNQLQKSAFIGSLWD | SEQ ID NO:222 |
| BM00292 | ERKQATFEIWELPNLNQQKGAFIASLWD | SEQ ID NO:223 |
| BM00293 | ERKRATFEIWELPNLNRTQKAAFISSLWD | SEQ ID NO:224 |

Figure 1I

| | | |
|---|---|---|
| Z00234 | VDNKFNKEKYLASYEIWQLPNLNRRQKAAFIASLFDDPSQSANLLAEAKKLNDAQAPK | SEQ ID NO:850 |
| Z00235 | VDNKFNKEKYSATFEIWQLPNLNQRQKAAFISSLWDDPSQSANLLAEAKKLNDAQAPK | SEQ ID NO:851 |
| Z00237 | VDNKFNKEKYAASFEIWQLPNLNTHQKAAFISSLWDDPSQSANLLAEAKKLNDAQAPK | SEQ ID NO:852 |
| Z00238 | VDNKFNKEKYKASGEIWQLPNLNRLQRAAFIKSLFDDPSQSANLLAEAKKLNDAQAPK | SEQ ID NO:853 |
| Z00239 | VDNKFNKEKYSASGEIWQLPNLNRTQKAAFIKSLWDDPSQSANLLAEAKKLNDAQAPK | SEQ ID NO:854 |
| Z00243 | VDNKFNKEKYHAAGEIWELPNLNRLQKAAFIRSLWDDPSQSANLLAEAKKLNDAQAPK | SEQ ID NO:855 |
| Z00244 | VDNKFNKEKYRAAGEIWELPNLNRRQQKAAFIRSLFDDPSQSANLLAEAKKLNDAQAPK | SEQ ID NO:856 |
| Z00245 | VDNKFNKEKYQASGEIWELPNLNRLQKAAFIRSLWDDPSQSANLLAEAKKLNDAQAPK | SEQ ID NO:857 |
| Z00246 | VDNKFNKEKYKATGEIWELPNLNRIQKAAFIRSLWDDPSQSANLLAEAKKLNDAQAPK | SEQ ID NO:858 |
| Z00247 | VDNKFNKEKYQASFEIWELPNLNRSQKAAFIKSLWDDPSQSANLLAEAKKLNDAQAPK | SEQ ID NO:859 |
| Z00248 | VDNKFNKERKVAAVEIWQLPNLNRWQRGAFISSLFDDPSQSANLLAEAKKLNDAQAPK | SEQ ID NO:860 |
| Z00249 | VDNKFNKERKLAAVEIWELPNLNQYQRGAFISSLWDDPSQSANLLAEAKKLNDAQAPK | SEQ ID NO:861 |
| Z00250 | VDNKFNKERKKASVEIWELPNLNRYQKGAFISSLFDDPSQSANLLAEAKKLNDAQAPK | SEQ ID NO:862 |
| Z00253 | VDNKFNKERKHAAWEIWELPNLNRHQKGAFISSLWDDPSQSANLLAEAKKLNDAQAPK | SEQ ID NO:863 |
| Z00254 | VDNKFNKERKHAAVEIWELPNLNRWQKGAFIGSLWDDPSQSANLLAEAKKLNDAQAPK | SEQ ID NO:864 |
| Z00255 | VDNKFNKERKHAAVEIWELPNLNVFQRGAFIASLYDDPSQSANLLAEAKKLNDAQAPK | SEQ ID NO:865 |
| Z00256 | VDNKFNKERKHAAVEIWELPNLNRLQRGAFIASLYDDPSQSANLLAEAKKLNDAQAPK | SEQ ID NO:866 |
| Z00258 | VDNKFNKEWKTAAVEIWELPNLNRRQKAAFIGSLYDDPSQSANLLAEAKKLNDAQAPK | SEQ ID NO:867 |
| Z00261 | VDNKFNKERKVAAFEIWELPNLNRGQKAAFIGSLFDDPSQSANLLAEAKKLNDAQAPK | SEQ ID NO:868 |
| Z00262 | VDNKFNKEKRNAAVEIWELPNLNRRQRGAAFISSLFDDPSQSANLLAEAKKLNDAQAPK | SEQ ID NO:869 |
| Z00263 | VDNKFNKERRNAAVEIWELPNLNRHQRAAFISSLWDDPSQSANLLAEAKKLNDAQAPK | SEQ ID NO:870 |
| Z00264 | VDNKFNKEKRQASVEIWELPNLNRIQKAAFISSLFDDPSQSANLLAEAKKLNDAQAPK | SEQ ID NO:871 |
| Z00265 | VDNKFNKEKRRAAVEIWELPNLNRIQKSAFIASLWDDPSQSANLLAEAKKLNDAQAPK | SEQ ID NO:872 |
| Z00266 | VDNKFNKEKRHAAWEIWELPNLNRAQKSAFIKSLWDDPSQSANLLAEAKKLNDAQAPK | SEQ ID NO:873 |
| Z00267 | VDNKFNKEKRNATVEIWELPNLNRIQRAAFIASLWDDPSQSANLLAEAKKLNDAQAPK | SEQ ID NO:874 |

Figure 1II

| | | |
|---|---|---|
| BM00294 | ERKTATFEIWELPNLNRVQKAAFISSLWD | SEQ ID NO:225 |
| BM00295 | ERKLATWEIWELPNLNRSQKAAFIISLWD | SEQ ID NO:226 |
| BM00299 | ERKVAAVEIWELPNLNRIQKAAFIRSLFD | SEQ ID NO:227 |
| BM00300 | ERKEAAVEIWELPNLNRLQKAAFIRSLFD | SEQ ID NO:228 |
| BM00302 | ERKRAAVEIWELPNLNRGQKAAFIKSLFD | SEQ ID NO:229 |
| BM00303 | ERKLAAVEIWELPNLNRTQKAAFIKSLFD | SEQ ID NO:230 |
| BM00304 | ERKVAAVEIWELPNLNRVQKAAFIKSLFD | SEQ ID NO:231 |
| BM00305 | ERKEAAVEIWELPNLNRVQKAAFIKSLYD | SEQ ID NO:232 |
| BM00309 | ERKAATVEIWELPNLNRRQKAAFIASLFD | SEQ ID NO:233 |
| BM00312 | EKRHASWEIWELPNLNQWQKAAFIRSLFD | SEQ ID NO:234 |
| BM00313 | ERKSATWEIWELPNLNQLQKAAFIRSLFD | SEQ ID NO:235 |
| BM00314 | EKKKAAVEIWELPNLNQRQKAAFIGSLWD | SEQ ID NO:236 |
| BM00315 | EKKLASFEIWELPNLNQRQKAAFIRSLWD | SEQ ID NO:237 |
| BM00316 | ERKVATVEIWELPNLNRVQAAAFIKSLWD | SEQ ID NO:238 |
| BM00317 | ERKTATVEIWELPNLNRIQKAAFIKSLWD | SEQ ID NO:239 |
| BM00320 | ERKSATVEIWELPNLNRVQKAAFISSLWD | SEQ ID NO:240 |
| BM00321 | ERKVATVEIWELPNLNRGQKAAFISSLWD | SEQ ID NO:241 |
| BM00322 | ERKQATVEIWELPNLNRRQRAAFISSLWD | SEQ ID NO:242 |
| BM00323 | ERKKATVEIWELPNLNRRQKGAFIASLWD | SEQ ID NO:243 |
| BM00324 | ERKVATVEIWELPNLNRRQKGAFIASLWD | SEQ ID NO:244 |
| BM00328 | ERKLATVEIWELPNLNRYQKGAFIASLWD | SEQ ID NO:245 |
| BM00332 | ERKAATVEIWELPNLNRLQKGAFIASLWD | SEQ ID NO:246 |
| BM00333 | ERKIATVEIWELPNLNRVQKSAFIASLWD | SEQ ID NO:247 |
| BM00334 | ERKNATVEIWELPNLNRAQKAAFIASLWD | SEQ ID NO:248 |
| BM00335 | ERKNATVEIWELPNLNRSQKAAFIGSLWD | SEQ ID NO:249 |

Figure 1J

| | | |
|---|---|---|
| Z00268 | VDNKFNKEKRAATVEIWELPNLNRLQKGAFIASLWDDPSQSANLLAEAKKLNDAQAPK | SEQ ID NO:875 |
| Z00269 | VDNKFNKERRGAAVEIWELPNLNRQQKAAFIASLWDDPSQSANLLAEAKKLNDAQAPK | SEQ ID NO:876 |
| Z00270 | VDNKFNKERRKATVEIWELPNLNRQQKAAFISSLWDDPSQSANLLAEAKKLNDAQAPK | SEQ ID NO:877 |
| Z00271 | VDNKFNKEKSTAAVEIWELPNLNRIQKAAFIKSLFDDPSQSANLLAEAKKLNDAQAPK | SEQ ID NO:878 |
| Z00272 | VDNKFNKEKSTAAVEIWELPNLNRYQKAAFIKSLFDDPSQSANLLAEAKKLNDAQAPK | SEQ ID NO:879 |
| Z00273 | VDNKFNKEKSHAAVEIWELPNLNRWQKAAFIKSLYDDPSQSANLLAEAKKLNDAQAPK | SEQ ID NO:880 |
| Z00274 | VDNKFNKERSSAAVEIWELPNLNRFQKAAFIKSLFDDPSQSANLLAEAKKLNDAQAPK | SEQ ID NO:881 |
| Z00275 | VDNKFNKEKRIAAAEIWELPNLNRVQKAAFIKSLFDDPSQSANLLAEAKKLNDAQAPK | SEQ ID NO:882 |
| Z00276 | VDNKFNKEKRHAAGEIWELPNLNRIQKAAFIKSLFDDPSQSANLLAEAKKLNDAQAPK | SEQ ID NO:883 |
| Z00277 | VDNKFNKEKRIAAVEIWELPNLNRVQKAAFIASLYDDPSQSANLLAEAKKLNDAQAPK | SEQ ID NO:884 |
| Z00278 | VDNKFNKEKRIASYEIWELPNLNRRQRAAFIASLWDDPSQSANLLAEAKKLNDAQAPK | SEQ ID NO:885 |
| Z00279 | VDNKFNKEKRNATFEIWELPNLNRSQKGAFISSLYDDPSQSANLLAEAKKLNDAQAPK | SEQ ID NO:886 |
| Z00282 | VDNKFNKERKVATFEIWELPNLNSRQKAAFIKSLFDDPSQSANLLAEAKKLNDAQAPK | SEQ ID NO:887 |
| Z00283 | VDNKFNKERKNATFEIWELPNLNQRQKSAFIASLWDDPSQSANLLAEAKKLNDAQAPK | SEQ ID NO:888 |
| Z00284 | VDNKFNKERSAATFEIWELPNLNQRQKSAFIKSLFDDPSQSANLLAEAKKLNDAQAPK | SEQ ID NO:889 |
| Z00285 | VDNKFNKERKHATFEIWELPNLNQLQKSAFIGSLWDDPSQSANLLAEAKKLNDAQAPK | SEQ ID NO:890 |
| Z00292 | VDNKFNKERKQATFEIWELPNLNQQQKGAFIASLWDDPSQSANLLAEAKKLNDAQAPK | SEQ ID NO:891 |
| Z00293 | VDNKFNKERKRATFEIWELPNLNRTQKAAFIKSLFDDPSQSANLLAEAKKLNDAQAPK | SEQ ID NO:892 |
| Z00294 | VDNKFNKERKTATFEIWELPNLNRVQKAAFISSLWDDPSQSANLLAEAKKLNDAQAPK | SEQ ID NO:893 |
| Z00295 | VDNKFNKERKLATWEIWELPNLNRSQKAAFIISLWDDPSQSANLLAEAKKLNDAQAPK | SEQ ID NO:894 |
| Z00299 | VDNKFNKERKVAAVEIWELPNLNRIQKAAFIRSLFDDPSQSANLLAEAKKLNDAQAPK | SEQ ID NO:895 |
| Z00300 | VDNKFNKERKEAAVEIWELPNLNRLQKAAFIRSLFDDPSQSANLLAEAKKLNDAQAPK | SEQ ID NO:896 |
| Z00302 | VDNKFNKERKRAAVEIWELPNLNRGQKAAFIKSLFDDPSQSANLLAEAKKLNDAQAPK | SEQ ID NO:897 |
| Z00303 | VDNKFNKERKLAAVEIWELPNLNRTQKAAFIKSLFDDPSQSANLLAEAKKLNDAQAPK | SEQ ID NO:898 |
| Z00304 | VDNKFNKERKVAAVEIWELPNLNRVQKAAFIKSLFDDPSQSANLLAEAKKLNDAQAPK | SEQ ID NO:899 |

Figure 1JJ

| | | |
|---|---|---|
| BM00338 | ERKTATVEIWELPNLNRGQKAAFIASLFD | SEQ ID NO:250 |
| BM00339 | ERKHAAVEIWELPNLNRIQRAAFIASLFD | SEQ ID NO:251 |
| BM00340 | ERKIATVEIWELPNLNRIQRAAFIASLFD | SEQ ID NO:252 |
| BM00341 | ERKIAAVEIWELPNLNRIQAAAFIASLWD | SEQ ID NO:253 |
| BM00342 | ERKSATVEIWELPNLNRTQRAAFIASLWD | SEQ ID NO:254 |
| BM00343 | ERKSAAVEIWELPNLNRTQKAAFIASLWD | SEQ ID NO:255 |
| BM00344 | EKKSATVEIWELPNLNRIQKAAFIGSLWD | SEQ ID NO:256 |
| BM00345 | EKKSAYVEIWELPNLNRYQKAAFIKSLFD | SEQ ID NO:257 |
| BM00349 | ERKIATYEIWELPNLNQRQKAAFIASLWD | SEQ ID NO:258 |
| BM00350 | ERSVATWEIWQLPNLNQRQKAAFIASLWD | SEQ ID NO:259 |
| BM00355 | EKRKATGEIWQLPNLNQRQKGAFIASLWD | SEQ ID NO:260 |
| BM00356 | ERKEARFEIWELPNLNQRQAAAFISSLFD | SEQ ID NO:261 |
| BM00357 | ERKAASWEIWELPNLNQRQKAAFISSLYD | SEQ ID NO:262 |
| BM00359 | EWKHAAGEIWELPNLNRSQKVAFIASLED | SEQ ID NO:263 |
| BM00360 | EWKRAAGEIWELPNLNRAQKVAFIASLAD | SEQ ID NO:264 |
| BM00362 | EWKIAAGEIWELPNLNQRQKVAFIRSLQD | SEQ ID NO:265 |
| BM00363 | EWKTAAYEIWELPNLNTYQKVAFIRSLQD | SEQ ID NO:266 |
| BM00364 | EWKVAAGEIWELPNLNRTQKVAFIRSLSD | SEQ ID NO:267 |
| BM00365 | EWKVAAGEIWELPNLNRWQKVAFIRSLSD | SEQ ID NO:268 |
| BM00366 | EWKQAAGEIWELPNLNRLQKVAFIRSLSD | SEQ ID NO:269 |
| BM00367 | EWKVAAGEIWELPNLNVWQKAAFIRSLSD | SEQ ID NO:270 |
| BM00368 | EWKVAAWEIWELPNLNRGQKVAFIRSLQD | SEQ ID NO:271 |
| BM00369 | EWKRAAFEIWELPNLNQAQKVAFITSLSD | SEQ ID NO:272 |
| BM00370 | EWKKAAGEIWLLPNLNRRQRGAFIASLAD | SEQ ID NO:273 |
| BM00371 | EWKKAAGEIWELPNLNSRQKGAFIASLAD | SEQ ID NO:274 |

Figure 1K

| | | |
|---|---|---|
| Z00305 | VDNKFNKERKEAAVEIWELPNLNRVQKAAFIKSLYDDPSQSANLLAEAKKLNDAQAPK | SEQ ID NO:900 |
| Z00309 | VDNKFNKERKAATVEIWELPNLNRRQKAAFIASLFDDPSQSANLLAEAKKLNDAQAPK | SEQ ID NO:901 |
| Z00312 | VDNKFNKEKRHASWEIWELPNLNQWQKAAFIRSLFDDPSQSANLLAEAKKLNDAQAPK | SEQ ID NO:902 |
| Z00313 | VDNKFNKERKSATWEIWELPNLNQLQKAAFIRSLFDDPSQSANLLAEAKKLNDAQAPK | SEQ ID NO:903 |
| Z00314 | VDNKFNKEKKAAVEIWELPNLNQRQKAAFIGSLWDDPSQSANLLAEAKKLNDAQAPK | SEQ ID NO:904 |
| Z00315 | VDNKFNKEKKLASFEIWELPNLNQRQKAAFIRSLWDDPSQSANLLAEAKKLNDAQAPK | SEQ ID NO:905 |
| Z00316 | VDNKFNKERKVATVEIWELPNLNRVQAAFIKSLWDDPSQSANLLAEAKKLNDAQAPK | SEQ ID NO:906 |
| Z00317 | VDNKFNKERKTATVEIWELPNLNRIQKAAFIKSLWDDPSQSANLLAEAKKLNDAQAPK | SEQ ID NO:907 |
| Z00320 | VDNKFNKERKSATVEIWELPNLNRVQKAAFISSLWDDPSQSANLLAEAKKLNDAQAPK | SEQ ID NO:908 |
| Z00321 | VDNKFNKERKVATVEIWELPNLNRGQKAAFISSLWDDPSQSANLLAEAKKLNDAQAPK | SEQ ID NO:909 |
| Z00322 | VDNKFNKERKQATVEIWELPNLNRRQRAAFISSLWDDPSQSANLLAEAKKLNDAQAPK | SEQ ID NO:910 |
| Z00323 | VDNKFNKERKKATVEIWELPNLNRQKGAFIASLWDDPSQSANLLAEAKKLNDAQAPK | SEQ ID NO:911 |
| Z00324 | VDNKFNKERKVATVEIWELPNLNRRQKGAFIASLWDDPSQSANLLAEAKKLNDAQAPK | SEQ ID NO:912 |
| Z00328 | VDNKFNKERKLATVEIWELPNLNRYQKGAFIASLWDDPSQSANLLAEAKKLNDAQAPK | SEQ ID NO:913 |
| Z00332 | VDNKFNKERKAATVEIWELPNLNRLQKGAFIASLWDDPSQSANLLAEAKKLNDAQAPK | SEQ ID NO:914 |
| Z00333 | VDNKFNKERKIATVEIWELPNLNRVQKSAFIASLWDDPSQSANLLAEAKKLNDAQAPK | SEQ ID NO:915 |
| Z00334 | VDNKFNKERKNATVEIWELPNLNRAQKAAFIASLWDDPSQSANLLAEAKKLNDAQAPK | SEQ ID NO:916 |
| Z00335 | VDNKFNKERKNATVEIWELPNLNRSQKAAFIGSLWDDPSQSANLLAEAKKLNDAQAPK | SEQ ID NO:917 |
| Z00338 | VDNKFNKERKTATVEIWELPNLNRGQKAAFIASLFDDPSQSANLLAEAKKLNDAQAPK | SEQ ID NO:918 |
| Z00339 | VDNKFNKERKHAAVEIWELPNLNRIQRAAFIASLFDDPSQSANLLAEAKKLNDAQAPK | SEQ ID NO:919 |
| Z00340 | VDNKFNKERKIATVEIWELPNLNRIQAAAFIASLWDDPSQSANLLAEAKKLNDAQAPK | SEQ ID NO:920 |
| Z00341 | VDNKFNKERKIAAVEIWELPNLNRIQAAAFIASLWDDPSQSANLLAEAKKLNDAQAPK | SEQ ID NO:921 |
| Z00342 | VDNKFNKERKSATVEIWELPNLNRTQRAAFIASLWDDPSQSANLLAEAKKLNDAQAPK | SEQ ID NO:922 |
| Z00343 | VDNKFNKERKSAAVEIWELPNLNRTQKAFIASLWDDPSQSANLLAEAKKLNDAQAPK | SEQ ID NO:923 |
| Z00344 | VDNKFNKEKKSATVEIWELPNLNRIQKAFIGSLWDDPSQSANLLAEAKKLNDAQAPK | SEQ ID NO:924 |

Figure 1KK

| | | |
|---|---|---|
| BM00372 | EWRGAAGEIWELPNLNRRQRAAFIASLAD | SEQ ID NO:275 |
| BM00373 | EWKVAAGEIWQLPNLNRRQRAAFIASLAD | SEQ ID NO:276 |
| BM00374 | EWKIAAVEIWELPNLNTRQKGAFIASLSD | SEQ ID NO:277 |
| BM00375 | EWKIAAFEIWELPNLNVRQRSAFISSLSD | SEQ ID NO:278 |
| BM00376 | EWKTAAYEIWELPNLNQRQRGAFIASLQD | SEQ ID NO:279 |
| BM00377 | EWKTAAGEIWELPNLNSRQKAAFIGSLAD | SEQ ID NO:280 |
| BM00378 | EWKTAAGEIWELPNLNVGQKAAFIGSLAD | SEQ ID NO:281 |
| BM00379 | EWKHAAGEIWELPNLNRTQKAAFIRSLAD | SEQ ID NO:282 |
| BM00380 | EWKRAAGEIWELPNLNRLQKAAFIRSLAD | SEQ ID NO:283 |
| BM00381 | EWKQAAGEIWELPNLNRGQKAAFISSLAD | SEQ ID NO:284 |
| BM00382 | EWKQAAGEIWELPNLNRGQKAAFITSLAD | SEQ ID NO:285 |
| BM00383 | EWKEAAGEIWELPNLNRGQKAAFIKSLAD | SEQ ID NO:286 |
| BM00384 | EWKTAAGEIWELPNLNRRQKAAFIASLQD | SEQ ID NO:287 |
| BM00385 | EWKRAAGEIWELPNLNRAQKAAFISSLQD | SEQ ID NO:288 |
| BM00386 | EWKHAAFEIWELPNLNVRQKAAFIGSLQD | SEQ ID NO:289 |
| BM00387 | EWKNAAFEIWELPNLNVSQKAAFIRSLQD | SEQ ID NO:290 |
| BM00388 | EWKAAAYEIWELPNLNVNWQKAAFISSLQD | SEQ ID NO:291 |
| BM00389 | EWKVAAGEIWELPNLNRWQKGAFITSLYD | SEQ ID NO:292 |
| BM00390 | EWKVAAGEIWELPNLNRWQKAAFIASLYD | SEQ ID NO:293 |
| BM00391 | EWKVAAGEIWELPNLNRLQRAAFIKSLYD | SEQ ID NO:294 |
| BM00392 | EWKVAAYEIWELPNLNRLQKAAFIASLYD | SEQ ID NO:295 |
| BM00393 | EWKVAAFEIWELPNLNRLQKAAFIISLQD | SEQ ID NO:296 |
| BM00394 | EWKTAAVEIWELPNLNRTQRAAFITSLYD | SEQ ID NO:297 |
| BM00395 | EWKTAAFEIWELPNLNRLQKAAFITSLSD | SEQ ID NO:298 |
| BM00396 | EWKTAAFEIWELPNLNRGQKAAFIRSLSD | SEQ ID NO:299 |

Figure 1L

| | | |
|---|---|---|
| Z00345 | VDNKFNKEKKSAYVEIWELPNLNRYQKAAFIKSLFDDPSQSANLLAEAKKLNDAQAPK | SEQ ID NO:925 |
| Z00349 | VDNKFNKERKIATYEIWELPNLNQRQKAAFIASLWDDPSQSANLLAEAKKLNDAQAPK | SEQ ID NO:926 |
| Z00350 | VDNKFNKERSVATWEIWQLPNLNQRQKAAFIASLWDDPSQSANLLAEAKKLNDAQAPK | SEQ ID NO:927 |
| Z00355 | VDNKFNKEKRKATGEIWQLPNLNQRQKGAAFIASLWDDPSQSANLLAEAKKLNDAQAPK | SEQ ID NO:928 |
| Z00356 | VDNKFNKERKEARFEIWELPNLNQRQAAAFISSLFDDPSQSANLLAEAKKLNDAQAPK | SEQ ID NO:929 |
| Z00357 | VDNKFNKERKAASWEIWELPNLNQRQKAAFISSLYDDPSQSANLLAEAKKLNDAQAPK | SEQ ID NO:930 |
| Z00359 | VDNKFNKEWKHAAGEIWELPNLNRSQKVAFIASLEDDPSQSANLLAEAKKLNDAQAPK | SEQ ID NO:931 |
| Z00360 | VDNKFNKEWKRAAGEIWELPNLNRAQKVAFIASLADDPSQSANLLAEAKKLNDAQAPK | SEQ ID NO:932 |
| Z00362 | VDNKFNKEWKIAAGEIWELPNLNQRQKVAFIRSLQDDPSQSANLLAEAKKLNDAQAPK | SEQ ID NO:933 |
| Z00363 | VDNKFNKEWKTAAYEIWELPNLNTYQKVAFIRSLQDDPSQSANLLAEAKKLNDAQAPK | SEQ ID NO:934 |
| Z00364 | VDNKFNKEWKVAAGEIWELPNLNRTQKVAFIRSLSDDPSQSANLLAEAKKLNDAQAPK | SEQ ID NO:935 |
| Z00365 | VDNKFNKEWKVAAGEIWELPNLNRWQKVAFIRSLSDDPSQSANLLAEAKKLNDAQAPK | SEQ ID NO:936 |
| Z00366 | VDNKFNKEWKQAAGEIWELPNLNRLQKVAFIRSLSDDPSQSANLLAEAKKLNDAQAPK | SEQ ID NO:937 |
| Z00367 | VDNKFNKEWKVAAGEIWELPNLNVWQKAAFIRSLSDDPSQSANLLAEAKKLNDAQAPK | SEQ ID NO:938 |
| Z00368 | VDNKFNKEWKVAAWEIWELPNLNRGQKVAFIRSLQDDPSQSANLLAEAKKLNDAQAPK | SEQ ID NO:939 |
| Z00369 | VDNKFNKEWKRAAFEIWELPNLNQAQKVAFITSLSDDPSQSANLLAEAKKLNDAQAPK | SEQ ID NO:940 |
| Z00370 | VDNKFNKEWKKAAGEIWLLPNLNRRQRGAFIASLADDPSQSANLLAEAKKLNDAQAPK | SEQ ID NO:941 |
| Z00371 | VDNKFNKEWKKAAGEIWELPNLNSRQKGAFIASLADDPSQSANLLAEAKKLNDAQAPK | SEQ ID NO:942 |
| Z00372 | VDNKFNKEWRGAAGEIWELPNLNRRQRAAFIASLADDPSQSANLLAEAKKLNDAQAPK | SEQ ID NO:943 |
| Z00373 | VDNKFNKEWKVAAGEIWQLPNLNRRQRAAFIASLADDPSQSANLLAEAKKLNDAQAPK | SEQ ID NO:944 |
| Z00374 | VDNKFNKEWKIAAVEIWELPNLNTRQKGAFIASLSDDPSQSANLLAEAKKLNDAQAPK | SEQ ID NO:945 |
| Z00375 | VDNKFNKEWKIAAFEIWELPNLNVRQRSAFISSLSDDPSQSANLLAEAKKLNDAQAPK | SEQ ID NO:946 |
| Z00376 | VDNKFNKEWKTAAYEIWELPNLNQRQRGAFIASLQDDPSQSANLLAEAKKLNDAQAPK | SEQ ID NO:947 |
| Z00377 | VDNKFNKEWKTAAGEIWELPNLNSRQKAAFIGSLADDPSQSANLLAEAKKLNDAQAPK | SEQ ID NO:948 |
| Z00378 | VDNKFNKEWKTAAGEIWELPNLNVGQKAAFIGSLADDPSQSANLLAEAKKLNDAQAPK | SEQ ID NO:949 |

Figure 1LL

| | | |
|---|---|---|
| BM00400 | EWKRAAFEIWELPNLNRLQKSAFIASLSD | SEQ ID NO:300 |
| BM00401 | EWKQAAFEIWELPNLNRYQAAAFIGSLQD | SEQ ID NO:301 |
| BM00402 | EWKHAAFEIWELPNLNRRQAGAFIASLQD | SEQ ID NO:302 |
| BM00403 | EWKQASGEIWELPNLNVRQKAAFISSLAD | SEQ ID NO:303 |
| BM00404 | EWKQASFEIWELPNLNVRQKAAFISSLSD | SEQ ID NO:304 |
| BM00405 | EWKLAAGEIWELPNLNVRQKAAFIASLQD | SEQ ID NO:305 |
| BM00406 | EWKIAAGEIWELPNLNVRQKAAFIASLSD | SEQ ID NO:306 |
| BM00407 | EWKHAAGEIWQLPNLNVTQKAAFIASLSD | SEQ ID NO:307 |
| BM00411 | EWKIAAGEIWELPNLNRRQAAAFIVSLSD | SEQ ID NO:308 |
| BM00412 | EWKSAAGEIWELPNLNRAQKAAFIISLSD | SEQ ID NO:309 |
| BM00413 | EWKHAAVEIWQLPNLNRFQKAAFIASLSD | SEQ ID NO:310 |
| BM00414 | EWKQAAWEIWQLPNLNTGQKAAFIRSLSD | SEQ ID NO:311 |
| BM00415 | EWKQASWEIWELPNLNRGQKAAFIASLSD | SEQ ID NO:312 |
| BM00416 | EWKTASYEIWQLPNLNRRQAAAFIASLSD | SEQ ID NO:313 |
| BM00417 | EWKNASFEIWLLPNLNRIQKAAFIASLSD | SEQ ID NO:314 |
| BM00418 | EWKNAAFEIWLLPNLNQRQKAAFIASLSD | SEQ ID NO:315 |
| BM00419 | EWRGAAFEIWQLPNLNQRQKAAFIASLYD | SEQ ID NO:316 |
| BM00420 | EWKVASWEIWQLPNLNQRQKAAFIGSLAD | SEQ ID NO:317 |
| BM00421 | EWKLASWEIWQLPNLNRMQKAAFIGSLSD | SEQ ID NO:318 |
| BM00422 | EWKRASVEIWELPNLNRQQKAAFIGSLSD | SEQ ID NO:319 |
| BM00425 | EWKRASFEIWQLPNLNRLQKAAFIASLAD | SEQ ID NO:320 |
| BM00428 | EWKGAAGEIWQLPNLNRRQKAAFISSLYD | SEQ ID NO:321 |
| BM00429 | EWKVAAFEIWQLPNLNRAQKAAFISSLAD | SEQ ID NO:322 |
| BM00430 | EWKHAAGEIWQLPNLNRAQKAAFISSLAD | SEQ ID NO:323 |
| BM00431 | EWKKAAYEIWQLPNLNRAQKAAFISSLYD | SEQ ID NO:324 |

Figure 1M

| | | |
|---|---|---|
| Z00379 | VDNKFNKEWKHAAGEIWELPNLNRTQKAAFIRSLADDPSQSANLLAEAKKLNDAQAPK | SEQ ID NO:950 |
| Z00380 | VDNKFNKEWKRAAGEIWELPNLNRLQKAAFIRSLADDPSQSANLLAEAKKLNDAQAPK | SEQ ID NO:951 |
| Z00381 | VDNKFNKEWKQAAGEIWELPNLNRGQKAAFISSLADDPSQSANLLAEAKKLNDAQAPK | SEQ ID NO:952 |
| Z00382 | VDNKFNKEWKQAAGEIWELPNLNRGQKAAFITSLADDPSQSANLLAEAKKLNDAQAPK | SEQ ID NO:953 |
| Z00383 | VDNKFNKEWKEAAGEIWELPNLNRGQKAAFIKSLADDPSQSANLLAEAKKLNDAQAPK | SEQ ID NO:954 |
| Z00384 | VDNKFNKEWKTAAGEIWELPNLNRRQKAAFIASLQDDPSQSANLLAEAKKLNDAQAPK | SEQ ID NO:955 |
| Z00385 | VDNKFNKEWKRAAGEIWELPNLNRAQKAAFISSLQDDPSQSANLLAEAKKLNDAQAPK | SEQ ID NO:956 |
| Z00386 | VDNKFNKEWKHAAFEIWELPNLNVRQKAAFIGSLQDDPSQSANLLAEAKKLNDAQAPK | SEQ ID NO:957 |
| Z00387 | VDNKFNKEWKNAAFEIWELPNLNVSQKAAFIRSLQDDPSQSANLLAEAKKLNDAQAPK | SEQ ID NO:958 |
| Z00388 | VDNKFNKEWKAAAYEIWELPNLNVWQKAAFISSLQDDPSQSANLLAEAKKLNDAQAPK | SEQ ID NO:959 |
| Z00389 | VDNKFNKEWKVAAGEIWELPNLNRWQKGAFITSLYDDPSQSANLLAEAKKLNDAQAPK | SEQ ID NO:960 |
| Z00390 | VDNKFNKEWKVAAGEIWELPNLNRWQKAAFITSLYDDPSQSANLLAEAKKLNDAQAPK | SEQ ID NO:961 |
| Z00391 | VDNKFNKEWKVAAGEIWELPNLNRLQRAAFIKSLYDDPSQSANLLAEAKKLNDAQAPK | SEQ ID NO:962 |
| Z00392 | VDNKFNKEWKVAAYEIWELPNLNRLQKAAFIASLYDDPSQSANLLAEAKKLNDAQAPK | SEQ ID NO:963 |
| Z00393 | VDNKFNKEWKVAAFEIWELPNLNRTQRAAFITSLQDDPSQSANLLAEAKKLNDAQAPK | SEQ ID NO:964 |
| Z00394 | VDNKFNKEWKTAAVEIWELPNLNRLQKAAFITSLSDDPSQSANLLAEAKKLNDAQAPK | SEQ ID NO:965 |
| Z00395 | VDNKFNKEWKTAAVEIWELPNLNRLQKAAFIGSLSDDPSQSANLLAEAKKLNDAQAPK | SEQ ID NO:966 |
| Z00396 | VDNKFNKEWKTAAFEIWELPNLNRGQKAAFIRSLSDDPSQSANLLAEAKKLNDAQAPK | SEQ ID NO:967 |
| Z00400 | VDNKFNKEWKRAAFEIWELPNLNRLQKSAFIASLSDDPSQSANLLAEAKKLNDAQAPK | SEQ ID NO:968 |
| Z00401 | VDNKFNKEWKQAAFEIWELPNLNRYQAAAFIGSLQDDPSQSANLLAEAKKLNDAQAPK | SEQ ID NO:969 |
| Z00402 | VDNKFNKEWKHAAFEIWELPNLNRROAGAFIASLQDDPSQSANLLAEAKKLNDAQAPK | SEQ ID NO:970 |
| Z00403 | VDNKFNKEWKHAAFEIWELPNLNVRQKAAFISSLADDPSQSANLLAEAKKLNDAQAPK | SEQ ID NO:971 |
| Z00404 | VDNKFNKEWKQASGEIWELPNLNVRQKAAFISSLSDDPSQSANLLAEAKKLNDAQAPK | SEQ ID NO:972 |
| Z00405 | VDNKFNKEWKQASFEIWELPNLNVRQKAAFIASLQDDPSQSANLLAEAKKLNDAQAPK | SEQ ID NO:973 |
| Z00406 | VDNKFNKEWKIAAGEIWELPNLNVRQKAAFIASLSDDPSQSANLLAEAKKLNDAQAPK | SEQ ID NO:974 |

Figure 1MM

| | | |
|---|---|---|
| BM00432 | EWKLAAYEIWQLPNLNRHQKAAFISSLSD | SEQ ID NO:325 |
| BM00433 | EWKRAAFEIWQLPNLNRSQKAAFISSLAD | SEQ ID NO:326 |
| BM00435 | EWKTAAFEIWQLPNLNRSQKAAFIASLAD | SEQ ID NO:327 |
| BM00437 | EWKIAAFEIWQLPNLNRIQKAAFIGSLAD | SEQ ID NO:328 |
| BM00438 | EWKQAAFEIWQLPNLNRIQKAAFITSLSD | SEQ ID NO:329 |
| BM00439 | EWKQAAFEIWQLPNLNRVQKAAFIVSLQD | SEQ ID NO:330 |
| BM00440 | EWKVAAGEIWQLPNLNRIQKAAFIGSLSD | SEQ ID NO:331 |
| BM00441 | EWKIAAFEIWQLPNLNRWQKAAFISSLQD | SEQ ID NO:332 |
| BM00442 | EWKEAAGEIWQLPNLNRYQKAAFIASLQD | SEQ ID NO:333 |
| BM00443 | EWKTASFEIWQLPNLNRYQKAAFISSLQD | SEQ ID NO:334 |
| HM01748 | KEKVAATGEIWDLPNLNTRQKNAFIGSLWDDPSQSANLLAEAKKLNDAQ | SEQ ID NO:335 |
| HM01749 | KEWRWAAHEIWDLPNLNVYQRAAFIRSLEDDPSQSANLLAEAKKLNDAQ | SEQ ID NO:336 |
| HM01750 | KERRLASVEIWELPNLNAVQKSAFISSLFDDPSQSANLLAEAKKLNDAQ | SEQ ID NO:337 |
| HM01751 | KEVKEARFEIWDLPNLNRTQKHAFIVSLEDDPSQSANLLAEAKKLNDAQ | SEQ ID NO:338 |
| HM01753 | KEWKGAAGEIWNLPNLNVSQRVAFIGSLADDPSQSANLLAEAKKLNDAQ | SEQ ID NO:339 |
| HM01754 | KEKYKAAHEIWELPNLNRDQRAAFTSLTDDPSQSANLLAEAKKLNDAQ | SEQ ID NO:340 |
| HM01813 | KERSLASFEIWELPNLNPKQKAAFIVSLFDDPSQSANLLAEAKKLNDAQ | SEQ ID NO:341 |
| HM01814 | KEWKRASWEIWELPNLNNAQKRAFISSLSDDPSQSANLLAEAKKLNDAQ | SEQ ID NO:342 |
| HM01815 | KEKYKAMTEIWILPNLNQRQKVAFIGSLDDDPSQSANLLAEAKKLNDAQ | SEQ ID NO:343 |
| HM01817 | KEWRGAAGEIWALPNLNNRQKGAFTESLPDDPSQSANLLAEAKKLNDAQ | SEQ ID NO:344 |
| HM01818 | KERWEATVEIWDLPNLNRNQKAAFIASLQDDPSQSANLLAEAKKLNDAQ | SEQ ID NO:345 |
| HM01820 | KEKYNAYAEIWLLPNLNRYQKGAFIKSLSDDPSQSANLLAEAKKLNDAQ | SEQ ID NO:346 |
| HM01821 | KERSVAQKEIWELPNLNRWQAGAFIKSLYDDPSQSANLLAEAKKLNDAQ | SEQ ID NO:347 |
| HM01824 | KEKMDAMGEIWDLPNLNRGQASAFIASLQDDPSQSANLLAEAKKLNDAQ | SEQ ID NO:348 |
| HM01825 | KEKRNAQVEIWTLPNLNSKQRAAFIKSLYDDPSQSANLLAEAKKLNDAQ | SEQ ID NO:349 |

Figure 1N

| | | |
|---|---|---|
| Z00407 | VDNKFNKEWKHAAGEIWQLPNLNVTQKAAFIASLSDDPSQSANLLAEAKKLNDAQAPK | SEQ ID NO:975 |
| Z00411 | VDNKFNKEWKIAAGEIWELPNLNRRQAAAFIVSLSDDPSQSANLLAEAKKLNDAQAPK | SEQ ID NO:976 |
| Z00412 | VDNKFNKEWKSAAGEIWELPNLNRAQKAAFIISLSDDPSQSANLLAEAKKLNDAQAPK | SEQ ID NO:977 |
| Z00413 | VDNKFNKEWKHAAVEIWQLPNLNRFQKAAFIASLSDDPSQSANLLAEAKKLNDAQAPK | SEQ ID NO:978 |
| Z00414 | VDNKFNKEWKQAAWEIWQLPNLNTGQKAAFIRSLSDDPSQSANLLAEAKKLNDAQAPK | SEQ ID NO:979 |
| Z00415 | VDNKFNKEWKQASWEIWELPNLNRGQKAAFIASLSDDPSQSANLLAEAKKLNDAQAPK | SEQ ID NO:980 |
| Z00416 | VDNKFNKEWKTASYEIWQLPNLNRRQAAAFIASLSDDPSQSANLLAEAKKLNDAQAPK | SEQ ID NO:981 |
| Z00417 | VDNKFNKEWKNASFEIWLLPNLNRIQKAAFIASLSDDPSQSANLLAEAKKLNDAQAPK | SEQ ID NO:982 |
| Z00418 | VDNKFNKEWKNAAFEIWLLPNLNRQRQKAAFIASLSDDPSQSANLLAEAKKLNDAQAPK | SEQ ID NO:983 |
| Z00419 | VDNKFNKEWRGAAFEIWQLPNLNQRQKAAFTASLYDDPSQSANLLAEAKKLNDAQAPK | SEQ ID NO:984 |
| Z00420 | VDNKFNKEWKVASWEIWQLPNLNRQQKAAFIGSLADDPSQSANLLAEAKKLNDAQAPK | SEQ ID NO:985 |
| Z00421 | VDNKFNKEWKLASWEIWQLPNLNRWQKAAFIGSLSDDPSQSANLLAEAKKLNDAQAPK | SEQ ID NO:986 |
| Z00422 | VDNKFNKEWKRASVEIWELPNLNRQQKAAFIGSLSDDPSQSANLLAEAKKLNDAQAPK | SEQ ID NO:987 |
| Z00425 | VDNKFNKEWKRASFEIWQLPNLNRLQKAAFTASLADDPSQSANLLAEAKKLNDAQAPK | SEQ ID NO:988 |
| Z00428 | VDNKFNKEWKGAAGEIWQLPNLNRRQAAFISSLYDDPSQSANLLAEAKKLNDAQAPK | SEQ ID NO:989 |
| Z00429 | VDNKFNKEWKVAAFEIWQLPNLNRAQKAAFISSLADDPSQSANLLAEAKKLNDAQAPK | SEQ ID NO:990 |
| Z00430 | VDNKFNKEWKHAAGEIWQLPNLNRAQKAAFISSLADDPSQSANLLAEAKKLNDAQAPK | SEQ ID NO:991 |
| Z00431 | VDNKFNKEWKKAAYEIWQLPNLNRAQYIWQLPNLNRAQKAAFISSLYDDPSQSANLLAEAKKLNDAQAPK | SEQ ID NO:992 |
| Z00432 | VDNKFNKEWKLAAYEIWQLPNLNRHQKAAFISSLSDDPSQSANLLAEAKKLNDAQAPK | SEQ ID NO:993 |
| Z00433 | VDNKFNKEWKRAAFEIWQLPNLNRSQKAAFISSLADDPSQSANLLAEAKKLNDAQAPK | SEQ ID NO:994 |
| Z00435 | VDNKFNKEWKTAAFEIWQLPNLNRSQKAAFIASLADDPSQSANLLAEAKKLNDAQAPK | SEQ ID NO:995 |
| Z00437 | VDNKFNKEWKIAAFEIWQLPNLNRIQKAAFIGSLADDPSQSANLLAEAKKLNDAQAPK | SEQ ID NO:996 |
| Z00438 | VDNKFNKEWKQAAFEIWQLPNLNRIQKAAFITSLSDDPSQSANLLAEAKKLNDAQAPK | SEQ ID NO:997 |
| Z00439 | VDNKFNKEWKQAAFEIWQLPNLNRVQKAAFIVSLQDDPSQSANLLAEAKKLNDAQAPK | SEQ ID NO:998 |
| Z00440 | VDNKFNKEWKVAAGEIWQLPNLNRIQKAAFIGSLSDDPSQSANLLAEAKKLNDAQAPK | SEQ ID NO:999 |

Figure 1NN

| | | |
|---|---|---|
| HM01826 | KERRDARFEIWELPNLNKYQRAAFISSLDDPSQSANLLAEAKKLNDAQ | SEQ ID NO:350 |
| HM01828 | KERSMARFEIWELPNLNRGQKSAFIASLEDDPSQSANLLAEAKKLNDAQ | SEQ ID NO:351 |
| HM01830 | KEWHGAASEIWELPNLNKSQKSAFIKSLPDDPSQSANLLAEAKKLNDAQ | SEQ ID NO:352 |
| HM02009 | KEWKQAEEIWDLPNLNRRQGAFITSLQDDPSQSANLLAEAKKLNDAQ | SEQ ID NO:353 |
| HM02010 | KEKVQASEEIWNLPNLNRRQRAAFIGSLYDDPSQSANLLAEAKKLNDAQ | SEQ ID NO:354 |
| HM02011 | KERYSATVEIWDLPNLNTLQKSAFIGSLQDDPSQSANLLAEAKKLNDAQ | SEQ ID NO:355 |
| HM05403 | KERYSAYYEIWQLPNLNRIQKAAFISSLQDDPSQSANLLAEAKKLNDAQ | SEQ ID NO:356 |
| HM05404 | KERYRAYFEIWQLPNLNRLQKAAFISSLEDDPSQSANLLAEAKKLNDAQ | SEQ ID NO:357 |
| HM05405 | KEKYKAYGEIWQLPNLNRVQKAAFIASLSDDPSQSANLLAEAKKLNDAQ | SEQ ID NO:358 |
| HM05406 | KERKQATFEIWELPNLNQROKAAFIKSLWDDPSQSANLLAEAKKLNDAQ | SEQ ID NO:359 |
| HM05407 | KEWKIAAGEIWQLPNLNRHQKGAFISSLYDDPSQSANLLAEAKKLNDAQ | SEQ ID NO:360 |
| HM05408 | KEKYKAYVEIWQLPNLNRYQRAAFIGSLQDDPSQSANLLAEAKKLNDAQ | SEQ ID NO:361 |
| HM05409 | KERKAATFEIWELPNLNRIQKAAFIASLFDDPSQSANLLAEAKKLNDAQ | SEQ ID NO:362 |
| HM05410 | KEKYKAYGEIWQLPNLNRIQKAAFISSLQDDPSQSANLLAEAKKLNDAQ | SEQ ID NO:363 |
| HM05411 | KEKRIATWEIWQLPNLNQHQKAAFISSLWDDPSQSANLLAEAKKLNDAQ | SEQ ID NO:364 |
| HM05412 | KEKYKAYVEIWQLPNLNRGQKAAFISSLQDDPSQSANLLAEAKKLNDAQ | SEQ ID NO:365 |
| HM05413 | KERYLAYYEIWQLPNLNRTQKAAFIGSLQDDPSQSANLLAEAKKLNDAQ | SEQ ID NO:366 |
| HM05414 | KERYIAYWEIWQLPNLNRRQKAAFISSLQDDPSQSANLLAEAKKLNDAQ | SEQ ID NO:367 |
| HM05415 | KERYRAYGEIWQLPNLNRGQKAAFIASLQDDPSQSANLLAEAKKLNDAQ | SEQ ID NO:368 |
| HM05416 | KEKYTAYFEIWQLPNLNVRQKAAFISSLQDDPSQSANLLAEAKKLNDAQ | SEQ ID NO:369 |
| HM05417 | KERYSAYYEIWQLPNLNVRQKAAFIGSLQDDPSQSANLLAEAKKLNDAQ | SEQ ID NO:370 |
| HM05418 | KEKYAAYGEIWQLPNLNRSQKAAFIGSLSDDPSQSANLLAEAKKLNDAQ | SEQ ID NO:371 |
| HM05419 | KERKRATVEIWELPNLNRLQRGAFIASLWDDPSQSANLLAEAKKLNDAQ | SEQ ID NO:372 |
| HM05420 | KEWKQASFEIWELPNLNRLQKAAFIGSLADDPSQSANLLAEAKKLNDAQ | SEQ ID NO:373 |
| HM05421 | KERKHATVEIWELPNLNRVQKAAFISSLWDDPSQSANLLAEAKKLNDAQ | SEQ ID NO:374 |

| | | |
|---|---|---|
| HM05422 | KEKYKAVVEIWQLPNLNQRQKAAFIGSLADDPSQSANLLAEAKKLNDAQ | SEQ ID NO:375 |
| HM05423 | KEKYVAYGEIWQLPNLNRTQKAAFISSLSDDPSQSANLLAEAKKLNDAQ | SEQ ID NO:376 |
| HM05424 | KERYIAYYEIWQLPNLNRYQKAAFIASLSDDPSQSANLLAEAKKLNDAQ | SEQ ID NO:377 |
| HM05425 | KEKYNAYGEIWQLPNLNVRQKAAFISSLADDPSQSANLLAEAKKLNDAQ | SEQ ID NO:378 |
| HM05426 | KERKAATVEIWELPNLNRVQKAAFIKSLFDDPSQSANLLAEAKKLNDAQ | SEQ ID NO:379 |
| HM05427 | KERYVAYYEIWELPNLNQRQKAAFIGSLQDDPSQSANLLAEAKKLNDAQ | SEQ ID NO:380 |
| HM05428 | KERYRAYYEIWQLPNLNQRQKAAFIGSLSDDPSQSANLLAEAKKLNDAQ | SEQ ID NO:381 |
| HM05429 | KEWKSAAFEIWELPNLNRLQKAAFIRSLSDDPSQSANLLAEAKKLNDAQ | SEQ ID NO:382 |
| HM05430 | KERKQATFEIWELPNLNRHQKGAFIASLWDDPSQSANLLAEAKKLNDAQ | SEQ ID NO:383 |
| HM05431 | KEWKIAAGEIWQLPNLNRRQKAAFIASLSDDPSQSANLLAEAKKLNDAQ | SEQ ID NO:384 |
| HM05432 | KERYLAYYEIWQLPNLNVRQKAAFIKSLFDDPSQSANLLAEAKKLNDAQ | SEQ ID NO:385 |
| HM05433 | KERYHAYYEIWELPNLNRLQKAAFISSLSDDPSQSANLLAEAKKLNDAQ | SEQ ID NO:386 |
| HM05434 | KEKYKAYAEIWQLPNLNRTQKAAFISSLQDDPSQSANLLAEAKKLNDAQ | SEQ ID NO:387 |
| HM05435 | KEKYVAYYEIWQLPNLNRQQKAAFISSLQDDPSQSANLLAEAKKLNDAQ | SEQ ID NO:388 |
| HM05436 | KERKLATFEIWELPNLNTSQKGAFIASLQDDPSQSANLLAEAKKLNDAQ | SEQ ID NO:389 |
| HM05437 | KERYVAYYEIWQLPNLNVQQKAAFIASLQDDPSQSANLLAEAKKLNDAQ | SEQ ID NO:390 |
| HM05438 | KERSIASVEIWELPNLNQRQKGAFIASLWDDPSQSANLLAEAKKLNDAQ | SEQ ID NO:391 |
| HM05439 | KERKIAAIEIWELPNLNVRQKAAFIRSLFDDPSQSANLLAEAKKLNDAQ | SEQ ID NO:392 |
| HM05440 | KEKKIAAFEIWELPNLNQWQKAAFIASLFDDPSQSANLLAEAKKLNDAQ | SEQ ID NO:393 |
| HM05441 | KERKIATVEIWELPNLNRIQKGAFIASLWDDPSQSANLLAEAKKLNDAQ | SEQ ID NO:394 |
| HM05442 | KEKYRAAGEIWELPNLNVLQKAAFIKSLWDDPSQSANLLAEAKKLNDAQ | SEQ ID NO:395 |
| HM05443 | KERKIAAVEIWELPNLNRYQKAAFIKSLFDDPSQSANLLAEAKKLNDAQ | SEQ ID NO:396 |
| HM05444 | KEKRTATWEIWQLPNLNQRQRAAFIGSLWDDPSQSANLLAEAKKLNDAQ | SEQ ID NO:397 |
| HM05445 | KERKIAAFEIWELPNLNRRQKAAFIASLWDDPSQSANLLAEAKKLNDAQ | SEQ ID NO:398 |
| HM05446 | KERKQAAVEIWELPNLNRIQKGAFIKSLWDDPSQSANLLAEAKKLNDAQ | SEQ ID NO:399 |

Figure 1P

| HER4-ECD | QSVCAGTENKLSLSDLEQQYRALRKYYENCEVVMGNLEITSIEHNRDLSFLRSVREVTGYVLVALNQFRYLPLENLRIIRGTKL<br>YEDRYALAIFLNYRKDGNFGLQELGLKNLTEILNGGVYVDQNKFLCYADTIHWQDIVRNPWPSNLTLVSTNGSSGCGRCHKSCTG<br>RCWGPTENHCQTLTRTVCAEQCDGRCYGPYVSDCCHRECAGGCSGPKDTCFACMNFNDSGACVTQCPQTFVYNPTTFQLEHNFN<br>AKYTYGAFCVKKCPHNFVVDSSSCVRACPSSKMEVEENGIKMCKPCTDICPKACDGIGTGSLMSAQTVDSSNIDKFINCTKINGN<br>LIFLVTGIHGDPYNAIEAIDPEKLNVFRTVREITGFLNIQSWPPNMTDFSVFSNLVTIGGRVLYSGLSLLILKQQGITSLQFQSL<br>KEISAGNIYITDNSNLCYHTINWTTLFSTINQRIVIRDNRKAENCTAEGMVCNHLCSSDGCWGPGPDQCLSCRRFSRGRICIES<br>CNLYDGEFREFENGSICVECDPQCEKMEDGLLTCHGPGPDNCTKCSHFKDGPNCVEKCPDGLQGANSFIFKYADPDRECHPCHPN<br>CTQGCNGPTSHDCIYYPWTGHSTLPQHARTP | SEQ ID<br>NO:1009 |

Figure 1PP

| | | |
|---|---|---|
| HM05447 | KERYIAYGEIWQLPNLNRRQKAAFIGSLSDDPSQSANLLAEAKKLNDAQ | SEQ ID NO:400 |
| HM00014 | KERYRAYYEIWQLPNLNRTQKVAFIGSLQDDPSQSANLLAEAKKLNDAQ | SEQ ID NO:401 |
| HM00015 | KERRLAYWEIWQLPNLNTTQKAAFIGSLQDDPSQSANLLAEAKKLNDAQ | SEQ ID NO:402 |
| HM00016 | KERRAYYEIWQLPNLNRIQKAAFIGSLQDDPSQSANLLAEAKKLNDAQ | SEQ ID NO:403 |
| HM00017 | KERLAYYEIWELPNLNVAQKAAFIGSLQDDPSQSANLLAEAKKLNDAQ | SEQ ID NO:404 |
| HM00018 | KERLAYYEIWELPNLNVRQKAAFIGSLQDDPSQSANLLAEAKKLNDAQ | SEQ ID NO:405 |
| HM00029 | KERYAAYYEIWQLPNLNSRQKAAFIGSLSDDPSQSANLLAEAKKLNDAQ | SEQ ID NO:406 |
| HM00030 | KERYLAYYEIWQLPNLNQLQKAAFIGSLADDPSQSANLLAEAKKLNDAQ | SEQ ID NO:407 |
| HM00031 | KERYLAYYEIWQLPNLNSWQKAAFIGSLQDDPSQSANLLAEAKKLNDAQ | SEQ ID NO:408 |
| HM00033 | KERYHAYYEIWQLPNLNSAQKAAFIGSLQDDPSQSANLLAEAKKLNDAQ | SEQ ID NO:409 |
| HM00034 | KERYEAYYEIWQLPNLNSVQKAAFIGSLQDDPSQSANLLAEAKKLNDAQ | SEQ ID NO:410 |
| HM00035 | KERYHAYYEIWQLPNLNRRQKAAFIGSLQDDPSQSANLLAEAKKLNDAQ | SEQ ID NO:411 |
| HM00036 | KERYTAYYEIWQLPNLNRAQKAAFIGSLQDDPSQSANLLAEAKKLNDAQ | SEQ ID NO:412 |
| HM00039 | KERYSAYYEIWQLPNLNRAQKAAFIGSLSDDPSQSANLLAEAKKLNDAQ | SEQ ID NO:413 |
| HM00042 | KERYSAYYEIWELPNLNRAQKAAFIGSLSDDPSQSANLLAEAKKLNDAQ | SEQ ID NO:414 |
| HM00043 | KERYHAYYEIWELPNLNRAQKAAFIGSLYDDPSQSANLLAEAKKLNDAQ | SEQ ID NO:415 |
| HM00044 | KERYSAYVEIWQLPNLNRGQKAAFIGSLYDDPSQSANLLAEAKKLNDAQ | SEQ ID NO:416 |
| HM00045 | KERYSAYFEIWQLPNLNRLQKAAFIGSLQDDPSQSANLLAEAKKLNDAQ | SEQ ID NO:417 |
| HM00046 | KERYSAYFEIWQLPNLNRYQKSAFIGSLQDDPSQSANLLAEAKKLNDAQ | SEQ ID NO:418 |
| HM00047 | KERYAAYFEIWQLPNLNVAQKAAFIGSLQDDPSQSANLLAEAKKLNDAQ | SEQ ID NO:419 |
| HM00048 | KERYQAYFEIWQLPNLNQWQKAAFIGSLQDDPSQSANLLAEAKKLNDAQ | SEQ ID NO:420 |
| HM00049 | KERYKAYWEIWQLPNLNQGQKAAFIGSLQDDPSQSANLLAEAKKLNDAQ | SEQ ID NO:421 |
| HM00050 | KERYIAYGEIWQLPNLNVGQKAAFIGSLQDDPSQSANLLAEAKKLNDAQ | SEQ ID NO:422 |
| HM00051 | KERYRAYVEIWQLPNLNRVQKAAFIGSLQDDPSQSANLLAEAKKLNDAQ | SEQ ID NO:423 |
| HM00052 | KERYKAYVEIWQLPNLNRTQKAAFIGSLQDDPSQSANLLAEAKKLNDAQ | SEQ ID NO:424 |

Figure 1Q

| | | |
|---|---|---|
| HM00053 | KEKYEAYGEIWELPNLNRSQKAAFIGSLEDDPSQSANLLAEAKKLNDAQ | SEQ ID NO:425 |
| HM00054 | KEKYQAYGEIWQLPNLNRSQKAAFITSLEDDPSQSANLLAEAKKLNDAQ | SEQ ID NO:426 |
| HM00058 | KEKYAAYGEIWLLPNLNRIQKAAFIGSLQDDPSQSANLLAEAKKLNDAQ | SEQ ID NO:427 |
| HM00060 | KEKYKAYGEIWELPNLNRRQKVAFISSLSDDPSQSANLLAEAKKLNDAQ | SEQ ID NO:428 |
| HM00061 | KEKYKAYGEIWELPNLNRSQKAAFIASLSDDPSQSANLLAEAKKLNDAQ | SEQ ID NO:429 |
| HM00072 | KEKYKAYGEIWQLPNLNQRQKAAFIASLSDDPSQSANLLAEAKKLNDAQ | SEQ ID NO:430 |
| HM00075 | KEKYKAYGEIWQLPNLNRSQKAAFISSLQDDPSQSANLLAEAKKLNDAQ | SEQ ID NO:431 |
| HM00076 | KEKYKAYGEIWQLPNLNRRQKAAFISSLADDPSQSANLLAEAKKLNDAQ | SEQ ID NO:432 |
| HM00077 | KEKYNAYGEIWQLPNLNRGQKAAFISSLSDDPSQSANLLAEAKKLNDAQ | SEQ ID NO:433 |
| HM00080 | KEKYVAYAEIWQLPNLNRVQKAAFIGSLSDDPSQSANLLAEAKKLNDAQ | SEQ ID NO:434 |
| HM00083 | KEKYQAYGEIWQLPNLNRVQKAAFIGSLSDDPSQSANLLAEAKKLNDAQ | SEQ ID NO:435 |
| HM00088 | KEKYHAYGEIWQLPNLNRIQKAAFIASLQDDPSQSANLLAEAKKLNDAQ | SEQ ID NO:436 |
| HM00092 | KEKYTAYGEIWQLPNLNRYQRAAFIASLSDDPSQSANLLAEAKKLNDAQ | SEQ ID NO:437 |
| HM00095 | KEKYKAYVEIWQLPNLNRGQKAAFIGSLSDDPSQSANLLAEAKKLNDAQ | SEQ ID NO:438 |
| HM00096 | KEKYVAYVEIWQLPNLNRTQKAAFIASLEDDPSQSANLLAEAKKLNDAQ | SEQ ID NO:439 |
| HM00097 | KEKYIAYVEIWQLPNLNRTQKAAFIASLSDDPSQSANLLAEAKKLNDAQ | SEQ ID NO:440 |
| HM00100 | KEKYKAYAEIWQLPNLNRAQKAAFIGSLYDDPSQSANLLAEAKKLNDAQ | SEQ ID NO:441 |
| HM00113 | KEKYTAYGEIWQLPNLNVRQKAAFISSLSDDPSQSANLLAEAKKLNDAQ | SEQ ID NO:442 |
| HM00116 | KEKYTAYGEIWQLPNLNQRQKAAFISSLQDDPSQSANLLAEAKKLNDAQ | SEQ ID NO:443 |
| HM00117 | KEKYTAYFEIWQLPNLNQGQKAAFIGSLQDDPSQSANLLAEAKKLNDAQ | SEQ ID NO:444 |
| HM00122 | KEKYQAYVEIWQLPNLNQRQKAAFIGSLADDPSQSANLLAEAKKLNDAQ | SEQ ID NO:445 |
| HM00123 | KEKYAAYVEIWQLPNLNQRQKAAFIGSLQDDPSQSANLLAEAKKLNDAQ | SEQ ID NO:446 |
| HM00126 | KEKYKAYVEIWQLPNLNQRQKAAFIGSLQDDPSQSANLLAEAKKLNDAQ | SEQ ID NO:447 |
| HM00127 | KEKYQAYAEIWQLPNLNTSQKAFIGSLQDDPSQSANLLAEAKKLNDAQ | SEQ ID NO:448 |
| HM00128 | KEKYQAYYEIWELPNLNVQQKSAFITTSLQDDPSQSANLLAEAKKLNDAQ | SEQ ID NO:449 |

Figure 1R

| | | |
|---|---|---|
| HM00129 | KEKYHAYYEIWQLPNLNVHQKAAFIRSLADDPSQSANLLAEAKKLNDAQ | SEQ ID NO:450 |
| HM00130 | KEKYQAYYEIWQLPNLNVAQKAAFIRSLSDDPSQSANLLAEAKKLNDAQ | SEQ ID NO:451 |
| HM00131 | KERYTAYYEIWQLPNLNRTQKAAFIGSLSDDPSQSANLLAEAKKLNDAQ | SEQ ID NO:452 |
| HM00137 | KERYRAYYEIWQLPNLNRQQKGAFIASLQDDPSQSANLLAEAKKLNDAQ | SEQ ID NO:453 |
| HM00138 | KEKYIAYYEIWQLPNLNRSOKGAFIGSLQDDPSQSANLLAEAKKLNDAQ | SEQ ID NO:454 |
| HM00139 | KEKYIAYYEIWQLPNLNRSQKGAFIGSLQDDPSQSANLLAEAKKLNDAQ | SEQ ID NO:455 |
| HM00140 | KEKYKAYYEIWQLPNLNRQQKGAFIGSLADDPSQSANLLAEAKKLNDAQ | SEQ ID NO:456 |
| HM00141 | KERYLAYYEIWQLPNLNQFQKAAFIASLQDDPSQSANLLAEAKKLNDAQ | SEQ ID NO:457 |
| HM00142 | KERYLAYYEIWQLPNLNREQKAAFIASLQDDPSQSANLLAEAKKLNDAQ | SEQ ID NO:458 |
| HM00146 | KERYVAYGEIWQLPNLNRYQKAAFIASLQDDPSQSANLLAEAKKLNDAQ | SEQ ID NO:459 |
| HM00147 | KERYTAYYEIWQLPNLNRAQKAAFIASLQDDPSQSANLLAEAKKLNDAQ | SEQ ID NO:460 |
| HM00152 | KERYQAYYEIWQLPNLNRIQKAAFIKSLQDDPSQSANLLAEAKKLNDAQ | SEQ ID NO:461 |
| HM00153 | KERYTAYYEIWQLPNLNTQQKAAFIRSLEDDPSQSANLLAEAKKLNDAQ | SEQ ID NO:462 |
| HM00154 | KERYQAYYEIWQLPNLNTIQKAAFIRSLQDDPSQSANLLAEAKKLNDAQ | SEQ ID NO:463 |
| HM00155 | KERYAAYAEIWQLPNLNRWQKAAFIASLQDDPSQSANLLAEAKKLNDAQ | SEQ ID NO:464 |
| HM00157 | KERYRAYAEIWQLPNLNRIQKAAFIGSLEDDPSQSANLLAEAKKLNDAQ | SEQ ID NO:465 |
| HM00158 | KERYRAYAEIWQLPNLNRIQKAAFIGSLQDDPSQSANLLAEAKKLNDAQ | SEQ ID NO:466 |
| HM00160 | KERYHAYAEIWQLPNLNRIQKAAFIASLSDDPSQSANLLAEAKKLNDAQ | SEQ ID NO:467 |
| HM00161 | KERYRAYYEIWQLPNLNRVQKAAFIASLSDDPSQSANLLAEAKKLNDAQ | SEQ ID NO:468 |
| HM00168 | KERYTAYYEIWQLPNLNRTQKAAFIASLSDDPSQSANLLAEAKKLNDAQ | SEQ ID NO:469 |
| HM00169 | KERYVAYYEIWQLPNLNRRQKAAFIASLSDDPSQSANLLAEAKKLNDAQ | SEQ ID NO:470 |
| HM00170 | KERYLAYYEIWQLPNLNRHQKGAFIASLEDDPSQSANLLAEAKKLNDAQ | SEQ ID NO:471 |
| HM00171 | KERYIAYFEIWQLPNLNRWQKGAFIASLEDDPSQSANLLAEAKKLNDAQ | SEQ ID NO:472 |
| HM00172 | KERYTAYFEIWQLPNLNRWQKGAFIASLEDDPSQSANLLAEAKKLNDAQ | SEQ ID NO:473 |
| HM00176 | KERYAAYFEIWQLPNLNRLQKAAFISSLEDDPSQSANLLAEAKKLNDAQ | SEQ ID NO:474 |

Figure 1S

| HM00177 | KERYVAYFEIWQLPNLNRSQKAAFISSLEDDPSQSANLLAEAKKLNDAQ | SEQ ID NO:475 |
| HM00178 | KERYGAYFEIWQLPNLNRTQKAAFIASLADDPSQSANLLAEAKKLNDAQ | SEQ ID NO:476 |
| HM00182 | KEKYIAYWEIWQLPNLNREQKAAFISSLQDDPSQSANLLAEAKKLNDAQ | SEQ ID NO:477 |
| HM00184 | KERYIAYWEIWQLPNLNRRQKAAFIASLEDDPSQSANLLAEAKKLNDAQ | SEQ ID NO:478 |
| HM00185 | KERYIAYWEIWQLPNLNQRQKAAFIASLADDPSQSANLLAEAKKLNDAQ | SEQ ID NO:479 |
| HM00186 | KERYIAYWEIWQLPNLNRLQKSAFIASLQDDPSQSANLLAEAKKLNDAQ | SEQ ID NO:480 |
| HM00187 | KERYHAYWEIWQLPNLNRAQKAAFIRSLQDDPSQSANLLAEAKKLNDAQ | SEQ ID NO:481 |
| HM00188 | KERYNAYWEIWQLPNLNRLQKAAFIRSLQDDPSQSANLLAEAKKLNDAQ | SEQ ID NO:482 |
| HM00189 | KERYTAYGEIWELPNLNRVQRAAFIASLADDPSQSANLLAEAKKLNDAQ | SEQ ID NO:483 |
| HM00190 | KERYTAYGEIWELPNLNRLQKAAFIGSLADDPSQSANLLAEAKKLNDAQ | SEQ ID NO:484 |
| HM00191 | KERYHAYGEIWELPNLNRRQKAAFITSLADDPSQSANLLAEAKKLNDAQ | SEQ ID NO:485 |
| HM00192 | KERYKAYGEIWQLPNLNRLQKAAFIGSLADDPSQSANLLAEAKKLNDAQ | SEQ ID NO:486 |
| HM00193 | KERYQAYGEIWQLPNLNRLQKAAFIGSLADDPSQSANLLAEAKKLNDAQ | SEQ ID NO:487 |
| HM00194 | KERYVAYGEIWQLPNLNRLQKAAFISSLADDPSQSANLLAEAKKLNDAQ | SEQ ID NO:488 |
| HM00197 | KERYIAYGEIWELPNLNRLQKAAFIGSLSDDPSQSANLLAEAKKLNDAQ | SEQ ID NO:489 |
| HM00198 | KERQAYGEIWQLPNLNRRQKAAFISSLQDDPSQSANLLAEAKKLNDAQ | SEQ ID NO:490 |
| HM00199 | KERRQAYFEIWELPNLNRYQKAAFISSLQDDPSQSANLLAEAKKLNDAQ | SEQ ID NO:491 |
| HM00200 | KERRAYYEIWELPNLNRIQKVAFIASLQDDPSQSANLLAEAKKLNDAQ | SEQ ID NO:492 |
| HM00201 | KEKYTAYGEIWELPNLNRIQKVAFIASLQDDPSQSANLLAEAKKLNDAQ | SEQ ID NO:493 |
| HM00202 | KEKYAAYVEIWELPNLNRRQKAAFIASLQDDPSQSANLLAEAKKLNDAQ | SEQ ID NO:494 |
| HM00203 | KERYRAYVEIWELPNLNRWQKAAFTRSLQDDPSQSANLLAEAKKLNDAQ | SEQ ID NO:495 |
| HM00208 | KERYRAYFEIWELPNLNRAQKAAFISSLSDDPSQSANLLAEAKKLNDAQ | SEQ ID NO:496 |
| HM00209 | KERYQAYFEIWQLPNLNRLQAGAFIASLSDDPSQSANLLAEAKKLNDAQ | SEQ ID NO:497 |
| HM00210 | KEKYQAYVEIWQLPNLNRLQKGAFIASLSDDPSQSANLLAEAKKLNDAQ | SEQ ID NO:498 |
| HM00211 | KEKAAYYEIWQLPNLNRSQKGAFIASLSDDPSQSANLLAEAKKLNDAQ | SEQ ID NO:499 |

Figure 1T

| | | |
|---|---|---|
| HM00212 | KEKYQAYYEIWELPNLNRGGQKAAFIASLSDDPSQSANLLAEAKKLNDAQ | SEQ ID NO:500 |
| HM00215 | KEKYNAYFEIWQLPNLNRLQKAAFITSLSDDPSQSANLLAEAKKLNDAQ | SEQ ID NO:501 |
| HM00217 | KEKYSAYFEIWQLPNLNTSQKAAFIASLSDDPSQSANLLAEAKKLNDAQ | SEQ ID NO:502 |
| HM00218 | KERYNAYFEIWELPNLNVRQKAAFIRSLSDDPSQSANLLAEAKKLNDAQ | SEQ ID NO:503 |
| HM00219 | KEKYEAYFEIWELPNLNSRQKAAFIGSLSDDPSQSANLLAEAKKLNDAQ | SEQ ID NO:504 |
| HM00220 | KERYRAYWEIWELPNLNQQQKVAFIRSLYDDPSQSANLLAEAKKLNDAQ | SEQ ID NO:505 |
| HM00222 | KERYNAYWEIWELPNLNQSQKVAFIRSLQDDPSQSANLLAEAKKLNDAQ | SEQ ID NO:506 |
| HM00224 | KERRHAYGEIWQLPNLNQROKVAFISSLQDDPSQSANLLAEAKKLNDAQ | SEQ ID NO:507 |
| HM00225 | KEKYVATWEIWELPNLNRAQKVAFIGSLWDDPSQSANLLAEAKKLNDAQ | SEQ ID NO:508 |
| HM00226 | KERRIARWEIWELPNLNRLQKVAFIGSLEDDPSQSANLLAEAKKLNDAQ | SEQ ID NO:509 |
| HM00227 | KEKYKAAGEIWQLPNLNRGQKVAFIGSLEDDPSQSANLLAEAKKLNDAQ | SEQ ID NO:510 |
| HM00228 | KEKYLAYGEIWQLPNLNQRHQKVAFIGSLDDDPSQSANLLAEAKKLNDAQ | SEQ ID NO:511 |
| HM00229 | KEKYQAYGEIWQLPNLNRQQKVAFISSLQDDPSQSANLLAEAKKLNDAQ | SEQ ID NO:512 |
| HM00231 | KEKYKAYGEIWQLPNLNRQQKVAFIISLQDDPSQSANLLAEAKKLNDAQ | SEQ ID NO:513 |
| HM00232 | KEKYAAAYEIWQLPNLNQROKGAFIASLFDDPSQSANLLAEAKKLNDAQ | SEQ ID NO:514 |
| HM00233 | KEKYAASYEIWELPNLNQRQKVAFIKSLFDDPSQSANLLAEAKKLNDAQ | SEQ ID NO:515 |
| HM00234 | KEKYLASYEIWQLPNLNRRQKAAFIASLFDDPSQSANLLAEAKKLNDAQ | SEQ ID NO:516 |
| HM00235 | KEKYSATFEIWQLPNLNQRQKAAFISSLWDDPSQSANLLAEAKKLNDAQ | SEQ ID NO:517 |
| HM00237 | KEKYAASFEIWQLPNLNRIQKAAFISSLWDDPSQSANLLAEAKKLNDAQ | SEQ ID NO:518 |
| HM00238 | KEKYKASGEIWQLPNLNRIQRAAFIKSLFDDPSQSANLLAEAKKLNDAQ | SEQ ID NO:519 |
| HM00239 | KEKYSASGEIWQLPNLNRTQKAAFIKSLWDDPSQSANLLAEAKKLNDAQ | SEQ ID NO:520 |
| HM00243 | KEKYHAAGEIWELPNLNRLQKAAFIRSLWDDPSQSANLLAEAKKLNDAQ | SEQ ID NO:521 |
| HM00244 | KEKYRAAGEIWELPNLNRQQKAAFIRSLFDDPSQSANLLAEAKKLNDAQ | SEQ ID NO:522 |
| HM00245 | KEKYQASGEIWELPNLNRLQKAAFIRSLFDDPSQSANLLAEAKKLNDAQ | SEQ ID NO:523 |
| HM00246 | KEKYKATGEIWELPNLNRIQKAAFIRSLWDDPSQSANLLAEAKKLNDAQ | SEQ ID NO:524 |

Figure 1U

| | | |
|---|---|---|
| HM00247 | KEKYQASFEIWELPNLNRSQKAAFIKSLWDDPSQSANLLAEAKKLNDAQ | SEQ ID NO:525 |
| HM00248 | KERKVAAVEIWQLPNLNRWQRGAFISSLFDDPSQSANLLAEAKKLNDAQ | SEQ ID NO:526 |
| HM00249 | KERKLAAVEIWELPNLNQYQRGAFISSLWDDPSQSANLLAEAKKLNDAQ | SEQ ID NO:527 |
| HM00250 | KERKKASVEIWELPNLNRYQKGAFISSLFDDPSQSANLLAEAKKLNDAQ | SEQ ID NO:528 |
| HM00253 | KERKHAAWEIWELPNLNRHQKGAFIKSLWDDPSQSANLLAEAKKLNDAQ | SEQ ID NO:529 |
| HM00254 | KERKHAAVEIWELPNLNRWQKGAFIGSLWDDPSQSANLLAEAKKLNDAQ | SEQ ID NO:530 |
| HM00255 | KERKHAAVEIWELPNLNVFQRGAFIASLYDDPSQSANLLAEAKKLNDAQ | SEQ ID NO:531 |
| HM00256 | KERKHAAVEIWELPNLNRLQRGAFIASLYDDPSQSANLLAEAKKLNDAQ | SEQ ID NO:532 |
| HM00258 | KEWKTAAVEIWELPNLNRRQKAAFIGSLYDDPSQSANLLAEAKKLNDAQ | SEQ ID NO:533 |
| HM00261 | KERKVAAFEIWELPNLNRGQKAAFIGSLYDDPSQSANLLAEAKKLNDAQ | SEQ ID NO:534 |
| HM00262 | KEKRNAAVEIWELPNLNRRQRAAFISSLFDDPSQSANLLAEAKKLNDAQ | SEQ ID NO:535 |
| HM00263 | KERRNAAVEIWELPNLNRHQRAAFISSLFDDPSQSANLLAEAKKLNDAQ | SEQ ID NO:536 |
| HM00264 | KEKRQASVEIWELPNLNRIQKAAFISSLFDDPSQSANLLAEAKKLNDAQ | SEQ ID NO:537 |
| HM00265 | KEKRRAAVEIWELPNLNRIQKSAFIASLWDDPSQSANLLAEAKKLNDAQ | SEQ ID NO:538 |
| HM00266 | KEKRHAAWEIWELPNLNRAQKSAFIKSLWDDPSQSANLLAEAKKLNDAQ | SEQ ID NO:539 |
| HM00267 | KEKRNATVEIWELPNLNRIQRAAFIASLWDDPSQSANLLAEAKKLNDAQ | SEQ ID NO:540 |
| HM00268 | KEKRAATVEIWELPNLNRLQKGAFIASLWDDPSQSANLLAEAKKLNDAQ | SEQ ID NO:541 |
| HM00269 | KERRGAAVEIWELPNLNRQQKAAFIASLWDDPSQSANLLAEAKKLNDAQ | SEQ ID NO:542 |
| HM00270 | KERRKATVEIWELPNLNRQQKAAFISSLWDDPSQSANLLAEAKKLNDAQ | SEQ ID NO:543 |
| HM00271 | KEKSTAAVEIWELPNLNRIQKAAFIKSLFDDPSQSANLLAEAKKLNDAQ | SEQ ID NO:544 |
| HM00272 | KEKSTAAVEIWELPNLNRYQKAAFIKSLFDDPSQSANLLAEAKKLNDAQ | SEQ ID NO:545 |
| HM00273 | KEKSHAAVEIWELPNLNRWQKAAFIKSLWDDPSQSANLLAEAKKLNDAQ | SEQ ID NO:546 |
| HM00274 | KERSSAAVEIWELPNLNRFQKAAFISLFDDPSQSANLLAEAKKLNDAQ | SEQ ID NO:547 |
| HM00275 | KEKRIAAAEIWELPNLNRVQKAAFIKSLFDDPSQSANLLAEAKKLNDAQ | SEQ ID NO:548 |
| HM00276 | KEKRHAAGEIWELPNLNRIQKAAFIKSLFDDPSQSANLLAEAKKLNDAQ | SEQ ID NO:549 |

Figure 1V

| | | |
|---|---|---|
| HM00277 | KEKRIAAVEIWELPNLNRVQKAAFIASLYDDPSQSANLLAEAKKLNDAQ | SEQ ID NO:550 |
| HM00278 | KEKRIASYEIWELPNLNRRQRAAFIASLYDDPSQSANLLAEAKKLNDAQ | SEQ ID NO:551 |
| HM00279 | KEKRNATFEIWELPNLNRSQKGAFISSLYDDPSQSANLLAEAKKLNDAQ | SEQ ID NO:552 |
| HM00282 | KEKRVATFEIWELPNLNSRQKAAFIKSLFDDPSQSANLLAEAKKLNDAQ | SEQ ID NO:553 |
| HM00283 | KEKRNATFEIWELPNLNQRQKSAFIASLWDDPSQSANLLAEAKKLNDAQ | SEQ ID NO:554 |
| HM00284 | KERSAATFEIWELPNLNRVQKSAFIASLWDDPSQSANLLAEAKKLNDAQ | SEQ ID NO:555 |
| HM00285 | KERKHATFEIWELPNLNQRQKSAFIGSLWDDPSQSANLLAEAKKLNDAQ | SEQ ID NO:556 |
| HM00292 | KERKQATFEIWELPNLNQQQKGAFIASLWDDPSQSANLLAEAKKLNDAQ | SEQ ID NO:557 |
| HM00293 | KERKRATFEIWELPNLNRTQKAAFISSLWDDPSQSANLLAEAKKLNDAQ | SEQ ID NO:558 |
| HM00294 | KERKTATFEIWELPNLNRVQKAAFIKSLFDDPSQSANLLAEAKKLNDAQ | SEQ ID NO:559 |
| HM00295 | KERKLATWEIWELPNLNRSQKAAFIISLWDDPSQSANLLAEAKKLNDAQ | SEQ ID NO:560 |
| HM00299 | KERKVAAVEIWELPNLNRIQKAAFIRSLFDDPSQSANLLAEAKKLNDAQ | SEQ ID NO:561 |
| HM00300 | KERKEAAVEIWELPNLNRLQKAAFIRSLFDDPSQSANLLAEAKKLNDAQ | SEQ ID NO:562 |
| HM00302 | KERKRAAVEIWELPNLNRGQKAAFIKSLFDDPSQSANLLAEAKKLNDAQ | SEQ ID NO:563 |
| HM00303 | KERKLAAVEIWELPNLNRTQKAAFIKSLFDDPSQSANLLAEAKKLNDAQ | SEQ ID NO:564 |
| HM00304 | KERKVAAVEIWELPNLNRVQKAAFIKSLFDDPSQSANLLAEAKKLNDAQ | SEQ ID NO:565 |
| HM00305 | KERKEAAVEIWELPNLNRVQKAAFIKSLYDDPSQSANLLAEAKKLNDAQ | SEQ ID NO:566 |
| HM00309 | KERKAATVEIWELPNLNRRQKAAFIASLFDDPSQSANLLAEAKKLNDAQ | SEQ ID NO:567 |
| HM00312 | KEKRHASWEIWELPNLNQWQKAAFIRSLFDDPSQSANLLAEAKKLNDAQ | SEQ ID NO:568 |
| HM00313 | KEKRSATWEIWELPNLNLQKAAFIRSLFDDPSQSANLLAEAKKLNDAQ | SEQ ID NO:569 |
| HM00314 | KEKKAAVEIWELPNLNQRQRQKAAFIGSLWDDPSQSANLLAEAKKLNDAQ | SEQ ID NO:570 |
| HM00315 | KEKKLASFEIWELPNLNQRQKAAFIRSLWDDPSQSANLLAEAKKLNDAQ | SEQ ID NO:571 |
| HM00316 | KERKVATVEIWELPNLNRVQAAAFIKSLWDDPSQSANLLAEAKKLNDAQ | SEQ ID NO:572 |
| HM00317 | KERKTATVEIWELPNLNRIQKAAFIKSLWDDPSQSANLLAEAKKLNDAQ | SEQ ID NO:573 |
| HM00320 | KERKSATVEIWELPNLNRVQKAAFISSLWDDPSQSANLLAEAKKLNDAQ | SEQ ID NO:574 |

Figure 1W

| | | |
|---|---|---|
| HM00321 | KERKVATVEIWELPNLNRGQKAAFISSLWDDPSQSANLLAEAKKLNDAQ | SEQ ID NO:575 |
| HM00322 | KERKQATVEIWELPNLNRRQRAAFISSLWDDPSQSANLLAEAKKLNDAQ | SEQ ID NO:576 |
| HM00323 | KERKKATVEIWELPNLNRRQKGAFIASLWDDPSQSANLLAEAKKLNDAQ | SEQ ID NO:577 |
| HM00324 | KERKVATVEIWELPNLNRRQKGAFIASLWDDPSQSANLLAEAKKLNDAQ | SEQ ID NO:578 |
| HM00328 | KERKLATVEIWELPNLNRYQKGAFIASLWDDPSQSANLLAEAKKLNDAQ | SEQ ID NO:579 |
| HM00332 | KERKAATVEIWELPNLNRLQKGAFIASLWDDPSQSANLLAEAKKLNDAQ | SEQ ID NO:580 |
| HM00333 | KERKIATVEIWELPNLNRVQKSAFIASLWDDPSQSANLLAEAKKLNDAQ | SEQ ID NO:581 |
| HM00334 | KERKNATVEIWELPNLNRAQKAAFIASLWDDPSQSANLLAEAKKLNDAQ | SEQ ID NO:582 |
| HM00335 | KERKNATVEIWELPNLNRSQKAAFIGSLWDDPSQSANLLAEAKKLNDAQ | SEQ ID NO:583 |
| HM00338 | KERKTATVEIWELPNLNRGQKAAFIASLFDDPSQSANLLAEAKKLNDAQ | SEQ ID NO:584 |
| HM00339 | KERKHAAVEIWELPNLNRIQRAAFIASLFDDPSQSANLLAEAKKLNDAQ | SEQ ID NO:585 |
| HM00340 | KERKIATVEIWELPNLNRIQRAAFIASLWDDPSQSANLLAEAKKLNDAQ | SEQ ID NO:586 |
| HM00341 | KERKIAAVEIWELPNLNRIQAAAFIASLWDDPSQSANLLAEAKKLNDAQ | SEQ ID NO:587 |
| HM00342 | KERKSATVEIWELPNLNRTQRAAFIASLWDDPSQSANLLAEAKKLNDAQ | SEQ ID NO:588 |
| HM00343 | KERKSAAVEIWELPNLNRTQKAAFIASLWDDPSQSANLLAEAKKLNDAQ | SEQ ID NO:589 |
| HM00344 | KEKKSATVEIWELPNLNRIQKAAFIGSLWDDPSQSANLLAEAKKLNDAQ | SEQ ID NO:590 |
| HM00345 | KEKKSAYVEIWELPNLNRYQKAAFIKSLFDDPSQSANLLAEAKKLNDAQ | SEQ ID NO:591 |
| HM00349 | KERKIATYEIWELPNLNQRQKAAFIASLWDDPSQSANLLAEAKKLNDAQ | SEQ ID NO:592 |
| HM00350 | KERSVATWEIWQLPNLNQRQKAAFIASLWDDPSQSANLLAEAKKLNDAQ | SEQ ID NO:593 |
| HM00355 | KEKRKATGEIWQLPNLNQRQKGAFIASLWDDPSQSANLLAEAKKLNDAQ | SEQ ID NO:594 |
| HM00356 | KERKEARFEIWELPNLNQRQAAAFISSLFDDPSQSANLLAEAKKLNDAQ | SEQ ID NO:595 |
| HM00357 | KERKAASWEIWELPNLNQRQKAAFISSLYDDPSQSANLLAEAKKLNDAQ | SEQ ID NO:596 |
| HM00359 | KEWKHAAGEIWELPNLNRSQKVAFIASLEDDPSQSANLLAEAKKLNDAQ | SEQ ID NO:597 |
| HM00360 | KEWKRAAGEIWELPNLNRAQKVAFIASLADDPSQSANLLAEAKKLNDAQ | SEQ ID NO:598 |
| HM00362 | KEWKIAAGEIWELPNLNQRQKVAFIRSLQDDPSQSANLLAEAKKLNDAQ | SEQ ID NO:599 |

Figure 1X

| | | |
|---|---|---|
| HM00363 | KEWKTAAYEIWELPNLNTYQKVAFIRSLQDDPSQSANLLAEAKKLNDAQ | SEQ ID NO:600 |
| HM00364 | KEWKVAAGEIWELPNLNRTQKVAFIRSLSDDPSQSANLLAEAKKLNDAQ | SEQ ID NO:601 |
| HM00365 | KEWKVAAGEIWELPNLNRWQKVAFIRSLSDDPSQSANLLAEAKKLNDAQ | SEQ ID NO:602 |
| HM00366 | KEWKQAAGEIWELPNLNRLQKVAFIRSLSDDPSQSANLLAEAKKLNDAQ | SEQ ID NO:603 |
| HM00367 | KEWKVAAGEIWELPNLNVWQKAAFIRSLSDDPSQSANLLAEAKKLNDAQ | SEQ ID NO:604 |
| HM00368 | KEWKVAAWEIWELPNLNRGQKVAFIRSLQDDPSQSANLLAEAKKLNDAQ | SEQ ID NO:605 |
| HM00369 | KEWKRAAFEIWELPNLNQAQKVAFITSLSDDPSQSANLLAEAKKLNDAQ | SEQ ID NO:606 |
| HM00370 | KEWKKAAGEIWLLPNLNRRQRGAFTASLADDPSQSANLLAEAKKLNDAQ | SEQ ID NO:607 |
| HM00371 | KEWKKAAGEIWELPNLNSRQKGAFTASLADDPSQSANLLAEAKKLNDAQ | SEQ ID NO:608 |
| HM00372 | KEWRGAAGEIWELPNLNRRQRAAFIASLADDPSQSANLLAEAKKLNDAQ | SEQ ID NO:609 |
| HM00373 | KEWKVAAGEIWQLPNLNRRQRAAFIASLADDPSQSANLLAEAKKLNDAQ | SEQ ID NO:610 |
| HM00374 | KEWKTAAVEIWELPNLNTRQKGAFIASLSDDPSQSANLLAEAKKLNDAQ | SEQ ID NO:611 |
| HM00375 | KEWKIAAFEIWELPNLNVRQRSAFISSLSDDPSQSANLLAEAKKLNDAQ | SEQ ID NO:612 |
| HM00376 | KEWKTAAYEIWELPNLNRQRQRGAFTASLQDDPSQSANLLAEAKKLNDAQ | SEQ ID NO:613 |
| HM00377 | KEWKTAAGEIWELPNLNSRQKAAFIGSLADDPSQSANLLAEAKKLNDAQ | SEQ ID NO:614 |
| HM00378 | KEWKHAAGEIWELPNLNVGQKAAFIGSLADDPSQSANLLAEAKKLNDAQ | SEQ ID NO:615 |
| HM00379 | KEWKTAAGEIWELPNLNRTQKAAFIRSLADDPSQSANLLAEAKKLNDAQ | SEQ ID NO:616 |
| HM00380 | KEWKRAAGEIWELPNLNRLQKAAFIRSLADDPSQSANLLAEAKKLNDAQ | SEQ ID NO:617 |
| HM00381 | KEWKQAAGEIWELPNLNRGQKAAFISSLADDPSQSANLLAEAKKLNDAQ | SEQ ID NO:618 |
| HM00382 | KEWKQAAGEIWELPNLNRGQKAAFITSLADDPSQSANLLAEAKKLNDAQ | SEQ ID NO:619 |
| HM00383 | KEWKEAAGEIWELPNLNRGQKAAFIKSLADDPSQSANLLAEAKKLNDAQ | SEQ ID NO:620 |
| HM00384 | KEWKTAAGEIWELPNLNRRQKAAFIASLQDDPSQSANLLAEAKKLNDAQ | SEQ ID NO:621 |
| HM00385 | KEWKRAAGEIWELPNLNRAQKAAFISSLQDDPSQSANLLAEAKKLNDAQ | SEQ ID NO:622 |
| HM00386 | KEWKHAAFEIWELPNLNVRQKAAFIGSLQDDPSQSANLLAEAKKLNDAQ | SEQ ID NO:623 |
| HM00387 | KEWKNAAFEIWELPNLNVSQKAAFIRSLQDDPSQSANLLAEAKKLNDAQ | SEQ ID NO:624 |

Figure 1Y

| HM00388 | KEWKAAAYEIWELPNLNVWQKAAFISSLQDDPSQSANLLAEAKKLNDAQ | SEQ ID NO:625 |
|---|---|---|
| HM00389 | KEWKVAAGEIWELPNLNRWQKGAFITSLYDDPSQSANLLAEAKKLNDAQ | SEQ ID NO:626 |
| HM00390 | KEWKVAAGEIWELPNLNRWQKAAFIASLYDDPSQSANLLAEAKKLNDAQ | SEQ ID NO:627 |
| HM00391 | KEWKVAAGEIWELPNLNRLQRAAFIKSLYDDPSQSANLLAEAKKLNDAQ | SEQ ID NO:628 |
| HM00392 | KEWKVAAYEIWELPNLNRLIQKAAFIASLYDDPSQSANLLAEAKKLNDAQ | SEQ ID NO:629 |
| HM00393 | KEWKVAAFEIWELPNLNRTQRAAFIISLQDDPSQSANLLAEAKKLNDAQ | SEQ ID NO:630 |
| HM00394 | KEWKTAAVEIWELPNLNRLQKAAFITSLSDDPSQSANLLAEAKKLNDAQ | SEQ ID NO:631 |
| HM00395 | KEWKTAAVEIWELPNLNRLQKAAFIGSLSDDPSQSANLLAEAKKLNDAQ | SEQ ID NO:632 |
| HM00396 | KEWKTAAFEIWELPNLNRGQKAAFIRSLSDDPSQSANLLAEAKKLNDAQ | SEQ ID NO:633 |
| HM00400 | KEWKRAAFEIWELPNLNRLQKSAFIASLSDDPSQSANLLAEAKKLNDAQ | SEQ ID NO:634 |
| HM00401 | KEWKQAAFEIWELPNLNRYQAAAFIGSLQDDPSQSANLLAEAKKLNDAQ | SEQ ID NO:635 |
| HM00402 | KEWKHAAFEIWELPNLNRRQAGAFIASLQDDPSQSANLLAEAKKLNDAQ | SEQ ID NO:636 |
| HM00403 | KEWKQASGEIWELPNLNVRQKAAFIASLADDPSQSANLLAEAKKLNDAQ | SEQ ID NO:637 |
| HM00404 | KEWKQASFEIWELPNLNVRQKAAFISSLSDDPSQSANLLAEAKKLNDAQ | SEQ ID NO:638 |
| HM00405 | KEWKLAAGEIWELPNLNVRQKAAFIASLQDDPSQSANLLAEAKKLNDAQ | SEQ ID NO:639 |
| HM00406 | KEWKIAAGEIWQLPNLNVTQKAAFIASLSDDPSQSANLLAEAKKLNDAQ | SEQ ID NO:640 |
| HM00407 | KEWKHAAGEIWQLPNLNRRQAAAFIVSLDDPSQSANLLAEAKKLNDAQ | SEQ ID NO:641 |
| HM00411 | KEWKIAAGEIWELPNLNRAQKAAFIISLSDDPSQSANLLAEAKKLNDAQ | SEQ ID NO:642 |
| HM00412 | KEWKSAAGEIWELPNLNRFQKAAFIASLSDDPSQSANLLAEAKKLNDAQ | SEQ ID NO:643 |
| HM00413 | KEWKHAAVEIWQLPNLNRNTGQKAAFIRSLSDDPSQSANLLAEAKKLNDAQ | SEQ ID NO:644 |
| HM00414 | KEWKQAAWEIWQLPNLNTGQKAAFIASLSDDPSQSANLLAEAKKLNDAQ | SEQ ID NO:645 |
| HM00415 | KEWKQASMEIWELPNLNRGQKAAFIASLSDDPSQSANLLAEAKKLNDAQ | SEQ ID NO:646 |
| HM00416 | KEWKTASYEIWQLPNLNRRQAAAFIASLSDDPSQSANLLAEAKKLNDAQ | SEQ ID NO:647 |
| HM00417 | KEWKNASFEIWLLPNLNRIQKAAFIASLSDDPSQSANLLAEAKKLNDAQ | SEQ ID NO:648 |
| HM00418 | KEWKNAAFEIWLLPNLNQRQKAAFIASLSDDPSQSANLLAEAKKLNDAQ | SEQ ID NO:649 |

Figure 1Z

HER3 BINDING POLYPEPTIDES

CROSS-REFERENCE TO RELATED APPLICATIONS

This application is a U.S. National Stage application of International Application PCT/SE2010/051164 filed 27 Oct. 2010, which claims benefit of EP 09175025.7 filed 4 Nov. 2009.

FIELD OF THE INVENTION

This invention relates to polypeptides which bind to Human Epidermal Growth Factor Receptor 3 (herein referred to as HER3) and to use of such polypeptides in imaging and therapy. The invention also relates to bispecific ligands having binding affinity for both HER3 and HER2, or HER3 and EGFR.

BACKGROUND

The epidermal growth factor family of transmembrane tyrosine kinase receptors, including EGFR (ErbB1 or HER1), ErbB2 (HER2), ErbB3 (ERBB3 or HER3) and ErbB4 (HER4) are involved in regulating key cellular functions (e.g. cell proliferation, survival, differentiation and migration) through a complex network of intracellular signaling pathways. Today, it is well established that abnormal expression and signaling of these receptors are associated with development and progression of several types of cancer, making them important targets for development of novel cancer therapeutics. So far, the EGFR and HER2 receptors have been the most extensively studied, with several targeting agents approved by regulatory authorities for diagnosis or treatment of human cancers. HER3 lacks tyrosine kinase activity and must therefore form heterodimers with other ErbB receptors (Citri et al, Exp Cell Res 284(1):54-65 (2003)), e.g. with HER2 to exert its signaling function. The HER2-HER3 heterodimer is considered to be a potent oncogenic unit (Holbro et al, Proc Natl Acad Sci 100(15): 8933-8 (2003)) and HER3 has recently gained increased attention as the preferred heterodimerization partner for HER2. Dimerization with HER2 leads to activation of the PI3K/Akt pathway and promotion of tumor cell survival and proliferation (Hynes et al, Nat Rev Cancer 5(5):341-54 (2005)). HER3 is expressed in a number of human cancers, including breast (Bobrow et al, Eur J Cancer 33(11):1846-50 (1997)), ovarian and bladder cancer (Rajkumar et al, Clin Mol Pathol 49(4) (1996)), and play an important role in signaling in other cancers (Stove et al, Clin Exp Metastasis 21(8):665-84 (2004)), including some lung cancers (Engelman et al, Proc Natl Acad Sci 102(10):3788-93 (2005)) and prostate cancer (Gregory et al, Clin Cancer Res 11(5):1704-12 (2005)). In addition, HER3 expression has a prognostic value, since high levels of receptor expression are associated with significantly shorter survival time compared with patients that overexpress HER2 (Tanner et al, J Clin Oncol 24(26):4317-23 (2006), Reschke et al, Clin Cancer Res 14(16):5188-97 (2008)). HER3 has indeed been suggested to be a key node in ligand-induced activation of the ErbB receptor-P13K signaling axis (Schoeberl et al, Sci Signal 2(77):ra 31 (2009)).

A relatively large fraction of the more recently approved therapies directed towards the EGFR and HER2 receptors is based on monoclonal antibodies. One of the reasons behind the success for this new class of biological agents in cancer therapy is that antibodies offer new and unique mechanisms of action previously unachievable using small chemical drugs. In addition to more traditional agonistic (e.g. stimulation of a cell surface receptor) and antagonistic (e.g. blocking of natural protein-protein interactions) therapeutic effects, antibodies can also be employed as targeting agents in order to specifically direct a range of immunological defense mechanisms against the cancerous cells, as well as to achieve specific delivery of various imaging or therapeutic conjugates (e.g. chemotherapeutic drugs, radionuclides and toxins). In contrast to the well investigated EGFR and HER2 receptor members of the ErbB-family, there are relatively few reports on the use of anti-HER3 antibodies.

Ullrich and co-workers have however reported that anti-HER3 monoclonal antibodies inhibit HER3 mediated signaling in cell models of breast cancer (van der Horst et al, Int J Cancer 115(4):519-27 (2005)), and there are currently two monoclonal anti-HER3 antibodies in Phase I clinical trials (AMG 888, Baselga et al, Nat Rev Cancer 9(7):463-75 (2009), and MM-121, Schoeberl et al, supra).

However, although several successful cancer therapy studies have been reported using full-length monoclonal antibodies, this class of agents is not always optimal for targeting solid tumors (neither for diagnostic nor for therapeutic pay-load purposes). Therapeutic effect is dependent on an efficient distribution of the drug throughout the tumor, and molecular imaging depends on a high ratio between tumor uptake and surrounding normal tissue. Since tumor penetration rate (including extravasation) is negatively associated with the size of the molecule, the relatively large IgG molecule inherently has poor tissue distribution and penetration capacity. Moreover, for molecular imaging, the extraordinarily long in vivo half-life of antibodies results in relatively high blood signals and thereby relatively poor tumor-to-blood contrasts.

Since HER3 may be expressed on the same tumor cell as other members of the EGF family, production of bispecific molecules targeting HER3 and another member of the EGF family has recently attracted some interest. Such bispecific molecules could for example be utilized as targeting vehicles for increasing the specificity of targeting in molecular imaging applications and simultaneously targeting HER3 and another antigen expressed on tumors.

It is however complicated to produce bispecific monoclonal antibodies which bind to two separate targets. When the genes encoding the four required polypeptide chains are produced in a cell as many as 10 different combinations are possible, and only one combination represents the desired bispecific antibody. Therefore, the concept of bispecific binding has not been fully explored using antibodies. Instead, antibody fragments and other binding molecules have been more widely utilized for making bispecific binding molecules, including bispecific Z variants (Friedman et al, Biotechnol Appl Biochem 54:121-31 (2009)).

DESCRIPTION OF THE INVENTION

It is an object of the present invention to provide novel HER3 binding agents which for example may be used in targeting HER3 expressing cells, molecular imaging of such HER3 expressing cells and treatment of HER3 related conditions.

A further object of the invention is to provide targeting agents with high specificity for lesions expressing both HER2 and HER3.

According to one aspect, there is provided a HER3 binding polypeptide, comprising a HER3 binding motif, BM, which motif consists of the amino acid sequence selected from i) EX$_2$X$_3$X$_4$A X$_6$X$_7$EIW X$_{11}$LPNL X$_{16}$X$_{17}$X$_{18}$QX$_{20}$ X$_{21}$AFIX$_{25}$ X$_{26}$LX$_{28}$D, (SEQ ID NO:1010)

wherein, independently of each other,

X$_2$ is selected from R, K, L, W and V;
X$_3$ is selected from R, H, K, M, S, W, Y and V;
X$_4$ is selected from A, R, N, D, Q, E, G, H, I, L, K, M, S, T, W and V;
X$_6$ is selected from A, R, Q, M, S, T and Y;
X$_7$ is selected from A, E, G, H, K, F, S, T, W, Y and V;
X$_{11}$ is selected from A, N, D, Q, E, I, L and T;
X$_{16}$ is selected from N and T;
X$_{17}$ is selected from A, R, N, Q, K, P, S, T and V;
X$_{18}$ is selected from A, R, N, E, F, D, Q, G, H, I, L, K, S, T, W, Y and V;
X$_{20}$ is selected from A, R and K;
X$_{21}$ is selected from A, R, N, G, H, S and V;
X$_{25}$ is selected from A, R, E, G, I, K, S, T and V;
X$_{26}$ is selected from S and K;
X$_{28}$ is selected from A, D, Q, E, F, P, S, T, W and Y;
and ii) an amino acid sequence which has at least 90% identity to the sequence defined in i), wherein the polypeptide binds to the extra-cellular domain of HER3 (HER3-ECD).

The polypeptides as described herein present good binding affinity for HER3 in that they bind well to HER3. The above definition of a class of sequence related HER3 binding polypeptides is based on an analysis of a number of random polypeptide variants of a parent scaffold that were selected for their interaction with HER3 in selection experiments. The identified HER3 binding motif, or "BM", corresponds to the target binding region of the parent scaffold, which region constitutes two alpha helices within a three-helical bundle protein domain. In the parent scaffold, the varied amino acid residues of the two BM helices constitute a binding surface for interaction with the constant Fc part of antibodies. By random variation of binding surface residues and subsequent selection of variants, the Fc interaction capacity of the binding surface has been replaced with a capacity for interaction with HER3.

As the skilled person will realize, the function of any polypeptide, such as the HER3 binding capacity of the polypeptides as defined herein, is dependent on the tertiary structure of the polypeptide. It is therefore possible to make minor changes to the amino acid sequence of a polypeptide without largely affecting the tertiary structure and the function thereof. Thus, in one embodiment, the polypeptide comprises modified variants of the BM of i), which are such that the resulting sequence is at least 90% identical to a sequence belonging to the class defined by i), such as at least 93% identical, such as at least 97% identical to a sequence belonging to the class defined by i). In some embodiments, minor changes may be made in all positions of the sequences of the HER3 binding polypeptides as disclosed herein. In other embodiments, minor changes may be made only in the non-variable positions, also denoted as scaffold amino acid residues. In such cases, changes are not allowed in the variable positions, i.e. positions denoted with an "X" (e.g. $X_2$, $X_3$, $X_4$, $X_6$, $X_7$, $X_{11}$, $X_{16}$, $X_{17}$, $X_{18}$, $X_{20}$, $X_{21}$, $X_{25}$, $X_{26}$ and $X_{28}$ of the above defined BM). For example, it is possible that an amino acid residue belonging to a certain functional grouping of amino acid residues (e.g. hydrophobic, hydrophilic, polar etc) could be exchanged for another amino acid residue from the same functional group.

The term "% identity", as used throughout the specification and the appended claims, is calculated as follows. The query sequence is aligned to the target sequence using the CLUSTAL W algorithm (Thompson, J. D., Higgins, D. G. and Gibson, T. J., Nucleic Acids Research, 22: 4673-4680 (1994)). A comparison is made over the window corresponding to the shortest of the aligned sequences. The shortest of the aligned sequences may in some instances be the target sequence, such as the 29 amino acid residue HER3 binding motif. In other instances, the query sequence may constitute the shortest of the aligned sequences. The query sequence may for example consist of at least 10 amino acid residues, such as at least 20 amino acid residues. The amino acid residues at each position are compared, and the percentage of positions in the query sequence that have identical correspondences in the target sequence is reported as % identity.

The term "% similarity", as used throughout the specification and the appended claims, is calculated in the following way. Sequence alignment and comparison are basically performed as described in relation to the % identity calculation. "Similarity" should however be interpreted as follows. Two amino acid residues are considered similar if they belong to the same group of amino acid residues. Non-limiting examples of groups of amino acid residues are the hydrophobic group, comprising the amino acid residues Ala, Val, Phe, Pro, Leu, Ile, Trp, Met and Cys; the basic group, comprising the amino acid residues Lys, Arg and His; the acidic group, comprising the amino acid residues Glu and Asp; the hydrophilic group, comprising the uncharged amino acid residues Gln, Asn, Ser, Thr and Tyr; and the natural group, comprising the amino acid residue Gly. Thus, the amino acid residues at each position are compared, and the percentage of positions in the query sequence that have similar correspondences in the target sequence is reported as % similarity.

Throughout this description, alternative embodiments according to the invention fulfill, instead of the specified percentage of identity, the corresponding percentage of similarity. Other alternative embodiments fulfill the specified percentage of identity as well as another, higher percentage of similarity, selected from the group of preferred percentages of identity for each sequence. For example, a sequence may be 70% similar to another sequence; or it may be 70% identical to another sequence; or it may be 70% identical and 90% similar to another sequence.

In one embodiment of the above disclosed polypeptide, $X_2$ is selected from R, K and W.

In a further embodiment of the above disclosed polypeptide, $X_3$ is selected from R, K, S and Y.

In a further embodiment of the above disclosed polypeptide, $X_4$ is selected from A, R, N, Q, H, I, L, K, S, T and V.

In a further embodiment of the above disclosed polypeptide, $X_6$ is selected from A, S, T and Y.

In a further embodiment of the above disclosed polypeptide, $X_7$ is selected from A, G, F, W, Y and V.

In a further embodiment of the above disclosed polypeptide, $X_{11}$ is selected from Q and E.

In a further embodiment of the above disclosed polypeptide, $X_{17}$ is selected from R, Q, T and V.

In a further embodiment of the above disclosed polypeptide, $X_{18}$ is selected from R, Q, G, H, I, L, S, T, W, Y and V.

In a further embodiment of the above disclosed polypeptide, $X_{20}$ is selected from R and K.

In a further embodiment of the above disclosed polypeptide, $X_{21}$ is selected from A and G.

In a further embodiment of the above disclosed polypeptide, $X_{25}$ is selected from A, R, G, K and S.

In a further embodiment of the above disclosed polypeptide, $X_{28}$ is selected from A, Q, E, F, S, W and Y.

In a further embodiment of the above disclosed polypeptide, $X_2$ is selected from R and K.

In a further embodiment of the above disclosed polypeptide, $X_3$ is selected from K and Y.

In a further embodiment of the above disclosed polypeptide, $X_4$ is selected from A, R, N, Q, H, L, K, S, T and V.

In a further embodiment of the above disclosed polypeptide, $X_6$ is selected from T and Y.

In a further embodiment of the above disclosed polypeptide, $X_7$ is selected from A, G, F, Y and V.

In a further embodiment of the above disclosed polypeptide, $X_{17}$ is selected from R, Q and V.

In a further embodiment of the above disclosed polypeptide, $X_{18}$ is selected from R, Q, I, L, T, Y and V.

In a further embodiment of the above disclosed polypeptide, $X_{25}$ is selected from A, G, K and S.

In a further embodiment of the above disclosed polypeptide, $X_{28}$ is selected from A, Q, E, F, S and W.

In one embodiment of the above disclosed HER3 binding polypeptide, the polypeptide comprises a HER3 binding motif, BM, which motif consists of the amino acid sequence selected from i) EX$_2$X$_3$X$_4$A YX$_7$EIW X$_{11}$LPNL X$_{16}$X$_{17}$X$_{18}$QX$_{20}$ X$_{21}$AFIX$_{26}$ X$_{26}$LX$_{28}$D, (SEQ ID NO:1040)
wherein, independently of each other,
$X_2$ is selected from K, R and W;
$X_3$ is selected from K, R, and Y;
$X_4$ is selected from A, D, E, G, H, I, K, L, M, N, Q, R, S, T, V and W;
$X_7$ is selected from A, E, F, G, H, K, S, T, V, W and Y;
$X_{11}$ is selected from E and Q;
$X_{16}$ is selected from N and T;
$X_{17}$ is selected from R, T and V;
$X_{18}$ is selected from R, T and V;
$X_{20}$ is selected from K and R;
$X_{21}$ is selected from A and G;
$X_{25}$ is selected from A, G, K, R and S;
$X_{26}$ is selected from S and K;
$X_{28}$ is selected from A, D, E, F, P, Q, S, T, W and Y;
and
ii) an amino acid sequence which has at least 93% identity to the sequence defined in i), wherein the polypeptide binds to the extra-cellular domain of HER3.

In a further embodiment of the above disclosed polypeptide, $X_2X_3$ is selected from KY, RY, WK and WR.

In a further embodiment of the above disclosed polypeptide, $X_{11}$ is Q.

In a further embodiment of the above disclosed polypeptide, $X_{17}X_{18}$ is selected from RV, RT, VR and RR.

In a further embodiment of the above disclosed polypeptide, $X_{20}$ is K.

In a further embodiment of the above disclosed polypeptide, $X_{21}$ is A.

In a further embodiment of the above disclosed polypeptide, $X_2X_3$ is selected from KY and RY.

In a further embodiment of the above disclosed polypeptide, $X_4$ is selected from K, L, S and T.

In a further embodiment of the above disclosed polypeptide, $X_7$ is selected from F, G and Y.

In a further embodiment of the above disclosed polypeptide, $X_{17}X_{18}$ is selected from RV, RT and VR.

In a further embodiment of the above disclosed polypeptide, $X_{25}$ is selected from A, G and S.

In yet a further embodiment of the above disclosed polypeptide, the amino acid sequence i) fulfils at least one of the following four conditions I, II, III and IV:
I) $X_2X_3$ is selected from KY and RY;
II) $X_{11}$ is Q;
III) $X_{20}$ is K;
IV) $X_{21}$ is A.
The amino acid sequence i) may for example fulfill at least two, such as at least three or all, of the four conditions I, II, III and IV As described in detail in the experimental section to follow, the selection of HER3 binding variants has led to the identification of individual HER3 binding motif (BM) sequences. These sequences constitute individual embodiments of HER3 binding polypeptides according to this aspect. The sequences of individual HER3 binding motifs are presented in FIG. 1A-N and as SEQ ID NO:1-334. In some embodiments of this aspect, the BM sequence i) is selected from any one of SEQ ID NO:1 to SEQ ID NO:66, such as from any one of SEQ ID NO:22-66, such as from SEQ ID NO:23-25, SEQ ID NO:27-28, SEQ ID NO:32, SEQ ID NO:35-36, SEQ ID NO:40, SEQ ID NO:42, SEQ ID NO:44-45, SEQ ID NO:53-54 and SEQ ID NO:56.

In particular embodiments, the HER3 binding motif (BM) thus forms part of a three-helix bundle protein domain. For example, the BM may essentially constitute two alpha helices with an interconnecting loop, within said three-helix bundle protein domain. In these embodiments, the HER3 binding polypeptide of the invention may comprise an amino acid sequence selected from:
i) K-[BM]-DPSQS X$_a$X$_b$LLX$_c$ EAKKL NDX$_d$Q (SEQ ID NO:1011);
wherein
[BM] is a HER3 binding motif as defined above;
$X_a$ is selected from A and S;
$X_b$ is selected from N and E;
$X_c$ is selected from A, S and C;
$X_d$ is selected from A and S;
and
ii) an amino acid sequence which has at least 80% identity to any one of the sequences defined above. Said amino acid sequence may have at least 82%, such as at least 84%, such as at least 86%, such as at least 88%, such as at least 90%, such as at least 92%, such as at least 94%, such as at least 96%, such as at least 98% identity to any one of the sequences defined above.

In one embodiment of the HER3 binding polypeptide as described above, $X_a$ is A; $X_b$ is N; $X_c$ is A and $X_d$ is A.

In a further embodiment of the HER3 binding polypeptide as described above, $X_a$ is A; $X_b$ is N; $X_c$ is C and $X_d$ is A.

In a further embodiment of the HER3 binding polypeptide as described above, $X_a$ is S; $X_b$ is E; $X_c$ is S and $X_d$ is S.

In a further embodiment of the HER3 binding polypeptide as described above, $X_a$ is S; $X_b$ is E; $X_c$ is C and $X_d$ is S.

In yet a further embodiment, the amino acid sequence of the HER3 binding polypeptide as defined above is selected from SEQ ID NO:335-668, in particular from SEQ ID NO:335-400, such as from SEQ ID NO:356-400, such as from SEQ ID NO:357-359, SEQ ID NO:361-362, SEQ ID NO:366, SEQ ID NO:369-370, SEQ ID NO:374, SEQ ID NO:376, SEQ ID NO:378-379, SEQ ID NO:387-388 and SEQ ID NO:390.

In particular embodiments, said three-helix bundle protein domain is selected from domains of bacterial receptor proteins. Non-limiting examples of such domains are the five different three-helical domains of Protein A from *Staphylococcus aureus*, such as domain B, and derivatives thereof. In some embodiments, the three-helical bundle protein domain is a variant of protein Z, which is derived from said domain B of staphylococcal Protein A.

Thus, in a further embodiment, there is provided a HER3 binding polypeptide which comprises an amino acid sequence selected from:
i) YAK[BM]-DPSQS SELLX$_c$ EAKKL NDSQA P (SEQ ID NO:1012);
wherein [BM] is a HER3 binding motif as defined above and
X$_c$ is selected from S and C; and
ii) an amino acid sequence which has at least 80% identity to any one of the sequences defined in i) above.
Alternatively, there is provided a HER3 binding polypeptide which comprises an amino acid sequence selected from:
i) FNK-[BM]-DPSQS ANLLX$_c$ EAKKL NDAQA P (SEQ ID NO:1013);
wherein [BM] is a HER3 binding motif as defined above and
X$_c$ is selected from A and C; and
ii) an amino acid sequence which has at least 80% identity to any one of the sequences defined in i) above.

As discussed above, polypeptides comprising minor changes as compared to the above amino acid sequences are also within the scope of the present application. Thus, in some embodiments, the HER3 binding polypeptides as defined above may for example have a sequence which is at least 82%, at least 83%, at least 85%, at least 87%, at least 89%, at least 91%, at least 92% at least 94%, at least 96% or at least 98% identical to the sequence described herein.

In some embodiments and as disclosed in the Experimental section below, the HER3 binding motif may form part of a 58 amino acid polypeptide. Such a polypeptide may e.g. comprise a sequence selected from any one of SEQ ID NO:669-1002, in particular a sequence selected from SEQ ID NO:669-734, such as selected from SEQ ID NO:690-734, such as from SEQ ID NO:691-693, SEQ ID NO:695-696, SEQ ID NO:700, SEQ ID NO:703-704, SEQ ID NO:708, SEQ ID NO:710, SEQ ID NO:712-713, SEQ ID NO:721, SEQ ID NO:722 and SEQ ID NO:724.

A HER3 binding polypeptide according to any aspect described herein may bind to HER3 such that the K$_D$ value of the interaction is at most $1 \times 10^{-6}$ M, or such as at most $1 \times 10^{-7}$ M, such as at most $1 \times 10^{-8}$ M. The terms HER3 binding" and "binding affinity for HER3" as used in this specification refers to a property of a polypeptide which may be tested for example by the use of surface plasmon resonance technology, such as in a Biacore instrument (GE Healthcare). HER3 binding affinity may e.g. be tested in an experiment in which HER3 is immobilized on a sensor chip of a Biacore instrument, and the sample containing the polypeptide to be tested is passed over the chip. Alternatively, and as described in the Examples below, HER3 binding affinity may be tested in an on-cell experiment. An on-cell experiment may for example be performed by incubating varying concentrations of labeled HER3 with cells displaying the polypeptide to be tested. The cell populations may thereafter be analyzed in a flow cytometer, such as in a fluorescence activated cell-sorting system (FACS), and the mean fluorescence intensity data may be determined. Mean fluorescence may subsequently be plotted against the HER3 concentrations and fitted to a one-site binding model in order to determine the apparent equilibrium dissociation constant, K$_D$. The HER3 or fragment thereof used in the K$_D$ determination may for example comprise the amino acid sequence represented by SEQ ID NO:1007 (HER3-ECD).

As accounted for in the following Examples, selection of HER3 binding variants may for example be achieved by phage display for selection of naïve variants of a protein scaffold optionally followed by affinity maturation and cell display for selection of affinity maturated HER3 binding variants. It is however understood that any selection system, whether phage-based, cell-based or other, may be used for selection of HER3 binding polypeptides. In the following Examples, an expression system for cell surface display of recombinant proteins on the Gram-positive bacterium *Staphylococcus carnosus* was used (Jonsson et al, Biotechnol Applied Biochem 54:93-103 (2009)). As compared to the size of a phage particle, the larger size of a cell however generally enables use of fluorescence-activated cell sorting (FACS) for high-throughput screening and selection from cell-displayed protein libraries.

As compared to the IgG molecule, the HER3 binding polypeptides of the invention are relatively small, which, apart from rendering the HER3 binding polypeptides useful in a wide range of applications, may enable production using solid-phase peptide synthesis. A solid-phase synthesis route may e.g. facilitate site-specific conjugation of non-biological groups such as chelators used for radiolabeling in molecular imaging.

Thus, the skilled person will appreciate that various modifications and/or additions can be made to a HER3 binding polypeptide according to any aspect disclosed herein in order to tailor the polypeptide to a specific application without departing from the scope of the present invention. For example, a HER3 binding polypeptide according to any aspect may comprise further C terminal and/or N terminal amino acids. Such a polypeptide should be comprehended as a polypeptide having additional amino acids residues at the very first and/or the very last position in the polypeptide chain, i.e. at the N- and/or C-terminus. Thus, a HER3 binding polypeptide may comprise any suitable number of additional amino acid residues, for example at least one additional amino acid residue. Each additional amino acid residue may individually or collectively be added in order to, for example, improve production, purification, stabilization in vivo or in vitro, coupling, or detection of the polypeptide. Such additional amino acid residues may comprise one or more amino acid residues added for the purpose of chemical coupling. One example of this is the addition of a cysteine residue. Such additional amino acid residues may also provide a "tag" for purification or detection of the polypeptide such as a His$_6$ tag or a "myc" (c-myc) tag or a "FLAG" tag for interaction with antibodies specific to the tag or immobilized metal affinity chromatography (IMAC) in the case of the His$_6$-tag.

The further amino acids as discussed above may be coupled to the HER3 binding polypeptide by means of chemical conjugation (using known organic chemistry methods) or by any other means, such as expression of the HER3 binding polypeptide as a fusion protein.

The further amino acids as discussed above may for example comprise one or more polypeptide domain(s). A further polypeptide domain may provide the HER3 binding polypeptide with another function, such as for example another binding function, or an enzymatic function, or a toxic function (e.g. an immunotoxin), or a fluorescent signaling function, or combinations thereof.

In some embodiments, the further polypeptide domain(s) may comprise a half life extending moiety which increases half life of the HER3 binding polypeptide in vivo. As understood by the skilled person, increased, or extended, half life means slowed clearance of a particular molecule from blood. A half life extending moiety may for example comprise a peptide or protein that will allow in vivo association to serum albumins. In particular, the half life extending moiety may be an albumin binding moiety. An albumin binding moiety may e.g. consist of a naturally occurring polypeptide, or an albumin binding fragment thereof, or an engineered polypeptide. An engineered polypeptide may be derived from a naturally occurring starting polypeptide through subjecting it to protein engineering techniques, such as mutations and alterations in a site-directed or randomized approach, with a view to create novel or enhanced properties, such as binding affinity for a molecule such as albumin.

Such an engineered albumin binding polypeptide may for example be a variant of a protein scaffold, which variant has been selected for its specific binding affinity for albumin. In a specific embodiment, the protein scaffold may be selected from domains of streptococcal Protein G or derivatives thereof, such as for example domain GA1, domain GA2 and domain GA3 of Protein G from *Streptococcus* strain G148, in particular domain GA3. Accordingly, in one embodiment of the HER3 binding polypeptide, the further amino acids comprise an albumin binding domain (ABD) of streptococcal Protein G, or a derivative thereof. One example of an albumin binding domain which may be comprised as a further polypeptide domain in the HER3 binding polypeptide of the invention is set out in SEQ ID NO:1005. Other examples of suitable albumin binding domains are disclosed in WO2009/016043. Such an ABD-extended polypeptide binds to serum albumin in vivo, and benefits from its longer half life, which increases the net half life of the polypeptide itself (see e.g. WO91/01743).

When a HER3 binding polypeptide according to the invention comprises an albumin binding moiety as defined above, the overall size of the HER3 binding polypeptide is relatively small. When administered for example to a mammalian subject, such as a human subject, the albumin binding part of the HER3 binding polypeptide will associate non-covalently with serum albumin and the polypeptide may thereby benefit from decreased renal clearance and increased recirculation in epithelial cells. Tissue penetration may however still be fast due to extravasating properties of serum albumin. Furthermore, a HER3 binding polypeptide comprising a half life extending moiety may not only display an extended half life in vivo, but also a reduced immunologic response in vivo, as compared to a polypeptide lacking a corresponding half life extending moiety (see e.g. WO2005/097202).

A further polypeptide domain may moreover provide the HER3 binding polypeptide with the same binding function. Thus, in a further embodiment, there is provided a HER3 binding polypeptide comprising at least two HER3 binding polypeptide monomer units, the amino acid sequences of which may be the same or different. Multimeric forms of the polypeptides may comprise a suitable number of domains, each having a HER3 binding motif, and each forming a "monomer" within the multimer. These domains may all have the same amino acid sequence, but alternatively, they may have different amino acid sequences. In particular, the HER3 binding polypeptide of the invention may form homo- or heterodimers.

The further polypeptide domain(s) as described above may be joined to the HER3 binding polypeptide by covalent coupling using known organic chemistry methods. Alternatively, the HER3 binding polypeptide comprising the further polypeptide domain(s) may be expressed as one or more fusion polypeptides, for example in a system for recombinant expression of polypeptides, or joined in any other fashion, either directly or via a linker, for example an amino acid linker.

In one embodiment of the HER3 binding polypeptide, the polypeptide binds to the same epitope as the naturally occurring HER3 ligands, or sufficiently close to it to block binding of the naturally occurring HER3 ligands, e.g. Neuregulins-1 and 2, to HER3. The HER3 binding polypeptide may thus be used as a HER3 blocking agent and/or to inhibit HER3 mediated cell signaling in vivo.

In a further aspect, there is provided a polynucleotide encoding a HER3 binding polypeptide as described above. An expression vector comprising such a polynucleotide may enable production of a HER3 binding polypeptide, for example by expression in a host cell.

A HER3 binding polypeptide may be used as an alternative to conventional antibodies or low molecular weight substances in various medical, veterinary and diagnostic applications. The skilled addressee will understand that the polypeptide of the invention may be useful in any method requiring affinity for HER3 of a reagent. Thus, the HER3 binding polypeptide may be used as a detection reagent, a capture reagent or a separation reagent in such methods. In addition, the HER3 binding polypeptide may be employed in diagnostics in order to reveal, diagnose and examine the presence of a disease characterized by HER3 expression on the cell surface in e.g. a mammalian subject. Thus, HER3 expression may diagnostically be monitored in vivo by use of a polypeptide of the invention. Diagnostic monitoring may for example be accomplished by delivery of diagnostic nuclides for assessment of HER3 expression by molecular imaging. A HER3 binding polypeptide according to the invention may also be useful as a therapeutic or diagnostic agent in its own right or as a means for targeting other therapeutic or diagnostic agents, with direct (e.g. toxic molecules, including radionuclides such as yttrium-90, lutetium-177 and thorium-227, toxins, such as maytansinoid) or indirect (e.g. cancer vaccines, immunostimulatory molecules) effects on the HER3 protein. The therapeutic effect may potentially be mediated by blocking the receptor interaction, or alternatively by using the HER3 binding polypeptide as a target for delivering a potent payload to a tumor cell.

In a further aspect, there is provided a ligand having binding affinity for HER3 and for HER2, comprising a HER3 binding polypeptide as defined above; a HER2-binding polypeptide; and a linking moiety for linking the HER3 binding polypeptide with the HER2 binding polypeptide. Such a ligand should be comprehended as an example of a bispecific heterodimer comprising two different binding functions: one binding function for HER3, provided by a polypeptide as disclosed above, and one binding function for HER2, provided by a HER2 binding polypeptide. It is to be understood that any HER3 binding polypeptide according to the invention may be comprised in the ligand. The two binding functions are comprised in the ligand as two separate monomer units.

Such a bispecific ligand according to the invention may be useful in detecting, characterizing and/or diagnosing cancer that involves both HER3 and HER2. Detection, characterization and/or diagnosis may for example be accomplished by molecular imaging using gamma or positron emitting nuclides or by using near infrared fluorescent probes. As described above, HER3 is a preferred heterodimerization partner for HER2, and critical for driving the proliferation of tumors characterized by over-expression of HER2. HER2 lacks a known ligand and is currently believed to be dependent on other receptors in the HER family for ligand induced signaling. A bispecific ligand according to the invention may however be used not only for diagnostic but also for targeted therapeutic payload applications. Compounds used in payload applications include, among others, radionuclides, prodrug enzymes, cytokines, chemical toxic molecules, toxins and photosensitizers. For targeted payload applications, high discrimination between normal and diseased tissue is extremely important.

By fine tuning the affinity of both binding polypeptides comprised in the bispecific ligand binding two different receptors, the ligand may preferentially locate to and accumulate only in lesions expressing both receptors simultaneously. Accordingly, HER2 and HER3 binding functions may provide the ligand with two equally strong binding functions for their individual targets. Thus, the binding affinity of the HER3 binding polypeptide for HER3 may be approximately of the same order as the binding affinity of the HER2 binding polypeptide for HER2. In one embodiment, the HER2 binding polypeptide may bind to HER2 such that the $K_D$ value of the interaction is at most $1 \times 10^{-6}$ M, such as at most $1 \times 10^{-7}$ M, such as at most $1 \times 10^{-8}$ M. In another embodiment, binding of the HER2 binding polypeptide to HER2 may be as strong or stronger than the corresponding binding of the HER3 binding polypeptide to HER3. Thus, the $K_D$ value of the interaction between the HER2 binding polypeptide and HER2 is no more than the $K_D$ value of the interaction between the HER3 binding polypeptide and HER3. The $K_D$ value of the interaction between the HER3 binding polypeptide and HER3 may for example be 5 times, 10 times or 100 times the $K_D$ value of the interaction between the HER2 binding polypeptide and HER2.

In one embodiment, the HER2 binding polypeptide of the bispecific ligand is an engineered polypeptide. The HER2 binding polypeptide may be an engineered polypeptide which is a variant of a protein scaffold, which variant has been selected for its specific binding affinity for HER2. Non-limiting examples of a protein scaffold are selected from the group consisting of staphylococcal protein A, and domains and derivatives thereof. In some embodiments, the HER2 binding polypeptide is an engineered protein derived from domain B of Protein A from *Staphylococcus aureus*. The engineered protein may in particular comprise a protein Z derivative, which is a variant of protein Z which is derived from said domain B of Protein A.

In some embodiments of the ligand, the engineered HER2 binding protein comprises an amino acid sequence selected from
i) YAKEM RNAYW EIALL PNLTN QQKRA FIRKL YDDPS QSSEL LSEAK KLNDS Q, corresponding to SEQ ID NO:1003; and
ii) an amino acid sequence which has at least 80% identity to the sequence defined in i).

Linking of the HER3 binding polypeptide and the HER2 binding polypeptide may for example be provided by a peptide linker comprising from 1 up to 45 amino acids. A linking moiety may in particular be arranged for coupling the N- and/or C-terminals of the HER3 binding polypeptide and the HER2 binding polypeptide. The linking thus provided may be selected from C- to C-terminal linking, C- to N-terminal linking or N- to C-terminal linking. Coupling of the linking moiety to the HER3 binding polypeptide and the HER2 binding polypeptide may e.g. be accomplished by means of chemical conjugation (using known organic chemistry methods) or by any other means, such as expression of the ligand as a fusion protein.

The ligand may, as described above, further comprise a half life extending moiety for extension of ligand half life in vivo. Half life extension may be accomplished by a number of different half life extending moieties, and non-limiting examples of such moieties are selected from albumin, albumin binding moieties as defined above in connection with the HER3 binding polypeptide, the Fc-part from IgG, and polymeric compounds such as polyethylene glycol (PEG). Coupling of the ligand to serum albumin, which is the most abundant protein in mammalian sera, may provide extension of ligand half life in vivo.

In particular, the albumin binding moiety may be an engineered protein derived from domain GA3 of streptococcal Protein G, such as an albumin binding moiety comprising an amino acid sequence selected from
i) LAEAK VLANR ELDKY GVSDF YKRLI NKAKT VEGVE ALKLH ILAAL P; as set out in SEQ ID NO:1005; and
ii) an amino acid sequence which has at least 80% identity to the sequence defined in i).

The half life extending moiety may for example be connected to the remainder of the ligand by covalent coupling using known organic chemistry methods, or joined in any other fashion, directly or mediated by a linker comprising a number of amino acids. When the half life extending moiety is represented by albumin or an albumin binding moiety, the ligand may in itself be expressed as one or more fusion polypeptides in a system for recombinant expression of polypeptides. In one embodiment, the half life extending moiety is attached to the remainder of the ligand via a cysteine residue present in the ligand. In particular, the half life extending moiety may be attached to a cysteine residue of the HER3 or the HER2 binding polypeptide, introduced at a site distant from the binding motif. In another embodiment, the half life extending moiety is attached to the remainder of the ligand via the linking moiety.

In a specific embodiment, the linking moiety comprises a half life extending moiety as defined above. Thus, albumin, albumin binding moieties or PEG may for example be employed for connecting the HER3 binding polypeptide with the HER2 binding polypeptide.

In some embodiments, a ligand according to the invention may comprise further C terminal or N terminal amino acids. Such further amino acids may, as described above as regards the HER3 binding polypeptide, individually or collectively be added in order to for example, improve production, purification, stabilization in vivo or in vitro, coupling, or detection of the polypeptide. In certain embodiments, the further amino acids may constitute one or more polypeptide domain(s). The function of such a further polypeptide domain may be the same as, or different from, the functions already comprised in the ligand. A further polypeptide domain may for example provide the ligand with another HER3 binding function and/or another HER2 binding function. Thus, a bispecific ligand according to the invention may comprise multimers of HER3 binding functions and/or multimers of HER2 binding functions. One example of bispecific ligand comprising multimeric binding functions is a ligand comprising two HER3 binding polypeptides and two HER2 binding polypeptides.

A ligand as defined above may, in one embodiment, prevent dimerization of HER2 and HER3 in vivo. More specifically, the ligand may, e.g. by binding to HER2 and/or HER3 expressed on a cell surface in a mammalian subject, inhibit HER3 mediated signaling in the subject. Due to the bispecific nature of the ligand, it may bind to and block the two receptors in a position such that they are no longer able to exert signaling. As the skilled addressee will understand, a ligand according to the invention may accordingly be utilized for the treatment of conditions associated with expression, and in particular over-expression, of HER2 and/or HER3 on the cell surface.

HER3 can however also form heterodimers with EGFR, thus forming an active signaling unit activating the PI3K/Akt pathway (Engelman et al, Proc Natl Acad Sci 102(10): 3788-93 (2005)). Indeed, HER3 is over-expressed in non-small cell lung cancer (NSCLC), apparently because of up-regulation of ErbB ligands (Fujimoto et al, Cancer Res 65(24):11478-85 (2005)), whereas HER3 is not expressed in normal lung epithelium. Thus, in a related aspect, there is provided a ligand having binding affinity for HER3 and for EGFR, comprising a HER3 binding polypeptide as defined above; an EGFR binding polypeptide; and a linking moiety for linking the HER3 binding polypeptide with the EGFR binding polypeptide. It should be understood that features described in the above aspects of the invention are also applicable to this aspect of the invention. In particular, such a bispecific ligand may target HER3 and EGFR and exert similar, or the same, modes of action as described above for the bispecific ligand binding to HER3 and HER2. Examples of a bispecific ligand binding to HER3 and EGFR may comprise an EGFR binding polypeptide selected from
i) YAKEM WIAWE EIRNL PNLNG WQMTA FIAKL LDDPS QSSEL LSEAK KLNDS Q, corresponding to SEQ ID NO:1004; and
ii) an amino acid sequence which has at least 80% identity to the sequence defined in i).

Other examples of EGFR binding polypeptides that may be used in a HER3 and EGFR binding ligand are disclosed in WO2007/065635.

In other embodiments, the HER3 binding polypeptide or bispecific ligand according to the invention may be used in targeting therapeutic or diagnostic agents to cells expressing HER3, both in vivo and in vitro, particularly to cells which over-express HER3. As discussed above, a ligand according to the invention may be utilized in targeting cells that express, or over-express, HER3 and/or HER2, or HER3 and/or EGFR. In a related aspect, there is thus provided a combination of a HER3 binding polypeptide as defined herein, or a ligand as defined above, and a therapeutic agent. Non-limiting examples of therapeutic agents are selected from cytotoxic payloads, such as radionuclides, small molecular drugs or toxins. Such therapeutic agents may be chemically conjugated or otherwise bound to the HER3 binding polypeptide or ligand.

A combination, a HER3 binding polypeptide or a ligand according to the invention, may furthermore be used as a medicament in therapy, for example for the treatment of a HER3 related condition, such as a HER3 related condition in a mammal, such as a human subject, selected from cancer disease, such as colon cancer, endometrial cancer, gastric cancer, glioma, breast cancer, pancreas cancer, head and neck squamous carcinoma, lung cancer, melanoma, medulloblastoma, neuroepithelioma, ovarian cancer, Paget's disease, papillary thyroid cancer, prostate cancer, skin squamous cell carcinoma, transitional cell carcinoma and vestibular schwannoma. Thus, use of a HER3 binding polypeptide or a ligand according to the invention for the manufacture of a medicament for treatment of a HER3 related condition, such as the HER3 related conditions mentioned above, is also within the scope of the present invention.

In a related aspect, there is provided a method of treatment of a HER3 related condition, comprising administering of a HER3 binding polypeptide, or ligand or combination as described above to a mammalian subject in need thereof. Consequently, in the method of treatment, the subject is treated with a HER3 binding polypeptide, a ligand or a combination according to the invention. In a more specific embodiment of said method, the binding of the HER3 binding polypeptide, the ligand or the combination to a HER3 expressed on a cell surface in the subject inhibits receptor activation. Said binding may for example inhibit HER3 mediated signaling. In one embodiment of the method of treatment, said HER3 related condition is selected from cancer disease, such as colon cancer, endometrial cancer, gastric cancer, glioma, breast cancer, pancreas cancer, head and neck squamous carcinoma, lung cancer, melanoma, medulloblastoma, neuroepithelioma, ovarian cancer, Paget's disease, papillary thyroid cancer, prostate cancer, skin squamous cell carcinoma, transitional cell carcinoma and vestibular schwannoma.

In another embodiment, there is provided a method of treatment of a HER3 and/or HER2 related condition, comprising administering of a ligand according to the invention to a mammalian subject in need thereof.

As understood by the skilled person and as discussed above, a HER3 binding polypeptide or a ligand according to the invention may be used in diagnosis, such as in the diagnosis of a HER3 or a HER3 and/or HER2 related condition. A HER3 binding polypeptide according to the invention may be employed separately or in combination with a diagnostic agent. Such a combination may be used in the diagnosis of a HER3 related condition, for example in molecular imaging of cells over-expressing HER3.

The invention will now be further illustrated by the following non-limiting Examples.

BRIEF DESCRIPTION OF THE FIGURES

FIG. 1A-PP is a listing of the amino acid sequences of examples of HER3 binding motifs comprised in HER3 binding polypeptides of the invention (SEQ ID NO:1-334; FIG. 1A-N), examples of 49-mer HER3 binding polypeptides according to the invention (SEQ ID NO:335-668; FIG. 1N-AA) and examples of 58-mer HER3 binding polypeptides according to the invention (SEQ ID NO:669-1002; FIG. 1AA-OO), an example of a HER2 binding polypeptide (SEQ ID NO:1003; FIG. 1OO) comprised in a ligand according to the invention, an example of an albumin binding moiety (SEQ ID NO:1005; FIG. 1OO) as may be comprised in one embodiment of a ligand according of the invention, an example of an EGFR binding polypeptide (SEQ ID NO:1004; FIG. 1OO) which may be comprised in one embodiment of a ligand according to the invention, as well as the sequences of protein Z (SEQ ID NO:1006; FIG. 1OO), and the sequences of the extracellular domain of HER3 (SEQ ID NO:1007; FIG. 1PP), the extracellular domain of HER2 (SEQ ID NO:1008; FIG. 1PP) and the extracellular domain of HER4 (SEQ ID NO:1009; FIG. 1PP).

Figure 2:
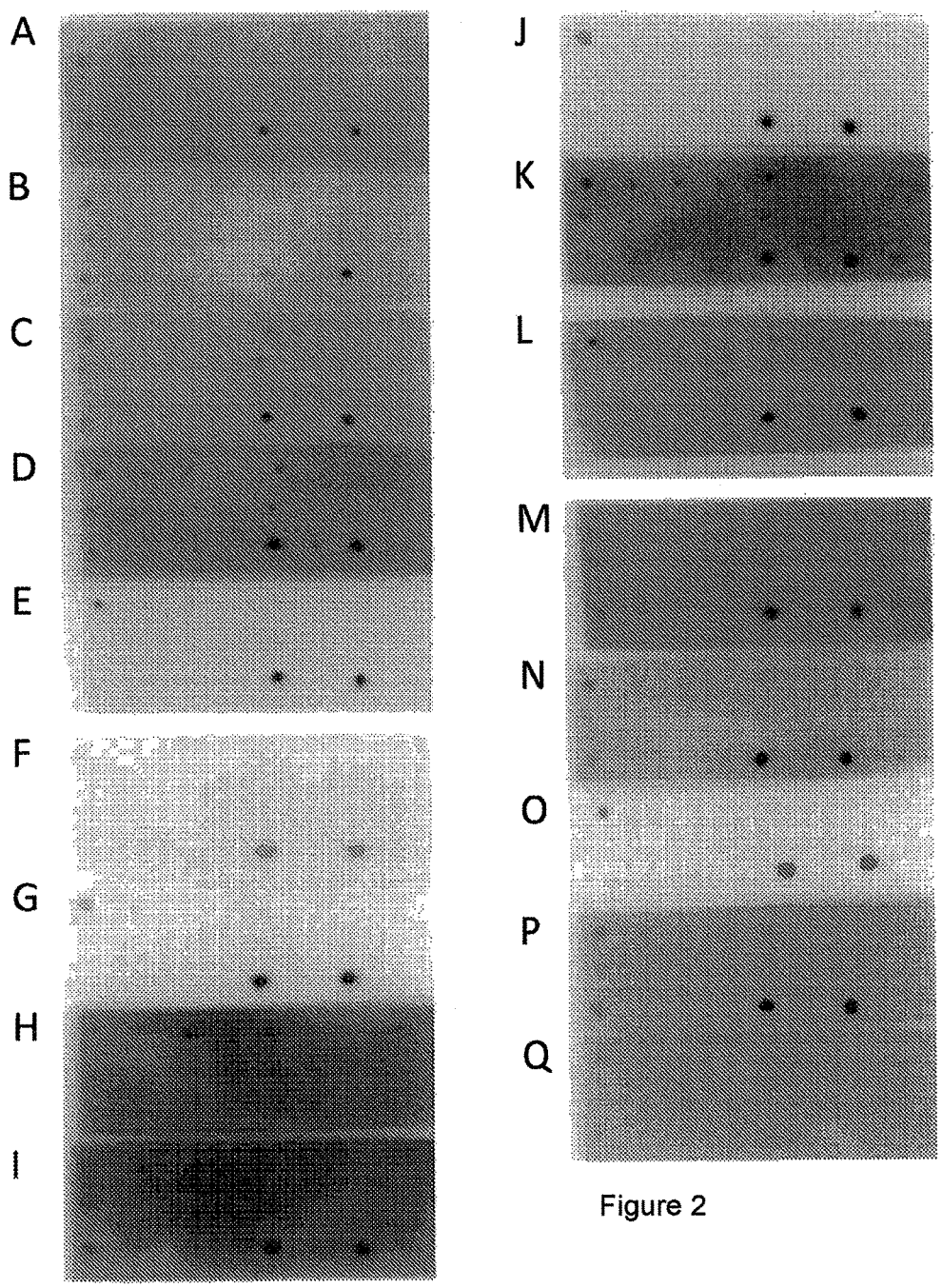
FIG. 2A-Q show the result of a dot blot assay performed using periplasmic fractions from individual HER3 binding Z variants expressed as fusions to the HSA binding domain ABD. The potential background binding to 21 control proteins as well as binding to HER3-ECD and HER3-Fc were analyzed. Proteins were dotted on the membrane in three rows from left to right in the following order.

Row 1: HSA, IgG, IgM, IgA, alpha-2 macroglobulin, fibrinogen, holo-transferrin, alpha-1-antitrypsin, Row 2: C3, haptoglobulin, alpha-1 acid glycoprotein, alpha-1 antichymotrypsin, C4, mouse IgE kappa, hemopexin, transthyretin, Row 3: streptavidin, neutravidin, HER2-ECD, HER3-Fc, HER4-Fc, HER3-ECD and HER4-ECD.

The images show response of A) Z01748, B) Z01813, C) Z01814, D) Z01815, E) Z02009, F) Z01821, G) Z02010, H) Z01824, I) Z01825, J) Z01817, K) Z01818, L) Z01820, M) Z01826, N) Z01828, 0) Z02011, P) Z01830, and Q) the product from pAY01247, which expresses only ABD, as a negative control.

FIG. 3A-F show images from the immunofluorescence experiment described in Example 2. HER3 positive AU566 cells (A-D) and HER2 positive and HER3 negative SKOV-3 cells (E-F) were stained with HER3 specific Z variants or controls according to the following: A) $His_6$-(Z01814)$_2$-cys (SEQ ID NO: 1019), B) $His_6$-(Z01820)$_2$-cys (SEQ ID NO: 1020), C) anti-HER3 antibody (positive control), D) (Z01154)$_2$ (negative control Z variant), E) $His_6$-(Z01814)$_2$-cys, (SEQ ID NO: 1019), F) $His_6$-(Z01820)$_2$-cys (SEQ ID NO: 1020).

FIG. 4 is a schematic representation of the staphylococcal display vector (A) used for cell display of HER3 binding polypeptides of the invention on the surface of S. carnosus (B). The vector pSCZ1 (A) contains: i) a promoter and secretion signal (S) from a lipase gene (expressed on the surface of the related Staphylococcus hyicus), ii) a gene fragment encoding a propeptide (PP) from the same lipase gene, which has been demonstrated to be important for efficient translocation of recombinant proteins, iii) a cell-wall anchoring region (XM), originating from staphylococcal Protein A, iv) an albumin binding protein (ABP, Samuelson et al, J Bacteriology 177(6):1470-1476, (1995)) from streptococcal Protein G introduced to provide surface expression level normalization of the target binding signal, v) a staphylococcal origin of replication and chloramphenicol acetyl transferase gene (Cml$^r$) for stable replication and expression in staphylococci, and vi) an origin of replication for E. coli (OriE) as well as a β-lactamase gene (Bla), facilitating subcloning work in E. coli.

FIG. 5 shows density plots as a result from flow-cytometric sortings of Sc:$Z_{HER3LIB}$. The plots show FL-4 channel fluorescence intensity corresponding to surface expression level (monitored via HSA binding) on the x-axis and FL-1 channel fluorescence corresponding to HER3 binding on the y-axis. The density plots show the staphylococcal library before flow-cytometric sorting round 1, 2, 3 and 4, respectively, with the regions used in gating outlined as a box in each plot.

FIG. 6A-D show histogram representations of a cell-based flow cytometry assay where FACS isolated cells displaying Z variants in fusion to an albumin binding protein (ABP) were incubated with fluorescently labeled HER3-Fc and fluorescently labeled HSA. The ratio of HER3 binding signal (MFI, FL-1) and HSA binding signal (MFI, FL-4) is on the y-axis. All FL-1/FL-4 ratios are normalized; A) with the FL-1/FL-4 ratio of Z05405 and B-D) with the FL-1/FL-4 ratio of a first generation binder (Z01753). 45 individual clones were analyzed in 4 separate assays (A-D) where Z05405 and Z05409 were included in all assays for comparison. A) shows cell-based flow cytometry assay results of Z05403-Z05415, B) shows cell-based flow cytometry assay results of Z05416-Z05426, C) shows cell-based flow cytometry assay results of Z05427-Z05434 and D) shows cell-based flow cytometry assay results of Z05435-Z05447.

FIG. 7A-D show sensorgrams from surface plasmon resonance (SPR) kinetic analyses of four different Z variants in four different concentrations. The uppermost curve in each sensorgram corresponds to the highest concentration of injected Z variant, the second curve from the top corresponds to the second highest concentration, the third curve from the top corresponds to the third highest concentration etc. The Z variants Z05405 (A) in concentrations of 46, 15, 1.5 and 1.5 nM, Z05413 (B), in concentrations of 57, 19, 6.3 and 1.9 nM, Z05416 (C), in concentrations of 67, 22, 7.5 and 2.2 nM and Z05417 (D), in concentrations of 59, 20, 6.5 and 2 nM, were injected over a surface immobilized with human HER3-Fc and dissociation constants based on $k_0$ and $k_{off}$ were determined.

FIG. 8A-B show sensorgrams from SPR competition analyses of Z05417 with heregulin. A) shows a sensorgram resulting from injections of HER3-Fc, alone and preincubated with 40-fold molar excess of Z05417, over a surface immobilized with human heregulin. B) shows a sensorgram resulting from co-injection of Z05417 with heregulin over a surface immobilized with human HER3-Fc. Z05417 was injected in duplicates in five different concentrations, 10 nM, 5 nM, 1 nM, 0.5 nM and 0 nM. The uppermost curve corresponds to the highest concentration of injected Z05417, the second curve from the top corresponds to the second highest concentration, the third curve from the top corresponds to the third highest concentration etc.

FIG. 9 shows a diagram over the percentage of HER3 phosphorylation in the absence and presence of HER3 binding Z variants. MCF-7 cells were stimulated with 5 nM heregulin in the absence of Z variants (100% phosphorylation, filled bars) and in the presence of the HER3 binding Z variants Z05416 and Z05417 and the negative control Z01155 (tag polymerase binding Z variant, striped bars) or with medium alone (open bars). The diagram shows the percentage of HER3 phosphorylation in the presence of Z variants or medium compared to heregulin-induced HER3 phosphorylation (100%).

EXAMPLES

Example 1: Selection and Screening of HER3 Binding Polypeptides

Material and Methods
Labeling of HER3 and HSA:

Biotinylation of recombinant human HER3/Fc chimera (R&D Systems, #348-RB-050), here denoted HER3-Fc, was performed using the Biotin-XX Microscale Protein Labeling Kit (Invitrogen, #630010) according to the supplier's recommendations. The extracellular domain of HER3 (SEQ ID NO:1007), here denoted HER3-ECD, was biotinylated using EZ-LINK™-Sulfo-NHS-LC-LC-Biotin (sulfosuccinimidyl-6-[biotin-amido]hexanoate) (Pierce, #21338) according to the supplier's recommendations. Human serum albumin (HSA; Sigma, #A-3782) was fluorescently labeled using ALEXA FLUOR® 647 succinimidyl ester (Invitrogen, #A20006; isomer-free, amine-reactive dye with excitation/emission maxima of ~650/668 nm) according to the supplier's recommendations. The protein buffer was changed to PBS (10 mM phosphate, 137 mM NaCl, 2.68 mM KCl, pH 7.4) or PBS supplemented with 0.1% PLURONIC® F108 NF Surfactant (PBSP; BASF Corporation, #30085231HO $(C_2H_4O)_a(C_3H_6O)_b(C_2H_4O)_aH$ with a=141 and b=44) in order to remove any excess biotin or fluorophore.

Phage Display Selection of HER3 Binding Polypeptides:

A library of random variants of Z molecules displayed on bacteriophage, denoted Zlib2002, constructed in phagemid pAffi1/pAY00065 as described in Grönwall et al, J Biotechnol 128:162-183 (2007), was used to select HER3-ECD-binding polypeptides. Preparation of phage stocks from the phagemid library, as well as between rounds of selection, was performed according to previously described procedures (Nord et al, Nat Biotech 15:772-777 (1997); Hansson et al, Immunotechnology 4:237-252 (1999)) using the helper phage M13K07 (New England Biolabs, #N0315S). The *Escherichia coli* amber suppressor strain RR1ΔM15 (Rüther, Nucleic Acids Res 10:5765-5772, 1982) was used for all cloning procedures and as host for phage production.

The phage selection was performed in solution using biotinylated HER3 protein and streptavidin-coated paramagnetic beads (DYNABEADS® M-280 Streptavidin, Dynal #112.06) for capture of bound phages. In addition, phage selection was performed on solid phase using HER3-ECD immobilized on MaxiSorp immunotubes (Nunc). Unspecific binding of phage particles was minimized by pre-treatment of all tubes and beads with PBST 0.1-gelatin (PBS supplemented with 0.1% TWEEN-20 (Polyethylene glycol sorbitan monolaurate) and 0.1% gelatin). Selection was performed in four cycles. All selections were performed in PBST 0.1-gelatin and in a volume of 1 ml.

For the selection performed in solution, four cycles of selection were performed at room temperature (RT) using different concentrations of biotinylated recombinant HER3-ECD as target protein. Phage stocks used in cycle 1 and 2 were pre-incubated with 0.1 mg streptavidin coated beads for 1 h to remove streptavidin binding phages. In cycle 1, phage particles from the Zlib2002 library were incubated with 100 nM of biotinylated HER3-ECD in PBST 0.1-gelatin for 2 hours. The subsequent selection cycles were divided into two selection tracks for which the target concentration was lowered to 50 (track 1) or 20 nM (track 2) for cycle 2, 20 (track 1) or 10 nM (track 2) for cycle 3 and 20 (track 1) or 5 nM (track 2) for cycle 4. The bound phages were captured with streptavidin-coated M-280 DYNABEADS® (paramagnetic beads), allowing an immobilization of 4 µg of HER3-ECD per milligram of beads.

For selection on solid phase, immunotubes were immobilized with 1 ml HER3-ECD, 10 µg/ml in 50 mM sodium carbonate buffer, pH 9.6 for 1.5 h at RT and thereafter blocked with 3 ml PBST 0.1-gelatin for 1 h at RT. Phage stock was added to the tube and incubated for 2 h.

For both selection strategies, the number of washes with PBST 0.1-gelatin was increased between rounds in order to increase selection stringency. Therefore, washes were performed twice in cycle 1, three times in cycle 2, six times in cycle 3 and 12 times in cycle 4. The bound phage particles were eluted with 0.1 M glycine-HCl (pH 2.2) followed by immediate neutralization with 1 M Tris-HCl (pH 8). The phage-containing eluate was used to infect log phase RR1ΔM15 cells and phagemid particles were rescued from infected cells using helper phage M13K07. The selection process was monitored by titration of phage stocks before each selection round and after elution from target protein. Serial dilutions of phage solutions were used for infection of log phase RR1ΔM15 cells.

ELISA Screening of Z Variants:

To test if the Z variant molecules could indeed interact with HER3, two different ELISA were performed, one using biotinylated HER3-ECD and the second using HER3-Fc as target protein. The Z variants were produced by inoculating single colonies, prepared as described above, in 1 ml TSB-YE medium (30 g/l TSB, 5 g/l yeast extract) supplemented with 100 µg/ml ampicillin and 0.1 mM isopropyl-β-D-1-thiogalactopyranoside (IPTG) in deep-well plates (Nunc #278752). As a negative control, an insulin-binding Z variant (Z00801) was inoculated and grown in each plate. The plates were incubated for 18-24 h at 37° C. After incubation, replica plates were made by transferring a small fraction of each culture to 96-well plates with 15% glycerol for storage at −20° C. Remaining cells were pelleted by centrifugation, re-suspended in 300 µl PBST 0.05 (PBS supplemented with 0.05% Tween 20) and frozen at −80° C. to release the periplasmic fraction of the cells. Frozen samples were thawed in a water bath and cells were pelleted by centrifugation. The periplasmic supernatant contained the Z variants as fusions to the albumin binding domain from GA3 of Protein G from *Streptococcus* strain G148, expressed as AQHDEALE-[Z#####]-VDYV-[ABD]-YVPG (SEQ ID NO: 1021) (Gronwall et al, supra). Z###### refers to individual Z variants.

Half area 96 well ELISA plates (Costar #3690) were coated with 50 µl/well of coating buffer (50 mM sodium carbonate, pH 9.6) containing 6 µg/ml human serum albumin (HSA, Sigma #A3782), and incubated over night (ON). The HSA solution was poured off and the wells were blocked with 100 µl of PBST 0.1 supplemented with 2% non-fat dry milk solution (Semper AB) for 1 h at RT. The blocking solution was discarded and 50 µl of periplasmic solution was added to each well and incubated for 1.5 h at RT under slow shaking. The supernatants were poured off and the wells were washed 4 times with PBST 0.05. 50 µl of HER3-Fc at a concentration of 0.5 µg/ml in PBST 0.05 or biotinylated HER3-ECD at a concentration of 1 µg/ml in PBS were added to each well. The plates were incubated for 1.5 h at RT followed by wash 4× in PBST 0.05. In HER3-Fc plates, an antibody against human Fc (DAKO Cytomation, #P0214), labeled with horseradish peroxidase (HRP) and diluted 1:4000 in PBST 0.05, was added to the wells and incubated for 1 h at RT. In the plates with biotinylated HER3-ECD, streptavidin conjugated with HRP (DAKO, #P0397) was added to each well diluted 1:5000 in PBST 0.05. After washing as described above, 50 µl IMMUNOPURE TMB substrate (Pierce #34021) was added to the wells and the plates were treated according to the manufacturer's recommendations. All steps from blocking to reading were performed in a Tecan Genesis Freedom 200 robot (Tecan Group LTD). Absorbance of the wells was read at 450 nm in an ELISA reader Tecan Ultra 384 (Tecan) and evaluated with Magellan v. 5.0 software (Tecan).

Sequencing:

Based on the ELISA screening, a part of all clones regarded as positive were picked for sequencing. PCR fragments were amplified from single colonies using a standard PCR program and the primers AFFI-21 (5'-tgcttc-cggctcgtatgttgtgtg, SEQ ID NO:1014) and AFFI-22 (5'-cggaaccagagccaccaccgg, SEQ ID NO:1015). Sequencing of amplified fragments was performed using the biotinylated oligonucleotide AFFI-72 (5'-biotin-cggaaccagagccaccaccgg, SEQ ID NO:1016) and a BIGDYE® Terminator v3.1 Cycle Sequencing Kit (Applied Biosystems), used in accordance with the manufacturer's protocol. The sequencing reactions were purified by binding to magnetic streptavidin coated beads using a Magnatrix 8000 (Magnetic Biosolution), and analyzed on ABI PRISM® 3100 Genetic Analyzer (PE Applied Biosystems). The sequencing results were imported and analyzed with an ALD LIMS NAUTILUS™ 2003 R2 B3 software (Thermo Electronics Corp.).

Dot Blot Analysis:

The produced HER3 binding Z variants were tested for specificity by dot blot analysis against alpha-2 macroglobulin (MP biomedicals/Cappel, #55833), alpha-1 acid glycoprotein (RDI, #RDI-SCP-153-1), alpha-1 antichymotrypsin (RDI, #RDI-SCP-159-0), alpha-1-antitrypsin (RDI, #RDI-SCP-165-5), C3 complement (RDI, #RDI-SCP-150-0), C4 complement (RDI, #RDI-SCP-151-0), fibrinogen (Enzyme research, #031015E), haptoglobulin (RDI, #RDI-SCP-119-1), hemopexin (Agilent), holo-transferrin (Sigma, #T0665), human IgA (Bethyl, #P80-102), mouse IgE kappa (BD, #55079), human IgG (Sigma, #G4386), human IgM (Sigma, #18260), human serum albumin (HSA, Sigma, #A3782), neutravidin (Pierce, #31000), streptavidin (Pierce, #21122), transthyretin (Sigma, #P1742), HER2-ECD (SEQ ID NO:1008), HER3-ECD (SEQ ID NO:1007), HER3-Fc (R&D Systems), HER4-ECD (SEQ ID NO:1009), HER4-Fc (R&D Systems).

The Z variants were produced in essentially the same manner as described under ELISA screening in order to obtain periplasmic supernatants containing soluble protein. The supernatants were filtered using 0.45 µm membranes.

Nitrocellulose membranes (Invitrogen) were dotted with 1 µl of each protein at a concentration of 0.25 mg/ml, except for HER3-ECD and HER4-ECD that had a concentration of 0.29 mg/ml and 0.14 mg/ml, respectively. The membranes were blocked ON in PBST 0.1 supplemented with 0.5% casein (blocking solution) at 4° C. After removal of the solution, the membranes were incubated for 1 h with periplasmic supernatants supplemented with 0.5% casein. The membranes were washed 3 times very briefly and 4×5 minutes in PBST 0.1. The Z variants were detected with a ABD fused hyperimmune polyclonal rabbit Ig against an epitope common for all Z variants (produced in house) diluted 1:5000 in PBST blocking solution by incubation for 1 h at RT. After washing as above an antibody against rabbit IgG conjugated with HRP (DAKO Cytomation, #P0448), diluted 1:5000 in blocking solution, was added to the membranes, followed by incubation of the membranes for 1 h at RT. The membranes were washed, rinsed in PBS and soaked with SUPERSIGNAL (Pierce #34075; luminol-based chemiluminescent Horseradish Peroxidase substrate). Light emissions were photographed with a CHEMIL-MAGER 5500 (Alpha Innotech Corp.)

Subcloning of Z variants: Dimeric Z variants were amplified from pAffi1/pAY00065 vectors. A PCR was performed using different primer pairs and the resulting gene fragments were purified and hybridized in ligase buffer. The hybridized gene fragments were subcloned in the pAY00430 vector, providing an N-terminal His$_6$ tag and a C-terminal cysteine (His$_6$-(Z######)$_2$-Cys (SEQ ID NO: 1022)). The HER3 binding Z variants were subcloned as dimers and the constructs encoded by the expression vectors were MGSSHH-HHHHLQ-[Z######][Z######]-VDC (SEQ ID NO: 1023). A three parts ligation was used for insertion of both insert fragments into the vector at the same step. Hybridized gene fragments and AccI-digested and dephosphorylated expression vectors were ligated in ligase buffer and electroporated into electrocompetent E. coli TOP10 cells. The transformed cells were spread on TBAB plates (30 g/l tryptose blood agar base) supplemented with 50 µg/ml of kanamycin, followed by incubation at 37° C. overnight. The colonies were screened using PCR and the lengths of the PCR fragments were verified on agarose gels. To verify the sequences, sequencing was performed as described above. Plasmid DNA stock was prepared from the sequenced clones and deposited in −80° C. In addition, E. coli BL21(DE3) cells were transformed with the plasmids through electroporation.

Results

Phage Display Selection of HER3 Binding Polypeptides:

Four rounds of phage display selection were run against biotinylated or non-biotinylated human HER3-ECD. The four selection cycles were performed in solution with biotinylated target at two different target concentrations or on solid phase with non-biotinylated target. In solution, phage particle target complexes were captured onto streptavidin-coated beads. For each selection cycle, the number of washes was increased. The phage particle titers and yields were calculated after each selection cycle. The phage particle yield (phage particles out/phage particles in) increased for the third or last cycle indicating an enrichment in target binding clones.

ELISA Screening of Z Variants:

The clones obtained after four cycles of selection were produced in 96-well plates and screened for HER3-ECD and HER3-Fc-binding activity in an ELISA. In total, 93 clones from each selection track were screened. The absorbance measurements showed that, independently of selection strategy, approximately 90% of the clones were positive for HER3, defined as a response two times the signal for the negative control. A Z variant molecule binding to insulin was used in negative and positive control experiments. The positive control was detected with biotinylated insulin and for the negative control the target protein was omitted.

Sequencing:

Sequencing was performed for clones selected on the basis of having varying signal absorbance values against HER3-Fc in ELISA screening, thus obtaining many different representative binders for the sequencing. In total, 135 HER3 positive clones were sequenced. Half of the clones were found in several copies resulting in total 23 new clones whereof two were identified as background binders. Each variant was given a unique identification number #####, and individual variants are referred to as Z#####. The amino acid sequences of the 58-mer Z variants are listed in FIG. 1AA-BB and in the sequence listing as SEQ ID NO:669-689. The deduced HER3 binding motifs of these Z variants are listed in FIGS. 1A and 1n the sequence listing as SEQ ID NO:1-21. The amino acid sequences of the 49-mer polypeptides predicted to constitute the complete three-helix bundle within each of these Z variants are listed in FIG. 1N-0 and in the sequence listing as SEQ ID NO:335-355.

Dot Blot Analysis:

The specificities of 16 of the sequenced unique HER3-binding polypeptides (in the form AQHDEALE-[Z#####]-VDYV-[ABD]-YVPG (SEQ ID NO: 1021)) were tested using dot blot analysis. 23 different proteins were blotted onto nitrocellulose membranes. The 23 proteins included 16 highly abundant human serum proteins, HER2-ECD, HER3-ECD and HER3-Fc and HER4-ECD and HER4-Fc. All Z variant fusion proteins except Z01824 bound to human to HSA as well as HER3-ECD and HER3-Fc in a specific way. Thus, the specificity of the tested Z variants was satisfying (FIG. 2).

Subcloning of Z Variants:

16 of the unique clones were chosen for subcloning in the expression vector pAY004308 as dimers. The cloning resulted in 15 dimers of HER3-binding Z variants (dimers of Z01748, Z01749, Z01751, Z01753, Z01814, Z01815, Z01817, Z01820, Z01821, Z01826, Z01828, Z01830, Z02009, Z02010 and Z02011).

Example 2: Production and Characterization of Z Variants

Materials and Methods

Protein expression and purification: Transformed E. coli BL21(DE3) cultures as subcloned in Example 1 were grown in TSB-YE to an optical density of approximately 1. The protein expression was then induced by addition of 1 M IPTG to a final concentration of 0.5 mM. Cultures were harvested 5 h after induction by centrifugation. The supernatants were discarded and the cell pellets were collected and stored at −20° C.

The HER3 binding Z variants were purified from cell pellets under denatured conditions on 1.5 ml Ni-NTA Superflow Columns (Qiagen) and buffer was exchanged to PBS using PD-10 columns (GE Healthcare). Purified Z variants were aliquoted and stored at −80° C.

Protein Characterization:

The concentration of purified Z variants (in $His_6$-$(Z\#\#\#\#\#)_2$-Cys form (SEQ ID NO 1022)) was determined by absorbance measurements at 280 nm. The purity was estimated by SDS-PAGE analysis on 10 wells 4-12% NuPAGE™ gels (Invitrogen) using Coomassie blue staining. To verify the identity and to determine the molecular weights of purified Z variants, LC/MS-analyses were performed on an Agilent 1100 LC/MSD system (Agilent Technologies).

Cd Analysis:

The purified Z variants were thawed and diluted to 0.5 mg/ml in PBS. For each diluted Z variant, a CD spectrum at 250-195 nm was obtained at 20° C. In addition, a variable temperature measurement (VTM) was performed to determine the melting temperature (Tm). In the VTM, the absorbance was measured at 220 nm while the temperature was raised from 20 to 90° C., with a temperature slope of 5° C./min. The CD measurements were performed on a Jasco J-810 spectropolarimeter (Jasco Scandinavia AB) using a cell with an optical path-length of 1 mm.

Immunofluorescence Staining:

The HER3 positive human mammary gland cell line AU565 (ATCC, #CRL-2351) and HER3 negative human ovary carcinoma cell line SKOV-3 (Ecacc, #91091004) were cultured as recommended by the supplier. The day before assay, 25000 cells were added to each well of multi well slides (eight wells per slide, Histolab #ER-201-1B) and allowed to grow ON in a $CO_2$ incubator to take on a flattened morphology. The slides were gently washed in PBS by adding droplets onto the slide with a Pasteur pipette.

Two experiments were performed. In the first, AU565 cells were stained with 11 different HER3 specific Z variants; $His_6$-$(Z01748)_2$-Cys (SEQ ID NO: 1024), $His_6$-$(Z01749)_2$-Cys (SEQ ID NO: 1025), $His_6$-$(Z01751)_2$-Cys (SEQ ID NO: 1026), $His_6$-$(Z01753)_2$-Cys (SEQ ID NO: 1027), $His_6$-$(Z01814)_2$-Cys (SEQ ID NO: 1019), $His_6$-$(Z01815)_2$-Cys (SEQ ID NO: 1028), $His_6$-$(Z01817)_2$-Cys (SEQ ID NO: 1029), $His_6$-$(Z01820)_2$-Cys (SEQ ID NO: 1020), $His_6$-$(Z01828)_2$-Cys (SEQ ID NO: 1030), $His_6$-$(Z01830)_2$-Cys (SEQ ID NO: 1031) and $His_6$-$(Z02011)_2$-Cys (SEQ ID NO: 1032). The second experiment was performed with $His_6$-$(Z01814)_2$-Cys (SEQ ID NO: 1019) and $His_6$-$(Z01820)_2$-Cys (SEQ ID NO: 1020), and with $(Z01154)_2$ as a negative control Z variant. The staining was performed on slides with HER3 positive AU565 and HER3 negative SKOV-3 cells. An anti-HER3 antibody from R&D Systems (#AF234) was included as a positive control in both experiments.

In both experiments, the Z variants were added to the wells at a concentration of 15 µg/ml in PBS and all dilutions of reagents were made in PBS as well as all washes. After 1 hour of incubation at RT, the multiwell slides were gently washed as described above and goat anti-Affibody molecule Ig (Affibody AB, #20.1000.01.0005) was added to each well at a concentration of 5 µg/ml. After 45 minutes of incubation at RT, the slides were gently washed as described above and 5 µg/ml of a chicken anti-goat Alexa Fluor488 (Invitrogen, #A21467) was added to each well. After an additional 45 minutes of incubation, the slides were gently washed. The positive control, goat anti-HER3 antibody was used at a concentration of 15 µg/ml followed by 5 µg/ml of chicken anti-goat Alexa Fluor488. After completed staining, the cells were fixed in 3% formaldehyde (Sigma, #1365) in PBS for 10 minutes at RT. Slides were then rinsed twice, dried and mounted with anti-fading solution containing DAPI (4',6-diamidine-2-phenyl indole, Vector laboratories, #H1200). The staining was documented using a LEICA DMLA microscope equipped with a video camera for live imaging.

On-Cell Affinity Ranking Using Flow Cytometry:

The full gene sequences encoding Z variants Z01751, Z01753, Z01814 and Z01820 were PCR amplified from their corresponding pAY00430 vector constructs and ligated to the staphylococcal display vector pSCZ1 (Kronqvist et al, Protein Eng Des Sel 21:247-255 (2008)), previously digested with restriction enzymes XhoI and SalI (New England Biolabs). The E. coli strain RR1ΔM15 was used as host for plasmid construction and preparation and the constructs were transformed to electrocompetent Staphylococcus carnosus TM300 (Götz, Soc Appl Bacteriol Symp Ser. 19:49-53 (1990)) according to a previously described protocol (Löfblom et al, J Appl Microbiol 102:736-747 (2007)). Staphylococcal cells individually displaying the four different Z variants were inoculated to 10 ml TSB-YE supplemented with 20 µg/ml chloramphenicol and grown ON at 37° C. and 150 rpm. From the cultures, $10^6$ cells were washed with 1 ml PBSP. The cells were pelleted by centrifugation (3500×g, 4° C., 6 min) and resuspended in 100 µl of PBSP containing different concentrations of biotinylated HER3-Fc (5, 20, 50 and 100 nM; see Example 1 for biotinylation). Equilibrium binding was reached by incubation at RT for 1 h with gentle mixing. The cells were washed once with 1 ml ice-cold PBSP, followed by incubation on ice in 100 µl ice-cold PBSP containing 1.25 µg/ml ALEXA FLUOR® 488-conjugated strepavidin (Invitrogen, #S32354) and 225 nM ALEXA FLUOR® 647-conjugated HSA (see Example 1) for 40 min. Following one wash with 1 ml ice-cold PBSP, cells were resuspended in 300 µl ice-cold PBSP prior to flow-cytometric analysis. The mean fluorescence intensity (MFI) was measured using a FACS VANTAGE SE (BD Biosciences) flow cytometer.

Results

Protein Expression and Purification:

The 15 dimeric Z variant molecules (in $His_6$-$(Z\#\#\#\#\#)_2$-Cys (SEQ ID NO: 1022) form) yielded acceptable production levels of soluble product and the purity of produced batches was estimated to exceed 90% by SDS-PAGE analysis, except for two Z variants ($His_6$-$(Z01826)_2$-Cys (SEQ ID NO: 1033) and $His_6$-$(Z02009)_2$-Cys (SEQ ID NO: 1034)) that did not meet that criteria. The LC/MS analysis verified the correct molecular weight for all pure Z variant molecules.

Cd Analysis:

The CD spectrums showed that the Z variant molecules had a-helical structures at 20° C. This result was also verified in the variable temperature measurements where the melting temperatures (Tm) were determined (Table 1).

TABLE 1

| Melting temperatures for the Z variants | |
|---|---|
| Z variant | Tm (° C.) |
| $His_6$-$(Z01748)_2$-Cys (SEQ ID NO: 1024) | 44 |
| $His_6$-$(Z01749)_2$-Cys (SEQ ID NO: 1025) | 63 |
| $His_6$-$(Z01751)_2$-Cys (SEQ ID NO: 1026) | 52 |
| $His_6$-$(Z01753)_2$-Cys (SEQ ID NO: 1027) | 56 |
| $His_6$-$(Z01814)_2$-Cys (SEQ ID NO: 1019) | 58 |
| $His_6$-$(Z01815)_2$-Cys (SEQ ID NO: 1028) | 56 |
| $His_6$-$(Z01817)_2$-Cys (SEQ ID NO: 1029) | 40 |

TABLE 1-continued

Melting temperatures for the Z variants

| Z variant | Tm (° C.) |
|---|---|
| His$_6$-(Z01820)$_2$-Cys (SEQ ID NO: 1020) | 55 |
| His$_6$-(Z01821)$_2$-Cys (SEQ ID NO: 1033) | 44 |
| His$_6$-(Z01828)$_2$-Cys (SEQ ID NO: 1030) | 49 |
| His$_6$-(Z01830)$_2$-Cys (SEQ ID NO: 1031) | 46 |
| His$_6$-(Z02010)$_2$-Cys (SEQ ID NO: 1035) | 51 |
| His$_6$-(Z02011)$_2$-Cys (SEQ ID NO: 1032) | 46 |

Figure 3:
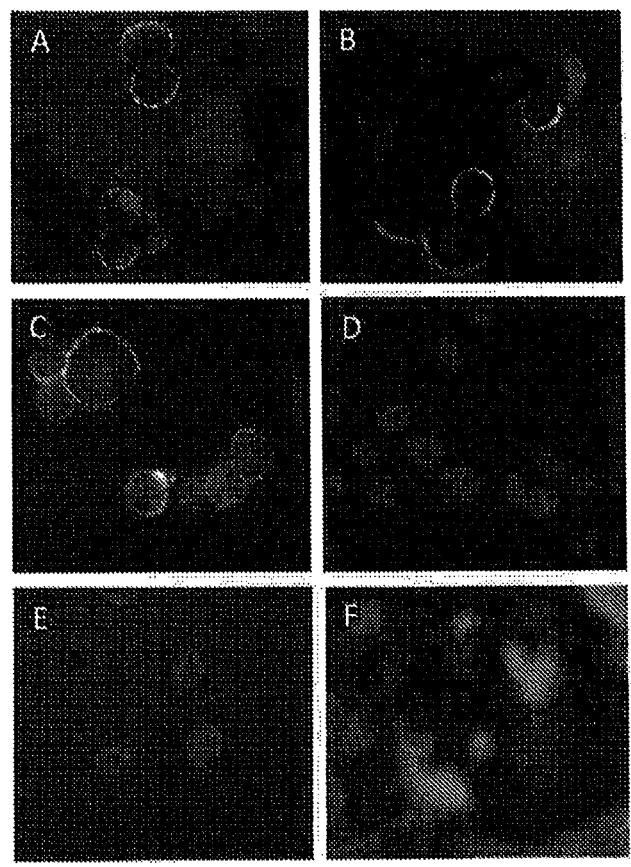

Immunofluorescence Staining:

Immunofluorescence microscopy was employed for characterization of specificity and binding activity to native HER3 expressed on human cancer cells. Eleven clones, showing positive signals in the ELISA screening of Example 1, were produced as dimers fused to an N-terminal His$_6$-tag and a C-terminal cysteine. Each Z variant was incubated on HER3 positive AU565 cells (human mammary mammary gland cell line). An anti-HER3 antibody was used as positive control. The cells were fixed after the staining procedure. Of eleven binders, 6 gave a membrane bound staining pattern. The background was high for some Z variants and in some cases it was difficult to judge if they were specific or not. Two of the HER3 specific molecules, His$_6$-(Z01814)$_2$-Cys (SEQ ID NO: 1019) and His$_6$-(Z01820)$_2$-Cys (SEQ ID NO: 1020) were selected for additional analysis on both HER3 positive AU565 cells and HER2 positive- and HER3 negative SKOV-3 cells (human ovary carcinoma cell line). Distinct cell membrane staining was obtained on AU565 but not on SKOV-3 cells demonstrating selectivity of the Z variants for HER3 over HER2 (FIG. 3).

On-Cell Affinity Ranking Using Flow Cytometry:

To further characterize the HER3 binding molecules and to verify functional expression on bacterial cells, four of the HER3 binding molecules showing specificity for HER3 in immunofluorescence staining were employed for an on-cell affinity ranking experiment using staphylococcal cell display and flow cytometry. Monomer constructs of the four variants were subcloned to the staphylococcal display vector for subsequent transformation to the staphylococcal host. Staphylococcal cells displaying the four Z variants, respectively, were incubated with four concentrations of biotinylated HER3-Fc ranging from 5-100 nM. Cells were analyzed using flow cytometry, revealing efficient expression on the cell surface and specific binding to HER3 for all four variants with no significant difference in relative affinity among the clones (data not shown). Biotinylated HER2 was used as negative control in the experiments and no cross-specificity was observed, confirming the results from the dot blot made with periplasmic supernatants in Example 1 and the immunofluorescence staining in this Example.

Example 3: Design and Construction of a Maturated Library of HER3 Binding Z Variants In this Example, a maturated library was constructed. The library was used for selections of HER3 binding polypeptides. Selections from maturated libraries are usually expected to result in binders with increased affinity (Orlova et al, Cancer Res 66(8):4339-48 (2006). Traditional oligonucleotide synthesis techniques using mononucleotides and degenerate codons may however limit the design since staphylococcal strains are not able to suppress amber stop codons. In this study, randomized double stranded linkers were instead generated by the SLONOMICS® technique which enables incorporation of randomized sets of trinucleotide building blocks using ligations and restrictions of the subsequently built up double stranded DNA.

Materials and Methods

Library Design:

The library was based on the sequences of the HER3 binding Z variants described in Examples 1 and 2. In the new library, 13 variable positions in the Z molecule scaffold were biased towards certain amino acid residues, according to a strategy based on the binding motifs of the Z variant sequences defined in SEQ ID NO:1-21. A SLONOMAX® library containing a mixture of 131 bp double stranded linkers, encoding partially randomized positions in helix 1 and 2 of the HER3 binding polypeptide, e.g. 5'-GAA NNN NNN NNN GCG NNN NNN GAG ATC TGG NNN TTA CCT AAC TTA AAC NNN NNN CAA NNN NNN GCC TTC ATC NNN AGT TTA NNN GAT GAC CCA AGC CAA AGC GCT AAC TT-3'(SEQ ID NO: 1036) (randomized codons are illustrated as NNN) flanked with restriction sites XhoI and NheI, was ordered from Sloning BioTechnology GmbH. The theoretical distributions of amino acid residues in the new library for the 13 variable Z positions are given in Table 3:

TABLE 3

Library design

| Amino acid position in the Z variant molecule | Randomization (amino acid abbreviations) | No of amino acids | Proportion |
|---|---|---|---|
| 2 | W, R, K | 3 | 1/3 |
| 3 | Y, R, K, S | 4 | 1/4 |
| 4 | A, V, I, L, G, S, T, K, R, E, Q, N, H | 13 | 1/13 |
| 6 | A, S, R, Y, T | 5 | 1/5 |
| 7 | W, Y, F, A, V, G | 6 | 1/6 |
| 10 | W | 1 | 1/1 |
| 11 | E, L, Q | 3 | 1/3 |
| 17 | R, Q, V, S, T | 5 | 1/5 |
| 18 | A, V, I, L, G, S, T, R, E, Q, H, W, F, Y | 14 | 1/14 |
| 20 | K, R, A | 3 | 1/3 |
| 21 | A, S, G, V | 4 | 1/4 |
| 25 | A, V, I, L, G, S, T, K, R | 9 | 1/9 |
| 28 | E, Q, F, Y, W, A, S | 7 | 1/7 |

Library Construction and Cloning:

The library was amplified using PHUSION DNA polymerase (Finnzymes, #F530L) during 8 cycles of PCR and pooled products were purified with QIAQUICK PCR Purification Kit (QIAGEN) according to the supplier's recommendations. The purified pool of randomized library fragments was digested with restriction enzymes XhoI and NheI (New England Biolabs) and purified using preparative gel electrophoresis on a 2% agarose gel. The E. coli strain RR1ΔM15 was used as host strain for plasmid production of the staphylococcal display vector pSCZ1 (FIG. 4A) with Jetstar Maxi Kit (Genomed, #220020).

The vector was digested with the same enzymes, XhoI and NheI, and purified using preparative gel electrophoresis on a 1% agarose gel. Ligation of pSCZ1 with the randomized library fragments was performed at a 1:4 molar ratio of vector to fragment using T4 DNA ligase (New England Biolabs, #M0202T). The ligation mixture was purified using QIAQUICK PCR Purification Kit according to the supplier's recommendations prior to transformation to electrocompetent E. coli DH5a cells (Invitrogen, #18263-012). Individual clones, plated directly after transformation as well as after ON amplification, were PCR amplified for sequence verification using BIGDYE Thermo Cycle Sequencing reactions and an ABI PRISM 3700 instrument (PE Applied Biosystems). Plasmids were prepared from ON cultures of *E. coli* using Jetstar Maxi Kit and transformed to electrocompetent *S. carnosus* as described previously (Löfblom et al, supra). The staphylococcal-displayed library is hereinafter denoted SC:$Z_{HER3LIB}$.

Library Quality Analysis:

An aliquot of SC:$Z_{HER3LIB}$ (at least ten times the library size, i.e. more than $1.3 \times 10^8$) was inoculated to 100 ml TSB-YE with 20 µg/ml chloramphenicol and grown ON at 37° C. and 150 rpm. After 16 hours, $10^7$ cells were washed once with 1 ml PBSP. The cells were pelleted by centrifugation (3500×g, 4° C., 6 min) and resuspended in PBSP containing 225 nM ALEXA FLUOR® 647-conjugated HSA and incubated for 1 hour at RT in the dark. Following one wash with 1 ml ice-cold PBSP, cells were resuspended in 300 µl ice-cold PBSP prior to flow-cytometric analysis. The mean fluorescence intensity (MFI) was measured using a FACS VANTAGE SE (BD Biosciences) flow cytometer.

Results
Library Construction and Cloning:

The new library was designed based on a set of HER3 binding Z variants (SEQ ID NO:669-689) with verified binding properties (Example 1 and 2). The theoretical size of the designed library was $7.4 \times 10^8$ Z variants. The library of DNA fragments was cloned into the staphylococcal expression vector and transformed into *S. carnosus* to generate a cell-displayed library containing around $1.3 \times 10^7$ individual clones. Sequence analysis of individual library members revealed a distribution of codons in accordance with the theoretical design and a low proportion of unexpected codons, multiple inserts and frame shifts.

Library Quality Analysis:

In order to verify that the Z variant maturation library was functionally displayed on the bacterial surface, staphylococcal cells from the library were incubated with fluorescently labeled HSA and analyzed using flow cytometry. The result showed that around 72% of the library expressed full-length proteins with functional ABP fusions on the cell surface (data not shown). A maturated library of HER3 binding polypeptides was thus successfully constructed.

Example 4: Selection, Screening and Characterization of Z Variants from a Staphylococcal Surface Display Library Materials and Methods
Cell Labeling and Staphylococcal Cell Sorting Using FACS:

An aliquot of SC:$Z_{HER3LIB}$ (at least ten times the library size, i.e. more than $1.3 \times 10^8$) was inoculated to 100 ml TSB-YE with 20 µg/ml chloramphenicol and grown ON at 37° C. and 150 rpm. After 16 hours, cells (at least four times the subsequent sampling number) were washed with 1 ml PBSP. The cells were pelleted by centrifugation (3500×g, 4° C., 6 min) and resuspended in PBSP containing biotinylated HER3-Fc and incubated at RT with gentle mixing for 2 hours to reach equilibrium binding. The cells were thereafter washed with ice-cold PBSP followed by incubation in 1 ml PBSP containing 1.25 µg/ml ALEXA FLUOR® 488 (fluoresecent dye)-conjugated streptavidin (Invitrogen) and 225 nM ALEXA FLUOR® 647-conjugated HSA for 1 hour on ice in the dark. After a final washing step in 1 ml of ice-cold PBSP, the cells were resuspended in ice-cold PBSP before sorting. Cells were sorted using a FACSVANTAGE SE (BD Biosciences) flow cytometer. The sort gate was set to sort out the top fraction of Z variant displaying cells (typically 0.1%) showing the highest ALEXA FLUOR® 488 to ALEXA FLUOR® 647 fluorescence intensity ratio. The cells were sorted directly into 0.5 ml TSB-YE medium and thereafter inoculated to TSB containing 10 µg/ml chloramphenicol and incubated at 37° C. for 16 hours in order to amplify isolated cells by growth for the next round of labeling and FACS. The procedure was repeated four times.

Sequencing:

Sequencing of individual staphylococcal clones was performed after cell sorting cycle 3 and 4 as described in under Library construction in Example 3.

On-Cell Affinity Ranking and $K_D$ Determination:

HER3-Fc was biotinylated and HSA conjugated with ALEXA FLUOR® 647 as described in Example 1. Staphylococcal cells displaying the different Z variants, respectively, were inoculated to 10 ml TSB-YE and 20 µg/ml chloramphenicol and grown ON at 37° C. and 150 rpm. From the cultures, $10^6$ cells were washed with 1 ml PBSP. The cells were pelleted by centrifugation (3500×g, 4° C., 6 min) and resuspended in PBSP containing different concentrations of biotinylated HER3-Fc (135, 90, 27, 9, 2.7, 0.9, 0.45, 0.22, 0.11 and 0.054 nM for Z05405, Z05413, Z05416 and Z05417; 670, 334, 110, 45, 18, 6.7, 2.2, 1.1, 0.37 and 0.27 nM for Z01820) spanning the estimated $K_D$. Equilibrium binding was reached by incubation at RT for one hour with gentle mixing. The cells were washed with 1 ml ice-cold PBSP, followed by incubation on ice in 100 µl ice-cold PBSP containing 1.25 µg/ml ALEXA FLUOR® 488-conjugated streptavidin, (Invitrogen) and, in the ranking experiment, 225 nM ALEXA FLUOR® 647-conjugated HSA, for 40 min. Following a wash with 1 ml ice-cold PBSP, cells were resuspended in 300 µl ice-cold PBSP prior to flow cytometric analysis. The mean fluorescence intensity (MFI) was measured using a FACS VANTAGE SE (BD Biosciences) flow cytometer.

Results
Flow-Cytometric Sorting for Isolation of Improved Z Variants:

For isolation of matured HER3 binding Z variants, the staphylococcal library was subjected to four rounds of fluorescence-activated cell sorting (FACS) with alternating rounds of amplification by cell growth.

Briefly cells were incubated with biotinylated HER3-Fc at concentrations around 10-fold lower compared to the estimated $K_D$ of the Z variants from Example 1 and 2. Cells were thereafter washed and incubated with fluorescently labeled streptavidin for subsequent fluorescence-mediated detection of cell-bound HER3 as well as fluorescently labeled HSA for monitoring of surface expression levels. The incubation of secondary reagents and HSA was performed on ice in order to reduce the dissociation rate of bound HER3. After an additional washing, the labeled cell library was screened and sorted in a flow cytometer. Selection stringency in terms of target concentration, sorting parameters and sorting gates was increased with each sorting round and typically, the top 0.1% of the library, demonstrating highest target binding to surface expression ratio, was gated and isolated for amplification and subsequent rounds of sorting. The visualization of the target-binding properties of the library in the flow cytometer revealed an enrichment of HER3-positive clones in each sorting round, and essentially only HER3-positive clones in the last round (FIG. 5). After up to four rounds of FACS, isolated cells were spread on semi-solid medium for sequencing and characterization of individual candidates.

Sequencing:

576 individual clones were sequenced resulting in 443 readable sequences, out of which 45 clones appeared more than once in the same sorting round (SEQ ID NO:690-734). Each variant was given a unique identification number #####, and individual variants are referred to as Z#####. The amino acid sequences of the 58-mer Z variants are listed in FIG. 1BB-OO and in the sequence listing as SEQ ID NO:690-1002. The deduced HER3 binding motifs of these Z variants are listed in FIG. 1A-N and in the sequence listing as SEQ ID NO:22-334. The amino acid sequences of the 49-mer polypeptides predicted to constitute the complete three-helix bundle within each of these Z variants are listed in FIG. 1O-AA and in the sequence listing as SEQ ID NO:356-668.

On-Cell Affinity Ranking:

On the basis of the sequencing results, the 45 clones that appeared more than once were subjected to a whole-cell ELISA assay in order to rank the variants with respect to affinity for HER3. The staphylococcal cell populations were analyzed using flow cytometry and one Z variant from Example 1 and 2 (Z01753) surface displayed on staphylococcal cells was included in the analysis for comparison. All 45 candidates were positive for HER3 binding in the assay and, moreover, 43 demonstrated a higher signal compared to the Z variant from Example 1 and 2 (FIG. 6A-D). The highest signals in the assay were seen with the four clones that appeared most frequently after sequencing, demonstrating quantitative isolation of Z variants in the flow-cytometric sorting.

$K_D$-Determination:

The apparent equilibrium dissociation constant ($K_D$) was determined on-cell for four Z variants (FIG. 4B) and one HER3 binding Z variant from Example 1 and 2 (Z01820). Staphylococcal cells displaying the four variants and Z01820 were incubated in varying concentrations of labeled HER3-Fc spanning the estimated $K_D$. The cell populations were analyzed in the flow cytometer and the mean fluorescence intensity data was subsequently plotted against the HER3-Fc concentrations and fitted to a one-site binding model in order to determine the $K_D$. All four maturated Z variants demonstrated low nanomolar apparent $K_D$. The strongest binder demonstrated a 15-fold improvement in affinity for HER3-Fc compared to the Z variant from Example 1 and 2 (Table 3).

TABLE 3

Affinities of HER3-Fc binding Z variants on cell using flow cytometry

| Z variant | $K_D$ (on-cell analysis, nM, mean ± SD) |
|---|---|
| Z05405 | 2.7 ± 0.6 |
| Z05413 | 2.3 ± 0.7 |
| Z05416 | 3.1 ± 0.6 |
| Z05417 | 3.2 ± 0.2 |
| Z01820 | 33.7 ± 1.3 |

Example 5: Surface Plasmon Resonance KD Determination of Z Variants

Materials and Methods
Surface Plasmon Resonance Analysis:

Surface plasmon resonance (SPR) analysis was performed for the HER3 binding Z variants Z05405, Z05413, Z05416 and Z05417 on a BIACORE 2000 surface plasmon resonance instrument (GE Healthcare). Human HER3-Fc (R&D Systems) and mouse HER3-Fc (R&D systems) were immobilized by NHS/ECD amine-coupling chemistry on a CM-5 sensor chip (GE Healthcare). The immobilization was performed in 10 mM NaAc (pH 4.5) at a flow rate of 30 µl/min and with receptor concentrations of 10 µg/ml, aiming for an immobilization level of 4000 RU. PBSP was used as running buffer at a flow rate of 20 µl/min (unless stated otherwise) and 5 mM NaOH for regeneration.

For determination of the kinetics, 250 µl of four different concentrations (1.5-67 nM diluted in PBSP) of the four HER3 binding Z variants were injected over HER3-Fc immobilized on the CM-5 chip surface. The surfaces were regenerated by four injections of 15 µl of 5 mM NaOH and extensive washing with running buffer. Each sample was measured in duplicates and the response from the blank surface was subtracted from the response from each Z variant at each concentration. The obtained sensorgrams were fitted to a one-site binding model for determination of $K_D$ values based on mean association ($k_{on}$) and dissociation rates ($k_{off}$).

Control Experiments:

To verify that the Z variants were not selected for affinity to the Fc part of HER3-Fc, each Z variant (50 nM) was incubated with a 10-fold molar excess of human polyclonal IgG (500 nM) for 1 h at room temperature prior to injection of 100 µl of each sample (in the above concentrations) over HER3-Fc immobilized on the biosensor chip surface. In an additional control experiment, the Z variants were injected over HER3-ECD immobilized on the sensor chip surface.

Results
Surface Plasmon Resonance Analysis:

The dissociation equilibrium constant ($K_D$) of the four Z variants Z05405, Z05413, Z05416 and Z05417 was determined by SPR technology. The affinity was determined from the association and dissociation rates of the Z variants using non-linear regression to a one-site binding model, resulting in dissociation constants of 1.61 nM for Z05405, 0.78 nM for Z05413, 0.78 nM for Z05416 and 0.69 nM for Z05417 (FIG. 7, Table 4). In Table 4, all values are means of duplicates of each concentration performed on the same day.

TABLE 4

Affinities of five HER3 binding Z variants for human/mouse HER3

| | Human HER3 | | | Mouse HER3 | | |
|---|---|---|---|---|---|---|
| Z variant | $K_D$ (nM) | $k_a$ (M$^{-1}$s$^{-1}$) | $k_d$ (s$^{-1}$) | $K_D$ (nM) | $k_a$ (M$^{-1}$s$^{-1}$) | $k_d$ (s$^{-1}$) |
| Z05405 | 1.6 | 1.8 × 10$^6$ | 2.8 × 10$^{-3}$ | 2.4 | 1.4 × 10$^6$ | 3.3 × 10$^{-3}$ |
| Z05413 | 0.8 | 1.7 × 10$^6$ | 1.3 × 10$^{-3}$ | 2.0 | 1.4 × 10$^6$ | 3.0 × 10$^{-3}$ |
| Z05416 | 0.8 | 1.9 × 10$^6$ | 1.5 × 10$^{-3}$ | 2.0 | 1.6 × 10$^6$ | 3.2 × 10$^{-3}$ |
| Z05417 | 0.7 | 1.9 × 10$^6$ | 1.3 × 10$^{-3}$ | 1.7 | 1.6 × 10$^6$ | 2.7 × 10$^{-3}$ |

Control Experiments:

Since the analysis of the HER3 binding Z variants was performed with HER3 fused to the human IgG Fc-region, two control experiments were performed in order to verify that the Z variants were not selected for affinity to the Fc part of HER3-Fc. No difference in response could be observed between Z variants pre-incubated with IgG and the samples containing only Z variants (data not shown). Moreover, the Z variants injected over a surface with HER3-ECD showed specific binding for all four variants (data not shown). Taken together, the two experiments clearly demonstrate that Fc is not part of the Z variants' binding site on HER3-Fc.

Example 6: Competition Assay for Heregulin and HER3 Binding Z Variants

In this Example, the ability of HER3 binding Z variants to block binding of the ligand heregulin to HER3 was investigated by SPR in a competition assay.

Materials and Method

Competition between the natural ligand heregulin (HRG1-β1, EGF-like domain, R&D Systems) and the four HER3 specific Z variants Z05405, Z05413, Z05416 and Z05417 was analyzed using SPR in two different assays.

In a first assay, 2.5 nM HER3-Fc was pre-incubated with 100 nM of each of the four HER3 specific Z variants (40-fold molar excess) for 1 h at room temperature. Thereafter, 75 µl of each mixture of HER3-Fc and Z variant was injected over a sensor chip surface with immobilized heregulin. Additionally, HER3-Fc not pre-incubated with Z variants was injected over the chip surface with immobilized heregulin.

In a second assay, 100 µl of each Z variant at five different concentrations (0-10 nM) was injected over the sensor chip surface with immobilized HER3, immediately followed by injection of 100 µl of 250 nM heregulin (using the BIACORE COINJECT command). All samples were injected in duplicates and an HER2 specific Z variant was injected using the same setup as a negative control. The surfaces were regenerated with two injections of 5 mM NaOH and extensive washing with running buffer.

Results

Competition of the HER3 specific Z variants Z05405, Z05413, Z05416 and Z05417 with the natural HER3 ligand heregulin for HER3 was investigated by SPR technology.

The results of the first assay, using heregulin immobilized on the chip surface, showed a nearly complete reduction in response level when injecting HER3-Fc pre-incubated with Z variants compared to injecting HER3-Fc not pre-incubated with Z variants (FIG. 8A).

The results of the second assay, using HER3-Fc immobilized on the chip surface, indicated a concentration-dependent competition with the interaction between the HER3 receptor and its natural ligand (FIG. 8B). The same pattern was observed for mouse HER3-Fc (data not shown). No competition between the negative control and heregulin could be observed for either human or mouse HER3 (data not shown).

The results demonstrate that the HER3 specific Z variants interact with the same binding site on HER3 as the natural ligand heregulin and can hence compete with the binding between the ligand and the receptor in vitro. This effect may be exploited in future therapeutic in vivo applications.

Example 7: Inhibition of Heregulin-Induced HER3 Phosphorylation In Vitro

In this Example, the ability of HER3 binding Z variants to prevent heregulin-induced HER3 phosphorylation was investigated in a cell assay.

Materials and Methods

Stimulation:

MCF-7 (ACC115, DSMZ) breast carcinoma cells were cultured in RPMI medium (BE12-167F, Lonza) supplemented with L-glutamine (BE17-605E, Cambrex), non-essential amino acids (BE13-114E, Cambrex), sodium pyruvate (BE13-115E, Cambrex) and 10% fetal bovine serum (FBS, 10108-165, Gibco). The day before stimulation, $1 \times 10^6$ cells were seeded in 6 mm Petri dishes (430168, BD Biosciences) in 5 ml of the above medium.

One hour prior to stimulation, the medium was changed to a medium consisting of RPMI+L-glutamine+2% dialyzed FBS (26400-036, Gibco). Phosphorylation of HER3 was induced with 5 nM heregulin (HRG1-β, 396-HB, R&D systems). HER3 binding Z variants Z05416 and Z05417, each comprising an N-terminal his-tag and a C-terminal cysteine ($His_6$-Z05416-cys (SEQ ID NO: 1037) and $His_6$-Z05417-cys (SEQ ID NO: 1038)), were added simultaneously with heregulin in 10 or 100 times molar excess. A taq polymerase specific Z variant ($His_6$-Z01155-cys (SEQ ID NO: 1039)) was used as a negative control and was added according to the same procedure as described above.

Following incubation for 10 minutes at 37° C., cellular processes were stopped by placing the petri dishes on ice and by subsequent washing with ice-cold PBS. After washing, 2 ml PBS containing 1 mM activated orthovanadate (450243, Sigma) was added to each dish and the cells were detached using a cell scraper. The cell solution was transferred to a 10 ml tube and the cells were pelleted by spinning in a pre-cooled centrifuge at 1000 rpm for 3 minutes. The dry pellet was dissolved in 100 µl ice cold lysing buffer (1% NP-40 (Sigma 13021), 20 mM Tris (pH 8.0), 137 mM NaCl, 10% glycerol, 2 mM EDTA, 1 mM activated sodium orthovanadate) to lyse the cells. The lysate was incubated end-over-end at 4° C. for 30 minutes and centrifuged at 13000 rpm for 15 minutes. The supernatant was collected and stored at −80° C. until further analysis.

pHER3-ELISA:

The presence of phosphorylated HER3 protein (pHER3) in cell lysates was analyzed using a DUOSET IC phospo ErbB3 sandwich ELISA (DYC-1769, R&D Systems).

96 well half area plates (Costar 3690) were coated over night with 50 µl/well of 2 µg/ml capture antibody diluted in PBS. The next day, the plate was washed four times with PBS+0.05% TWEEN (PBST) in an automated ELISA washer. The wells were blocked with PBS containing 1% BSA (100 µl/well) for 2 hours at RT and washed as previously described.

50 µl/well of cell lysates, diluted two or four times in IC Diluent #12 (1% NP-40, 20 mM Tris (pH 8.0), 137 mM NaCl, 10% glycerol, 2 mM EDTA, and 1 mM activated sodium orthovanadate), were added. Positive controls, provided by the manufacturer, were also added to the wells. The plate was subsequently incubated for 2 hours.

After washing, 50 µl/well of detection antibody was added, diluted according to manufacturer protocol in IC diluent #14 (20 mM Tris, 137 mM NaCl, 0.05% TWEEN 20, 0.1% BSA, pH 7.2-7.4), and the plate was incubated for another 2 hours. Following incubation, the plate was washed and 50 µl/well of TMB (IMMUNOPURE, THERMO Fisher Scientific) was added. The reaction was stopped after 20 minutes by addition of 50 µl/well of 2 M $H_2SO_4$ and the absorbance was measured at 450 nm using a VICTOR[3] ELISA plate reader.

Results

The HER3-specific Z variants Z05416 and Z05417 were, together with the negative control (taq polymerase specific Z01155), assessed for their ability to block heregulin-induced phosphorylation of HER3. The relative content of pHER3(%) was determined as the relation of blocked culture (OD-value obtained from a culture containing a Z variant) to heregulin-stimulated culture (OD-value obtained from heregulin-stimulated cultures). FIG. 9 shows that the HER3 binding variants Z05416 and Z05417 inhibited heregulin-induced phosphorylation in a dose dependent manner, whereas the taq polymerase binding variant Z01155 did not have any effect.

Example 8: Bispecific Z Variants Binding to HER3 and HER2

As described in the Background section, HER3 is a preferred heterodimerization partner for HER2, and HER2 is dependent on other receptors in the HER family for ligand induced signaling. A bispecific HER3 and HER2 targeting ligand (for example a HER3-HER2 binding Z variant), might block the receptor signal driving tumor growth on tumors expressing both receptors.

Different molecular constructs for the bispecific molecules, optionally comprising various linker lengths, are contemplated. Examples of constructs are N- or C-terminal positioning of the HER3 binding polypeptide to the HER2 binding polypeptide. If a linker is introduced between the two binding polypeptides, it can comprise 1-60 amino acid residues, such as 1-45 amino acids. In addition, the bispecific construct may be provided with a half life extension moiety, e.g. by albumin fusion, coupling to an albumin binding moiety or a molecule such as PEG, at the N- or C-terminal part of the molecule or within the linker region. Alternatively, the half life extending moiety may in itself be utilized as a linker, or a spacer, between the two binding polypeptides.

Material and Methods

A dimeric bispecific Z variant molecule is engineered as previously reported in Friedman et al, Biotechnol Appl Biochem, 54(2):121-31 (2009). Although Friedman et al describes production of tetrameric Z variants specific for two members of the HER family, the construction of a HER3 and HER2 bispecific Z variant in principle follows the same protocol. A person skilled in the field will easily understand how to apply the procedure based on Friedman et al. For construction of a heterodimeric Z variant binding to HER3 and HER2, a gene fragment encoding a HER3 binding variant is genetically fused in-frame with a gene fragment encoding a HER2 binding Z variant using a 40 aa peptide linker between the two binding polypeptides by following the procedure described by Jonsson, et al, supra.

The gene encoding the bispecific protein is constructed by cloning of vectors encoding the HER3-HER2 binding Z variants. The HER3 binding Z variant is selected from SEQ ID NO:669-1002, in particular a sequence selected from SEQ ID NO:669-734, such as selected from SEQ ID NO:690-734, such as from SEQ ID NO:691-693, SEQ ID NO:695-696, SEQ ID NO:700, SEQ ID NO:703-704, SEQ ID NO:708, SEQ ID NO:710, SEQ ID NO:712-713, SEQ ID NO:721, SEQ ID NO:722 and SEQ ID NO:724, and the HER2 binding Z variant is selected from SEQ ID NO:1003. The HER2 and the HER3 binding Z variants can have different affinities for the different receptors. Constructs may also be made from vectors encoding Z variants having various affinity for the same receptor. The vectors encoding the bispecific HER3-HER2 binding Z variants are cleaved using suitable endonucleases (e.g. SfiI, AccI, PstI, BamHI, New England Biolabs) and the gene fragments encoding HER3-HER2 specific Z variants are recovered and ligated to form the gene encoding the bispecific molecule. The HER3 and HER2 binding polypeptides may individually form a monomeric unit or a multimeric unit, such as a dimer, trimer or tetramer, within the gene fragment.

For introduction of a peptide linker, multiples of gene fragments encoding a linker region (e.g. GGGS, (SEQ ID NO:1017), or GGGGSGGGGLVGLGSGGGGS, (SEQ ID NO:1018)) are introduced to create constructs with different linker lengths. The linker region can also contain an albumin gene or the gene for an albumin binding domain (ABD). Here, the ABD gene is amplified using PCR, and a linker encoding unit is introduced. This is followed by BamHI restriction digestion and ligation into the dimeric HER3-HER2 bispecific gene between the HER binding polypeptides. This is essentially conducted as described for creating trimeric TNF constructs by Jonsson et al, supra, however replacing the central TNF molecules described in Jonsson with an ABD. Alternatively, the gene fragments encoding HER3-HER2 binding Z variants are amplified using suitable PCR primers that also introduce the desired linker regions and restriction sites for cloning of the bispecific molecule in various formats. Different formats of the bispecific molecule are for example N- or C-terminal positioning, various lengths of linkers between the binding Z variants and/or the ABD gene in between. Another possibility for construction of genes encoding for the desired bispecific molecule is simply to purchase the fully synthetic gene from companies offering such services, such as e.g. Geneart A G.

The resulting gene fragments encoding the HER3 binding Z variant, the HER2 binding Z variant, the peptide linker and optionally ABD, are ligated into an expression vector, transformed into expression cells (e.g. *E. coli*). Proteins are expressed for example as described in Example 2. Expression vectors are used that encode an additional his-tag and/or a unique cysteine for labeling purposes, and the expressed protein is purified as for example described in Example 2. The methods used for protein expression and purification are standard methods known to the person skilled in the field.

The resulting bispecific proteins are then tested for simultaneous binding in vitro, as described in Friedman et al, supra, by using Biosensor analysis (BIACORE, GE Healthcare). Human HER3-Fc (hHER3-Fc) and human HER2-Fc (hHER2-Fc, both from R&D Systems) are immobilized by amine coupling on the carboxylated dextran layer of a CM5 sensor chip (GE Healthcare), according to the manufacturer's instructions. Another flow-cell surface is activated and de-activated as a reference surface. The bispecific HER3-HER2 molecule is diluted in a running buffer, HBS (10 mM Hepes, 150 mM NaCl, 3.4 mM EDTA and 0.005% surfactant P20, pH 7.4), before binding analysis is performed at 25° C. In a first experiment, the bispecific HER3-HER2 molecule is injected at concentrations ranging from 125 nM to 2 µM over all surfaces with a flow rate of 30 µl/min. A HER3 binding Z variant and a HER2 binding Z variant are also injected as controls. After each injection the flow cells are regenerated by the injection of 10 ml of 10 mM HCl.

In a second experiment, 5 µM HER3-HER2 molecule is injected over flow-cell surfaces having immobilized hHER3-Fc or hHER2-Fc (R&D Systems) by amine coupling on the carboxylated dextran layer of a CM5 sensor chip. Following a short dissociation time of 1 min, 115 nM hHER3-Fc and hHER2-Fc (diluted in the running buffer) is injected and the ability of the bispecific molecules to simultaneously bind both their targets is monitored.

By incubating a fluorescently labeled bispecific HER3-HER2 molecule with cells expressing either HER3 and not HER2, or HER2 and not HER3, binding ability of the HER3-HER2 molecule on live cells is monitored using fluorescence microscopy and flow cytometry analysis, as described in Friedman et al, supra. Differences in specificity are investigated at the same time, to find out if different constructs, having different affinities for their respective receptors, will differentiate between different receptor expression levels on cells.

The biological effect of binding bispecific Z variants to cells is tested by exposing cell cultures to various amounts, ranging from 0.05 nM up to 5000 nM, of the bispecific Z variants and analyzing cell growth rate and survival, and by analyzing phosphorylation patterns of important cell signaling pathways using western blot analysis, as described for a HER2 specific Z variant by Ekerljung et al (in Tumour Biol 27(4):201-10 (2006) and in Biochem Biophys Res Commun 377(2):489-94 (2008)). Cell lines that can be tested include MDA-MB-361, NCI-N87, CALU-3 and SKOV-3. Also HER3 transduced BT-474 and ZR75-cells can be used.

To test the effect of the HER3-HER2 Z variants in vivo, the bispecific constructs are evaluated for tumor targeting and for biological effect in a tumor. The bispecific HER3-HER2 binding Z variants are radiolabeled as previously described (Ahlgren et al, Bioconjug Chem 19(1):235-43 (2008)), and characterized for in vitro cellular uptake, retention and internalization using described methods (Steffen et al, Cancer Biother Radiopharm 20(3):239-48(2005)). Animals bearing xenografted tumors expressing HER3 and HER2 receptors (e.g. MDA-MB-361, NCI-N87, CALU-3 and SKOV-3) are in a biodistribution study injected with the radiolabeled HER3-HER2 binding Z variants and monitored for tumor uptake and contrast to other organs. For constructs not having a half life extending moiety, the distribution of the radioactivity in the xenografted mice is typically assessed at 1, 2, 4, 8, 24, 48 and 72 hours following injection of the radiolabeled bispecific HER3-HER2 binding Z variant. For constructs having a half life extending moiety, the distribution of the radioactivity is typically assessed at 1, 4, 12, 24, 48, 72, 168 and 332 hours following injection of the radiolabeled bispecific HER3-HER2 binding Z variant, essentially as described in Tolmachev et al (Cancer Res 67(6):2773-82 (2007)). The uptake of the radiolabeled bispecific Z variants is compared to the uptake of HER2 and/or HER3 binding Z variants alone. In cases where the bispecific Z variants have superior uptake and retention and/or specificity in tumors in vivo as compared to the monospecific counterparts, the bispecific variants may be suitable for targeted payload therapy. Such therapy will utilize a potent effector function, e.g. radionuclides, toxic chemical molecules, toxins, cytokines or photosensitizers, fused or conjugated to the bispecific molecule.

The bispecific Z variants are furthermore characterized for intrinsic effect in vivo. Mice are grafted with tumor cells expressing both receptors, or as control, only one or none of the receptors, and subjected to a single or multiple injections of the bispecific Z variants. Tumor growth is monitored over time and versus control groups, including a vehicle group receiving only the injection buffer but no active compound, i.e. the bispecific HER3-HER2 binding molecule.

Example 9: Z Variants with Bispecific Binding to HER3 and EGFR

As described in the introduction, HER3 is a preferred heterodimerization partner for HER2. It is however, in certain conditions, also an important dimerization partner for the EGF-receptor (EGFR or HER1). By using a bispecific HER3 and EGFR targeting ligand, tumors expressing both receptors will be targeted, and the tumor driving receptor signaling may be blocked.

Bispecific HER3 and EGFR binding Z variants are engineered essentially as described above in Example 8. The resulting construct can be tested in cell lines expressing HER3 and EGFR receptors, such as A431-cells, in a similar fashion as described in Example 8 for bispecific HER3 and HER2 binding Z variants.

The invention claimed is:

1. HER3 binding polypeptide, comprising a HER3 binding motif (BM), wherein the amino acid sequence of the BM is selected from the group consisting of SEQ ID NOs: 1 to 334, and
    wherein the HER3 binding polypeptide binds to the extra-cellular domain of HER3.

2. HER3 binding polypeptide according to claim 1, wherein the amino acid sequence of the BM is selected from the group consisting of SEQ ID NOs: 1 to 66.

3. HER3 binding polypeptide according to claim 2, wherein the amino acid sequence of the BM is SEQ ID NO: 23-25, 27-28, 32, 35-36, 40, 42, 44-45, 53-54 or 56.

4. HER3 binding polypeptide according to claim 1, which comprises the polypeptide sequence:
    K-[BM]-DPSQS $X_aX_b$LLX$_C$ EAKKL NDX$_d$Q (SEQ ID NO:1011); wherein
    [BM] is the HER3 binding motif as defined in claim 1;
    $X_a$ is selected from A and S;
    $X_b$ is selected from N and E;
    $X_c$ is selected from A, S and C;
    $X_d$ is selected from A and S.

5. HER3 binding polypeptide according to claim 4, wherein $X_a$ is A; $X_b$ is N; $X_c$ is A and $X_d$ is A.

6. HER3 binding polypeptide according to claim 4, wherein $X_a$ is A; $X_b$ is N; $X_c$ is C and $X_d$ is A.

7. HER3 binding polypeptide according to claim 4, wherein $X_a$ is S; $X_b$ is E; $X_c$ is S and $X_d$ is S.

8. HER3 binding polypeptide according to claim 4, wherein $X_a$ is S; $X_b$ is E; $X_c$ is C and $X_d$ is S.

9. HER3 binding polypeptide according to claim 4, wherein the HER3 binding polypeptide sequence comprises SEQ ID NO: 335-667 or 668.

10. HER3 binding polypeptide according to claim 9, wherein the HER3 binding polypeptide sequence comprises SEQ ID NO: 335-399, or 400.

11. HER3 binding polypeptide according to claim 10, wherein the HER3 binding polypeptide sequence comprises SEQ ID NO: 357-359, 361-362, 366-370, 374, 376, 378-379, 387-388, or 390.

12. HER3 binding polypeptide according to claim 1, which comprises the polypeptide sequence:
    YAK-[BM]-DPSQS SELLX$_c$ EAKKL NDSQA P (SEQ ID NO:1012);
        wherein [BM] is a HER3 binding motif as defined in claim 1 and $X_c$ is selected from S and C.

13. HER3 binding polypeptide according to claim 1, which comprises the polypeptide sequence:
    FNK-[BM]-DPSQS ANLLX$_C$ EAKKL NDAQA P (SEQ ID NO:1013);
        wherein [BM] is a HER3 binding motif as defined in claim 1 and $X_c$ is selected from A and C.

14. HER3 binding polypeptide according to claim 1, the HER3 binding polypeptide comprising SEQ ID NO: 669-1001 or 1002.

15. HER3 binding polypeptide according to claim 14, wherein the HER3 binding polypeptide comprises SEQ ID NO: 669-733, or 734.

16. HER3 binding polypeptide according to claim 15, wherein the HER3 binding polypeptide comprises SEQ ID NO:691-693, 695-696, 700, 703-704, 708, 710, 712-713, 721, 722, or 724.

17. HER3 binding polypeptide according to claim 1, wherein the HER3 binding polypeptide binds to HER3 such that the $K_D$ value of the interaction is at most $1\times10^{-6}$ M.

18. HER3 binding polypeptide according to claim 1 comprising further C terminal and/or N terminal amino acids.

19. HER3 binding polypeptide according to claim 18, in which the further C terminal and/or N terminal amino acids improve production, purification, stability in vivo or in vitro, binding, or detection of the polypeptide.

20. HER3 binding polypeptide according to claim 1 in multimeric form, comprising at least two HER3 binding polypeptide monomer units, the amino acid sequences of which may be the same or different.

21. HER3 binding polypeptide according to claim 20, in dimeric form.

22. A composition comprising the HER3 binding polypeptide according to claim 1 and a second moiety comprising a therapeutic agent.

23. The HER3 binding polypeptide according to claim 17, wherein the HER3 binding polypeptide binds to HER3 such that the $K_D$ value of the interaction is at most $1\times10^{-7}$ M.

24. The HER3 binding polypeptide according to claim 23, wherein the HER3 binding polypeptide binds to HER3 such that the $K_D$ value of the interaction is at most $1\times10^{-8}$ M.

25. A ligand having binding affinity for HER3 and for HER2, comprising a HER3 binding polypeptide according to claim 1; a HER2 binding polypeptide comprising an engineered protein comprising a protein Z derivative; and a linking moiety for linking the HER3 binding polypeptide with the HER2 binding polypeptide.

26. The ligand according to claim 25, wherein the HER2 binding polypeptide binds to HER2 such that the $K_D$ value of the interaction is at most $1\times10^{-6}$ M.

27. The ligand according to claim 25, wherein the engineered protein comprises the amino acid sequence
    YAKEM RNAYW EIALL PNLTN QQKRA FIRKL YDDPS QSSEL LSEAK KLNDS Q (SEQ ID NO:1003).

28. The ligand according to claim 25, wherein the linking moiety is a peptide comprising from 1 to 45 amino acids.

29. The ligand according to claim 25, further comprising a half-life extending moiety for extension of ligand half-life in vivo.

30. The ligand according to claim 29, wherein the half-life extending moiety is albumin.

31. The ligand according to claim 29, wherein the half-life extending moiety is an albumin binding moiety.

32. The ligand according to claim 31, wherein the albumin binding moiety is an engineered protein derived from domain GA3 of streptococcal Protein G.

33. The ligand according to claim 32, wherein the albumin binding moiety comprises the amino acid sequence
LAEAK VLANR ELDKY GVSDF YKRLI NKAKT VEGVE ALKLH ILAAL P (SEQ ID NO:1005).

34. The ligand according to claim 29, wherein the half-life extending moiety is polyethylene glycol.

35. The ligand according to claim 29, wherein the ligand comprises at least one cysteine residue and the half-life extending moiety is attached to the ligand via said at least one cysteine residue.

36. The ligand according to claim 29, wherein the half-life extending moiety is attached to the ligand via the linking moiety.

37. The ligand according to claim 25, wherein the linking moiety comprises a half-life extending moiety.

38. The ligand according to claim 25 wherein the linking moiety is an amino acid linker.

39. A ligand having binding affinity for HER3 and for EGFR, comprising a HER3 binding polypeptide according to claim 1; an EGFR-binding polypeptide; and a linking moiety for linking the HER3 binding polypeptide with the EGFR binding polypeptide.

* * * * *

SEQUENCE LISTING

<160> NUMBER OF SEQ ID NOS: 1040

<210> SEQ ID NO 1
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 1

Glu Lys Val Ala Ala Thr Gly Glu Ile Trp Asp Leu Pro Asn Leu Asn
1               5                   10                  15

Thr Arg Gln Lys Asn Ala Phe Ile Gly Ser Leu Trp Asp
            20                  25

<210> SEQ ID NO 2
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 2

Glu Trp Arg Trp Ala Ala His Glu Ile Trp Asp Leu Pro Asn Leu Asn
1               5                   10                  15

Val Tyr Gln Arg Ala Ala Phe Ile Arg Ser Leu Glu Asp
            20                  25

<210> SEQ ID NO 3
<211> LENGTH: 29

```
<212> TYPE: PRT
<213> ORGANISM: Artificial Sequence
<220> FEATURE:
<223> OTHER INFORMATION: Engineered polypeptide

<400> SEQUENCE: 3

Glu Arg Arg Leu Ala Ser Val Glu Ile Trp Glu Leu Pro Asn Leu Asn
1               5                   10                  15

Ala Val Gln Lys Ser Ala Phe Ile Ser Ser Leu Phe Asp
            20                  25

<210> SEQ ID NO 4
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 4

Glu Val Lys Glu Ala Arg Phe Glu Ile Trp Asp Leu Pro Asn Leu Asn
1               5                   10                  15

Arg Thr Gln Lys His Ala Phe Ile Val Ser Leu Glu Asp
            20                  25

<210> SEQ ID NO 5
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 5

Glu Trp Lys Gly Ala Ala Gly Glu Ile Trp Asn Leu Pro Asn Leu Asn
1               5                   10                  15

Val Ser Gln Arg Val Ala Phe Ile Gly Ser Leu Ala Asp
            20                  25

<210> SEQ ID NO 6
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 6

Glu Lys Tyr Lys Ala Ala His Glu Ile Trp Glu Leu Pro Asn Leu Asn
1               5                   10                  15

Arg Asp Gln Arg Ala Ala Phe Ile Thr Ser Leu Thr Asp
            20                  25

<210> SEQ ID NO 7
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 7

Glu Arg Ser Leu Ala Ser Phe Glu Ile Trp Glu Leu Pro Asn Leu Asn
1               5                   10                  15

Pro Lys Gln Lys Ala Ala Phe Ile Val Ser Leu Phe Asp
            20                  25

<210> SEQ ID NO 8
```

```
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 8

Glu Trp Lys Arg Ala Ser Trp Glu Ile Trp Glu Leu Pro Asn Leu Asn
1               5                   10                  15

Asn Ala Gln Lys Arg Ala Phe Ile Ser Ser Leu Ser Asp
            20                  25

<210> SEQ ID NO 9
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 9

Glu Lys Tyr Lys Ala Met Thr Glu Ile Trp Ile Leu Pro Asn Leu Asn
1               5                   10                  15

Gln Arg Gln Lys Val Ala Phe Ile Gly Ser Leu Asp Asp
            20                  25

<210> SEQ ID NO 10
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 10

Glu Trp Arg Gly Ala Ala Gly Glu Ile Trp Ala Leu Pro Asn Leu Asn
1               5                   10                  15

Asn Arg Gln Lys Gly Ala Phe Ile Glu Ser Leu Pro Asp
            20                  25

<210> SEQ ID NO 11
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 11

Glu Arg Trp Glu Ala Thr Val Glu Ile Trp Asp Leu Pro Asn Leu Asn
1               5                   10                  15

Arg Asn Gln Lys Ala Ala Phe Ile Ala Ser Leu Gln Asp
            20                  25

<210> SEQ ID NO 12
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 12

Glu Lys Tyr Asn Ala Tyr Ala Glu Ile Trp Leu Leu Pro Asn Leu Asn
1               5                   10                  15

Arg Tyr Gln Lys Ala Ala Phe Ile Gly Ser Leu Ser Asp
            20                  25
```

```
<210> SEQ ID NO 13
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 13

Glu Arg Ser Val Ala Gln Lys Glu Ile Trp Glu Leu Pro Asn Leu Asn
1               5                   10                  15

Arg Trp Gln Ala Gly Ala Phe Ile Lys Ser Leu Tyr Asp
            20                  25

<210> SEQ ID NO 14
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 14

Glu Lys Met Asp Ala Met Gly Glu Ile Trp Asp Leu Pro Asn Leu Asn
1               5                   10                  15

Arg Gly Gln Ala Ser Ala Phe Ile Ala Ser Leu Gln Asp
            20                  25

<210> SEQ ID NO 15
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 15

Glu Lys Arg Asn Ala Gln Val Glu Ile Trp Thr Leu Pro Asn Leu Asn
1               5                   10                  15

Ser Lys Gln Arg Ala Ala Phe Ile Lys Ser Leu Tyr Asp
            20                  25

<210> SEQ ID NO 16
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 16

Glu Arg Arg Asp Ala Arg Phe Glu Ile Trp Glu Leu Pro Asn Leu Asn
1               5                   10                  15

Lys Tyr Gln Arg Ala Ala Phe Ile Ser Ser Leu Asp Asp
            20                  25

<210> SEQ ID NO 17
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 17

Glu Arg Ser Met Ala Arg Phe Glu Ile Trp Glu Leu Pro Asn Leu Asn
1               5                   10                  15

Arg Gly Gln Lys Ser Ala Phe Ile Ala Ser Leu Glu Asp
            20                  25
```

```
<210> SEQ ID NO 18
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 18

Glu Trp His Gly Ala Ala Ser Glu Ile Trp Glu Leu Pro Asn Leu Asn
1               5                   10                  15

Lys Ser Gln Lys Ser Ala Phe Ile Lys Ser Leu Pro Asp
            20                  25

<210> SEQ ID NO 19
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 19

Glu Trp Lys Gln Ala Ala Glu Glu Ile Trp Asp Leu Pro Asn Leu Asn
1               5                   10                  15

Arg Arg Gln Ala Gly Ala Phe Ile Thr Ser Leu Gln Asp
            20                  25

<210> SEQ ID NO 20
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 20

Glu Lys Val Gln Ala Ser Glu Glu Ile Trp Asn Leu Pro Asn Leu Asn
1               5                   10                  15

Arg Arg Gln Arg Ala Ala Phe Ile Gly Ser Leu Tyr Asp
            20                  25

<210> SEQ ID NO 21
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 21

Glu Arg Tyr Ser Ala Thr Val Glu Ile Trp Asp Leu Pro Asn Leu Asn
1               5                   10                  15

Thr Leu Gln Lys Ser Ala Phe Ile Gly Ser Leu Gln Asp
            20                  25

<210> SEQ ID NO 22
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 22

Glu Arg Tyr Ser Ala Tyr Tyr Glu Ile Trp Gln Leu Pro Asn Leu Asn
1               5                   10                  15

Arg Ile Gln Lys Ala Ala Phe Ile Ser Ser Leu Gln Asp
            20                  25
```

```
<210> SEQ ID NO 23
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 23

Glu Arg Tyr Arg Ala Tyr Phe Glu Ile Trp Gln Leu Pro Asn Leu Asn
1               5                   10                  15

Arg Leu Gln Lys Ala Ala Phe Ile Ser Ser Leu Glu Asp
            20                  25

<210> SEQ ID NO 24
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 24

Glu Lys Tyr Lys Ala Tyr Gly Glu Ile Trp Gln Leu Pro Asn Leu Asn
1               5                   10                  15

Arg Val Gln Lys Ala Ala Phe Ile Ala Ser Leu Ser Asp
            20                  25

<210> SEQ ID NO 25
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 25

Glu Arg Lys Gln Ala Thr Phe Glu Ile Trp Glu Leu Pro Asn Leu Asn
1               5                   10                  15

Gln Arg Gln Lys Ala Ala Phe Ile Lys Ser Leu Trp Asp
            20                  25

<210> SEQ ID NO 26
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 26

Glu Trp Lys Ile Ala Ala Gly Glu Ile Trp Gln Leu Pro Asn Leu Asn
1               5                   10                  15

Arg His Gln Lys Gly Ala Phe Ile Ser Ser Leu Tyr Asp
            20                  25

<210> SEQ ID NO 27
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 27

Glu Lys Tyr Lys Ala Tyr Val Glu Ile Trp Gln Leu Pro Asn Leu Asn
1               5                   10                  15

Arg Tyr Gln Arg Ala Ala Phe Ile Gly Ser Leu Gln Asp
```

20                  25

<210> SEQ ID NO 28
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 28

Glu Arg Lys Ala Ala Thr Phe Glu Ile Trp Glu Leu Pro Asn Leu Asn
1               5                   10                  15

Arg Ile Gln Lys Ala Ala Phe Ile Ala Ser Leu Phe Asp
                20                  25

<210> SEQ ID NO 29
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 29

Glu Lys Tyr Lys Ala Tyr Gly Glu Ile Trp Gln Leu Pro Asn Leu Asn
1               5                   10                  15

Arg Ile Gln Lys Ala Ala Phe Ile Ser Ser Leu Gln Asp
                20                  25

<210> SEQ ID NO 30
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 30

Glu Lys Arg Ile Ala Thr Trp Glu Ile Trp Gln Leu Pro Asn Leu Asn
1               5                   10                  15

Gln His Gln Lys Ala Ala Phe Ile Ser Ser Leu Trp Asp
                20                  25

<210> SEQ ID NO 31
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 31

Glu Lys Tyr Lys Ala Tyr Val Glu Ile Trp Gln Leu Pro Asn Leu Asn
1               5                   10                  15

Arg Gly Gln Lys Ala Ala Phe Ile Ser Ser Leu Gln Asp
                20                  25

<210> SEQ ID NO 32
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 32

Glu Arg Tyr Leu Ala Tyr Tyr Glu Ile Trp Gln Leu Pro Asn Leu Asn
1               5                   10                  15

Arg Thr Gln Lys Ala Ala Phe Ile Gly Ser Leu Gln Asp
            20                  25

<210> SEQ ID NO 33
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 33

Glu Arg Tyr Ile Ala Tyr Trp Glu Ile Trp Gln Leu Pro Asn Leu Asn
1               5                   10                  15

Arg Arg Gln Lys Ala Ala Phe Ile Ser Ser Leu Gln Asp
            20                  25

<210> SEQ ID NO 34
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 34

Glu Lys Tyr Arg Ala Tyr Gly Glu Ile Trp Gln Leu Pro Asn Leu Asn
1               5                   10                  15

Arg Gly Gln Lys Ala Ala Phe Ile Ala Ser Leu Gln Asp
            20                  25

<210> SEQ ID NO 35
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 35

Glu Lys Tyr Thr Ala Tyr Phe Glu Ile Trp Gln Leu Pro Asn Leu Asn
1               5                   10                  15

Val Arg Gln Lys Ala Ala Phe Ile Ser Ser Leu Gln Asp
            20                  25

<210> SEQ ID NO 36
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 36

Glu Arg Tyr Ser Ala Tyr Tyr Glu Ile Trp Gln Leu Pro Asn Leu Asn
1               5                   10                  15

Val Arg Gln Lys Ala Ala Phe Ile Gly Ser Leu Gln Asp
            20                  25

<210> SEQ ID NO 37
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 37

Glu Lys Tyr Ala Ala Tyr Gly Glu Ile Trp Gln Leu Pro Asn Leu Asn
1               5                   10                  15

Arg Ser Gln Lys Ala Ala Phe Ile Gly Ser Leu Ser Asp
            20                  25

<210> SEQ ID NO 38
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 38

Glu Arg Lys Arg Ala Thr Val Glu Ile Trp Glu Leu Pro Asn Leu Asn
1               5                   10                  15

Arg Leu Gln Arg Gly Ala Phe Ile Ala Ser Leu Trp Asp
            20                  25

<210> SEQ ID NO 39
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 39

Glu Trp Lys Gln Ala Ser Phe Glu Ile Trp Glu Leu Pro Asn Leu Asn
1               5                   10                  15

Arg Leu Gln Lys Ala Ala Phe Ile Gly Ser Leu Ala Asp
            20                  25

<210> SEQ ID NO 40
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 40

Glu Arg Lys His Ala Thr Val Glu Ile Trp Glu Leu Pro Asn Leu Asn
1               5                   10                  15

Arg Val Gln Lys Ala Ala Phe Ile Ser Ser Leu Trp Asp
            20                  25

<210> SEQ ID NO 41
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 41

Glu Lys Tyr Lys Ala Tyr Val Glu Ile Trp Gln Leu Pro Asn Leu Asn
1               5                   10                  15

Gln Arg Gln Lys Ala Ala Phe Ile Gly Ser Leu Ala Asp
            20                  25

<210> SEQ ID NO 42
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 42

Glu Lys Tyr Val Ala Tyr Gly Glu Ile Trp Gln Leu Pro Asn Leu Asn

```
              1               5                   10                  15
Arg Thr Gln Lys Ala Ala Phe Ile Ser Ser Leu Ser Asp
            20                  25
```

<210> SEQ ID NO 43
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 43

```
Glu Arg Tyr Ile Ala Tyr Tyr Glu Ile Trp Gln Leu Pro Asn Leu Asn
1               5                   10                  15
Arg Tyr Gln Lys Ala Ala Phe Ile Ala Ser Leu Ser Asp
            20                  25
```

<210> SEQ ID NO 44
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 44

```
Glu Lys Tyr Asn Ala Tyr Gly Glu Ile Trp Gln Leu Pro Asn Leu Asn
1               5                   10                  15
Val Arg Gln Lys Ala Ala Phe Ile Ser Ser Leu Ala Asp
            20                  25
```

<210> SEQ ID NO 45
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 45

```
Glu Arg Lys Ala Ala Thr Val Glu Ile Trp Glu Leu Pro Asn Leu Asn
1               5                   10                  15
Arg Val Gln Lys Ala Ala Phe Ile Lys Ser Leu Phe Asp
            20                  25
```

<210> SEQ ID NO 46
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 46

```
Glu Arg Tyr Val Ala Tyr Tyr Glu Ile Trp Glu Leu Pro Asn Leu Asn
1               5                   10                  15
Gln Arg Gln Lys Ala Ala Phe Ile Gly Ser Leu Gln Asp
            20                  25
```

<210> SEQ ID NO 47
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 47

```
Glu Arg Tyr Arg Ala Tyr Tyr Glu Ile Trp Gln Leu Pro Asn Leu Asn
1               5                   10                  15

Gln Arg Gln Lys Ala Ala Phe Ile Gly Ser Leu Ser Asp
            20                  25
```

<210> SEQ ID NO 48
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 48

```
Glu Trp Lys Ser Ala Ala Phe Glu Ile Trp Glu Leu Pro Asn Leu Asn
1               5                   10                  15

Arg Leu Gln Lys Ala Ala Phe Ile Arg Ser Leu Ser Asp
            20                  25
```

<210> SEQ ID NO 49
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 49

```
Glu Arg Lys Gln Ala Thr Phe Glu Ile Trp Glu Leu Pro Asn Leu Asn
1               5                   10                  15

Arg His Gln Lys Gly Ala Phe Ile Ala Ser Leu Trp Asp
            20                  25
```

<210> SEQ ID NO 50
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 50

```
Glu Trp Lys Ile Ala Ala Gly Glu Ile Trp Gln Leu Pro Asn Leu Asn
1               5                   10                  15

Arg Arg Gln Lys Ala Ala Phe Ile Ala Ser Leu Ser Asp
            20                  25
```

<210> SEQ ID NO 51
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 51

```
Glu Arg Tyr Leu Ala Tyr Tyr Glu Ile Trp Gln Leu Pro Asn Leu Asn
1               5                   10                  15

Arg Arg Gln Lys Ala Ala Phe Ile Gly Ser Leu Gln Asp
            20                  25
```

<210> SEQ ID NO 52
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 52

Glu Arg Tyr His Ala Tyr Tyr Glu Ile Trp Glu Leu Pro Asn Leu Asn
1               5                   10                  15

Arg Leu Gln Lys Ala Ala Phe Ile Ser Ser Leu Ser Asp
            20                  25

<210> SEQ ID NO 53
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 53

Glu Lys Tyr Lys Ala Tyr Ala Glu Ile Trp Gln Leu Pro Asn Leu Asn
1               5                   10                  15

Arg Thr Gln Lys Ala Ala Phe Ile Ser Ser Leu Gln Asp
            20                  25

<210> SEQ ID NO 54
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 54

Glu Arg Tyr Lys Ala Tyr Tyr Glu Ile Trp Gln Leu Pro Asn Leu Asn
1               5                   10                  15

Arg Gln Gln Lys Gly Ala Phe Ile Ser Ser Leu Gln Asp
            20                  25

<210> SEQ ID NO 55
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 55

Glu Arg Lys Leu Ala Thr Phe Glu Ile Trp Glu Leu Pro Asn Leu Asn
1               5                   10                  15

Thr Ser Gln Lys Gly Ala Phe Ile Ser Ser Leu Trp Asp
            20                  25

<210> SEQ ID NO 56
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 56

Glu Arg Tyr Val Ala Tyr Tyr Glu Ile Trp Gln Leu Pro Asn Leu Asn
1               5                   10                  15

Val Gln Gln Lys Ala Ala Phe Ile Ala Ser Leu Gln Asp
            20                  25

<210> SEQ ID NO 57
<211> LENGTH: 29
<212> TYPE: PRT
<213> ORGANISM: Artificial Sequence
<220> FEATURE:
<223> OTHER INFORMATION: Engineered polypeptide

```
<400> SEQUENCE: 57

Glu Arg Ser Ile Ala Ser Val Glu Ile Trp Glu Leu Pro Asn Leu Asn
1               5                   10                  15

Gln Arg Gln Lys Gly Ala Phe Ile Ala Ser Leu Trp Asp
            20                  25

<210> SEQ ID NO 58
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 58

Glu Arg Lys Gln Ala Ala Val Glu Ile Trp Glu Leu Pro Asn Leu Asn
1               5                   10                  15

Val Arg Gln Lys Ala Ala Phe Ile Arg Ser Leu Phe Asp
            20                  25

<210> SEQ ID NO 59
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 59

Glu Lys Lys Ile Ala Ala Phe Glu Ile Trp Glu Leu Pro Asn Leu Asn
1               5                   10                  15

Gln Trp Gln Lys Ala Ala Phe Ile Ala Ser Leu Phe Asp
            20                  25

<210> SEQ ID NO 60
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 60

Glu Arg Lys Ile Ala Thr Val Glu Ile Trp Glu Leu Pro Asn Leu Asn
1               5                   10                  15

Arg Ile Gln Lys Gly Ala Phe Ile Ala Ser Leu Trp Asp
            20                  25

<210> SEQ ID NO 61
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 61

Glu Lys Tyr Arg Ala Ala Gly Glu Ile Trp Glu Leu Pro Asn Leu Asn
1               5                   10                  15

Val Leu Gln Lys Ala Ala Phe Ile Lys Ser Leu Trp Asp
            20                  25

<210> SEQ ID NO 62
<211> LENGTH: 29
<212> TYPE: PRT
<213> ORGANISM: Artificial Sequence
<220> FEATURE:
<223> OTHER INFORMATION: Engineered polypeptide
```

```
<400> SEQUENCE: 62

Glu Arg Lys Ile Ala Ala Val Glu Ile Trp Glu Leu Pro Asn Leu Asn
1               5                   10                  15

Arg Tyr Gln Lys Ala Ala Phe Ile Lys Ser Leu Phe Asp
            20                  25

<210> SEQ ID NO 63
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 63

Glu Lys Arg Thr Ala Thr Trp Glu Ile Trp Gln Leu Pro Asn Leu Asn
1               5                   10                  15

Gln Arg Gln Arg Ala Ala Phe Ile Gly Ser Leu Trp Asp
            20                  25

<210> SEQ ID NO 64
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 64

Glu Arg Lys Thr Ala Thr Val Glu Ile Trp Glu Leu Pro Asn Leu Asn
1               5                   10                  15

Arg Arg Gln Lys Ala Ala Phe Ile Ala Ser Leu Trp Asp
            20                  25

<210> SEQ ID NO 65
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 65

Glu Arg Lys Gln Ala Ala Val Glu Ile Trp Glu Leu Pro Asn Leu Asn
1               5                   10                  15

Arg Ile Gln Lys Gly Ala Phe Ile Lys Ser Leu Trp Asp
            20                  25

<210> SEQ ID NO 66
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 66

Glu Arg Tyr Ile Ala Tyr Gly Glu Ile Trp Gln Leu Pro Asn Leu Asn
1               5                   10                  15

Arg Arg Gln Lys Ala Ala Phe Ile Gly Ser Leu Ser Asp
            20                  25

<210> SEQ ID NO 67
<211> LENGTH: 29
<212> TYPE: PRT
<213> ORGANISM: Artificial Sequence
<220> FEATURE:
```

<223> OTHER INFORMATION: Engineered polypeptide

<400> SEQUENCE: 67

Glu Arg Tyr Arg Ala Tyr Tyr Glu Ile Trp Gln Leu Pro Asn Leu Asn
1               5                   10                  15

Arg Thr Gln Lys Val Ala Phe Ile Gly Ser Leu Gln Asp
            20                  25

<210> SEQ ID NO 68
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 68

Glu Arg Arg Leu Ala Tyr Trp Glu Ile Trp Gln Leu Pro Asn Leu Asn
1               5                   10                  15

Thr Thr Gln Lys Ala Ala Phe Ile Gly Ser Leu Gln Asp
            20                  25

<210> SEQ ID NO 69
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 69

Glu Arg Arg Arg Ala Tyr Tyr Glu Ile Trp Gln Leu Pro Asn Leu Asn
1               5                   10                  15

Arg Ile Gln Lys Ala Ala Phe Ile Gly Ser Leu Gln Asp
            20                  25

<210> SEQ ID NO 70
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 70

Glu Arg Arg Leu Ala Tyr Tyr Glu Ile Trp Glu Leu Pro Asn Leu Asn
1               5                   10                  15

Val Ala Gln Lys Ala Ala Phe Ile Gly Ser Leu Gln Asp
            20                  25

<210> SEQ ID NO 71
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 71

Glu Arg Tyr Leu Ala Tyr Tyr Glu Ile Trp Glu Leu Pro Asn Leu Asn
1               5                   10                  15

Val Arg Gln Lys Ala Ala Phe Ile Gly Ser Leu Gln Asp
            20                  25

<210> SEQ ID NO 72
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 72

Glu Arg Tyr Ala Ala Tyr Tyr Glu Ile Trp Gln Leu Pro Asn Leu Asn
1               5                   10                  15

Ser Arg Gln Lys Ala Ala Phe Ile Gly Ser Leu Ser Asp
            20                  25

<210> SEQ ID NO 73
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 73

Glu Arg Tyr Leu Ala Tyr Tyr Glu Ile Trp Gln Leu Pro Asn Leu Asn
1               5                   10                  15

Gln Leu Gln Lys Ala Ala Phe Ile Gly Ser Leu Ala Asp
            20                  25

<210> SEQ ID NO 74
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 74

Glu Arg Tyr His Ala Tyr Tyr Glu Ile Trp Gln Leu Pro Asn Leu Asn
1               5                   10                  15

Ser Trp Gln Lys Ala Ala Phe Ile Gly Ser Leu Gln Asp
            20                  25

<210> SEQ ID NO 75
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 75

Glu Arg Tyr His Ala Tyr Tyr Glu Ile Trp Gln Leu Pro Asn Leu Asn
1               5                   10                  15

Ser Ala Gln Lys Ala Ala Phe Ile Gly Ser Leu Gln Asp
            20                  25

<210> SEQ ID NO 76
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 76

Glu Arg Tyr Glu Ala Tyr Tyr Glu Ile Trp Gln Leu Pro Asn Leu Asn
1               5                   10                  15

Ser Val Gln Lys Ala Ala Phe Ile Gly Ser Leu Gln Asp
            20                  25

<210> SEQ ID NO 77
<211> LENGTH: 29
<212> TYPE: PRT

```
<213> ORGANISM: Artificial Sequence
<220> FEATURE:
<223> OTHER INFORMATION: Engineered polypeptide

<400> SEQUENCE: 77

Glu Arg Tyr His Ala Tyr Tyr Glu Ile Trp Gln Leu Pro Asn Leu Asn
1               5                   10                  15

Arg Arg Gln Lys Ala Ala Phe Ile Gly Ser Leu Gln Asp
            20                  25

<210> SEQ ID NO 78
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 78

Glu Arg Tyr Thr Ala Tyr Tyr Glu Ile Trp Gln Leu Pro Asn Leu Asn
1               5                   10                  15

Arg Ala Gln Lys Ala Ala Phe Ile Gly Ser Leu Gln Asp
            20                  25

<210> SEQ ID NO 79
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 79

Glu Arg Tyr Ser Ala Tyr Tyr Glu Ile Trp Gln Leu Pro Asn Leu Asn
1               5                   10                  15

Arg Ala Gln Lys Ala Ala Phe Ile Gly Ser Leu Ser Asp
            20                  25

<210> SEQ ID NO 80
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 80

Glu Arg Tyr Ser Ala Tyr Tyr Glu Ile Trp Glu Leu Pro Asn Leu Asn
1               5                   10                  15

Arg Ala Gln Lys Ala Ala Phe Ile Gly Ser Leu Ser Asp
            20                  25

<210> SEQ ID NO 81
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 81

Glu Arg Tyr His Ala Tyr Tyr Glu Ile Trp Gln Leu Pro Asn Leu Asn
1               5                   10                  15

Arg Ala Gln Lys Ala Ala Phe Ile Gly Ser Leu Tyr Asp
            20                  25

<210> SEQ ID NO 82
<211> LENGTH: 29
```

```
<212> TYPE: PRT
<213> ORGANISM: Artificial Sequence
<220> FEATURE:
<223> OTHER INFORMATION: Engineered polypeptide

<400> SEQUENCE: 82

Glu Arg Tyr Ser Ala Tyr Val Glu Ile Trp Gln Leu Pro Asn Leu Asn
1               5                   10                  15

Arg Gly Gln Lys Ala Ala Phe Ile Gly Ser Leu Tyr Asp
            20                  25

<210> SEQ ID NO 83
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 83

Glu Arg Tyr Ser Ala Tyr Phe Glu Ile Trp Gln Leu Pro Asn Leu Asn
1               5                   10                  15

Arg Leu Gln Lys Ala Ala Phe Ile Gly Ser Leu Gln Asp
            20                  25

<210> SEQ ID NO 84
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 84

Glu Arg Tyr Asn Ala Tyr Phe Glu Ile Trp Gln Leu Pro Asn Leu Asn
1               5                   10                  15

Arg Tyr Gln Lys Ser Ala Phe Ile Gly Ser Leu Gln Asp
            20                  25

<210> SEQ ID NO 85
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 85

Glu Arg Tyr Ala Ala Tyr Phe Glu Ile Trp Gln Leu Pro Asn Leu Asn
1               5                   10                  15

Val Ala Gln Lys Ala Ala Phe Ile Gly Ser Leu Gln Asp
            20                  25

<210> SEQ ID NO 86
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 86

Glu Arg Tyr Gln Ala Tyr Phe Glu Ile Trp Gln Leu Pro Asn Leu Asn
1               5                   10                  15

Gln Trp Gln Lys Ala Ala Phe Ile Gly Ser Leu Gln Asp
            20                  25

<210> SEQ ID NO 87
```

```
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 87

Glu Arg Tyr Lys Ala Tyr Trp Glu Ile Trp Gln Leu Pro Asn Leu Asn
1               5                   10                  15

Gln Gly Gln Lys Ala Ala Phe Ile Gly Ser Leu Gln Asp
            20                  25

<210> SEQ ID NO 88
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 88

Glu Arg Tyr Ile Ala Tyr Gly Glu Ile Trp Gln Leu Pro Asn Leu Asn
1               5                   10                  15

Val Gly Gln Lys Ala Ala Phe Ile Gly Ser Leu Gln Asp
            20                  25

<210> SEQ ID NO 89
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 89

Glu Arg Tyr Arg Ala Tyr Val Glu Ile Trp Gln Leu Pro Asn Leu Asn
1               5                   10                  15

Arg Val Gln Lys Ala Ala Phe Ile Gly Ser Leu Gln Asp
            20                  25

<210> SEQ ID NO 90
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 90

Glu Arg Tyr Lys Ala Tyr Val Glu Ile Trp Gln Leu Pro Asn Leu Asn
1               5                   10                  15

Arg Thr Gln Lys Ala Ala Phe Ile Gly Ser Leu Gln Asp
            20                  25

<210> SEQ ID NO 91
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 91

Glu Lys Tyr Glu Ala Tyr Gly Glu Ile Trp Glu Leu Pro Asn Leu Asn
1               5                   10                  15

Arg Ser Gln Lys Ala Ala Phe Ile Gly Ser Leu Glu Asp
            20                  25
```

```
<210> SEQ ID NO 92
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 92

Glu Lys Tyr Gln Ala Tyr Gly Glu Ile Trp Gln Leu Pro Asn Leu Asn
1               5                   10                  15

Arg Ser Gln Lys Ala Ala Phe Ile Thr Ser Leu Glu Asp
            20                  25

<210> SEQ ID NO 93
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 93

Glu Lys Tyr Ala Ala Tyr Gly Glu Ile Trp Leu Leu Pro Asn Leu Asn
1               5                   10                  15

Arg Ile Gln Lys Ala Ala Phe Ile Gly Ser Leu Gln Asp
            20                  25

<210> SEQ ID NO 94
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 94

Glu Lys Tyr Lys Ala Tyr Gly Glu Ile Trp Glu Leu Pro Asn Leu Asn
1               5                   10                  15

Arg Arg Gln Lys Val Ala Phe Ile Ser Ser Leu Ser Asp
            20                  25

<210> SEQ ID NO 95
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 95

Glu Lys Tyr Lys Ala Tyr Gly Glu Ile Trp Glu Leu Pro Asn Leu Asn
1               5                   10                  15

Arg Ser Gln Lys Ala Ala Phe Ile Ala Ser Leu Ser Asp
            20                  25

<210> SEQ ID NO 96
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 96

Glu Lys Tyr Lys Ala Tyr Gly Glu Ile Trp Gln Leu Pro Asn Leu Asn
1               5                   10                  15

Gln Arg Gln Lys Ala Ala Phe Ile Ala Ser Leu Ser Asp
            20                  25
```

<210> SEQ ID NO 97
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 97

```
Glu Lys Tyr Lys Ala Tyr Gly Glu Ile Trp Gln Leu Pro Asn Leu Asn
1               5                   10                  15

Arg Ser Gln Lys Ala Ala Phe Ile Ser Ser Leu Gln Asp
            20                  25
```

<210> SEQ ID NO 98
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 98

```
Glu Lys Tyr Lys Ala Tyr Gly Glu Ile Trp Gln Leu Pro Asn Leu Asn
1               5                   10                  15

Arg Arg Gln Lys Ala Ala Phe Ile Ser Ser Leu Ala Asp
            20                  25
```

<210> SEQ ID NO 99
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 99

```
Glu Lys Tyr Asn Ala Tyr Gly Glu Ile Trp Gln Leu Pro Asn Leu Asn
1               5                   10                  15

Arg Gly Gln Lys Ala Ala Phe Ile Ser Ser Leu Ser Asp
            20                  25
```

<210> SEQ ID NO 100
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 100

```
Glu Lys Tyr Val Ala Tyr Ala Glu Ile Trp Gln Leu Pro Asn Leu Asn
1               5                   10                  15

Arg Val Gln Lys Ala Ala Phe Ile Gly Ser Leu Ser Asp
            20                  25
```

<210> SEQ ID NO 101
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 101

```
Glu Lys Tyr Gln Ala Tyr Gly Glu Ile Trp Gln Leu Pro Asn Leu Asn
1               5                   10                  15

Arg Val Gln Lys Ala Ala Phe Ile Gly Ser Leu Ser Asp
            20                  25
```

```
<210> SEQ ID NO 102
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 102

Glu Lys Tyr His Ala Tyr Gly Glu Ile Trp Gln Leu Pro Asn Leu Asn
1               5                   10                  15

Arg Ile Gln Lys Ala Ala Phe Ile Ala Ser Leu Gln Asp
            20                  25

<210> SEQ ID NO 103
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 103

Glu Lys Tyr Thr Ala Tyr Val Glu Ile Trp Gln Leu Pro Asn Leu Asn
1               5                   10                  15

Arg Tyr Gln Arg Ala Ala Phe Ile Ala Ser Leu Ser Asp
            20                  25

<210> SEQ ID NO 104
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 104

Glu Lys Tyr Lys Ala Tyr Val Glu Ile Trp Gln Leu Pro Asn Leu Asn
1               5                   10                  15

Arg Gly Gln Lys Ala Ala Phe Ile Gly Ser Leu Ser Asp
            20                  25

<210> SEQ ID NO 105
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 105

Glu Lys Tyr Val Ala Tyr Val Glu Ile Trp Gln Leu Pro Asn Leu Asn
1               5                   10                  15

Arg Thr Gln Lys Ala Ala Phe Ile Ala Ser Leu Glu Asp
            20                  25

<210> SEQ ID NO 106
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 106

Glu Lys Tyr Ile Ala Tyr Val Glu Ile Trp Gln Leu Pro Asn Leu Asn
1               5                   10                  15

Arg Thr Gln Lys Ala Ala Phe Ile Ala Ser Leu Ser Asp
```

20                  25

<210> SEQ ID NO 107
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 107

Glu Lys Tyr Lys Ala Tyr Ala Glu Ile Trp Gln Leu Pro Asn Leu Asn
1               5                   10                  15

Arg Ala Gln Lys Ala Ala Phe Ile Gly Ser Leu Tyr Asp
            20                  25

<210> SEQ ID NO 108
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 108

Glu Lys Tyr Thr Ala Tyr Gly Glu Ile Trp Gln Leu Pro Asn Leu Asn
1               5                   10                  15

Val Arg Gln Lys Ala Ala Phe Ile Ser Ser Leu Ser Asp
            20                  25

<210> SEQ ID NO 109
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 109

Glu Lys Tyr Thr Ala Tyr Gly Glu Ile Trp Gln Leu Pro Asn Leu Asn
1               5                   10                  15

Gln Arg Gln Lys Ala Ala Phe Ile Ser Ser Leu Gln Asp
            20                  25

<210> SEQ ID NO 110
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 110

Glu Lys Tyr Thr Ala Tyr Phe Glu Ile Trp Gln Leu Pro Asn Leu Asn
1               5                   10                  15

Gln Gly Gln Lys Ala Ala Phe Ile Gly Ser Leu Gln Asp
            20                  25

<210> SEQ ID NO 111
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 111

Glu Lys Tyr Gln Ala Tyr Val Glu Ile Trp Gln Leu Pro Asn Leu Asn
1               5                   10                  15

```
Gln Arg Gln Lys Ala Ala Phe Ile Gly Ser Leu Ala Asp
            20                  25
```

```
<210> SEQ ID NO 112
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 112

Glu Lys Tyr Ala Ala Tyr Val Glu Ile Trp Gln Leu Pro Asn Leu Asn
1               5                   10                  15

Gln Arg Gln Lys Ala Ala Phe Ile Gly Ser Leu Gln Asp
            20                  25
```

```
<210> SEQ ID NO 113
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 113

Glu Lys Tyr Val Ala Tyr Val Glu Ile Trp Gln Leu Pro Asn Leu Asn
1               5                   10                  15

Thr Ser Gln Lys Ala Ala Phe Ile Gly Ser Leu Gln Asp
            20                  25
```

```
<210> SEQ ID NO 114
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 114

Glu Lys Tyr Gln Ala Tyr Ala Glu Ile Trp Gln Leu Pro Asn Leu Asn
1               5                   10                  15

Val Arg Gln Lys Ser Ala Phe Ile Gly Ser Leu Gln Asp
            20                  25
```

```
<210> SEQ ID NO 115
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 115

Glu Lys Tyr Gln Ala Tyr Tyr Glu Ile Trp Glu Leu Pro Asn Leu Asn
1               5                   10                  15

Val Gln Gln Lys Ser Ala Phe Ile Thr Ser Leu Gln Asp
            20                  25
```

```
<210> SEQ ID NO 116
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 116

Glu Lys Tyr His Ala Tyr Tyr Glu Ile Trp Gln Leu Pro Asn Leu Asn
1               5                   10                  15
```

```
Val His Gln Lys Ala Ala Phe Ile Arg Ser Leu Ala Asp
            20                  25

<210> SEQ ID NO 117
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 117

Glu Lys Tyr Gln Ala Tyr Tyr Glu Ile Trp Gln Leu Pro Asn Leu Asn
1               5                   10                  15

Val Ala Gln Lys Ala Ala Phe Ile Arg Ser Leu Ser Asp
            20                  25

<210> SEQ ID NO 118
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 118

Glu Lys Tyr Thr Ala Tyr Tyr Glu Ile Trp Gln Leu Pro Asn Leu Asn
1               5                   10                  15

Arg Thr Gln Lys Ala Ala Phe Ile Gly Ser Leu Ser Asp
            20                  25

<210> SEQ ID NO 119
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 119

Glu Arg Tyr Arg Ala Tyr Tyr Glu Ile Trp Gln Leu Pro Asn Leu Asn
1               5                   10                  15

Arg Gln Gln Lys Gly Ala Phe Ile Ala Ser Leu Gln Asp
            20                  25

<210> SEQ ID NO 120
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 120

Glu Lys Tyr Lys Ala Tyr Tyr Glu Ile Trp Gln Leu Pro Asn Leu Asn
1               5                   10                  15

Arg Ser Gln Lys Gly Ala Phe Ile Gly Ser Leu Gln Asp
            20                  25

<210> SEQ ID NO 121
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 121

Glu Lys Tyr Ile Ala Tyr Tyr Glu Ile Trp Gln Leu Pro Asn Leu Asn
```

```
                1               5                   10                  15
Arg Ser Gln Lys Gly Ala Phe Ile Gly Ser Leu Gln Asp
            20                  25

<210> SEQ ID NO 122
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 122

Glu Arg Tyr Lys Ala Tyr Tyr Glu Ile Trp Gln Leu Pro Asn Leu Asn
1               5                   10                  15

Arg Gln Gln Lys Ala Ala Phe Ile Gly Ser Leu Ala Asp
            20                  25

<210> SEQ ID NO 123
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 123

Glu Arg Tyr Leu Ala Tyr Tyr Glu Ile Trp Gln Leu Pro Asn Leu Asn
1               5                   10                  15

Gln Phe Gln Lys Ala Ala Phe Ile Ala Ser Leu Gln Asp
            20                  25

<210> SEQ ID NO 124
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 124

Glu Arg Tyr Leu Ala Tyr Tyr Glu Ile Trp Gln Leu Pro Asn Leu Asn
1               5                   10                  15

Arg Glu Gln Lys Ala Ala Phe Ile Ala Ser Leu Gln Asp
            20                  25

<210> SEQ ID NO 125
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 125

Glu Arg Tyr Val Ala Tyr Gly Glu Ile Trp Gln Leu Pro Asn Leu Asn
1               5                   10                  15

Arg Tyr Gln Lys Ala Ala Phe Ile Ala Ser Leu Gln Asp
            20                  25

<210> SEQ ID NO 126
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 126
```

```
Glu Arg Tyr Ile Ala Tyr Tyr Glu Ile Trp Gln Leu Pro Asn Leu Asn
1               5                   10                  15

Arg Ala Gln Lys Ala Ala Phe Ile Ala Ser Leu Gln Asp
            20                  25
```

<210> SEQ ID NO 127
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 127

```
Glu Arg Tyr Gln Ala Tyr Tyr Glu Ile Trp Gln Leu Pro Asn Leu Asn
1               5                   10                  15

Arg Ile Gln Lys Ala Ala Phe Ile Lys Ser Leu Gln Asp
            20                  25
```

<210> SEQ ID NO 128
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 128

```
Glu Arg Tyr Thr Ala Tyr Tyr Glu Ile Trp Gln Leu Pro Asn Leu Asn
1               5                   10                  15

Thr Gln Gln Lys Ala Ala Phe Ile Arg Ser Leu Glu Asp
            20                  25
```

<210> SEQ ID NO 129
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 129

```
Glu Arg Tyr Gln Ala Tyr Tyr Glu Ile Trp Gln Leu Pro Asn Leu Asn
1               5                   10                  15

Thr Ile Gln Lys Ala Ala Phe Ile Arg Ser Leu Gln Asp
            20                  25
```

<210> SEQ ID NO 130
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 130

```
Glu Arg Tyr Ala Ala Tyr Ala Glu Ile Trp Gln Leu Pro Asn Leu Asn
1               5                   10                  15

Arg Trp Gln Lys Ala Ala Phe Ile Ser Ser Leu Gln Asp
            20                  25
```

<210> SEQ ID NO 131
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 131

Glu Arg Tyr Arg Ala Tyr Ala Glu Ile Trp Gln Leu Pro Asn Leu Asn
1               5                   10                  15

Arg Trp Gln Lys Ala Ala Phe Ile Ala Ser Leu Gln Asp
            20                  25

<210> SEQ ID NO 132
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 132

Glu Arg Tyr Arg Ala Tyr Ala Glu Ile Trp Gln Leu Pro Asn Leu Asn
1               5                   10                  15

Arg Ile Gln Lys Ala Ala Phe Ile Gly Ser Leu Glu Asp
            20                  25

<210> SEQ ID NO 133
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 133

Glu Arg Tyr His Ala Tyr Ala Glu Ile Trp Gln Leu Pro Asn Leu Asn
1               5                   10                  15

Arg Ile Gln Lys Ala Ala Phe Ile Gly Ser Leu Gln Asp
            20                  25

<210> SEQ ID NO 134
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 134

Glu Arg Tyr Arg Ala Tyr Tyr Glu Ile Trp Gln Leu Pro Asn Leu Asn
1               5                   10                  15

Arg Tyr Gln Lys Ala Ala Phe Ile Ala Ser Leu Ser Asp
            20                  25

<210> SEQ ID NO 135
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 135

Glu Arg Tyr Thr Ala Tyr Tyr Glu Ile Trp Gln Leu Pro Asn Leu Asn
1               5                   10                  15

Arg Val Gln Lys Ala Ala Phe Ile Ala Ser Leu Ser Asp
            20                  25

<210> SEQ ID NO 136
<211> LENGTH: 29
<212> TYPE: PRT
<213> ORGANISM: Artificial Sequence
<220> FEATURE:
<223> OTHER INFORMATION: Engineered polypeptide

```
<400> SEQUENCE: 136

Glu Arg Tyr His Ala Tyr Tyr Glu Ile Trp Gln Leu Pro Asn Leu Asn
1               5                   10                  15

Arg Thr Gln Lys Ala Ala Phe Ile Ala Ser Leu Ser Asp
            20                  25

<210> SEQ ID NO 137
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 137

Glu Arg Tyr Val Ala Tyr Tyr Glu Ile Trp Gln Leu Pro Asn Leu Asn
1               5                   10                  15

Arg Arg Gln Lys Ala Ala Phe Ile Ser Ser Leu Ser Asp
            20                  25

<210> SEQ ID NO 138
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 138

Glu Arg Tyr Leu Ala Tyr Phe Glu Ile Trp Gln Leu Pro Asn Leu Asn
1               5                   10                  15

Arg His Gln Lys Gly Ala Phe Ile Ala Ser Leu Glu Asp
            20                  25

<210> SEQ ID NO 139
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 139

Glu Arg Tyr Thr Ala Tyr Phe Glu Ile Trp Gln Leu Pro Asn Leu Asn
1               5                   10                  15

Arg Trp Gln Lys Gly Ala Phe Ile Ala Ser Leu Glu Asp
            20                  25

<210> SEQ ID NO 140
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 140

Glu Arg Tyr Ala Ala Tyr Phe Glu Ile Trp Gln Leu Pro Asn Leu Asn
1               5                   10                  15

Arg Leu Gln Lys Ala Ala Phe Ile Ser Ser Leu Glu Asp
            20                  25

<210> SEQ ID NO 141
<211> LENGTH: 29
<212> TYPE: PRT
<213> ORGANISM: Artificial Sequence
<220> FEATURE:
<223> OTHER INFORMATION: Engineered polypeptide
```

-continued

```
<400> SEQUENCE: 141

Glu Arg Tyr Val Ala Tyr Phe Glu Ile Trp Gln Leu Pro Asn Leu Asn
1               5                   10                  15

Arg Ser Gln Lys Ala Ala Phe Ile Ser Ser Leu Glu Asp
            20                  25

<210> SEQ ID NO 142
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 142

Glu Arg Tyr Gly Ala Tyr Phe Glu Ile Trp Gln Leu Pro Asn Leu Asn
1               5                   10                  15

Arg Thr Gln Lys Ala Ala Phe Ile Ala Ser Leu Ala Asp
            20                  25

<210> SEQ ID NO 143
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 143

Glu Lys Tyr Ile Ala Tyr Trp Glu Ile Trp Gln Leu Pro Asn Leu Asn
1               5                   10                  15

Arg Glu Gln Lys Ala Ala Phe Ile Ser Ser Leu Gln Asp
            20                  25

<210> SEQ ID NO 144
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 144

Glu Arg Tyr Ile Ala Tyr Ala Glu Ile Trp Gln Leu Pro Asn Leu Asn
1               5                   10                  15

Arg Arg Gln Lys Ala Ala Phe Ile Ala Ser Leu Glu Asp
            20                  25

<210> SEQ ID NO 145
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 145

Glu Arg Tyr Ile Ala Tyr Trp Glu Ile Trp Gln Leu Pro Asn Leu Asn
1               5                   10                  15

Gln Arg Gln Lys Ala Ala Phe Ile Ala Ser Leu Ala Asp
            20                  25

<210> SEQ ID NO 146
<211> LENGTH: 29
<212> TYPE: PRT
<213> ORGANISM: Artificial Sequence
<220> FEATURE:
```

<223> OTHER INFORMATION: Engineered polypeptide

<400> SEQUENCE: 146

Glu Arg Tyr Ile Ala Tyr Trp Glu Ile Trp Gln Leu Pro Asn Leu Asn
1               5                   10                  15

Arg Leu Gln Lys Ser Ala Phe Ile Ala Ser Leu Gln Asp
            20                  25

<210> SEQ ID NO 147
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 147

Glu Arg Tyr His Ala Tyr Trp Glu Ile Trp Gln Leu Pro Asn Leu Asn
1               5                   10                  15

Arg Ala Gln Lys Ala Ala Phe Ile Arg Ser Leu Gln Asp
            20                  25

<210> SEQ ID NO 148
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 148

Glu Arg Tyr Asn Ala Tyr Trp Glu Ile Trp Gln Leu Pro Asn Leu Asn
1               5                   10                  15

Arg Leu Gln Lys Ala Ala Phe Ile Arg Ser Leu Gln Asp
            20                  25

<210> SEQ ID NO 149
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 149

Glu Arg Tyr Thr Ala Tyr Gly Glu Ile Trp Glu Leu Pro Asn Leu Asn
1               5                   10                  15

Arg Val Gln Arg Ala Ala Phe Ile Ala Ser Leu Ala Asp
            20                  25

<210> SEQ ID NO 150
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 150

Glu Arg Tyr Thr Ala Tyr Gly Glu Ile Trp Glu Leu Pro Asn Leu Asn
1               5                   10                  15

Arg Leu Gln Lys Ala Ala Phe Ile Gly Ser Leu Ala Asp
            20                  25

<210> SEQ ID NO 151
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 151

Glu Arg Tyr His Ala Tyr Gly Glu Ile Trp Glu Leu Pro Asn Leu Asn
1               5                   10                  15

Arg Arg Gln Lys Ala Ala Phe Ile Thr Ser Leu Ala Asp
            20                  25

<210> SEQ ID NO 152
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 152

Glu Arg Tyr Lys Ala Tyr Gly Glu Ile Trp Gln Leu Pro Asn Leu Asn
1               5                   10                  15

Arg Leu Gln Lys Ala Ala Phe Ile Gly Ser Leu Ala Asp
            20                  25

<210> SEQ ID NO 153
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 153

Glu Arg Tyr Gln Ala Tyr Gly Glu Ile Trp Gln Leu Pro Asn Leu Asn
1               5                   10                  15

Arg Leu Gln Lys Ala Ala Phe Ile Gly Ser Leu Ala Asp
            20                  25

<210> SEQ ID NO 154
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 154

Glu Arg Tyr Val Ala Tyr Gly Glu Ile Trp Gln Leu Pro Asn Leu Asn
1               5                   10                  15

Arg Leu Gln Lys Ala Ala Phe Ile Ser Ser Leu Ala Asp
            20                  25

<210> SEQ ID NO 155
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 155

Glu Arg Tyr Ile Ala Tyr Gly Glu Ile Trp Glu Leu Pro Asn Leu Asn
1               5                   10                  15

Arg Leu Gln Lys Ala Ala Phe Ile Gly Ser Leu Ser Asp
            20                  25

<210> SEQ ID NO 156
<211> LENGTH: 29
<212> TYPE: PRT

```
<213> ORGANISM: Artificial Sequence
<220> FEATURE:
<223> OTHER INFORMATION: Engineered polypeptide

<400> SEQUENCE: 156

Glu Arg Tyr Gln Ala Tyr Gly Glu Ile Trp Gln Leu Pro Asn Leu Asn
1               5                   10                  15

Arg Arg Gln Lys Ala Ala Phe Ile Ser Ser Leu Gln Asp
            20                  25

<210> SEQ ID NO 157
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 157

Glu Arg Arg Gln Ala Tyr Phe Glu Ile Trp Glu Leu Pro Asn Leu Asn
1               5                   10                  15

Arg Tyr Gln Lys Ala Ala Phe Ile Ser Ser Leu Gln Asp
            20                  25

<210> SEQ ID NO 158
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 158

Glu Arg Tyr Arg Ala Tyr Val Glu Ile Trp Glu Leu Pro Asn Leu Asn
1               5                   10                  15

Arg Ile Gln Lys Val Ala Phe Ile Ala Ser Leu Gln Asp
            20                  25

<210> SEQ ID NO 159
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 159

Glu Lys Tyr Thr Ala Tyr Gly Glu Ile Trp Glu Leu Pro Asn Leu Asn
1               5                   10                  15

Arg Ile Gln Lys Val Ala Phe Ile Ala Ser Leu Gln Asp
            20                  25

<210> SEQ ID NO 160
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 160

Glu Lys Tyr Ala Ala Tyr Val Glu Ile Trp Glu Leu Pro Asn Leu Asn
1               5                   10                  15

Arg Arg Gln Lys Ala Ala Phe Ile Ala Ser Leu Gln Asp
            20                  25

<210> SEQ ID NO 161
<211> LENGTH: 29
```

```
<212> TYPE: PRT
<213> ORGANISM: Artificial Sequence
<220> FEATURE:
<223> OTHER INFORMATION: Engineered polypeptide

<400> SEQUENCE: 161

Glu Arg Tyr Arg Ala Tyr Val Glu Ile Trp Glu Leu Pro Asn Leu Asn
1               5                   10                  15

Arg Trp Gln Lys Ala Ala Phe Ile Arg Ser Leu Gln Asp
            20                  25

<210> SEQ ID NO 162
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 162

Glu Arg Tyr Arg Ala Tyr Phe Glu Ile Trp Glu Leu Pro Asn Leu Asn
1               5                   10                  15

Arg Ala Gln Lys Ala Ala Phe Ile Ser Ser Leu Ser Asp
            20                  25

<210> SEQ ID NO 163
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 163

Glu Arg Tyr Gln Ala Tyr Phe Glu Ile Trp Gln Leu Pro Asn Leu Asn
1               5                   10                  15

Arg Leu Gln Ala Gly Ala Phe Ile Ala Ser Leu Ser Asp
            20                  25

<210> SEQ ID NO 164
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 164

Glu Lys Tyr Gln Ala Tyr Val Glu Ile Trp Gln Leu Pro Asn Leu Asn
1               5                   10                  15

Arg Leu Gln Lys Gly Ala Phe Ile Ala Ser Leu Ser Asp
            20                  25

<210> SEQ ID NO 165
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 165

Glu Lys Tyr Ala Ala Tyr Tyr Glu Ile Trp Gln Leu Pro Asn Leu Asn
1               5                   10                  15

Arg Ser Gln Lys Gly Ala Phe Ile Ala Ser Leu Ser Asp
            20                  25

<210> SEQ ID NO 166
```

-continued

```
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 166

Glu Lys Tyr Gln Ala Tyr Tyr Glu Ile Trp Glu Leu Pro Asn Leu Asn
1               5                   10                  15

Arg Gly Gln Lys Ala Ala Phe Ile Ala Ser Leu Ser Asp
            20                  25

<210> SEQ ID NO 167
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 167

Glu Lys Tyr Asn Ala Tyr Phe Glu Ile Trp Gln Leu Pro Asn Leu Asn
1               5                   10                  15

Arg Leu Gln Lys Ala Ala Phe Ile Thr Ser Leu Ser Asp
            20                  25

<210> SEQ ID NO 168
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 168

Glu Lys Tyr Ser Ala Tyr Phe Glu Ile Trp Gln Leu Pro Asn Leu Asn
1               5                   10                  15

Thr Ser Gln Lys Ala Ala Phe Ile Ala Ser Leu Ser Asp
            20                  25

<210> SEQ ID NO 169
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 169

Glu Arg Tyr Asn Ala Tyr Phe Glu Ile Trp Glu Leu Pro Asn Leu Asn
1               5                   10                  15

Val Arg Gln Lys Ala Ala Phe Ile Arg Ser Leu Ser Asp
            20                  25

<210> SEQ ID NO 170
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 170

Glu Lys Tyr Glu Ala Tyr Phe Glu Ile Trp Glu Leu Pro Asn Leu Asn
1               5                   10                  15

Ser Arg Gln Lys Ala Ala Phe Ile Gly Ser Leu Ser Asp
            20                  25
```

```
<210> SEQ ID NO 171
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 171

Glu Arg Tyr Arg Ala Tyr Trp Glu Ile Trp Glu Leu Pro Asn Leu Asn
1               5                   10                  15

Gln Gln Gln Lys Val Ala Phe Ile Arg Ser Leu Tyr Asp
            20                  25

<210> SEQ ID NO 172
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 172

Glu Arg Tyr Asn Ala Tyr Trp Glu Ile Trp Glu Leu Pro Asn Leu Asn
1               5                   10                  15

Gln Gly Gln Lys Val Ala Phe Ile Arg Ser Leu Gln Asp
            20                  25

<210> SEQ ID NO 173
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 173

Glu Arg Arg His Ala Tyr Gly Glu Ile Trp Gln Leu Pro Asn Leu Asn
1               5                   10                  15

Gln Arg Gln Lys Val Ala Phe Ile Ser Ser Leu Gln Asp
            20                  25

<210> SEQ ID NO 174
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 174

Glu Lys Tyr Val Ala Thr Trp Glu Ile Trp Glu Leu Pro Asn Leu Asn
1               5                   10                  15

Arg Ala Gln Lys Val Ala Phe Ile Gly Ser Leu Trp Asp
            20                  25

<210> SEQ ID NO 175
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 175

Glu Arg Arg Ile Ala Arg Trp Glu Ile Trp Glu Leu Pro Asn Leu Asn
1               5                   10                  15

Arg Leu Gln Lys Val Ala Phe Ile Gly Ser Leu Glu Asp
            20                  25
```

<210> SEQ ID NO 176
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 176

Glu Lys Tyr Lys Ala Ala Gly Glu Ile Trp Gln Leu Pro Asn Leu Asn
1               5                   10                  15

Arg Gly Gln Lys Val Ala Phe Ile Gly Ser Leu Glu Asp
            20                  25

<210> SEQ ID NO 177
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 177

Glu Lys Tyr Leu Ala Tyr Gly Glu Ile Trp Gln Leu Pro Asn Leu Asn
1               5                   10                  15

Arg His Gln Lys Val Ala Phe Ile Gly Ser Leu Ser Asp
            20                  25

<210> SEQ ID NO 178
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 178

Glu Lys Tyr Gln Ala Tyr Gly Glu Ile Trp Gln Leu Pro Asn Leu Asn
1               5                   10                  15

Arg Gln Gln Lys Val Ala Phe Ile Ser Ser Leu Gln Asp
            20                  25

<210> SEQ ID NO 179
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 179

Glu Lys Tyr Lys Ala Tyr Gly Glu Ile Trp Gln Leu Pro Asn Leu Asn
1               5                   10                  15

Arg Gln Gln Lys Val Ala Phe Ile Ser Leu Gln Asp
            20                  25

<210> SEQ ID NO 180
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 180

Glu Lys Tyr Ala Ala Ala Tyr Glu Ile Trp Gln Leu Pro Asn Leu Asn
1               5                   10                  15

Gln Arg Gln Lys Gly Ala Phe Ile Ala Ser Leu Phe Asp
            20                  25

```
<210> SEQ ID NO 181
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 181

Glu Lys Tyr Ala Ala Ser Tyr Glu Ile Trp Glu Leu Pro Asn Leu Asn
1               5                   10                  15

Gln Arg Gln Lys Ala Ala Phe Ile Lys Ser Leu Phe Asp
            20                  25

<210> SEQ ID NO 182
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 182

Glu Lys Tyr Leu Ala Ser Tyr Glu Ile Trp Gln Leu Pro Asn Leu Asn
1               5                   10                  15

Arg Arg Gln Lys Ala Ala Phe Ile Ala Ser Leu Phe Asp
            20                  25

<210> SEQ ID NO 183
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 183

Glu Lys Tyr Ser Ala Thr Phe Glu Ile Trp Gln Leu Pro Asn Leu Asn
1               5                   10                  15

Gln Arg Gln Lys Ala Ala Phe Ile Ser Ser Leu Trp Asp
            20                  25

<210> SEQ ID NO 184
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 184

Glu Lys Tyr Ala Ala Ser Phe Glu Ile Trp Gln Leu Pro Asn Leu Asn
1               5                   10                  15

Thr His Gln Lys Ala Ala Phe Ile Ser Ser Leu Trp Asp
            20                  25

<210> SEQ ID NO 185
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 185

Glu Lys Tyr Lys Ala Ser Gly Glu Ile Trp Gln Leu Pro Asn Leu Asn
1               5                   10                  15

Arg Leu Gln Arg Ala Ala Phe Ile Lys Ser Leu Phe Asp
```

```
                20                  25

<210> SEQ ID NO 186
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 186

Glu Lys Tyr Ser Ala Ser Gly Glu Ile Trp Gln Leu Pro Asn Leu Asn
1               5                   10                  15

Arg Thr Gln Lys Ala Ala Phe Ile Lys Ser Leu Trp Asp
                20                  25

<210> SEQ ID NO 187
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 187

Glu Lys Tyr His Ala Ala Gly Glu Ile Trp Glu Leu Pro Asn Leu Asn
1               5                   10                  15

Arg Leu Gln Lys Ala Ala Phe Ile Arg Ser Leu Trp Asp
                20                  25

<210> SEQ ID NO 188
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 188

Glu Lys Tyr Arg Ala Ala Gly Glu Ile Trp Glu Leu Pro Asn Leu Asn
1               5                   10                  15

Arg Gln Gln Lys Ala Ala Phe Ile Arg Ser Leu Phe Asp
                20                  25

<210> SEQ ID NO 189
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 189

Glu Lys Tyr Gln Ala Ser Gly Glu Ile Trp Glu Leu Pro Asn Leu Asn
1               5                   10                  15

Arg Leu Gln Lys Ala Ala Phe Ile Arg Ser Leu Phe Asp
                20                  25

<210> SEQ ID NO 190
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 190

Glu Lys Tyr Lys Ala Thr Gly Glu Ile Trp Glu Leu Pro Asn Leu Asn
1               5                   10                  15
```

Arg Ile Gln Lys Ala Ala Phe Ile Arg Ser Leu Trp Asp
            20                  25

<210> SEQ ID NO 191
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 191

Glu Lys Tyr Gln Ala Ser Phe Glu Ile Trp Glu Leu Pro Asn Leu Asn
1               5                   10                  15

Arg Ser Gln Lys Ala Ala Phe Ile Lys Ser Leu Trp Asp
            20                  25

<210> SEQ ID NO 192
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 192

Glu Arg Lys Val Ala Ala Val Glu Ile Trp Gln Leu Pro Asn Leu Asn
1               5                   10                  15

Arg Trp Gln Arg Gly Ala Phe Ile Ser Ser Leu Phe Asp
            20                  25

<210> SEQ ID NO 193
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 193

Glu Arg Lys Leu Ala Ala Val Glu Ile Trp Glu Leu Pro Asn Leu Asn
1               5                   10                  15

Gln Tyr Gln Arg Gly Ala Phe Ile Ser Ser Leu Trp Asp
            20                  25

<210> SEQ ID NO 194
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 194

Glu Arg Lys Lys Ala Ser Val Glu Ile Trp Glu Leu Pro Asn Leu Asn
1               5                   10                  15

Arg Tyr Gln Lys Gly Ala Phe Ile Ser Ser Leu Phe Asp
            20                  25

<210> SEQ ID NO 195
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 195

Glu Arg Lys His Ala Ala Trp Glu Ile Trp Glu Leu Pro Asn Leu Asn
1               5                   10                  15

Arg His Gln Lys Gly Ala Phe Ile Lys Ser Leu Trp Asp
            20                  25

<210> SEQ ID NO 196
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 196

Glu Arg Lys His Ala Ala Val Glu Ile Trp Glu Leu Pro Asn Leu Asn
1               5                   10                  15

Arg Trp Gln Lys Gly Ala Phe Ile Gly Ser Leu Trp Asp
            20                  25

<210> SEQ ID NO 197
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 197

Glu Lys Arg His Ala Ala Val Glu Ile Trp Glu Leu Pro Asn Leu Asn
1               5                   10                  15

Val Phe Gln Arg Gly Ala Phe Ile Ala Ser Leu Tyr Asp
            20                  25

<210> SEQ ID NO 198
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 198

Glu Arg Lys His Ala Ala Val Glu Ile Trp Glu Leu Pro Asn Leu Asn
1               5                   10                  15

Arg Leu Gln Arg Gly Ala Phe Ile Ala Ser Leu Tyr Asp
            20                  25

<210> SEQ ID NO 199
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 199

Glu Trp Lys Thr Ala Ala Val Glu Ile Trp Glu Leu Pro Asn Leu Asn
1               5                   10                  15

Arg Arg Gln Lys Ala Ala Phe Ile Gly Ser Leu Tyr Asp
            20                  25

<210> SEQ ID NO 200
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 200

Glu Arg Lys Val Ala Ala Phe Glu Ile Trp Glu Leu Pro Asn Leu Asn

```
                1               5                  10                  15
Arg Gly Gln Lys Ala Ala Phe Ile Gly Ser Leu Tyr Asp
            20                  25
```

<210> SEQ ID NO 201
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 201

```
Glu Lys Arg Asn Ala Ala Val Glu Ile Trp Glu Leu Pro Asn Leu Asn
1               5                  10                  15
Arg Arg Gln Arg Ala Ala Phe Ile Ser Ser Leu Phe Asp
            20                  25
```

<210> SEQ ID NO 202
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 202

```
Glu Arg Arg Asn Ala Ala Val Glu Ile Trp Glu Leu Pro Asn Leu Asn
1               5                  10                  15
Arg His Gln Arg Ala Ala Phe Ile Ser Ser Leu Trp Asp
            20                  25
```

<210> SEQ ID NO 203
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 203

```
Glu Lys Arg Gln Ala Ser Val Glu Ile Trp Glu Leu Pro Asn Leu Asn
1               5                  10                  15
Arg Ile Gln Lys Ala Ala Phe Ile Ser Ser Leu Phe Asp
            20                  25
```

<210> SEQ ID NO 204
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 204

```
Glu Lys Arg Arg Ala Ala Val Glu Ile Trp Glu Leu Pro Asn Leu Asn
1               5                  10                  15
Arg Ile Gln Lys Ser Ala Phe Ile Ala Ser Leu Trp Asp
            20                  25
```

<210> SEQ ID NO 205
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 205

Glu Lys Arg His Ala Ala Trp Glu Ile Trp Glu Leu Pro Asn Leu Asn
1               5                   10                  15

Arg Ala Gln Lys Ser Ala Phe Ile Lys Ser Leu Trp Asp
            20                  25

<210> SEQ ID NO 206
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 206

Glu Lys Arg Asn Ala Thr Val Glu Ile Trp Glu Leu Pro Asn Leu Asn
1               5                   10                  15

Arg Ile Gln Arg Ala Ala Phe Ile Ala Ser Leu Trp Asp
            20                  25

<210> SEQ ID NO 207
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 207

Glu Lys Arg Ala Ala Thr Val Glu Ile Trp Glu Leu Pro Asn Leu Asn
1               5                   10                  15

Arg Leu Gln Lys Gly Ala Phe Ile Ala Ser Leu Trp Asp
            20                  25

<210> SEQ ID NO 208
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 208

Glu Arg Arg Gly Ala Ala Val Glu Ile Trp Glu Leu Pro Asn Leu Asn
1               5                   10                  15

Arg Gln Gln Lys Ala Ala Phe Ile Ala Ser Leu Trp Asp
            20                  25

<210> SEQ ID NO 209
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 209

Glu Arg Arg Lys Ala Thr Val Glu Ile Trp Glu Leu Pro Asn Leu Asn
1               5                   10                  15

Arg Gln Gln Lys Ala Ala Phe Ile Ser Ser Leu Trp Asp
            20                  25

<210> SEQ ID NO 210
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 210

Glu Lys Ser Thr Ala Ala Val Glu Ile Trp Glu Leu Pro Asn Leu Asn
1               5                   10                  15

Arg Ile Gln Lys Ala Ala Phe Ile Lys Ser Leu Phe Asp
            20                  25

<210> SEQ ID NO 211
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 211

Glu Lys Ser Thr Ala Ala Val Glu Ile Trp Glu Leu Pro Asn Leu Asn
1               5                   10                  15

Arg Tyr Gln Lys Ala Ala Phe Ile Lys Ser Leu Phe Asp
            20                  25

<210> SEQ ID NO 212
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 212

Glu Lys Ser His Ala Ala Val Glu Ile Trp Glu Leu Pro Asn Leu Asn
1               5                   10                  15

Arg Trp Gln Lys Ala Ala Phe Ile Lys Ser Leu Tyr Asp
            20                  25

<210> SEQ ID NO 213
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 213

Glu Arg Ser Ser Ala Ala Val Glu Ile Trp Glu Leu Pro Asn Leu Asn
1               5                   10                  15

Arg Phe Gln Lys Ala Ala Phe Ile Lys Ser Leu Phe Asp
            20                  25

<210> SEQ ID NO 214
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 214

Glu Lys Arg Ile Ala Ala Ala Glu Ile Trp Glu Leu Pro Asn Leu Asn
1               5                   10                  15

Arg Val Gln Lys Ala Ala Phe Ile Lys Ser Leu Phe Asp
            20                  25

<210> SEQ ID NO 215
<211> LENGTH: 29
<212> TYPE: PRT
<213> ORGANISM: Artificial Sequence
<220> FEATURE:
<223> OTHER INFORMATION: Engineered polypeptide

```
<400> SEQUENCE: 215

Glu Lys Arg His Ala Ala Gly Glu Ile Trp Glu Leu Pro Asn Leu Asn
1               5                   10                  15

Arg Ile Gln Lys Ala Ala Phe Ile Lys Ser Leu Phe Asp
            20                  25

<210> SEQ ID NO 216
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 216

Glu Lys Arg Ile Ala Ala Val Glu Ile Trp Glu Leu Pro Asn Leu Asn
1               5                   10                  15

Arg Val Gln Lys Ala Ala Phe Ile Ala Ser Leu Tyr Asp
            20                  25

<210> SEQ ID NO 217
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 217

Glu Lys Arg Ile Ala Ser Tyr Glu Ile Trp Glu Leu Pro Asn Leu Asn
1               5                   10                  15

Arg Arg Gln Arg Ala Ala Phe Ile Ala Ser Leu Trp Asp
            20                  25

<210> SEQ ID NO 218
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 218

Glu Lys Arg Asn Ala Thr Phe Glu Ile Trp Glu Leu Pro Asn Leu Asn
1               5                   10                  15

Arg Ser Gln Lys Gly Ala Phe Ile Ser Ser Leu Tyr Asp
            20                  25

<210> SEQ ID NO 219
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 219

Glu Arg Lys Val Ala Thr Phe Glu Ile Trp Glu Leu Pro Asn Leu Asn
1               5                   10                  15

Ser Arg Gln Lys Ala Ala Phe Ile Lys Ser Leu Phe Asp
            20                  25

<210> SEQ ID NO 220
<211> LENGTH: 29
<212> TYPE: PRT
<213> ORGANISM: Artificial Sequence
<220> FEATURE:
<223> OTHER INFORMATION: Engineered polypeptide
```

<400> SEQUENCE: 220

Glu Arg Lys Asn Ala Thr Phe Glu Ile Trp Glu Leu Pro Asn Leu Asn
1               5                   10                  15

Gln Arg Gln Lys Ser Ala Phe Ile Ala Ser Leu Trp Asp
            20                  25

<210> SEQ ID NO 221
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 221

Glu Arg Ser Ala Ala Thr Phe Glu Ile Trp Glu Leu Pro Asn Leu Asn
1               5                   10                  15

Gln Arg Gln Lys Ser Ala Phe Ile Ala Ser Leu Trp Asp
            20                  25

<210> SEQ ID NO 222
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 222

Glu Arg Lys His Ala Thr Phe Glu Ile Trp Glu Leu Pro Asn Leu Asn
1               5                   10                  15

Gln Leu Gln Lys Ser Ala Phe Ile Gly Ser Leu Trp Asp
            20                  25

<210> SEQ ID NO 223
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 223

Glu Arg Lys Gln Ala Thr Phe Glu Ile Trp Glu Leu Pro Asn Leu Asn
1               5                   10                  15

Gln Gln Gln Lys Gly Ala Phe Ile Ala Ser Leu Trp Asp
            20                  25

<210> SEQ ID NO 224
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 224

Glu Arg Lys Arg Ala Thr Phe Glu Ile Trp Glu Leu Pro Asn Leu Asn
1               5                   10                  15

Arg Thr Gln Lys Ala Ala Phe Ile Ser Ser Leu Trp Asp
            20                  25

<210> SEQ ID NO 225
<211> LENGTH: 29
<212> TYPE: PRT
<213> ORGANISM: Artificial Sequence
<220> FEATURE:

<223> OTHER INFORMATION: Engineered polypeptide

<400> SEQUENCE: 225

Glu Arg Lys Thr Ala Thr Phe Glu Ile Trp Glu Leu Pro Asn Leu Asn
1               5                   10                  15

Arg Val Gln Lys Ala Ala Phe Ile Ser Ser Leu Trp Asp
            20                  25

<210> SEQ ID NO 226
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 226

Glu Arg Lys Leu Ala Thr Trp Glu Ile Trp Glu Leu Pro Asn Leu Asn
1               5                   10                  15

Arg Ser Gln Lys Ala Ala Phe Ile Ile Ser Leu Trp Asp
            20                  25

<210> SEQ ID NO 227
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 227

Glu Arg Lys Val Ala Ala Val Glu Ile Trp Glu Leu Pro Asn Leu Asn
1               5                   10                  15

Arg Ile Gln Lys Ala Ala Phe Ile Arg Ser Leu Phe Asp
            20                  25

<210> SEQ ID NO 228
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 228

Glu Arg Lys Glu Ala Ala Val Glu Ile Trp Glu Leu Pro Asn Leu Asn
1               5                   10                  15

Arg Leu Gln Lys Ala Ala Phe Ile Arg Ser Leu Phe Asp
            20                  25

<210> SEQ ID NO 229
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 229

Glu Arg Lys Arg Ala Ala Val Glu Ile Trp Glu Leu Pro Asn Leu Asn
1               5                   10                  15

Arg Gly Gln Lys Ala Ala Phe Ile Lys Ser Leu Phe Asp
            20                  25

<210> SEQ ID NO 230
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 230

Glu Arg Lys Leu Ala Ala Val Glu Ile Trp Glu Leu Pro Asn Leu Asn
1               5                   10                  15

Arg Thr Gln Lys Ala Ala Phe Ile Lys Ser Leu Phe Asp
            20                  25

<210> SEQ ID NO 231
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 231

Glu Arg Lys Val Ala Ala Val Glu Ile Trp Glu Leu Pro Asn Leu Asn
1               5                   10                  15

Arg Val Gln Lys Ala Ala Phe Ile Lys Ser Leu Phe Asp
            20                  25

<210> SEQ ID NO 232
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 232

Glu Arg Lys Glu Ala Ala Val Glu Ile Trp Glu Leu Pro Asn Leu Asn
1               5                   10                  15

Arg Val Gln Lys Ala Ala Phe Ile Lys Ser Leu Tyr Asp
            20                  25

<210> SEQ ID NO 233
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 233

Glu Arg Lys Ala Ala Thr Val Glu Ile Trp Glu Leu Pro Asn Leu Asn
1               5                   10                  15

Arg Arg Gln Lys Ala Ala Phe Ile Ala Ser Leu Phe Asp
            20                  25

<210> SEQ ID NO 234
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 234

Glu Lys Arg His Ala Ser Trp Glu Ile Trp Glu Leu Pro Asn Leu Asn
1               5                   10                  15

Gln Trp Gln Lys Ala Ala Phe Ile Arg Ser Leu Phe Asp
            20                  25

<210> SEQ ID NO 235
<211> LENGTH: 29
<212> TYPE: PRT

<213> ORGANISM: Artificial Sequence
<220> FEATURE:
<223> OTHER INFORMATION: Engineered polypeptide

<400> SEQUENCE: 235

Glu Arg Lys Ser Ala Thr Trp Glu Ile Trp Glu Leu Pro Asn Leu Asn
1               5                   10                  15

Gln Leu Gln Lys Ala Ala Phe Ile Arg Ser Leu Phe Asp
            20                  25

<210> SEQ ID NO 236
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 236

Glu Lys Lys Lys Ala Ala Val Glu Ile Trp Glu Leu Pro Asn Leu Asn
1               5                   10                  15

Gln Arg Gln Lys Ala Ala Phe Ile Gly Ser Leu Trp Asp
            20                  25

<210> SEQ ID NO 237
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 237

Glu Lys Lys Leu Ala Ser Phe Glu Ile Trp Glu Leu Pro Asn Leu Asn
1               5                   10                  15

Gln Arg Gln Lys Ala Ala Phe Ile Arg Ser Leu Trp Asp
            20                  25

<210> SEQ ID NO 238
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 238

Glu Arg Lys Val Ala Thr Val Glu Ile Trp Glu Leu Pro Asn Leu Asn
1               5                   10                  15

Arg Val Gln Ala Ala Ala Phe Ile Lys Ser Leu Trp Asp
            20                  25

<210> SEQ ID NO 239
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 239

Glu Arg Lys Thr Ala Thr Val Glu Ile Trp Glu Leu Pro Asn Leu Asn
1               5                   10                  15

Arg Ile Gln Lys Ala Ala Phe Ile Lys Ser Leu Trp Asp
            20                  25

<210> SEQ ID NO 240
<211> LENGTH: 29

```
<212> TYPE: PRT
<213> ORGANISM: Artificial Sequence
<220> FEATURE:
<223> OTHER INFORMATION: Engineered polypeptide

<400> SEQUENCE: 240

Glu Arg Lys Ser Ala Thr Val Glu Ile Trp Glu Leu Pro Asn Leu Asn
1               5                   10                  15

Arg Val Gln Lys Ala Ala Phe Ile Ser Ser Leu Trp Asp
            20                  25

<210> SEQ ID NO 241
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 241

Glu Arg Lys Val Ala Thr Val Glu Ile Trp Glu Leu Pro Asn Leu Asn
1               5                   10                  15

Arg Gly Gln Lys Ala Ala Phe Ile Ser Ser Leu Trp Asp
            20                  25

<210> SEQ ID NO 242
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 242

Glu Arg Lys Gln Ala Thr Val Glu Ile Trp Glu Leu Pro Asn Leu Asn
1               5                   10                  15

Arg Arg Gln Arg Ala Ala Phe Ile Ser Ser Leu Trp Asp
            20                  25

<210> SEQ ID NO 243
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 243

Glu Arg Lys Lys Ala Thr Val Glu Ile Trp Glu Leu Pro Asn Leu Asn
1               5                   10                  15

Arg Arg Gln Lys Gly Ala Phe Ile Ala Ser Leu Trp Asp
            20                  25

<210> SEQ ID NO 244
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 244

Glu Arg Lys Val Ala Thr Val Glu Ile Trp Glu Leu Pro Asn Leu Asn
1               5                   10                  15

Arg Arg Gln Lys Gly Ala Phe Ile Ala Ser Leu Trp Asp
            20                  25

<210> SEQ ID NO 245
```

```
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 245

Glu Arg Lys Leu Ala Thr Val Glu Ile Trp Glu Leu Pro Asn Leu Asn
1               5                   10                  15

Arg Tyr Gln Lys Gly Ala Phe Ile Ala Ser Leu Trp Asp
            20                  25

<210> SEQ ID NO 246
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 246

Glu Arg Lys Ala Ala Thr Val Glu Ile Trp Glu Leu Pro Asn Leu Asn
1               5                   10                  15

Arg Leu Gln Lys Gly Ala Phe Ile Ala Ser Leu Trp Asp
            20                  25

<210> SEQ ID NO 247
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 247

Glu Arg Lys Ile Ala Thr Val Glu Ile Trp Glu Leu Pro Asn Leu Asn
1               5                   10                  15

Arg Val Gln Lys Ser Ala Phe Ile Ala Ser Leu Trp Asp
            20                  25

<210> SEQ ID NO 248
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 248

Glu Arg Lys Asn Ala Thr Val Glu Ile Trp Glu Leu Pro Asn Leu Asn
1               5                   10                  15

Arg Ala Gln Lys Ala Ala Phe Ile Ala Ser Leu Trp Asp
            20                  25

<210> SEQ ID NO 249
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 249

Glu Arg Lys Asn Ala Thr Val Glu Ile Trp Glu Leu Pro Asn Leu Asn
1               5                   10                  15

Arg Ser Gln Lys Ala Ala Phe Ile Gly Ser Leu Trp Asp
            20                  25
```

```
<210> SEQ ID NO 250
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 250

Glu Arg Lys Thr Ala Thr Val Glu Ile Trp Glu Leu Pro Asn Leu Asn
1               5                   10                  15

Arg Gly Gln Lys Ala Ala Phe Ile Ala Ser Leu Phe Asp
            20                  25

<210> SEQ ID NO 251
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 251

Glu Arg Lys His Ala Ala Val Glu Ile Trp Glu Leu Pro Asn Leu Asn
1               5                   10                  15

Arg Ile Gln Arg Ala Ala Phe Ile Ala Ser Leu Phe Asp
            20                  25

<210> SEQ ID NO 252
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 252

Glu Arg Lys Ile Ala Thr Val Glu Ile Trp Glu Leu Pro Asn Leu Asn
1               5                   10                  15

Arg Ile Gln Arg Ala Ala Phe Ile Ala Ser Leu Phe Asp
            20                  25

<210> SEQ ID NO 253
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 253

Glu Arg Lys Ile Ala Ala Val Glu Ile Trp Glu Leu Pro Asn Leu Asn
1               5                   10                  15

Arg Ile Gln Ala Ala Ala Phe Ile Ala Ser Leu Trp Asp
            20                  25

<210> SEQ ID NO 254
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 254

Glu Arg Lys Ser Ala Thr Val Glu Ile Trp Glu Leu Pro Asn Leu Asn
1               5                   10                  15

Arg Thr Gln Arg Ala Ala Phe Ile Ala Ser Leu Trp Asp
            20                  25
```

<210> SEQ ID NO 255
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 255

Glu Arg Lys Ser Ala Ala Val Glu Ile Trp Glu Leu Pro Asn Leu Asn
1               5                   10                  15

Arg Thr Gln Lys Ala Ala Phe Ile Ala Ser Leu Trp Asp
            20                  25

<210> SEQ ID NO 256
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 256

Glu Lys Lys Ser Ala Thr Val Glu Ile Trp Glu Leu Pro Asn Leu Asn
1               5                   10                  15

Arg Ile Gln Lys Ala Ala Phe Ile Gly Ser Leu Trp Asp
            20                  25

<210> SEQ ID NO 257
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 257

Glu Lys Lys Ser Ala Tyr Val Glu Ile Trp Glu Leu Pro Asn Leu Asn
1               5                   10                  15

Arg Tyr Gln Lys Ala Ala Phe Ile Lys Ser Leu Phe Asp
            20                  25

<210> SEQ ID NO 258
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 258

Glu Arg Lys Ile Ala Thr Tyr Glu Ile Trp Glu Leu Pro Asn Leu Asn
1               5                   10                  15

Gln Arg Gln Lys Ala Ala Phe Ile Ala Ser Leu Trp Asp
            20                  25

<210> SEQ ID NO 259
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 259

Glu Arg Ser Val Ala Thr Trp Glu Ile Trp Gln Leu Pro Asn Leu Asn
1               5                   10                  15

Gln Arg Gln Lys Ala Ala Phe Ile Ala Ser Leu Trp Asp
            20                  25

<210> SEQ ID NO 260
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 260

Glu Lys Arg Lys Ala Thr Gly Glu Ile Trp Gln Leu Pro Asn Leu Asn
1               5                   10                  15

Gln Arg Gln Lys Gly Ala Phe Ile Ala Ser Leu Trp Asp
            20                  25

<210> SEQ ID NO 261
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 261

Glu Arg Lys Glu Ala Arg Phe Glu Ile Trp Glu Leu Pro Asn Leu Asn
1               5                   10                  15

Gln Arg Gln Ala Ala Ala Phe Ile Ser Ser Leu Phe Asp
            20                  25

<210> SEQ ID NO 262
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 262

Glu Arg Lys Ala Ala Ser Trp Glu Ile Trp Glu Leu Pro Asn Leu Asn
1               5                   10                  15

Gln Arg Gln Lys Ala Ala Phe Ile Ser Ser Leu Tyr Asp
            20                  25

<210> SEQ ID NO 263
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 263

Glu Trp Lys His Ala Ala Gly Glu Ile Trp Glu Leu Pro Asn Leu Asn
1               5                   10                  15

Arg Ser Gln Lys Val Ala Phe Ile Ala Ser Leu Glu Asp
            20                  25

<210> SEQ ID NO 264
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 264

Glu Trp Lys Arg Ala Ala Gly Glu Ile Trp Glu Leu Pro Asn Leu Asn
1               5                   10                  15

Arg Ala Gln Lys Val Ala Phe Ile Ala Ser Leu Ala Asp 20                  25

<210> SEQ ID NO 265
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 265

Glu Trp Lys Ile Ala Ala Gly Glu Ile Trp Glu Leu Pro Asn Leu Asn
1               5                   10                  15

Gln Arg Gln Lys Val Ala Phe Ile Arg Ser Leu Gln Asp
            20                  25

<210> SEQ ID NO 266
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 266

Glu Trp Lys Thr Ala Ala Tyr Glu Ile Trp Glu Leu Pro Asn Leu Asn
1               5                   10                  15

Thr Tyr Gln Lys Val Ala Phe Ile Arg Ser Leu Gln Asp
            20                  25

<210> SEQ ID NO 267
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 267

Glu Trp Lys Val Ala Ala Gly Glu Ile Trp Glu Leu Pro Asn Leu Asn
1               5                   10                  15

Arg Thr Gln Lys Val Ala Phe Ile Arg Ser Leu Ser Asp
            20                  25

<210> SEQ ID NO 268
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 268

Glu Trp Lys Val Ala Ala Gly Glu Ile Trp Glu Leu Pro Asn Leu Asn
1               5                   10                  15

Arg Trp Gln Lys Val Ala Phe Ile Arg Ser Leu Ser Asp
            20                  25

<210> SEQ ID NO 269
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 269

Glu Trp Lys Gln Ala Ala Gly Glu Ile Trp Glu Leu Pro Asn Leu Asn
1               5                   10                  15

-continued

Arg Leu Gln Lys Val Ala Phe Ile Arg Ser Leu Ser Asp
            20                  25

<210> SEQ ID NO 270
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 270

Glu Trp Lys Val Ala Ala Gly Glu Ile Trp Glu Leu Pro Asn Leu Asn
1               5                   10                  15

Val Trp Gln Lys Ala Ala Phe Ile Arg Ser Leu Ser Asp
            20                  25

<210> SEQ ID NO 271
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 271

Glu Trp Lys Val Ala Ala Trp Glu Ile Trp Glu Leu Pro Asn Leu Asn
1               5                   10                  15

Arg Gly Gln Lys Val Ala Phe Ile Arg Ser Leu Gln Asp
            20                  25

<210> SEQ ID NO 272
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 272

Glu Trp Lys Arg Ala Ala Phe Glu Ile Trp Glu Leu Pro Asn Leu Asn
1               5                   10                  15

Gln Ala Gln Lys Val Ala Phe Ile Thr Ser Leu Ser Asp
            20                  25

<210> SEQ ID NO 273
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 273

Glu Trp Lys Lys Ala Ala Gly Glu Ile Trp Leu Leu Pro Asn Leu Asn
1               5                   10                  15

Arg Arg Gln Arg Gly Ala Phe Ile Ala Ser Leu Ala Asp
            20                  25

<210> SEQ ID NO 274
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 274

Glu Trp Lys Lys Ala Ala Gly Glu Ile Trp Glu Leu Pro Asn Leu Asn
1               5                   10                  15

Ser Arg Gln Lys Gly Ala Phe Ile Ala Ser Leu Ala Asp
            20                  25

<210> SEQ ID NO 275
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 275

Glu Trp Arg Gly Ala Ala Gly Glu Ile Trp Glu Leu Pro Asn Leu Asn
1               5                   10                  15

Arg Arg Gln Arg Ala Ala Phe Ile Ala Ser Leu Ala Asp
            20                  25

<210> SEQ ID NO 276
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 276

Glu Trp Lys Val Ala Ala Gly Glu Ile Trp Gln Leu Pro Asn Leu Asn
1               5                   10                  15

Arg Arg Gln Arg Ala Ala Phe Ile Ala Ser Leu Ala Asp
            20                  25

<210> SEQ ID NO 277
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 277

Glu Trp Lys Ile Ala Ala Val Glu Ile Trp Glu Leu Pro Asn Leu Asn
1               5                   10                  15

Thr Arg Gln Lys Gly Ala Phe Ile Ala Ser Leu Ser Asp
            20                  25

<210> SEQ ID NO 278
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 278

Glu Trp Lys Ile Ala Ala Phe Glu Ile Trp Glu Leu Pro Asn Leu Asn
1               5                   10                  15

Val Arg Gln Arg Ser Ala Phe Ile Ser Ser Leu Ser Asp
            20                  25

<210> SEQ ID NO 279
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 279

Glu Trp Lys Thr Ala Ala Tyr Glu Ile Trp Glu Leu Pro Asn Leu Asn

```
                1               5                   10                  15
Gln Arg Gln Arg Gly Ala Phe Ile Ala Ser Leu Gln Asp
            20                  25
```

<210> SEQ ID NO 280
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 280

```
Glu Trp Lys Thr Ala Ala Gly Glu Ile Trp Glu Leu Pro Asn Leu Asn
1               5                   10                  15
Ser Arg Gln Lys Ala Ala Phe Ile Gly Ser Leu Ala Asp
            20                  25
```

<210> SEQ ID NO 281
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 281

```
Glu Trp Lys Thr Ala Ala Gly Glu Ile Trp Glu Leu Pro Asn Leu Asn
1               5                   10                  15
Val Gly Gln Lys Ala Ala Phe Ile Gly Ser Leu Ala Asp
            20                  25
```

<210> SEQ ID NO 282
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 282

```
Glu Trp Lys His Ala Ala Gly Glu Ile Trp Glu Leu Pro Asn Leu Asn
1               5                   10                  15
Arg Thr Gln Lys Ala Ala Phe Ile Arg Ser Leu Ala Asp
            20                  25
```

<210> SEQ ID NO 283
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 283

```
Glu Trp Lys Arg Ala Ala Gly Glu Ile Trp Glu Leu Pro Asn Leu Asn
1               5                   10                  15
Arg Leu Gln Lys Ala Ala Phe Ile Arg Ser Leu Ala Asp
            20                  25
```

<210> SEQ ID NO 284
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 284

Glu Trp Lys Gln Ala Ala Gly Glu Ile Trp Glu Leu Pro Asn Leu Asn
1               5                   10                  15

Arg Gly Gln Lys Ala Ala Phe Ile Ser Ser Leu Ala Asp
            20                  25

<210> SEQ ID NO 285
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 285

Glu Trp Lys Gln Ala Ala Gly Glu Ile Trp Glu Leu Pro Asn Leu Asn
1               5                   10                  15

Arg Gly Gln Lys Ala Ala Phe Ile Thr Ser Leu Ala Asp
            20                  25

<210> SEQ ID NO 286
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 286

Glu Trp Lys Glu Ala Ala Gly Glu Ile Trp Glu Leu Pro Asn Leu Asn
1               5                   10                  15

Arg Gly Gln Lys Ala Ala Phe Ile Lys Ser Leu Ala Asp
            20                  25

<210> SEQ ID NO 287
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 287

Glu Trp Lys Thr Ala Ala Gly Glu Ile Trp Glu Leu Pro Asn Leu Asn
1               5                   10                  15

Arg Arg Gln Lys Ala Ala Phe Ile Ala Ser Leu Gln Asp
            20                  25

<210> SEQ ID NO 288
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 288

Glu Trp Lys Arg Ala Ala Gly Glu Ile Trp Glu Leu Pro Asn Leu Asn
1               5                   10                  15

Arg Ala Gln Lys Ala Ala Phe Ile Ser Ser Leu Gln Asp
            20                  25

<210> SEQ ID NO 289
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 289

```
Glu Trp Lys His Ala Ala Phe Glu Ile Trp Glu Leu Pro Asn Leu Asn
1               5                   10                  15

Val Arg Gln Lys Ala Ala Phe Ile Gly Ser Leu Gln Asp
            20                  25
```

<210> SEQ ID NO 290
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 290

```
Glu Trp Lys Asn Ala Ala Phe Glu Ile Trp Glu Leu Pro Asn Leu Asn
1               5                   10                  15

Val Ser Gln Lys Ala Ala Phe Ile Arg Ser Leu Gln Asp
            20                  25
```

<210> SEQ ID NO 291
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 291

```
Glu Trp Lys Ala Ala Ala Tyr Glu Ile Trp Glu Leu Pro Asn Leu Asn
1               5                   10                  15

Val Trp Gln Lys Ala Ala Phe Ile Ser Ser Leu Gln Asp
            20                  25
```

<210> SEQ ID NO 292
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 292

```
Glu Trp Lys Val Ala Ala Gly Glu Ile Trp Glu Leu Pro Asn Leu Asn
1               5                   10                  15

Arg Trp Gln Lys Gly Ala Phe Ile Thr Ser Leu Tyr Asp
            20                  25
```

<210> SEQ ID NO 293
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 293

```
Glu Trp Lys Val Ala Ala Gly Glu Ile Trp Glu Leu Pro Asn Leu Asn
1               5                   10                  15

Arg Trp Gln Lys Ala Ala Phe Ile Ala Ser Leu Tyr Asp
            20                  25
```

<210> SEQ ID NO 294
<211> LENGTH: 29
<212> TYPE: PRT
<213> ORGANISM: Artificial Sequence
<220> FEATURE:
<223> OTHER INFORMATION: Engineered polypeptide

```
<400> SEQUENCE: 294

Glu Trp Lys Val Ala Ala Gly Glu Ile Trp Glu Leu Pro Asn Leu Asn
1               5                   10                  15

Arg Leu Gln Arg Ala Ala Phe Ile Lys Ser Leu Tyr Asp
            20                  25

<210> SEQ ID NO 295
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 295

Glu Trp Lys Val Ala Ala Tyr Glu Ile Trp Glu Leu Pro Asn Leu Asn
1               5                   10                  15

Arg Leu Gln Lys Ala Ala Phe Ile Ala Ser Leu Tyr Asp
            20                  25

<210> SEQ ID NO 296
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 296

Glu Trp Lys Val Ala Ala Phe Glu Ile Trp Glu Leu Pro Asn Leu Asn
1               5                   10                  15

Arg Thr Gln Arg Ala Ala Phe Ile Ile Ser Leu Gln Asp
            20                  25

<210> SEQ ID NO 297
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 297

Glu Trp Lys Thr Ala Ala Val Glu Ile Trp Glu Leu Pro Asn Leu Asn
1               5                   10                  15

Arg Leu Gln Lys Ala Ala Phe Ile Thr Ser Leu Ser Asp
            20                  25

<210> SEQ ID NO 298
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 298

Glu Trp Lys Thr Ala Ala Val Glu Ile Trp Glu Leu Pro Asn Leu Asn
1               5                   10                  15

Arg Leu Gln Lys Ala Ala Phe Ile Gly Ser Leu Ser Asp
            20                  25

<210> SEQ ID NO 299
<211> LENGTH: 29
<212> TYPE: PRT
<213> ORGANISM: Artificial Sequence
<220> FEATURE:
<223> OTHER INFORMATION: Engineered polypeptide
```

<400> SEQUENCE: 299

Glu Trp Lys Thr Ala Ala Phe Glu Ile Trp Glu Leu Pro Asn Leu Asn
1               5                   10                  15

Arg Gly Gln Lys Ala Ala Phe Ile Arg Ser Leu Ser Asp
            20                  25

<210> SEQ ID NO 300
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 300

Glu Trp Lys Arg Ala Ala Phe Glu Ile Trp Glu Leu Pro Asn Leu Asn
1               5                   10                  15

Arg Leu Gln Lys Ser Ala Phe Ile Ala Ser Leu Ser Asp
            20                  25

<210> SEQ ID NO 301
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 301

Glu Trp Lys Gln Ala Ala Phe Glu Ile Trp Glu Leu Pro Asn Leu Asn
1               5                   10                  15

Arg Tyr Gln Ala Ala Ala Phe Ile Gly Ser Leu Gln Asp
            20                  25

<210> SEQ ID NO 302
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 302

Glu Trp Lys His Ala Ala Phe Glu Ile Trp Glu Leu Pro Asn Leu Asn
1               5                   10                  15

Arg Arg Gln Ala Gly Ala Phe Ile Ala Ser Leu Gln Asp
            20                  25

<210> SEQ ID NO 303
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 303

Glu Trp Lys Gln Ala Ser Gly Glu Ile Trp Glu Leu Pro Asn Leu Asn
1               5                   10                  15

Val Arg Gln Lys Ala Ala Phe Ile Ser Ser Leu Ala Asp
            20                  25

<210> SEQ ID NO 304
<211> LENGTH: 29
<212> TYPE: PRT
<213> ORGANISM: Artificial Sequence
<220> FEATURE:

<223> OTHER INFORMATION: Engineered polypeptide

<400> SEQUENCE: 304

Glu Trp Lys Gln Ala Ser Phe Glu Ile Trp Glu Leu Pro Asn Leu Asn
1               5                   10                  15

Val Arg Gln Lys Ala Ala Phe Ile Ser Ser Leu Ser Asp
            20                  25

<210> SEQ ID NO 305
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 305

Glu Trp Lys Leu Ala Ala Gly Glu Ile Trp Glu Leu Pro Asn Leu Asn
1               5                   10                  15

Val Arg Gln Lys Ala Ala Phe Ile Ala Ser Leu Gln Asp
            20                  25

<210> SEQ ID NO 306
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 306

Glu Trp Lys Ile Ala Ala Gly Glu Ile Trp Glu Leu Pro Asn Leu Asn
1               5                   10                  15

Val Arg Gln Lys Ala Ala Phe Ile Ala Ser Leu Ser Asp
            20                  25

<210> SEQ ID NO 307
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 307

Glu Trp Lys His Ala Ala Gly Glu Ile Trp Gln Leu Pro Asn Leu Asn
1               5                   10                  15

Val Thr Gln Lys Ala Ala Phe Ile Ala Ser Leu Ser Asp
            20                  25

<210> SEQ ID NO 308
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 308

Glu Trp Lys Ile Ala Ala Gly Glu Ile Trp Glu Leu Pro Asn Leu Asn
1               5                   10                  15

Arg Arg Gln Ala Ala Ala Phe Ile Val Ser Leu Ser Asp
            20                  25

<210> SEQ ID NO 309
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 309

Glu Trp Lys Ser Ala Ala Gly Glu Ile Trp Glu Leu Pro Asn Leu Asn
1               5                   10                  15

Arg Ala Gln Lys Ala Ala Phe Ile Ile Ser Leu Ser Asp
            20                  25

<210> SEQ ID NO 310
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 310

Glu Trp Lys His Ala Ala Val Glu Ile Trp Gln Leu Pro Asn Leu Asn
1               5                   10                  15

Arg Phe Gln Lys Ala Ala Phe Ile Ala Ser Leu Ser Asp
            20                  25

<210> SEQ ID NO 311
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 311

Glu Trp Lys Gln Ala Ala Trp Glu Ile Trp Gln Leu Pro Asn Leu Asn
1               5                   10                  15

Thr Gly Gln Lys Ala Ala Phe Ile Arg Ser Leu Ser Asp
            20                  25

<210> SEQ ID NO 312
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 312

Glu Trp Lys Gln Ala Ser Trp Glu Ile Trp Glu Leu Pro Asn Leu Asn
1               5                   10                  15

Arg Gly Gln Lys Ala Ala Phe Ile Ala Ser Leu Ser Asp
            20                  25

<210> SEQ ID NO 313
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 313

Glu Trp Lys Thr Ala Ser Tyr Glu Ile Trp Gln Leu Pro Asn Leu Asn
1               5                   10                  15

Arg Arg Gln Ala Ala Ala Phe Ile Ala Ser Leu Ser Asp
            20                  25

<210> SEQ ID NO 314
<211> LENGTH: 29
<212> TYPE: PRT

<213> ORGANISM: Artificial Sequence
<220> FEATURE:
<223> OTHER INFORMATION: Engineered polypeptide

<400> SEQUENCE: 314

Glu Trp Lys Asn Ala Ser Phe Glu Ile Trp Leu Leu Pro Asn Leu Asn
1               5                   10                  15

Arg Ile Gln Lys Ala Ala Phe Ile Ala Ser Leu Ser Asp
            20                  25

<210> SEQ ID NO 315
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 315

Glu Trp Lys Asn Ala Ala Phe Glu Ile Trp Leu Leu Pro Asn Leu Asn
1               5                   10                  15

Gln Arg Gln Lys Ala Ala Phe Ile Ala Ser Leu Ser Asp
            20                  25

<210> SEQ ID NO 316
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 316

Glu Trp Arg Gly Ala Ala Phe Glu Ile Trp Gln Leu Pro Asn Leu Asn
1               5                   10                  15

Gln Arg Gln Lys Ala Ala Phe Ile Ala Ser Leu Tyr Asp
            20                  25

<210> SEQ ID NO 317
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 317

Glu Trp Lys Val Ala Ser Trp Glu Ile Trp Gln Leu Pro Asn Leu Asn
1               5                   10                  15

Arg Gln Gln Lys Ala Ala Phe Ile Gly Ser Leu Ala Asp
            20                  25

<210> SEQ ID NO 318
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 318

Glu Trp Lys Leu Ala Ser Trp Glu Ile Trp Gln Leu Pro Asn Leu Asn
1               5                   10                  15

Arg Trp Gln Lys Ala Ala Phe Ile Gly Ser Leu Ser Asp
            20                  25

<210> SEQ ID NO 319
<211> LENGTH: 29

```
<212> TYPE: PRT
<213> ORGANISM: Artificial Sequence
<220> FEATURE:
<223> OTHER INFORMATION: Engineered polypeptide

<400> SEQUENCE: 319

Glu Trp Lys Arg Ala Ser Val Glu Ile Trp Glu Leu Pro Asn Leu Asn
1               5                   10                  15

Arg Gln Gln Lys Ala Ala Phe Ile Gly Ser Leu Ser Asp
            20                  25

<210> SEQ ID NO 320
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 320

Glu Trp Lys Arg Ala Ser Phe Glu Ile Trp Gln Leu Pro Asn Leu Asn
1               5                   10                  15

Arg Leu Gln Lys Ala Ala Phe Ile Ala Ser Leu Ala Asp
            20                  25

<210> SEQ ID NO 321
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 321

Glu Trp Lys Gly Ala Ala Gly Glu Ile Trp Gln Leu Pro Asn Leu Asn
1               5                   10                  15

Arg Arg Gln Lys Ala Ala Phe Ile Ser Ser Leu Tyr Asp
            20                  25

<210> SEQ ID NO 322
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 322

Glu Trp Lys Val Ala Ala Phe Glu Ile Trp Gln Leu Pro Asn Leu Asn
1               5                   10                  15

Arg Ala Gln Lys Ala Ala Phe Ile Ser Ser Leu Ala Asp
            20                  25

<210> SEQ ID NO 323
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 323

Glu Trp Lys His Ala Ala Gly Glu Ile Trp Gln Leu Pro Asn Leu Asn
1               5                   10                  15

Arg Ala Gln Lys Ala Ala Phe Ile Ser Ser Leu Ala Asp
            20                  25

<210> SEQ ID NO 324
```

```
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 324

Glu Trp Lys Lys Ala Ala Tyr Glu Ile Trp Gln Leu Pro Asn Leu Asn
1               5                   10                  15

Arg Ala Gln Lys Ala Ala Phe Ile Ser Ser Leu Tyr Asp
            20                  25

<210> SEQ ID NO 325
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 325

Glu Trp Lys Leu Ala Ala Tyr Glu Ile Trp Gln Leu Pro Asn Leu Asn
1               5                   10                  15

Arg His Gln Lys Ala Ala Phe Ile Ser Ser Leu Ser Asp
            20                  25

<210> SEQ ID NO 326
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 326

Glu Trp Lys Arg Ala Ala Phe Glu Ile Trp Gln Leu Pro Asn Leu Asn
1               5                   10                  15

Arg Ser Gln Lys Ala Ala Phe Ile Ser Ser Leu Ala Asp
            20                  25

<210> SEQ ID NO 327
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 327

Glu Trp Lys Thr Ala Ala Phe Glu Ile Trp Gln Leu Pro Asn Leu Asn
1               5                   10                  15

Arg Ser Gln Lys Ala Ala Phe Ile Ala Ser Leu Ala Asp
            20                  25

<210> SEQ ID NO 328
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 328

Glu Trp Lys Ile Ala Ala Phe Glu Ile Trp Gln Leu Pro Asn Leu Asn
1               5                   10                  15

Arg Ile Gln Lys Ala Ala Phe Ile Gly Ser Leu Ala Asp
            20                  25
```

```
<210> SEQ ID NO 329
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 329

Glu Trp Lys Gln Ala Ala Phe Glu Ile Trp Gln Leu Pro Asn Leu Asn
1               5                   10                  15

Arg Ile Gln Lys Ala Ala Phe Ile Thr Ser Leu Ser Asp
            20                  25

<210> SEQ ID NO 330
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 330

Glu Trp Lys Gln Ala Ala Phe Glu Ile Trp Gln Leu Pro Asn Leu Asn
1               5                   10                  15

Arg Val Gln Lys Ala Ala Phe Ile Val Ser Leu Gln Asp
            20                  25

<210> SEQ ID NO 331
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 331

Glu Trp Lys Val Ala Ala Gly Glu Ile Trp Gln Leu Pro Asn Leu Asn
1               5                   10                  15

Arg Ile Gln Lys Ala Ala Phe Ile Gly Ser Leu Ser Asp
            20                  25

<210> SEQ ID NO 332
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 332

Glu Trp Lys Ile Ala Ala Phe Glu Ile Trp Gln Leu Pro Asn Leu Asn
1               5                   10                  15

Arg Trp Gln Lys Ala Ala Phe Ile Ser Ser Leu Gln Asp
            20                  25

<210> SEQ ID NO 333
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 333

Glu Trp Lys Glu Ala Ala Gly Glu Ile Trp Gln Leu Pro Asn Leu Asn
1               5                   10                  15

Arg Tyr Gln Lys Ala Ala Phe Ile Ala Ser Leu Gln Asp
            20                  25
```

```
<210> SEQ ID NO 334
<211> LENGTH: 29
<212> TYPE: PRT
<213> ORGANISM: Artificial Sequence
<220> FEATURE:
<223> OTHER INFORMATION: Engineered polypeptide

<400> SEQUENCE: 334

Glu Trp Lys Thr Ala Ser Phe Glu Ile Trp Gln Leu Pro Asn Leu Asn
1               5                   10                  15

Arg Tyr Gln Lys Ala Ala Phe Ile Ser Ser Leu Gln Asp
            20                  25

<210> SEQ ID NO 335
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 335

Lys Glu Lys Val Ala Ala Thr Gly Glu Ile Trp Asp Leu Pro Asn Leu
1               5                   10                  15

Asn Thr Arg Gln Lys Asn Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 336
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 336

Lys Glu Trp Arg Trp Ala Ala His Glu Ile Trp Asp Leu Pro Asn Leu
1               5                   10                  15

Asn Val Tyr Gln Arg Ala Ala Phe Ile Arg Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 337
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 337

Lys Glu Arg Arg Leu Ala Ser Val Glu Ile Trp Glu Leu Pro Asn Leu
1               5                   10                  15

Asn Ala Val Gln Lys Ser Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 338
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 338

Lys Glu Val Lys Glu Ala Arg Phe Glu Ile Trp Asp Leu Pro Asn Leu
1               5                   10                  15

Asn Arg Thr Gln Lys His Ala Phe Ile Val Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 339
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 339

Lys Glu Trp Lys Gly Ala Ala Gly Glu Ile Trp Asn Leu Pro Asn Leu
1               5                   10                  15

Asn Val Ser Gln Arg Val Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 340
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 340

Lys Glu Lys Tyr Lys Ala Ala His Glu Ile Trp Glu Leu Pro Asn Leu
1               5                   10                  15

Asn Arg Asp Gln Arg Ala Ala Phe Ile Thr Ser Leu Thr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 341
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 341

Lys Glu Arg Ser Leu Ala Ser Phe Glu Ile Trp Glu Leu Pro Asn Leu
1               5                   10                  15

Asn Pro Lys Gln Lys Ala Ala Phe Ile Val Ser Leu Phe Asp Asp Pro
            20                  25                  30

-continued

```
Ser Gln Ser Ala Asn Leu Leu Ala Glu Ala Lys Lys Leu Asn Asp Ala
        35                  40                  45

Gln

<210> SEQ ID NO 342
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 342

Lys Glu Trp Lys Arg Ala Ser Trp Glu Ile Trp Glu Leu Pro Asn Leu
1               5                   10                  15

Asn Asn Ala Gln Lys Arg Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 343
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 343

Lys Glu Lys Tyr Lys Ala Met Thr Glu Ile Trp Ile Leu Pro Asn Leu
1               5                   10                  15

Asn Gln Arg Gln Lys Val Ala Phe Ile Gly Ser Leu Asp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 344
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 344

Lys Glu Trp Arg Gly Ala Ala Gly Glu Ile Trp Ala Leu Pro Asn Leu
1               5                   10                  15

Asn Asn Arg Gln Lys Gly Ala Phe Ile Glu Ser Leu Pro Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 345
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 345

Lys Glu Arg Trp Glu Ala Thr Val Glu Ile Trp Asp Leu Pro Asn Leu
```

```
                1               5                  10                  15
Asn Arg Asn Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 346
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 346

Lys Glu Lys Tyr Asn Ala Tyr Ala Glu Ile Trp Leu Leu Pro Asn Leu
1               5                  10                  15

Asn Arg Tyr Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 347
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 347

Lys Glu Arg Ser Val Ala Gln Lys Glu Ile Trp Glu Leu Pro Asn Leu
1               5                  10                  15

Asn Arg Trp Gln Ala Gly Ala Phe Ile Lys Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 348
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 348

Lys Glu Lys Met Asp Ala Met Gly Glu Ile Trp Asp Leu Pro Asn Leu
1               5                  10                  15

Asn Arg Gly Gln Ala Ser Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 349
<211> LENGTH: 49
<212> TYPE: PRT
<213> ORGANISM: Artificial Sequence
<220> FEATURE:
```

<223> OTHER INFORMATION: Engineered polypeptide

<400> SEQUENCE: 349

Lys Glu Lys Arg Asn Ala Gln Val Glu Ile Trp Thr Leu Pro Asn Leu
1               5                   10                  15

Asn Ser Lys Gln Arg Ala Ala Phe Ile Lys Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 350
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 350

Lys Glu Arg Arg Asp Ala Arg Phe Glu Ile Trp Glu Leu Pro Asn Leu
1               5                   10                  15

Asn Lys Tyr Gln Arg Ala Ala Phe Ile Ser Ser Leu Asp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 351
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 351

Lys Glu Arg Ser Met Ala Arg Phe Glu Ile Trp Glu Leu Pro Asn Leu
1               5                   10                  15

Asn Arg Gly Gln Lys Ser Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 352
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 352

Lys Glu Trp His Gly Ala Ala Ser Glu Ile Trp Glu Leu Pro Asn Leu
1               5                   10                  15

Asn Lys Ser Gln Lys Ser Ala Phe Ile Lys Ser Leu Pro Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 353
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 353

Lys Glu Trp Lys Gln Ala Ala Glu Glu Ile Trp Asp Leu Pro Asn Leu
1               5                   10                  15

Asn Arg Arg Gln Ala Gly Ala Phe Ile Thr Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 354
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 354

Lys Glu Lys Val Gln Ala Ser Glu Glu Ile Trp Asn Leu Pro Asn Leu
1               5                   10                  15

Asn Arg Arg Gln Arg Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 355
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 355

Lys Glu Arg Tyr Ser Ala Thr Val Glu Ile Trp Asp Leu Pro Asn Leu
1               5                   10                  15

Asn Thr Leu Gln Lys Ser Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 356
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 356

Lys Glu Arg Tyr Ser Ala Tyr Tyr Glu Ile Trp Gln Leu Pro Asn Leu
1               5                   10                  15

Asn Arg Ile Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
```

-continued

```
                      35                  40                  45
Gln

<210> SEQ ID NO 357
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 357

Lys Glu Arg Tyr Arg Ala Tyr Phe Glu Ile Trp Gln Leu Pro Asn Leu
1               5                   10                  15

Asn Arg Leu Gln Lys Ala Ala Phe Ile Ser Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 358
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 358

Lys Glu Lys Tyr Lys Ala Tyr Gly Glu Ile Trp Gln Leu Pro Asn Leu
1               5                   10                  15

Asn Arg Val Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 359
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 359

Lys Glu Arg Lys Gln Ala Thr Phe Glu Ile Trp Glu Leu Pro Asn Leu
1               5                   10                  15

Asn Gln Arg Gln Lys Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 360
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 360

Lys Glu Trp Lys Ile Ala Ala Gly Glu Ile Trp Gln Leu Pro Asn Leu
1               5                   10                  15
```

Asn Arg His Gln Lys Gly Ala Phe Ile Ser Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 361
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 361

Lys Glu Lys Tyr Lys Ala Tyr Val Glu Ile Trp Gln Leu Pro Asn Leu
1               5                   10                  15

Asn Arg Tyr Gln Arg Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 362
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 362

Lys Glu Arg Lys Ala Ala Thr Phe Glu Ile Trp Glu Leu Pro Asn Leu
1               5                   10                  15

Asn Arg Ile Gln Lys Ala Ala Phe Ile Ala Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 363
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 363

Lys Glu Lys Tyr Lys Ala Tyr Gly Glu Ile Trp Gln Leu Pro Asn Leu
1               5                   10                  15

Asn Arg Ile Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 364
<211> LENGTH: 49
<212> TYPE: PRT
<213> ORGANISM: Artificial Sequence
<220> FEATURE:
<223> OTHER INFORMATION: Engineered polypeptide -continued

<400> SEQUENCE: 364

Lys Glu Lys Arg Ile Ala Thr Trp Glu Ile Trp Gln Leu Pro Asn Leu
1               5                   10                  15

Asn Gln His Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 365
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 365

Lys Glu Lys Tyr Lys Ala Tyr Val Glu Ile Trp Gln Leu Pro Asn Leu
1               5                   10                  15

Asn Arg Gly Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 366
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 366

Lys Glu Arg Tyr Leu Ala Tyr Tyr Glu Ile Trp Gln Leu Pro Asn Leu
1               5                   10                  15

Asn Arg Thr Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 367
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 367

Lys Glu Arg Tyr Ile Ala Tyr Trp Glu Ile Trp Gln Leu Pro Asn Leu
1               5                   10                  15

Asn Arg Arg Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 368

```
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 368

Lys Glu Lys Tyr Arg Ala Tyr Gly Glu Ile Trp Gln Leu Pro Asn Leu
1               5                   10                  15

Asn Arg Gly Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 369
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 369

Lys Glu Lys Tyr Thr Ala Tyr Phe Glu Ile Trp Gln Leu Pro Asn Leu
1               5                   10                  15

Asn Val Arg Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 370
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 370

Lys Glu Arg Tyr Ser Ala Tyr Tyr Glu Ile Trp Gln Leu Pro Asn Leu
1               5                   10                  15

Asn Val Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 371
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 371

Lys Glu Lys Tyr Ala Ala Tyr Gly Glu Ile Trp Gln Leu Pro Asn Leu
1               5                   10                  15

Asn Arg Ser Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 372
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 372

```
Lys Glu Arg Lys Arg Ala Thr Val Glu Ile Trp Glu Leu Pro Asn Leu
1               5                   10                  15
Asn Arg Leu Gln Arg Gly Ala Phe Ile Ala Ser Leu Trp Asp Asp Pro
            20                  25                  30
Ser Gln Ser Ala Asn Leu Leu Ala Glu Ala Lys Lys Leu Asn Asp Ala
        35                  40                  45
Gln
```

<210> SEQ ID NO 373
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 373

```
Lys Glu Trp Lys Gln Ala Ser Phe Glu Ile Trp Glu Leu Pro Asn Leu
1               5                   10                  15
Asn Arg Leu Gln Lys Ala Ala Phe Ile Gly Ser Leu Ala Asp Asp Pro
            20                  25                  30
Ser Gln Ser Ala Asn Leu Leu Ala Glu Ala Lys Lys Leu Asn Asp Ala
        35                  40                  45
Gln
```

<210> SEQ ID NO 374
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 374

```
Lys Glu Arg Lys His Ala Thr Val Glu Ile Trp Glu Leu Pro Asn Leu
1               5                   10                  15
Asn Arg Val Gln Lys Ala Ala Phe Ile Ser Ser Leu Trp Asp Asp Pro
            20                  25                  30
Ser Gln Ser Ala Asn Leu Leu Ala Glu Ala Lys Lys Leu Asn Asp Ala
        35                  40                  45
Gln
```

<210> SEQ ID NO 375
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 375

```
Lys Glu Lys Tyr Lys Ala Tyr Val Glu Ile Trp Gln Leu Pro Asn Leu
1               5                   10                  15
```

Asn Gln Arg Gln Lys Ala Ala Phe Ile Gly Ser Leu Ala Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 376
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 376

Lys Glu Lys Tyr Val Ala Tyr Gly Glu Ile Trp Gln Leu Pro Asn Leu
1               5                   10                  15

Asn Arg Thr Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 377
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 377

Lys Glu Arg Tyr Ile Ala Tyr Tyr Glu Ile Trp Gln Leu Pro Asn Leu
1               5                   10                  15

Asn Arg Tyr Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 378
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 378

Lys Glu Lys Tyr Asn Ala Tyr Gly Glu Ile Trp Gln Leu Pro Asn Leu
1               5                   10                  15

Asn Val Arg Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 379
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 379

Lys Glu Arg Lys Ala Ala Thr Val Glu Ile Trp Glu Leu Pro Asn Leu
1               5                   10                  15

Asn Arg Val Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 380
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 380

Lys Glu Arg Tyr Val Ala Tyr Tyr Glu Ile Trp Glu Leu Pro Asn Leu
1               5                   10                  15

Asn Gln Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 381
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 381

Lys Glu Arg Tyr Arg Ala Tyr Tyr Glu Ile Trp Gln Leu Pro Asn Leu
1               5                   10                  15

Asn Gln Arg Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 382
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 382

Lys Glu Trp Lys Ser Ala Ala Phe Glu Ile Trp Glu Leu Pro Asn Leu
1               5                   10                  15

Asn Arg Leu Gln Lys Ala Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 383
<211> LENGTH: 49

```
<212> TYPE: PRT
<213> ORGANISM: Artificial Sequence
<220> FEATURE:
<223> OTHER INFORMATION: Engineered polypeptide

<400> SEQUENCE: 383

Lys Glu Arg Lys Gln Ala Thr Phe Glu Ile Trp Glu Leu Pro Asn Leu
1               5                   10                  15

Asn Arg His Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 384
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 384

Lys Glu Trp Lys Ile Ala Ala Gly Glu Ile Trp Gln Leu Pro Asn Leu
1               5                   10                  15

Asn Arg Arg Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 385
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 385

Lys Glu Arg Tyr Leu Ala Tyr Tyr Glu Ile Trp Gln Leu Pro Asn Leu
1               5                   10                  15

Asn Arg Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 386
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 386

Lys Glu Arg Tyr His Ala Tyr Tyr Glu Ile Trp Glu Leu Pro Asn Leu
1               5                   10                  15

Asn Arg Leu Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 387
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 387

Lys Glu Lys Tyr Lys Ala Tyr Ala Glu Ile Trp Gln Leu Pro Asn Leu
1               5                   10                  15

Asn Arg Thr Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 388
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 388

Lys Glu Arg Tyr Lys Ala Tyr Tyr Glu Ile Trp Gln Leu Pro Asn Leu
1               5                   10                  15

Asn Arg Gln Gln Lys Gly Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 389
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 389

Lys Glu Arg Lys Leu Ala Thr Phe Glu Ile Trp Glu Leu Pro Asn Leu
1               5                   10                  15

Asn Thr Ser Gln Lys Gly Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 390
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 390

Lys Glu Arg Tyr Val Ala Tyr Tyr Glu Ile Trp Gln Leu Pro Asn Leu
1               5                   10                  15

Asn Val Gln Gln Lys Ala Ala Phe Ile Ala Ser Leu Gln Asp Asp Pro

```
                    20                  25                  30

Ser Gln Ser Ala Asn Leu Leu Ala Glu Ala Lys Lys Leu Asn Asp Ala
        35                  40                  45

Gln

<210> SEQ ID NO 391
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 391

Lys Glu Arg Ser Ile Ala Ser Val Glu Ile Trp Glu Leu Pro Asn Leu
1               5                   10                  15

Asn Gln Arg Gln Lys Gly Ala Phe Ile Ala Ser Leu Trp Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 392
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 392

Lys Glu Arg Lys Gln Ala Ala Val Glu Ile Trp Glu Leu Pro Asn Leu
1               5                   10                  15

Asn Val Arg Gln Lys Ala Ala Phe Ile Arg Ser Leu Phe Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 393
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 393

Lys Glu Lys Lys Ile Ala Ala Phe Glu Ile Trp Glu Leu Pro Asn Leu
1               5                   10                  15

Asn Gln Trp Gln Lys Ala Ala Phe Ile Ala Ser Leu Phe Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 394
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 394
```

Lys Glu Arg Lys Ile Ala Thr Val Glu Ile Trp Glu Leu Pro Asn Leu
1               5                   10                  15

Asn Arg Ile Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 395
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 395

Lys Glu Lys Tyr Arg Ala Ala Gly Glu Ile Trp Glu Leu Pro Asn Leu
1               5                   10                  15

Asn Val Leu Gln Lys Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 396
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 396

Lys Glu Arg Lys Ile Ala Ala Val Glu Ile Trp Glu Leu Pro Asn Leu
1               5                   10                  15

Asn Arg Tyr Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 397
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 397

Lys Glu Lys Arg Thr Ala Thr Trp Glu Ile Trp Gln Leu Pro Asn Leu
1               5                   10                  15

Asn Gln Arg Gln Arg Ala Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 398
<211> LENGTH: 49
<212> TYPE: PRT

<213> ORGANISM: Artificial Sequence
<220> FEATURE:
<223> OTHER INFORMATION: Engineered polypeptide

<400> SEQUENCE: 398

| Lys | Glu | Arg | Lys | Thr | Ala | Thr | Val | Glu | Ile | Trp | Glu | Leu | Pro | Asn | Leu |
|---|---|---|---|---|---|---|---|---|---|---|---|---|---|---|---|
| 1 | | | | 5 | | | | | 10 | | | | | 15 | |

| Asn | Arg | Arg | Gln | Lys | Ala | Ala | Phe | Ile | Ala | Ser | Leu | Trp | Asp | Asp | Pro |
|---|---|---|---|---|---|---|---|---|---|---|---|---|---|---|---|
| | | | 20 | | | | | 25 | | | | | 30 | | |

| Ser | Gln | Ser | Ala | Asn | Leu | Leu | Ala | Glu | Ala | Lys | Lys | Leu | Asn | Asp | Ala |
|---|---|---|---|---|---|---|---|---|---|---|---|---|---|---|---|
| | | 35 | | | | | 40 | | | | | 45 | | | |

Gln

<210> SEQ ID NO 399
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 399

| Lys | Glu | Arg | Lys | Gln | Ala | Ala | Val | Glu | Ile | Trp | Glu | Leu | Pro | Asn | Leu |
|---|---|---|---|---|---|---|---|---|---|---|---|---|---|---|---|
| 1 | | | | 5 | | | | | 10 | | | | | 15 | |

| Asn | Arg | Ile | Gln | Lys | Gly | Ala | Phe | Ile | Lys | Ser | Leu | Trp | Asp | Asp | Pro |
|---|---|---|---|---|---|---|---|---|---|---|---|---|---|---|---|
| | | | 20 | | | | | 25 | | | | | 30 | | |

| Ser | Gln | Ser | Ala | Asn | Leu | Leu | Ala | Glu | Ala | Lys | Lys | Leu | Asn | Asp | Ala |
|---|---|---|---|---|---|---|---|---|---|---|---|---|---|---|---|
| | | 35 | | | | | 40 | | | | | 45 | | | |

Gln

<210> SEQ ID NO 400
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 400

| Lys | Glu | Arg | Tyr | Ile | Ala | Tyr | Gly | Glu | Ile | Trp | Gln | Leu | Pro | Asn | Leu |
|---|---|---|---|---|---|---|---|---|---|---|---|---|---|---|---|
| 1 | | | | 5 | | | | | 10 | | | | | 15 | |

| Asn | Arg | Arg | Gln | Lys | Ala | Ala | Phe | Ile | Gly | Ser | Leu | Ser | Asp | Asp | Pro |
|---|---|---|---|---|---|---|---|---|---|---|---|---|---|---|---|
| | | | 20 | | | | | 25 | | | | | 30 | | |

| Ser | Gln | Ser | Ala | Asn | Leu | Leu | Ala | Glu | Ala | Lys | Lys | Leu | Asn | Asp | Ala |
|---|---|---|---|---|---|---|---|---|---|---|---|---|---|---|---|
| | | 35 | | | | | 40 | | | | | 45 | | | |

Gln

<210> SEQ ID NO 401
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 401

| Lys | Glu | Arg | Tyr | Arg | Ala | Tyr | Tyr | Glu | Ile | Trp | Gln | Leu | Pro | Asn | Leu |
|---|---|---|---|---|---|---|---|---|---|---|---|---|---|---|---|
| 1 | | | | 5 | | | | | 10 | | | | | 15 | |

| Asn | Arg | Thr | Gln | Lys | Val | Ala | Phe | Ile | Gly | Ser | Leu | Gln | Asp | Asp | Pro |
|---|---|---|---|---|---|---|---|---|---|---|---|---|---|---|---|
| | | | 20 | | | | | 25 | | | | | 30 | | |

| Ser | Gln | Ser | Ala | Asn | Leu | Leu | Ala | Glu | Ala | Lys | Lys | Leu | Asn | Asp | Ala |
|---|---|---|---|---|---|---|---|---|---|---|---|---|---|---|---|
| | | 35 | | | | | 40 | | | | | 45 | | | |

Gln

<210> SEQ ID NO 402
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 402

Lys Glu Arg Arg Leu Ala Tyr Trp Glu Ile Trp Gln Leu Pro Asn Leu
1               5                   10                  15

Asn Thr Thr Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 403
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 403

Lys Glu Arg Arg Arg Ala Tyr Tyr Glu Ile Trp Gln Leu Pro Asn Leu
1               5                   10                  15

Asn Arg Ile Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 404
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 404

Lys Glu Arg Arg Leu Ala Tyr Tyr Glu Ile Trp Glu Leu Pro Asn Leu
1               5                   10                  15

Asn Val Ala Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 405
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 405

Lys Glu Arg Tyr Leu Ala Tyr Tyr Glu Ile Trp Glu Leu Pro Asn Leu
1               5                   10                  15

Asn Val Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 406
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 406

Lys Glu Arg Tyr Ala Ala Tyr Tyr Glu Ile Trp Gln Leu Pro Asn Leu
1               5                   10                  15

Asn Ser Arg Gln Lys Ala Ala Phe Ile Gly Ser Leu Ser Asp Asp Pro
        20                  25                  30

Ser Gln Ser Ala Asn Leu Leu Ala Glu Ala Lys Lys Leu Asn Asp Ala
        35                  40                  45

Gln

<210> SEQ ID NO 407
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 407

Lys Glu Arg Tyr Leu Ala Tyr Tyr Glu Ile Trp Gln Leu Pro Asn Leu
1               5                   10                  15

Asn Gln Leu Gln Lys Ala Ala Phe Ile Gly Ser Leu Ala Asp Asp Pro
        20                  25                  30

Ser Gln Ser Ala Asn Leu Leu Ala Glu Ala Lys Lys Leu Asn Asp Ala
        35                  40                  45

Gln

<210> SEQ ID NO 408
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 408

Lys Glu Arg Tyr His Ala Tyr Tyr Glu Ile Trp Gln Leu Pro Asn Leu
1               5                   10                  15

Asn Ser Trp Gln Lys Ala Ala Phe Ile Gly Ser Leu Gly Asp Asp Pro
        20                  25                  30

Ser Gln Ser Ala Asn Leu Leu Ala Glu Ala Lys Lys Leu Asn Asp Ala
        35                  40                  45

Gln

<210> SEQ ID NO 409
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 409

Lys Glu Arg Tyr His Ala Tyr Tyr Glu Ile Trp Gln Leu Pro Asn Leu
1               5                   10                  15

Asn Ser Ala Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 410
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 410

Lys Glu Arg Tyr Glu Ala Tyr Tyr Glu Ile Trp Gln Leu Pro Asn Leu
1               5                   10                  15

Asn Ser Val Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 411
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 411

Lys Glu Arg Tyr His Ala Tyr Tyr Glu Ile Trp Gln Leu Pro Asn Leu
1               5                   10                  15

Asn Arg Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 412
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 412

Lys Glu Arg Tyr Thr Ala Tyr Tyr Glu Ile Trp Gln Leu Pro Asn Leu
1               5                   10                  15

Asn Arg Ala Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 413
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 413

Lys Glu Arg Tyr Ser Ala Tyr Glu Ile Trp Gln Leu Pro Asn Leu
1               5                   10                  15

Asn Arg Ala Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 414
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 414

Lys Glu Arg Tyr Ser Ala Tyr Glu Ile Trp Gln Leu Pro Asn Leu
1               5                   10                  15

Asn Arg Ala Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 415
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 415

Lys Glu Arg Tyr His Ala Tyr Glu Ile Trp Gln Leu Pro Asn Leu
1               5                   10                  15

Asn Arg Ala Gln Lys Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 416
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 416

Lys Glu Arg Tyr Ser Ala Tyr Val Glu Ile Trp Gln Leu Pro Asn Leu
1               5                   10                  15

Asn Arg Gly Gln Lys Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 417
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 417

Lys Glu Arg Tyr Ser Ala Tyr Phe Glu Ile Trp Gln Leu Pro Asn Leu
1               5                   10                  15

Asn Arg Leu Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 418
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 418

Lys Glu Arg Tyr Asn Ala Tyr Phe Glu Ile Trp Gln Leu Pro Asn Leu
1               5                   10                  15

Asn Arg Tyr Gln Lys Ser Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 419
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 419

Lys Glu Arg Tyr Ala Ala Tyr Phe Glu Ile Trp Gln Leu Pro Asn Leu
1               5                   10                  15

Asn Val Ala Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 420
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 420

Lys Glu Arg Tyr Gln Ala Tyr Phe Glu Ile Trp Gln Leu Pro Asn Leu
1               5                   10                  15

Asn Gln Trp Gln Lys Ala Ala Phe Ile Gly Ser Leu Asp Asp Pro
            20                  25                  30

```
Ser Gln Ser Ala Asn Leu Leu Ala Glu Ala Lys Lys Leu Asn Asp Ala
        35                  40                  45

Gln
```

<210> SEQ ID NO 421
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 421

```
Lys Glu Arg Tyr Lys Ala Tyr Trp Glu Ile Trp Gln Leu Pro Asn Leu
1               5                   10                  15

Asn Gln Gly Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 422
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 422

```
Lys Glu Arg Tyr Ile Ala Tyr Gly Glu Ile Trp Gln Leu Pro Asn Leu
1               5                   10                  15

Asn Val Gly Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 423
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 423

```
Lys Glu Arg Tyr Arg Ala Tyr Val Glu Ile Trp Gln Leu Pro Asn Leu
1               5                   10                  15

Asn Arg Val Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 424
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 424

```
Lys Glu Arg Tyr Lys Ala Tyr Val Glu Ile Trp Gln Leu Pro Asn Leu
```

1               5                  10                 15
Asn Arg Thr Gln Lys Ala Ala Phe Ile Gly Ser Leu Gln Asp Asp Pro
            20                  25                 30

Ser Gln Ser Ala Asn Leu Leu Ala Glu Ala Lys Lys Leu Asn Asp Ala
        35                  40                  45

Gln

<210> SEQ ID NO 425
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 425

Lys Glu Lys Tyr Glu Ala Tyr Gly Glu Ile Trp Glu Leu Pro Asn Leu
1               5                  10                 15

Asn Arg Ser Gln Lys Ala Ala Phe Ile Gly Ser Leu Glu Asp Asp Pro
            20                  25                 30

Ser Gln Ser Ala Asn Leu Leu Ala Glu Ala Lys Lys Leu Asn Asp Ala
        35                  40                  45

Gln

<210> SEQ ID NO 426
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 426

Lys Glu Lys Tyr Gln Ala Tyr Gly Glu Ile Trp Gln Leu Pro Asn Leu
1               5                  10                 15

Asn Arg Ser Gln Lys Ala Ala Phe Ile Thr Ser Leu Glu Asp Asp Pro
            20                  25                 30

Ser Gln Ser Ala Asn Leu Leu Ala Glu Ala Lys Lys Leu Asn Asp Ala
        35                  40                  45

Gln

<210> SEQ ID NO 427
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 427

Lys Glu Lys Tyr Ala Ala Tyr Gly Glu Ile Trp Leu Leu Pro Asn Leu
1               5                  10                 15

Asn Arg Ile Gln Lys Ala Ala Phe Ile Gly Ser Leu Gln Asp Asp Pro
            20                  25                 30

Ser Gln Ser Ala Asn Leu Leu Ala Glu Ala Lys Lys Leu Asn Asp Ala
        35                  40                  45

Gln

<210> SEQ ID NO 428
<211> LENGTH: 49
<212> TYPE: PRT
<213> ORGANISM: Artificial Sequence
<220> FEATURE:

<223> OTHER INFORMATION: Engineered polypeptide

<400> SEQUENCE: 428

Lys Glu Lys Tyr Lys Ala Tyr Gly Glu Ile Trp Glu Leu Pro Asn Leu
1               5                   10                  15

Asn Arg Arg Gln Lys Val Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 429
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 429

Lys Glu Lys Tyr Lys Ala Tyr Gly Glu Ile Trp Glu Leu Pro Asn Leu
1               5                   10                  15

Asn Arg Ser Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 430
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 430

Lys Glu Lys Tyr Lys Ala Tyr Gly Glu Ile Trp Gln Leu Pro Asn Leu
1               5                   10                  15

Asn Gln Arg Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 431
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 431

Lys Glu Lys Tyr Lys Ala Tyr Gly Glu Ile Trp Gln Leu Pro Asn Leu
1               5                   10                  15

Asn Arg Ser Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 432
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 432

Lys Glu Lys Tyr Lys Ala Tyr Gly Glu Ile Trp Gln Leu Pro Asn Leu
1               5                   10                  15

Asn Arg Arg Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 433
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 433

Lys Glu Lys Tyr Asn Ala Tyr Gly Glu Ile Trp Gln Leu Pro Asn Leu
1               5                   10                  15

Asn Arg Gly Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 434
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 434

Lys Glu Lys Tyr Val Ala Tyr Ala Glu Ile Trp Gln Leu Pro Asn Leu
1               5                   10                  15

Asn Arg Val Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 435
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 435

Lys Glu Lys Tyr Gln Ala Tyr Gly Glu Ile Trp Gln Leu Pro Asn Leu
1               5                   10                  15

Asn Arg Val Gln Lys Ala Ala Phe Ile Gly Ser Leu Asp Asp Pro
            20                  25                  30

Ser Gln Ser Ala Asn Leu Leu Ala Glu Ala Lys Lys Leu Asn Asp Ala
```

-continued

```
                35                  40                  45

Gln

<210> SEQ ID NO 436
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 436

Lys Glu Lys Tyr His Ala Tyr Gly Glu Ile Trp Gln Leu Pro Asn Leu
1               5                   10                  15

Asn Arg Ile Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 437
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 437

Lys Glu Lys Tyr Thr Ala Tyr Val Glu Ile Trp Gln Leu Pro Asn Leu
1               5                   10                  15

Asn Arg Tyr Gln Arg Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 438
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 438

Lys Glu Lys Tyr Lys Ala Tyr Val Glu Ile Trp Gln Leu Pro Asn Leu
1               5                   10                  15

Asn Arg Gly Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 439
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 439

Lys Glu Lys Tyr Val Ala Tyr Val Glu Ile Trp Gln Leu Pro Asn Leu
1               5                   10                  15
```

Asn Arg Thr Gln Lys Ala Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 440
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 440

Lys Glu Lys Tyr Ile Ala Tyr Val Glu Ile Trp Gln Leu Pro Asn Leu
1               5                   10                  15

Asn Arg Thr Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 441
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 441

Lys Glu Lys Tyr Lys Ala Tyr Ala Glu Ile Trp Gln Leu Pro Asn Leu
1               5                   10                  15

Asn Arg Ala Gln Lys Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 442
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 442

Lys Glu Lys Tyr Thr Ala Tyr Gly Glu Ile Trp Gln Leu Pro Asn Leu
1               5                   10                  15

Asn Val Arg Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 443
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 443

Lys Glu Lys Tyr Thr Ala Tyr Gly Glu Ile Trp Gln Leu Pro Asn Leu
1               5                   10                  15

Asn Gln Arg Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 444
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 444

Lys Glu Lys Tyr Thr Ala Tyr Phe Glu Ile Trp Gln Leu Pro Asn Leu
1               5                   10                  15

Asn Gln Gly Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 445
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 445

Lys Glu Lys Tyr Gln Ala Tyr Val Glu Ile Trp Gln Leu Pro Asn Leu
1               5                   10                  15

Asn Gln Arg Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 446
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 446

Lys Glu Lys Tyr Ala Ala Tyr Val Glu Ile Trp Gln Leu Pro Asn Leu
1               5                   10                  15

Asn Gln Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 447

```
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 447

Lys Glu Lys Tyr Val Ala Tyr Val Glu Ile Trp Gln Leu Pro Asn Leu
1               5                  10                  15

Asn Thr Ser Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 448
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 448

Lys Glu Lys Tyr Gln Ala Tyr Ala Glu Ile Trp Gln Leu Pro Asn Leu
1               5                  10                  15

Asn Val Arg Gln Lys Ser Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 449
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 449

Lys Glu Lys Tyr Gln Ala Tyr Tyr Glu Ile Trp Glu Leu Pro Asn Leu
1               5                  10                  15

Asn Val Gln Gln Lys Ser Ala Phe Ile Thr Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 450
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 450

Lys Glu Lys Tyr His Ala Tyr Tyr Glu Ile Trp Gln Leu Pro Asn Leu
1               5                  10                  15

Asn Val His Gln Lys Ala Ala Phe Ile Arg Ser Leu Ala Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 451
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 451

Lys Glu Lys Tyr Gln Ala Tyr Tyr Glu Ile Trp Gln Leu Pro Asn Leu
1               5                   10                  15

Asn Val Ala Gln Lys Ala Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 452
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 452

Lys Glu Lys Tyr Thr Ala Tyr Tyr Glu Ile Trp Gln Leu Pro Asn Leu
1               5                   10                  15

Asn Arg Thr Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 453
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 453

Lys Glu Arg Tyr Arg Ala Tyr Tyr Glu Ile Trp Gln Leu Pro Asn Leu
1               5                   10                  15

Asn Arg Gln Gln Lys Gly Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 454
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 454

Lys Glu Lys Tyr Lys Ala Tyr Tyr Glu Ile Trp Gln Leu Pro Asn Leu
1               5                   10                  15

```
Asn Arg Ser Gln Lys Gly Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 455
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 455

```
Lys Glu Lys Tyr Ile Ala Tyr Tyr Glu Ile Trp Gln Leu Pro Asn Leu
1               5                   10                  15

Asn Arg Ser Gln Lys Gly Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 456
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 456

```
Lys Glu Arg Tyr Lys Ala Tyr Tyr Glu Ile Trp Gln Leu Pro Asn Leu
1               5                   10                  15

Asn Arg Gln Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 457
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 457

```
Lys Glu Arg Tyr Leu Ala Tyr Tyr Glu Ile Trp Gln Leu Pro Asn Leu
1               5                   10                  15

Asn Gln Phe Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 458
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 458

Lys Glu Arg Tyr Leu Ala Tyr Tyr Glu Ile Trp Gln Leu Pro Asn Leu
1               5                   10                  15

Asn Arg Glu Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 459
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 459

Lys Glu Arg Tyr Val Ala Tyr Gly Glu Ile Trp Gln Leu Pro Asn Leu
1               5                   10                  15

Asn Arg Tyr Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 460
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 460

Lys Glu Arg Tyr Ile Ala Tyr Tyr Glu Ile Trp Gln Leu Pro Asn Leu
1               5                   10                  15

Asn Arg Ala Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 461
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 461

Lys Glu Arg Tyr Gln Ala Tyr Tyr Glu Ile Trp Gln Leu Pro Asn Leu
1               5                   10                  15

Asn Arg Ile Gln Lys Ala Ala Phe Ile Lys Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 462
<211> LENGTH: 49

<212> TYPE: PRT
<213> ORGANISM: Artificial Sequence
<220> FEATURE:
<223> OTHER INFORMATION: Engineered polypeptide

<400> SEQUENCE: 462

Lys Glu Arg Tyr Thr Ala Tyr Tyr Glu Ile Trp Gln Leu Pro Asn Leu
1               5                   10                  15

Asn Thr Gln Gln Lys Ala Ala Phe Ile Arg Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 463
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 463

Lys Glu Arg Tyr Gln Ala Tyr Tyr Glu Ile Trp Gln Leu Pro Asn Leu
1               5                   10                  15

Asn Thr Ile Gln Lys Ala Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 464
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 464

Lys Glu Arg Tyr Ala Ala Tyr Ala Glu Ile Trp Gln Leu Pro Asn Leu
1               5                   10                  15

Asn Arg Trp Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 465
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 465

Lys Glu Arg Tyr Arg Ala Tyr Ala Glu Ile Trp Gln Leu Pro Asn Leu
1               5                   10                  15

Asn Arg Trp Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 466
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 466

Lys Glu Arg Tyr Arg Ala Tyr Ala Glu Ile Trp Gln Leu Pro Asn Leu
1               5                   10                  15

Asn Arg Ile Gln Lys Ala Ala Phe Ile Gly Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 467
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 467

Lys Glu Arg Tyr His Ala Tyr Ala Glu Ile Trp Gln Leu Pro Asn Leu
1               5                   10                  15

Asn Arg Ile Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 468
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 468

Lys Glu Arg Tyr Arg Ala Tyr Tyr Glu Ile Trp Gln Leu Pro Asn Leu
1               5                   10                  15

Asn Arg Tyr Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 469
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 469

Lys Glu Arg Tyr Thr Ala Tyr Tyr Glu Ile Trp Gln Leu Pro Asn Leu
1               5                   10                  15

Asn Arg Val Gln Lys Ala Ala Phe Ile Ala Ser Leu Ser Asp Asp Pro

```
                    20                  25                  30

Ser Gln Ser Ala Asn Leu Leu Ala Glu Ala Lys Lys Leu Asn Asp Ala
        35                  40                  45

Gln

<210> SEQ ID NO 470
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 470

Lys Glu Arg Tyr His Ala Tyr Tyr Glu Ile Trp Gln Leu Pro Asn Leu
 1               5                  10                  15

Asn Arg Thr Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 471
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 471

Lys Glu Arg Tyr Val Ala Tyr Tyr Glu Ile Trp Gln Leu Pro Asn Leu
 1               5                  10                  15

Asn Arg Arg Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 472
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 472

Lys Glu Arg Tyr Leu Ala Tyr Phe Glu Ile Trp Gln Leu Pro Asn Leu
 1               5                  10                  15

Asn Arg His Gln Lys Gly Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 473
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 473
```

Lys Glu Arg Tyr Thr Ala Tyr Phe Glu Ile Trp Gln Leu Pro Asn Leu
1               5                   10                  15

Asn Arg Trp Gln Lys Gly Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 474
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 474

Lys Glu Arg Tyr Ala Ala Tyr Phe Glu Ile Trp Gln Leu Pro Asn Leu
1               5                   10                  15

Asn Arg Leu Gln Lys Ala Ala Phe Ile Ser Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 475
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 475

Lys Glu Arg Tyr Val Ala Tyr Phe Glu Ile Trp Gln Leu Pro Asn Leu
1               5                   10                  15

Asn Arg Ser Gln Lys Ala Ala Phe Ile Ser Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 476
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 476

Lys Glu Arg Tyr Gly Ala Tyr Phe Glu Ile Trp Gln Leu Pro Asn Leu
1               5                   10                  15

Asn Arg Thr Gln Lys Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 477
<211> LENGTH: 49
<212> TYPE: PRT

<213> ORGANISM: Artificial Sequence
<220> FEATURE:
<223> OTHER INFORMATION: Engineered polypeptide

<400> SEQUENCE: 477

Lys Glu Lys Tyr Ile Ala Tyr Trp Glu Ile Trp Gln Leu Pro Asn Leu
1               5                   10                  15

Asn Arg Glu Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 478
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 478

Lys Glu Arg Tyr Ile Ala Tyr Ala Glu Ile Trp Gln Leu Pro Asn Leu
1               5                   10                  15

Asn Arg Arg Gln Lys Ala Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 479
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 479

Lys Glu Arg Tyr Ile Ala Tyr Trp Glu Ile Trp Gln Leu Pro Asn Leu
1               5                   10                  15

Asn Gln Arg Gln Lys Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 480
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 480

Lys Glu Arg Tyr Ile Ala Tyr Trp Glu Ile Trp Gln Leu Pro Asn Leu
1               5                   10                  15

Asn Arg Leu Gln Lys Ser Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 481
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 481

Lys Glu Arg Tyr His Ala Tyr Trp Glu Ile Trp Gln Leu Pro Asn Leu
1               5                   10                  15

Asn Arg Ala Gln Lys Ala Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 482
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 482

Lys Glu Arg Tyr Asn Ala Tyr Trp Glu Ile Trp Gln Leu Pro Asn Leu
1               5                   10                  15

Asn Arg Leu Gln Lys Ala Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 483
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 483

Lys Glu Arg Tyr Thr Ala Tyr Gly Glu Ile Trp Glu Leu Pro Asn Leu
1               5                   10                  15

Asn Arg Val Gln Arg Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 484
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 484

Lys Glu Arg Tyr Thr Ala Tyr Gly Glu Ile Trp Glu Leu Pro Asn Leu
1               5                   10                  15

Asn Arg Leu Gln Lys Ala Ala Phe Ile Gly Ser Leu Ala Asp Asp Pro
            20                  25                  30
```

Ser Gln Ser Ala Asn Leu Leu Ala Glu Ala Lys Lys Leu Asn Asp Ala
        35                  40                  45

Gln

<210> SEQ ID NO 485
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 485

Lys Glu Arg Tyr His Ala Tyr Gly Glu Ile Trp Glu Leu Pro Asn Leu
1               5                   10                  15

Asn Arg Arg Gln Lys Ala Ala Phe Ile Thr Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 486
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 486

Lys Glu Arg Tyr Lys Ala Tyr Gly Glu Ile Trp Gln Leu Pro Asn Leu
1               5                   10                  15

Asn Arg Leu Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 487
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 487

Lys Glu Arg Tyr Gln Ala Tyr Gly Glu Ile Trp Gln Leu Pro Asn Leu
1               5                   10                  15

Asn Arg Leu Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 488
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 488

Lys Glu Arg Tyr Val Ala Tyr Gly Glu Ile Trp Gln Leu Pro Asn Leu
1               5                   10                  15

Asn Arg Leu Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 489
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 489

Lys Glu Arg Tyr Ile Ala Tyr Gly Glu Ile Trp Glu Leu Pro Asn Leu
1               5                   10                  15

Asn Arg Leu Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 490
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 490

Lys Glu Arg Tyr Gln Ala Tyr Gly Glu Ile Trp Gln Leu Pro Asn Leu
1               5                   10                  15

Asn Arg Arg Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 491
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 491

Lys Glu Arg Arg Gln Ala Tyr Phe Glu Ile Trp Glu Leu Pro Asn Leu
1               5                   10                  15

Asn Arg Tyr Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 492
<211> LENGTH: 49
<212> TYPE: PRT
<213> ORGANISM: Artificial Sequence

```
<220> FEATURE:
<223> OTHER INFORMATION: Engineered polypeptide

<400> SEQUENCE: 492

Lys Glu Arg Tyr Arg Ala Tyr Val Glu Ile Trp Glu Leu Pro Asn Leu
1               5                   10                  15

Asn Arg Ile Gln Lys Val Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 493
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 493

Lys Glu Lys Tyr Thr Ala Tyr Gly Glu Ile Trp Glu Leu Pro Asn Leu
1               5                   10                  15

Asn Arg Ile Gln Lys Val Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 494
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 494

Lys Glu Lys Tyr Ala Ala Tyr Val Glu Ile Trp Glu Leu Pro Asn Leu
1               5                   10                  15

Asn Arg Arg Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 495
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 495

Lys Glu Arg Tyr Arg Ala Tyr Val Glu Ile Trp Glu Leu Pro Asn Leu
1               5                   10                  15

Asn Arg Trp Gln Lys Ala Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 496
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 496

Lys Glu Arg Tyr Arg Ala Tyr Phe Glu Ile Trp Glu Leu Pro Asn Leu
1               5                   10                  15

Asn Arg Ala Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 497
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 497

Lys Glu Arg Tyr Gln Ala Tyr Phe Glu Ile Trp Gln Leu Pro Asn Leu
1               5                   10                  15

Asn Arg Leu Gln Ala Gly Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 498
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 498

Lys Glu Lys Tyr Gln Ala Tyr Val Glu Ile Trp Gln Leu Pro Asn Leu
1               5                   10                  15

Asn Arg Leu Gln Lys Gly Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 499
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 499

Lys Glu Lys Tyr Ala Ala Tyr Tyr Glu Ile Trp Gln Leu Pro Asn Leu
1               5                   10                  15

Asn Arg Ser Gln Lys Gly Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 500
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 500

Lys Glu Lys Tyr Gln Ala Tyr Tyr Glu Ile Trp Glu Leu Pro Asn Leu
1               5                   10                  15

Asn Arg Gly Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 501
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 501

Lys Glu Lys Tyr Asn Ala Tyr Phe Glu Ile Trp Gln Leu Pro Asn Leu
1               5                   10                  15

Asn Arg Leu Gln Lys Ala Ala Phe Ile Thr Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 502
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 502

Lys Glu Lys Tyr Ser Ala Tyr Phe Glu Ile Trp Gln Leu Pro Asn Leu
1               5                   10                  15

Asn Thr Ser Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 503
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 503

Lys Glu Arg Tyr Asn Ala Tyr Phe Glu Ile Trp Glu Leu Pro Asn Leu

```
            1               5                  10                  15
Asn Val Arg Gln Lys Ala Ala Phe Ile Arg Ser Leu Ser Asp Asp Pro
                20                  25                  30
Ser Gln Ser Ala Asn Leu Leu Ala Glu Ala Lys Lys Leu Asn Asp Ala
                35                  40                  45
Gln
```

<210> SEQ ID NO 504
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 504

```
Lys Glu Lys Tyr Glu Ala Tyr Phe Glu Ile Trp Glu Leu Pro Asn Leu
1               5                   10                  15
Asn Ser Arg Gln Lys Ala Ala Phe Ile Gly Ser Leu Ser Asp Asp Pro
                20                  25                  30
Ser Gln Ser Ala Asn Leu Leu Ala Glu Ala Lys Lys Leu Asn Asp Ala
                35                  40                  45
Gln
```

<210> SEQ ID NO 505
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 505

```
Lys Glu Arg Tyr Arg Ala Tyr Trp Glu Ile Trp Glu Leu Pro Asn Leu
1               5                   10                  15
Asn Gln Gln Gln Lys Val Ala Phe Ile Arg Ser Leu Tyr Asp Asp Pro
                20                  25                  30
Ser Gln Ser Ala Asn Leu Leu Ala Glu Ala Lys Lys Leu Asn Asp Ala
                35                  40                  45
Gln
```

<210> SEQ ID NO 506
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 506

```
Lys Glu Arg Tyr Asn Ala Tyr Trp Glu Ile Trp Glu Leu Pro Asn Leu
1               5                   10                  15
Asn Gln Gly Gln Lys Val Ala Phe Ile Arg Ser Leu Gln Asp Asp Pro
                20                  25                  30
Ser Gln Ser Ala Asn Leu Leu Ala Glu Ala Lys Lys Leu Asn Asp Ala
                35                  40                  45
Gln
```

<210> SEQ ID NO 507
<211> LENGTH: 49
<212> TYPE: PRT
<213> ORGANISM: Artificial Sequence
<220> FEATURE:

<223> OTHER INFORMATION: Engineered polypeptide

<400> SEQUENCE: 507

Lys Glu Arg Arg His Ala Tyr Gly Glu Ile Trp Gln Leu Pro Asn Leu
1               5                   10                  15

Asn Gln Arg Gln Lys Val Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 508
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 508

Lys Glu Lys Tyr Val Ala Thr Trp Glu Ile Trp Glu Leu Pro Asn Leu
1               5                   10                  15

Asn Arg Ala Gln Lys Val Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 509
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 509

Lys Glu Arg Arg Ile Ala Arg Trp Glu Ile Trp Glu Leu Pro Asn Leu
1               5                   10                  15

Asn Arg Leu Gln Lys Val Ala Phe Ile Gly Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 510
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 510

Lys Glu Lys Tyr Lys Ala Ala Gly Glu Ile Trp Gln Leu Pro Asn Leu
1               5                   10                  15

Asn Arg Gly Gln Lys Val Ala Phe Ile Gly Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 511
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 511

Lys Glu Lys Tyr Leu Ala Tyr Gly Glu Ile Trp Gln Leu Pro Asn Leu
1               5                   10                  15

Asn Arg His Gln Lys Val Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 512
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 512

Lys Glu Lys Tyr Gln Ala Tyr Gly Glu Ile Trp Gln Leu Pro Asn Leu
1               5                   10                  15

Asn Arg Gln Gln Lys Val Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 513
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 513

Lys Glu Lys Tyr Lys Ala Tyr Gly Glu Ile Trp Gln Leu Pro Asn Leu
1               5                   10                  15

Asn Arg Gln Gln Lys Val Ala Phe Ile Ile Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 514
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 514

Lys Glu Lys Tyr Ala Ala Ala Tyr Glu Ile Trp Gln Leu Pro Asn Leu
1               5                   10                  15

Asn Gln Arg Gln Lys Gly Ala Phe Ile Ala Ser Leu Phe Asp Asp Pro
            20                  25                  30

Ser Gln Ser Ala Asn Leu Leu Ala Glu Ala Lys Lys Leu Asn Asp Ala
        35                  40                  45
```

-continued

```
                35                  40                  45

Gln

<210> SEQ ID NO 515
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 515

Lys Glu Lys Tyr Ala Ala Ser Tyr Glu Ile Trp Glu Leu Pro Asn Leu
1               5                   10                  15

Asn Gln Arg Gln Lys Ala Ala Phe Ile Lys Ser Leu Phe Asp Asp Pro
                20                  25                  30

Ser Gln Ser Ala Asn Leu Leu Ala Glu Ala Lys Lys Leu Asn Asp Ala
                35                  40                  45

Gln

<210> SEQ ID NO 516
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 516

Lys Glu Lys Tyr Leu Ala Ser Tyr Glu Ile Trp Gln Leu Pro Asn Leu
1               5                   10                  15

Asn Arg Arg Gln Lys Ala Ala Phe Ile Ala Ser Leu Phe Asp Asp Pro
                20                  25                  30

Ser Gln Ser Ala Asn Leu Leu Ala Glu Ala Lys Lys Leu Asn Asp Ala
                35                  40                  45

Gln

<210> SEQ ID NO 517
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 517

Lys Glu Lys Tyr Ser Ala Thr Phe Glu Ile Trp Gln Leu Pro Asn Leu
1               5                   10                  15

Asn Gln Arg Gln Lys Ala Ala Phe Ile Ser Ser Leu Trp Asp Asp Pro
                20                  25                  30

Ser Gln Ser Ala Asn Leu Leu Ala Glu Ala Lys Lys Leu Asn Asp Ala
                35                  40                  45

Gln

<210> SEQ ID NO 518
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 518

Lys Glu Lys Tyr Ala Ala Ser Phe Glu Ile Trp Gln Leu Pro Asn Leu
1               5                   10                  15
```

Asn Thr His Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 519
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 519

Lys Glu Lys Tyr Lys Ala Ser Gly Glu Ile Trp Gln Leu Pro Asn Leu
1               5                   10                  15

Asn Arg Leu Gln Arg Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 520
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 520

Lys Glu Lys Tyr Ser Ala Ser Gly Glu Ile Trp Gln Leu Pro Asn Leu
1               5                   10                  15

Asn Arg Thr Gln Lys Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 521
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 521

Lys Glu Lys Tyr His Ala Ala Gly Glu Ile Trp Glu Leu Pro Asn Leu
1               5                   10                  15

Asn Arg Leu Gln Lys Ala Ala Phe Ile Arg Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 522
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 522

Lys Glu Lys Tyr Arg Ala Ala Gly Glu Ile Trp Glu Leu Pro Asn Leu
1               5                   10                  15

Asn Arg Gln Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 523
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 523

Lys Glu Lys Tyr Gln Ala Ser Gly Glu Ile Trp Glu Leu Pro Asn Leu
1               5                   10                  15

Asn Arg Leu Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 524
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 524

Lys Glu Lys Tyr Lys Ala Thr Gly Glu Ile Trp Glu Leu Pro Asn Leu
1               5                   10                  15

Asn Arg Ile Gln Lys Ala Ala Phe Ile Arg Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 525
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 525

Lys Glu Lys Tyr Gln Ala Ser Phe Glu Ile Trp Glu Leu Pro Asn Leu
1               5                   10                  15

Asn Arg Ser Gln Lys Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 526

```
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 526

Lys Glu Arg Lys Val Ala Ala Val Glu Ile Trp Gln Leu Pro Asn Leu
1               5                   10                  15

Asn Arg Trp Gln Arg Gly Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 527
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 527

Lys Glu Arg Lys Leu Ala Ala Val Glu Ile Trp Glu Leu Pro Asn Leu
1               5                   10                  15

Asn Gln Tyr Gln Arg Gly Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 528
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 528

Lys Glu Arg Lys Lys Ala Ser Val Glu Ile Trp Glu Leu Pro Asn Leu
1               5                   10                  15

Asn Arg Tyr Gln Lys Gly Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 529
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 529

Lys Glu Arg Lys His Ala Ala Trp Glu Ile Trp Glu Leu Pro Asn Leu
1               5                   10                  15

Asn Arg His Gln Lys Gly Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45
```

Gln

<210> SEQ ID NO 530
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 530

```
Lys Glu Arg Lys His Ala Ala Val Glu Ile Trp Glu Leu Pro Asn Leu
1               5                   10                  15

Asn Arg Trp Gln Lys Gly Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 531
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 531

```
Lys Glu Lys Arg His Ala Ala Val Glu Ile Trp Glu Leu Pro Asn Leu
1               5                   10                  15

Asn Val Phe Gln Arg Gly Ala Phe Ile Ala Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 532
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 532

```
Lys Glu Arg Lys His Ala Ala Val Glu Ile Trp Glu Leu Pro Asn Leu
1               5                   10                  15

Asn Arg Leu Gln Arg Gly Ala Phe Ile Ala Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 533
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 533

```
Lys Glu Trp Lys Thr Ala Ala Val Glu Ile Trp Glu Leu Pro Asn Leu
1               5                   10                  15
```

Asn Arg Arg Gln Lys Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 534
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 534

Lys Glu Arg Lys Val Ala Ala Phe Glu Ile Trp Glu Leu Pro Asn Leu
1               5                   10                  15

Asn Arg Gly Gln Lys Ala Ala Phe Ile Gly Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 535
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 535

Lys Glu Lys Arg Asn Ala Ala Val Glu Ile Trp Glu Leu Pro Asn Leu
1               5                   10                  15

Asn Arg Arg Gln Arg Ala Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 536
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 536

Lys Glu Arg Arg Asn Ala Ala Val Glu Ile Trp Glu Leu Pro Asn Leu
1               5                   10                  15

Asn Arg His Gln Arg Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 537
<211> LENGTH: 49
<212> TYPE: PRT
<213> ORGANISM: Artificial Sequence
<220> FEATURE:
<223> OTHER INFORMATION: Engineered polypeptide

```
<400> SEQUENCE: 537

Lys Glu Lys Arg Gln Ala Ser Val Glu Ile Trp Glu Leu Pro Asn Leu
1               5                   10                  15

Asn Arg Ile Gln Lys Ala Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 538
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 538

Lys Glu Lys Arg Arg Ala Ala Val Glu Ile Trp Glu Leu Pro Asn Leu
1               5                   10                  15

Asn Arg Ile Gln Lys Ser Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 539
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 539

Lys Glu Lys Arg His Ala Ala Trp Glu Ile Trp Glu Leu Pro Asn Leu
1               5                   10                  15

Asn Arg Ala Gln Lys Ser Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 540
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 540

Lys Glu Lys Arg Asn Ala Thr Val Glu Ile Trp Glu Leu Pro Asn Leu
1               5                   10                  15

Asn Arg Ile Gln Arg Ala Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 541
<211> LENGTH: 49
```

```
<212> TYPE: PRT
<213> ORGANISM: Artificial Sequence
<220> FEATURE:
<223> OTHER INFORMATION: Engineered polypeptide

<400> SEQUENCE: 541

Lys Glu Lys Arg Ala Ala Thr Val Glu Ile Trp Glu Leu Pro Asn Leu
1               5                   10                  15

Asn Arg Leu Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 542
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 542

Lys Glu Arg Arg Gly Ala Ala Val Glu Ile Trp Glu Leu Pro Asn Leu
1               5                   10                  15

Asn Arg Gln Gln Lys Ala Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 543
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 543

Lys Glu Arg Arg Lys Ala Thr Val Glu Ile Trp Glu Leu Pro Asn Leu
1               5                   10                  15

Asn Arg Gln Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 544
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 544

Lys Glu Lys Ser Thr Ala Ala Val Glu Ile Trp Glu Leu Pro Asn Leu
1               5                   10                  15

Asn Arg Ile Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45
```

-continued

Gln

<210> SEQ ID NO 545
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 545

Lys Glu Lys Ser Thr Ala Ala Val Glu Ile Trp Glu Leu Pro Asn Leu
1               5                   10                  15

Asn Arg Tyr Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 546
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 546

Lys Glu Lys Ser His Ala Ala Val Glu Ile Trp Glu Leu Pro Asn Leu
1               5                   10                  15

Asn Arg Trp Gln Lys Ala Ala Phe Ile Lys Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 547
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 547

Lys Glu Arg Ser Ser Ala Ala Val Glu Ile Trp Glu Leu Pro Asn Leu
1               5                   10                  15

Asn Arg Phe Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 548
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 548

Lys Glu Lys Arg Ile Ala Ala Ala Glu Ile Trp Glu Leu Pro Asn Leu
1               5                   10                  15

Asn Arg Val Gln Lys Ala Ala Phe Ile Lys Ser Leu Phe Asp Asp Pro

```
                20                  25                  30

Ser Gln Ser Ala Asn Leu Leu Ala Glu Ala Lys Lys Leu Asn Asp Ala
        35                  40                  45

Gln

<210> SEQ ID NO 549
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 549

Lys Glu Lys Arg His Ala Ala Gly Glu Ile Trp Glu Leu Pro Asn Leu
1               5                   10                  15

Asn Arg Ile Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 550
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 550

Lys Glu Lys Arg Ile Ala Ala Val Glu Ile Trp Glu Leu Pro Asn Leu
1               5                   10                  15

Asn Arg Val Gln Lys Ala Ala Phe Ile Ala Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 551
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 551

Lys Glu Lys Arg Ile Ala Ser Tyr Glu Ile Trp Glu Leu Pro Asn Leu
1               5                   10                  15

Asn Arg Arg Gln Arg Ala Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 552
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 552
```

```
Lys Glu Lys Arg Asn Ala Thr Phe Glu Ile Trp Glu Leu Pro Asn Leu
1               5                   10                  15

Asn Arg Ser Gln Lys Gly Ala Phe Ile Ser Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 553
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 553

Lys Glu Arg Lys Val Ala Thr Phe Glu Ile Trp Glu Leu Pro Asn Leu
1               5                   10                  15

Asn Ser Arg Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 554
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 554

Lys Glu Arg Lys Asn Ala Thr Phe Glu Ile Trp Glu Leu Pro Asn Leu
1               5                   10                  15

Asn Gln Arg Gln Lys Ser Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 555
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 555

Lys Glu Arg Ser Ala Ala Thr Phe Glu Ile Trp Glu Leu Pro Asn Leu
1               5                   10                  15

Asn Gln Arg Gln Lys Ser Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 556
<211> LENGTH: 49
<212> TYPE: PRT
```

<213> ORGANISM: Artificial Sequence
<220> FEATURE:
<223> OTHER INFORMATION: Engineered polypeptide

<400> SEQUENCE: 556

Lys Glu Arg Lys His Ala Thr Phe Glu Ile Trp Glu Leu Pro Asn Leu
1               5                   10                  15

Asn Gln Leu Gln Lys Ser Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 557
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 557

Lys Glu Arg Lys Gln Ala Thr Phe Glu Ile Trp Glu Leu Pro Asn Leu
1               5                   10                  15

Asn Gln Gln Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 558
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 558

Lys Glu Arg Lys Arg Ala Thr Phe Glu Ile Trp Glu Leu Pro Asn Leu
1               5                   10                  15

Asn Arg Thr Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 559
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 559

Lys Glu Arg Lys Thr Ala Thr Phe Glu Ile Trp Glu Leu Pro Asn Leu
1               5                   10                  15

Asn Arg Val Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 560
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 560

Lys Glu Arg Lys Leu Ala Thr Trp Glu Ile Trp Glu Leu Pro Asn Leu
1               5                   10                  15

Asn Arg Ser Gln Lys Ala Ala Phe Ile Ile Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 561
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 561

Lys Glu Arg Lys Val Ala Ala Val Glu Ile Trp Glu Leu Pro Asn Leu
1               5                   10                  15

Asn Arg Ile Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 562
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 562

Lys Glu Arg Lys Glu Ala Ala Val Glu Ile Trp Glu Leu Pro Asn Leu
1               5                   10                  15

Asn Arg Leu Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 563
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 563

Lys Glu Arg Lys Arg Ala Ala Val Glu Ile Trp Glu Leu Pro Asn Leu
1               5                   10                  15

Asn Arg Gly Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 564
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 564

Lys Glu Arg Lys Leu Ala Ala Val Glu Ile Trp Glu Leu Pro Asn Leu
1               5                   10                  15

Asn Arg Thr Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 565
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 565

Lys Glu Arg Lys Val Ala Ala Val Glu Ile Trp Glu Leu Pro Asn Leu
1               5                   10                  15

Asn Arg Val Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 566
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 566

Lys Glu Arg Lys Glu Ala Ala Val Glu Ile Trp Glu Leu Pro Asn Leu
1               5                   10                  15

Asn Arg Val Gln Lys Ala Ala Phe Ile Lys Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 567
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 567

-continued

Lys Glu Arg Lys Ala Ala Thr Val Glu Ile Trp Glu Leu Pro Asn Leu
1               5                   10                  15

Asn Arg Arg Gln Lys Ala Ala Phe Ile Ala Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 568
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 568

Lys Glu Lys Arg His Ala Ser Trp Glu Ile Trp Glu Leu Pro Asn Leu
1               5                   10                  15

Asn Gln Trp Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 569
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 569

Lys Glu Arg Lys Ser Ala Thr Trp Glu Ile Trp Glu Leu Pro Asn Leu
1               5                   10                  15

Asn Gln Leu Gln Lys Ala Ala Phe Ile Arg Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 570
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 570

Lys Glu Lys Lys Lys Ala Ala Val Glu Ile Trp Glu Leu Pro Asn Leu
1               5                   10                  15

Asn Gln Arg Gln Lys Ala Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 571
<211> LENGTH: 49
<212> TYPE: PRT
<213> ORGANISM: Artificial Sequence

```
<220> FEATURE:
<223> OTHER INFORMATION: Engineered polypeptide

<400> SEQUENCE: 571

Lys Glu Lys Lys Leu Ala Ser Phe Glu Ile Trp Glu Leu Pro Asn Leu
1               5                   10                  15

Asn Gln Arg Gln Lys Ala Ala Phe Ile Arg Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 572
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 572

Lys Glu Arg Lys Val Ala Thr Val Glu Ile Trp Glu Leu Pro Asn Leu
1               5                   10                  15

Asn Arg Val Gln Ala Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 573
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 573

Lys Glu Arg Lys Thr Ala Thr Val Glu Ile Trp Glu Leu Pro Asn Leu
1               5                   10                  15

Asn Arg Ile Gln Lys Ala Ala Phe Ile Lys Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 574
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 574

Lys Glu Arg Lys Ser Ala Thr Val Glu Ile Trp Glu Leu Pro Asn Leu
1               5                   10                  15

Asn Arg Val Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 575
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 575

Lys Glu Arg Lys Val Ala Thr Val Glu Ile Trp Glu Leu Pro Asn Leu
1               5                   10                  15

Asn Arg Gly Gln Lys Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 576
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 576

Lys Glu Arg Lys Gln Ala Thr Val Glu Ile Trp Glu Leu Pro Asn Leu
1               5                   10                  15

Asn Arg Arg Gln Arg Ala Ala Phe Ile Ser Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 577
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 577

Lys Glu Arg Lys Lys Ala Thr Val Glu Ile Trp Glu Leu Pro Asn Leu
1               5                   10                  15

Asn Arg Arg Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 578
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 578

Lys Glu Arg Lys Val Ala Thr Val Glu Ile Trp Glu Leu Pro Asn Leu
1               5                   10                  15

Asn Arg Arg Gln Lys Gly Ala Phe Ile Ala Ser Leu Trp Asp Asp Pro
            20                  25                  30

```
Ser Gln Ser Ala Asn Leu Leu Ala Glu Ala Lys Lys Leu Asn Asp Ala
        35                  40                  45

Gln

<210> SEQ ID NO 579
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 579

Lys Glu Arg Lys Leu Ala Thr Val Glu Ile Trp Glu Leu Pro Asn Leu
1               5                   10                  15

Asn Arg Tyr Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 580
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 580

Lys Glu Arg Lys Ala Ala Thr Val Glu Ile Trp Glu Leu Pro Asn Leu
1               5                   10                  15

Asn Arg Leu Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 581
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 581

Lys Glu Arg Lys Ile Ala Thr Val Glu Ile Trp Glu Leu Pro Asn Leu
1               5                   10                  15

Asn Arg Val Gln Lys Ser Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 582
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 582

Lys Glu Arg Lys Asn Ala Thr Val Glu Ile Trp Glu Leu Pro Asn Leu
```

```
                1               5                  10                  15
Asn Arg Ala Gln Lys Ala Ala Phe Ile Ala Ser Leu Trp Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 583
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 583

Lys Glu Arg Lys Asn Ala Thr Val Glu Ile Trp Glu Leu Pro Asn Leu
1               5                   10                  15

Asn Arg Ser Gln Lys Ala Ala Phe Ile Gly Ser Leu Trp Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 584
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 584

Lys Glu Arg Lys Thr Ala Thr Val Glu Ile Trp Glu Leu Pro Asn Leu
1               5                   10                  15

Asn Arg Gly Gln Lys Ala Ala Phe Ile Ala Ser Leu Phe Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 585
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 585

Lys Glu Arg Lys His Ala Ala Val Glu Ile Trp Glu Leu Pro Asn Leu
1               5                   10                  15

Asn Arg Ile Gln Arg Ala Ala Phe Ile Ala Ser Leu Phe Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 586
<211> LENGTH: 49
<212> TYPE: PRT
<213> ORGANISM: Artificial Sequence
<220> FEATURE:
```

<223> OTHER INFORMATION: Engineered polypeptide

<400> SEQUENCE: 586

Lys Glu Arg Lys Ile Ala Thr Val Glu Ile Trp Glu Leu Pro Asn Leu
1               5                   10                  15
Asn Arg Ile Gln Arg Ala Ala Phe Ile Ala Ser Leu Phe Asp Asp Pro
            20                  25                  30
Ser Gln Ser Ala Asn Leu Leu Ala Glu Ala Lys Lys Leu Asn Asp Ala
        35                  40                  45
Gln

<210> SEQ ID NO 587
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 587

Lys Glu Arg Lys Ile Ala Ala Val Glu Ile Trp Glu Leu Pro Asn Leu
1               5                   10                  15
Asn Arg Ile Gln Ala Ala Ala Phe Ile Ala Ser Leu Trp Asp Asp Pro
            20                  25                  30
Ser Gln Ser Ala Asn Leu Leu Ala Glu Ala Lys Lys Leu Asn Asp Ala
        35                  40                  45
Gln

<210> SEQ ID NO 588
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 588

Lys Glu Arg Lys Ser Ala Thr Val Glu Ile Trp Glu Leu Pro Asn Leu
1               5                   10                  15
Asn Arg Thr Gln Arg Ala Ala Phe Ile Ala Ser Leu Trp Asp Asp Pro
            20                  25                  30
Ser Gln Ser Ala Asn Leu Leu Ala Glu Ala Lys Lys Leu Asn Asp Ala
        35                  40                  45
Gln

<210> SEQ ID NO 589
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 589

Lys Glu Arg Lys Ser Ala Ala Val Glu Ile Trp Glu Leu Pro Asn Leu
1               5                   10                  15
Asn Arg Thr Gln Lys Ala Ala Phe Ile Ala Ser Leu Trp Asp Asp Pro
            20                  25                  30
Ser Gln Ser Ala Asn Leu Leu Ala Glu Ala Lys Lys Leu Asn Asp Ala
        35                  40                  45
Gln

```
<210> SEQ ID NO 590
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 590
```

Lys Glu Lys Lys Ser Ala Thr Val Glu Ile Trp Glu Leu Pro Asn Leu
1               5                   10                  15

Asn Arg Ile Gln Lys Ala Ala Phe Ile Gly Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 591
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 591
```

Lys Glu Lys Lys Ser Ala Tyr Val Glu Ile Trp Glu Leu Pro Asn Leu
1               5                   10                  15

Asn Arg Tyr Gln Lys Ala Ala Phe Ile Lys Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 592
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 592
```

Lys Glu Arg Lys Ile Ala Thr Tyr Glu Ile Trp Glu Leu Pro Asn Leu
1               5                   10                  15

Asn Gln Arg Gln Lys Ala Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

```
<210> SEQ ID NO 593
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 593
```

Lys Glu Arg Ser Val Ala Thr Trp Glu Ile Trp Gln Leu Pro Asn Leu
1               5                   10                  15

Asn Gln Arg Gln Lys Ala Ala Phe Ile Ala Ser Leu Trp Asp Asp Pro
            20                  25                  30

Ser Gln Ser Ala Asn Leu Leu Ala Glu Ala Lys Lys Leu Asn Asp Ala

Gln

<210> SEQ ID NO 594
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 594

Lys Glu Lys Arg Lys Ala Thr Gly Glu Ile Trp Gln Leu Pro Asn Leu
1               5                   10                  15

Asn Gln Arg Gln Lys Gly Ala Phe Ile Ala Ser Leu Trp Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 595
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 595

Lys Glu Arg Lys Glu Ala Arg Phe Glu Ile Trp Glu Leu Pro Asn Leu
1               5                   10                  15

Asn Gln Arg Gln Ala Ala Ala Phe Ile Ser Ser Leu Phe Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 596
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 596

Lys Glu Arg Lys Ala Ala Ser Trp Glu Ile Trp Glu Leu Pro Asn Leu
1               5                   10                  15

Asn Gln Arg Gln Lys Ala Ala Phe Ile Ser Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 597
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 597

Lys Glu Trp Lys His Ala Ala Gly Glu Ile Trp Glu Leu Pro Asn Leu
1               5                   10                  15

-continued

```
Asn Arg Ser Gln Lys Val Ala Phe Ile Ala Ser Leu Glu Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 598
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 598

Lys Glu Trp Lys Arg Ala Ala Gly Glu Ile Trp Glu Leu Pro Asn Leu
1               5                   10                  15

Asn Arg Ala Gln Lys Val Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 599
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 599

Lys Glu Trp Lys Ile Ala Ala Gly Glu Ile Trp Glu Leu Pro Asn Leu
1               5                   10                  15

Asn Gln Arg Gln Lys Val Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 600
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 600

Lys Glu Trp Lys Thr Ala Ala Tyr Glu Ile Trp Glu Leu Pro Asn Leu
1               5                   10                  15

Asn Thr Tyr Gln Lys Val Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 601
<211> LENGTH: 49
<212> TYPE: PRT
<213> ORGANISM: Artificial Sequence
<220> FEATURE:
<223> OTHER INFORMATION: Engineered polypeptide
```

<400> SEQUENCE: 601

Lys Glu Trp Lys Val Ala Ala Gly Glu Ile Trp Glu Leu Pro Asn Leu
1               5                   10                  15

Asn Arg Thr Gln Lys Val Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 602
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 602

Lys Glu Trp Lys Val Ala Ala Gly Glu Ile Trp Glu Leu Pro Asn Leu
1               5                   10                  15

Asn Arg Trp Gln Lys Val Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 603
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 603

Lys Glu Trp Lys Gln Ala Ala Gly Glu Ile Trp Glu Leu Pro Asn Leu
1               5                   10                  15

Asn Arg Leu Gln Lys Val Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 604
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 604

Lys Glu Trp Lys Val Ala Ala Gly Glu Ile Trp Glu Leu Pro Asn Leu
1               5                   10                  15

Asn Val Trp Gln Lys Ala Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 605

```
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 605

Lys Glu Trp Lys Val Ala Ala Trp Glu Ile Trp Glu Leu Pro Asn Leu
1               5                   10                  15

Asn Arg Gly Gln Lys Val Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 606
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 606

Lys Glu Trp Lys Arg Ala Ala Phe Glu Ile Trp Glu Leu Pro Asn Leu
1               5                   10                  15

Asn Gln Ala Gln Lys Val Ala Phe Ile Thr Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 607
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 607

Lys Glu Trp Lys Lys Ala Ala Gly Glu Ile Trp Leu Leu Pro Asn Leu
1               5                   10                  15

Asn Arg Arg Gln Arg Gly Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 608
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 608

Lys Glu Trp Lys Lys Ala Ala Gly Glu Ile Trp Glu Leu Pro Asn Leu
1               5                   10                  15

Asn Ser Arg Gln Lys Gly Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45
```

-continued

Gln

<210> SEQ ID NO 609
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 609

Lys Glu Trp Arg Gly Ala Ala Gly Glu Ile Trp Glu Leu Pro Asn Leu
1               5                   10                  15

Asn Arg Arg Gln Arg Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 610
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 610

Lys Glu Trp Lys Val Ala Ala Gly Glu Ile Trp Gln Leu Pro Asn Leu
1               5                   10                  15

Asn Arg Arg Gln Arg Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 611
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 611

Lys Glu Trp Lys Ile Ala Ala Val Glu Ile Trp Glu Leu Pro Asn Leu
1               5                   10                  15

Asn Thr Arg Gln Lys Gly Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 612
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 612

Lys Glu Trp Lys Ile Ala Ala Phe Glu Ile Trp Glu Leu Pro Asn Leu
1               5                   10                  15

-continued

```
Asn Val Arg Gln Arg Ser Ala Phe Ile Ser Ser Leu Ser Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 613
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 613

```
Lys Glu Trp Lys Thr Ala Ala Tyr Glu Ile Trp Glu Leu Pro Asn Leu
1               5                   10                  15

Asn Gln Arg Gln Arg Gly Ala Phe Ile Ala Ser Leu Gln Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 614
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 614

```
Lys Glu Trp Lys Thr Ala Ala Gly Glu Ile Trp Glu Leu Pro Asn Leu
1               5                   10                  15

Asn Ser Arg Gln Lys Ala Ala Phe Ile Gly Ser Leu Ala Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 615
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 615

```
Lys Glu Trp Lys Thr Ala Ala Gly Glu Ile Trp Glu Leu Pro Asn Leu
1               5                   10                  15

Asn Val Gly Gln Lys Ala Ala Phe Ile Gly Ser Leu Ala Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 616
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 616

Lys Glu Trp Lys His Ala Ala Gly Glu Ile Trp Glu Leu Pro Asn Leu
1               5                   10                  15

Asn Arg Thr Gln Lys Ala Ala Phe Ile Arg Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 617
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 617

Lys Glu Trp Lys Arg Ala Ala Gly Glu Ile Trp Glu Leu Pro Asn Leu
1               5                   10                  15

Asn Arg Leu Gln Lys Ala Ala Phe Ile Arg Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 618
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 618

Lys Glu Trp Lys Gln Ala Ala Gly Glu Ile Trp Glu Leu Pro Asn Leu
1               5                   10                  15

Asn Arg Gly Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 619
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 619

Lys Glu Trp Lys Gln Ala Ala Gly Glu Ile Trp Glu Leu Pro Asn Leu
1               5                   10                  15

Asn Arg Gly Gln Lys Ala Ala Phe Ile Thr Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 620
<211> LENGTH: 49

<212> TYPE: PRT
<213> ORGANISM: Artificial Sequence
<220> FEATURE:
<223> OTHER INFORMATION: Engineered polypeptide

<400> SEQUENCE: 620

Lys Glu Trp Lys Glu Ala Ala Gly Glu Ile Trp Glu Leu Pro Asn Leu
1               5                   10                  15

Asn Arg Gly Gln Lys Ala Ala Phe Ile Lys Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 621
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 621

Lys Glu Trp Lys Thr Ala Ala Gly Glu Ile Trp Glu Leu Pro Asn Leu
1               5                   10                  15

Asn Arg Arg Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 622
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 622

Lys Glu Trp Lys Arg Ala Ala Gly Glu Ile Trp Glu Leu Pro Asn Leu
1               5                   10                  15

Asn Arg Ala Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 623
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 623

Lys Glu Trp Lys His Ala Ala Phe Glu Ile Trp Glu Leu Pro Asn Leu
1               5                   10                  15

Asn Val Arg Gln Lys Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 624
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 624

Lys Glu Trp Lys Asn Ala Ala Phe Glu Ile Trp Glu Leu Pro Asn Leu
1               5                   10                  15

Asn Val Ser Gln Lys Ala Ala Phe Ile Arg Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 625
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 625

Lys Glu Trp Lys Ala Ala Ala Tyr Glu Ile Trp Glu Leu Pro Asn Leu
1               5                   10                  15

Asn Val Trp Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 626
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 626

Lys Glu Trp Lys Val Ala Ala Gly Glu Ile Trp Glu Leu Pro Asn Leu
1               5                   10                  15

Asn Arg Trp Gln Lys Gly Ala Phe Ile Thr Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 627
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 627

Lys Glu Trp Lys Val Ala Ala Gly Glu Ile Trp Glu Leu Pro Asn Leu
1               5                   10                  15

Asn Arg Trp Gln Lys Ala Ala Phe Ile Ala Ser Leu Tyr Asp Asp Pro

```
                    20                  25                  30

Ser Gln Ser Ala Asn Leu Leu Ala Glu Ala Lys Lys Leu Asn Asp Ala
        35                  40                  45

Gln

<210> SEQ ID NO 628
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 628

Lys Glu Trp Lys Val Ala Ala Gly Glu Ile Trp Glu Leu Pro Asn Leu
1               5                   10                  15

Asn Arg Leu Gln Arg Ala Ala Phe Ile Lys Ser Leu Tyr Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 629
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 629

Lys Glu Trp Lys Val Ala Ala Tyr Glu Ile Trp Glu Leu Pro Asn Leu
1               5                   10                  15

Asn Arg Leu Gln Lys Ala Ala Phe Ile Ala Ser Leu Tyr Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 630
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 630

Lys Glu Trp Lys Val Ala Ala Phe Glu Ile Trp Glu Leu Pro Asn Leu
1               5                   10                  15

Asn Arg Thr Gln Arg Ala Ala Phe Ile Ile Ser Leu Gln Asp Asp Pro
                20                  25                  30

Ser Gln Ser Ala Asn Leu Leu Ala Glu Ala Lys Lys Leu Asn Asp Ala
        35                  40                  45

Gln

<210> SEQ ID NO 631
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 631
```

-continued

```
Lys Glu Trp Lys Thr Ala Ala Val Glu Ile Trp Glu Leu Pro Asn Leu
1               5                   10                  15

Asn Arg Leu Gln Lys Ala Ala Phe Ile Thr Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 632
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 632

Lys Glu Trp Lys Thr Ala Ala Val Glu Ile Trp Glu Leu Pro Asn Leu
1               5                   10                  15

Asn Arg Leu Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 633
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 633

Lys Glu Trp Lys Thr Ala Ala Phe Glu Ile Trp Glu Leu Pro Asn Leu
1               5                   10                  15

Asn Arg Gly Gln Lys Ala Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 634
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 634

Lys Glu Trp Lys Arg Ala Ala Phe Glu Ile Trp Glu Leu Pro Asn Leu
1               5                   10                  15

Asn Arg Leu Gln Lys Ser Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 635
<211> LENGTH: 49
<212> TYPE: PRT
```

<213> ORGANISM: Artificial Sequence
<220> FEATURE:
<223> OTHER INFORMATION: Engineered polypeptide

<400> SEQUENCE: 635

```
Lys Glu Trp Lys Gln Ala Ala Phe Glu Ile Trp Glu Leu Pro Asn Leu
1               5                   10                  15

Asn Arg Tyr Gln Ala Ala Ala Phe Ile Gly Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 636
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 636

```
Lys Glu Trp Lys His Ala Ala Phe Glu Ile Trp Glu Leu Pro Asn Leu
1               5                   10                  15

Asn Arg Arg Gln Ala Gly Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 637
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 637

```
Lys Glu Trp Lys Gln Ala Ser Gly Glu Ile Trp Glu Leu Pro Asn Leu
1               5                   10                  15

Asn Val Arg Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 638
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 638

```
Lys Glu Trp Lys Gln Ala Ser Phe Glu Ile Trp Glu Leu Pro Asn Leu
1               5                   10                  15

Asn Val Arg Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 639
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 639

Lys Glu Trp Lys Leu Ala Ala Gly Glu Ile Trp Glu Leu Pro Asn Leu
1               5                   10                  15

Asn Val Arg Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 640
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 640

Lys Glu Trp Lys Ile Ala Ala Gly Glu Ile Trp Glu Leu Pro Asn Leu
1               5                   10                  15

Asn Val Arg Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 641
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 641

Lys Glu Trp Lys His Ala Ala Gly Glu Ile Trp Gln Leu Pro Asn Leu
1               5                   10                  15

Asn Val Thr Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 642
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 642

Lys Glu Trp Lys Ile Ala Ala Gly Glu Ile Trp Glu Leu Pro Asn Leu
1               5                   10                  15

Asn Arg Arg Gln Ala Ala Ala Phe Ile Val Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 643
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 643

Lys Glu Trp Lys Ser Ala Ala Gly Glu Ile Trp Glu Leu Pro Asn Leu
1               5                   10                  15

Asn Arg Ala Gln Lys Ala Ala Phe Ile Ile Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 644
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 644

Lys Glu Trp Lys His Ala Ala Val Glu Ile Trp Gln Leu Pro Asn Leu
1               5                   10                  15

Asn Arg Phe Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 645
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 645

Lys Glu Trp Lys Gln Ala Ala Trp Glu Ile Trp Gln Leu Pro Asn Leu
1               5                   10                  15

Asn Thr Gly Gln Lys Ala Ala Phe Ile Arg Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 646
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 646

```
Lys Glu Trp Lys Gln Ala Ser Trp Glu Ile Trp Glu Leu Pro Asn Leu
1               5                   10                  15

Asn Arg Gly Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 647
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 647

Lys Glu Trp Lys Thr Ala Ser Tyr Glu Ile Trp Gln Leu Pro Asn Leu
1               5                   10                  15

Asn Arg Arg Gln Ala Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 648
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 648

Lys Glu Trp Lys Asn Ala Ser Phe Glu Ile Trp Leu Leu Pro Asn Leu
1               5                   10                  15

Asn Arg Ile Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 649
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 649

Lys Glu Trp Lys Asn Ala Ala Phe Glu Ile Trp Leu Leu Pro Asn Leu
1               5                   10                  15

Asn Gln Arg Gln Lys Ala Ala Phe Ile Ala Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 650
<211> LENGTH: 49
<212> TYPE: PRT
<213> ORGANISM: Artificial Sequence
```

```
<220> FEATURE:
<223> OTHER INFORMATION: Engineered polypeptide

<400> SEQUENCE: 650

Lys Glu Trp Arg Gly Ala Ala Phe Glu Ile Trp Gln Leu Pro Asn Leu
1               5                   10                  15

Asn Gln Arg Gln Lys Ala Ala Phe Ile Ala Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 651
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 651

Lys Glu Trp Lys Val Ala Ser Trp Glu Ile Trp Gln Leu Pro Asn Leu
1               5                   10                  15

Asn Arg Gln Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 652
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 652

Lys Glu Trp Lys Leu Ala Ser Trp Glu Ile Trp Gln Leu Pro Asn Leu
1               5                   10                  15

Asn Arg Trp Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 653
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 653

Lys Glu Trp Lys Arg Ala Ser Val Glu Ile Trp Glu Leu Pro Asn Leu
1               5                   10                  15

Asn Arg Gln Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln
```

<210> SEQ ID NO 654
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 654

Lys Glu Trp Lys Arg Ala Ser Phe Glu Ile Trp Gln Leu Pro Asn Leu
1               5                   10                  15

Asn Arg Leu Gln Lys Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 655
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 655

Lys Glu Trp Lys Gly Ala Ala Gly Glu Ile Trp Gln Leu Pro Asn Leu
1               5                   10                  15

Asn Arg Arg Gln Lys Ala Ala Phe Ile Ser Ser Leu Tyr Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 656
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 656

Lys Glu Trp Lys Val Ala Ala Phe Glu Ile Trp Gln Leu Pro Asn Leu
1               5                   10                  15

Asn Arg Ala Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 657
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 657

Lys Glu Trp Lys His Ala Ala Gly Glu Ile Trp Gln Leu Pro Asn Leu
1               5                   10                  15

Asn Arg Ala Gln Lys Ala Ala Phe Ile Ser Ser Leu Ala Asp Asp Pro
            20                  25                  30

```
Ser Gln Ser Ala Asn Leu Leu Ala Glu Ala Lys Lys Leu Asn Asp Ala
            35                  40                  45

Gln
```

<210> SEQ ID NO 658
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 658

```
Lys Glu Trp Lys Lys Ala Ala Tyr Glu Ile Trp Gln Leu Pro Asn Leu
1               5                   10                  15

Asn Arg Ala Gln Lys Ala Ala Phe Ile Ser Ser Leu Tyr Asp Asp Pro
            20                  25                  30

Ser Gln Ser Ala Asn Leu Leu Ala Glu Ala Lys Lys Leu Asn Asp Ala
            35                  40                  45

Gln
```

<210> SEQ ID NO 659
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 659

```
Lys Glu Trp Lys Leu Ala Ala Tyr Glu Ile Trp Gln Leu Pro Asn Leu
1               5                   10                  15

Asn Arg His Gln Lys Ala Ala Phe Ile Ser Ser Leu Ser Asp Asp Pro
            20                  25                  30

Ser Gln Ser Ala Asn Leu Leu Ala Glu Ala Lys Lys Leu Asn Asp Ala
            35                  40                  45

Gln
```

<210> SEQ ID NO 660
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 660

```
Lys Glu Trp Lys Arg Ala Ala Phe Glu Ile Trp Gln Leu Pro Asn Leu
1               5                   10                  15

Asn Arg Ser Gln Lys Ala Ala Phe Ile Ser Ser Leu Ala Asp Asp Pro
            20                  25                  30

Ser Gln Ser Ala Asn Leu Leu Ala Glu Ala Lys Lys Leu Asn Asp Ala
            35                  40                  45

Gln
```

<210> SEQ ID NO 661
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 661

```
Lys Glu Trp Lys Thr Ala Ala Phe Glu Ile Trp Gln Leu Pro Asn Leu
```

```
                1               5                   10                  15
Asn Arg Ser Gln Lys Ala Ala Phe Ile Ala Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 662
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 662

Lys Glu Trp Lys Ile Ala Ala Phe Glu Ile Trp Gln Leu Pro Asn Leu
1               5                   10                  15

Asn Arg Ile Gln Lys Ala Ala Phe Ile Gly Ser Leu Ala Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 663
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 663

Lys Glu Trp Lys Gln Ala Ala Phe Glu Ile Trp Gln Leu Pro Asn Leu
1               5                   10                  15

Asn Arg Ile Gln Lys Ala Ala Phe Ile Thr Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 664
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 664

Lys Glu Trp Lys Gln Ala Ala Phe Glu Ile Trp Gln Leu Pro Asn Leu
1               5                   10                  15

Asn Arg Val Gln Lys Ala Ala Phe Ile Val Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 665
<211> LENGTH: 49
<212> TYPE: PRT
<213> ORGANISM: Artificial Sequence
<220> FEATURE:
```

<223> OTHER INFORMATION: Engineered polypeptide

<400> SEQUENCE: 665

Lys Glu Trp Lys Val Ala Ala Gly Glu Ile Trp Gln Leu Pro Asn Leu
1               5                   10                  15

Asn Arg Ile Gln Lys Ala Ala Phe Ile Gly Ser Leu Ser Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 666
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 666

Lys Glu Trp Lys Ile Ala Ala Phe Glu Ile Trp Gln Leu Pro Asn Leu
1               5                   10                  15

Asn Arg Trp Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 667
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 667

Lys Glu Trp Lys Glu Ala Ala Gly Glu Ile Trp Gln Leu Pro Asn Leu
1               5                   10                  15

Asn Arg Tyr Gln Lys Ala Ala Phe Ile Ala Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

<210> SEQ ID NO 668
<211> LENGTH: 49
<212> TYPE: PRT
<213> ORGANISM: Artificial Sequence
<220> FEATURE:
<223> OTHER INFORMATION: Engineered polypeptide

<400> SEQUENCE: 668

Lys Glu Trp Lys Thr Ala Ser Phe Glu Ile Trp Gln Leu Pro Asn Leu
1               5                   10                  15

Asn Arg Tyr Gln Lys Ala Ala Phe Ile Ser Ser Leu Gln Asp Asp Pro
            20                  25                  30

Ser Gln Ser Ala Asn Leu Leu Ala Glu Ala Lys Lys Leu Asn Asp Ala
        35                  40                  45

Gln

-continued

```
<210> SEQ ID NO 669
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 669

Val Asp Asn Lys Phe Asn Lys Glu Lys Val Ala Ala Thr Gly Glu Ile
1               5                   10                  15

Trp Asp Leu Pro Asn Leu Asn Thr Arg Gln Lys Asn Ala Phe Ile Gly
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 670
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 670

Val Asp Asn Lys Phe Asn Lys Glu Trp Arg Trp Ala Ala His Glu Ile
1               5                   10                  15

Trp Asp Leu Pro Asn Leu Asn Val Tyr Gln Arg Ala Ala Phe Ile Arg
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 671
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 671

Val Asp Asn Lys Phe Asn Lys Glu Arg Arg Leu Ala Ser Val Glu Ile
1               5                   10                  15

Trp Glu Leu Pro Asn Leu Asn Ala Val Gln Lys Ser Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 672
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 672

Val Asp Asn Lys Phe Asn Lys Glu Val Lys Glu Ala Arg Phe Glu Ile
1               5                   10                  15

Trp Asp Leu Pro Asn Leu Asn Arg Thr Gln Lys His Ala Phe Ile Val
```

```
                    20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 673
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 673

Val Asp Asn Lys Phe Asn Lys Glu Trp Lys Gly Ala Ala Gly Glu Ile
1               5                   10                  15

Trp Asn Leu Pro Asn Leu Asn Val Ser Gln Arg Val Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 674
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 674

Val Asp Asn Lys Phe Asn Lys Glu Lys Tyr Lys Ala Ala His Glu Ile
1               5                   10                  15

Trp Glu Leu Pro Asn Leu Asn Arg Asp Gln Arg Ala Ala Phe Ile Thr
            20                  25                  30

Ser Leu Thr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 675
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 675

Val Asp Asn Lys Phe Asn Lys Glu Arg Ser Leu Ala Ser Phe Glu Ile
1               5                   10                  15

Trp Glu Leu Pro Asn Leu Asn Pro Lys Gln Lys Ala Ala Phe Ile Val
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 676
<211> LENGTH: 58
<212> TYPE: PRT
<213> ORGANISM: Artificial Sequence
```

<220> FEATURE:
<223> OTHER INFORMATION: Engineered polypeptide

<400> SEQUENCE: 676

Val Asp Asn Lys Phe Asn Lys Glu Trp Lys Arg Ala Ser Trp Glu Ile
1               5                   10                  15

Trp Glu Leu Pro Asn Leu Asn Asn Ala Gln Lys Arg Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 677
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 677

Val Asp Asn Lys Phe Asn Lys Glu Lys Tyr Lys Ala Met Thr Glu Ile
1               5                   10                  15

Trp Ile Leu Pro Asn Leu Asn Gln Arg Gln Lys Val Ala Phe Ile Gly
            20                  25                  30

Ser Leu Asp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 678
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 678

Val Asp Asn Lys Phe Asn Lys Glu Trp Arg Gly Ala Ala Gly Glu Ile
1               5                   10                  15

Trp Ala Leu Pro Asn Leu Asn Asn Arg Gln Lys Gly Ala Phe Ile Glu
            20                  25                  30

Ser Leu Pro Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 679
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 679

Val Asp Asn Lys Phe Asn Lys Glu Arg Trp Glu Ala Thr Val Glu Ile
1               5                   10                  15

Trp Asp Leu Pro Asn Leu Asn Arg Asn Gln Lys Ala Ala Phe Ile Ala
            20                  25                  30

Ser Leu Gln Asp Asp Pro Ser Gln Ser Ala Asn Leu Leu Ala Glu Ala
        35                  40                  45

```
Lys Lys Leu Asn Asp Ala Gln Ala Pro Lys
    50                  55

<210> SEQ ID NO 680
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 680

Val Asp Asn Lys Phe Asn Lys Glu Lys Tyr Asn Ala Tyr Ala Glu Ile
1               5                   10                  15

Trp Leu Leu Pro Asn Leu Asn Arg Tyr Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 681
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 681

Val Asp Asn Lys Phe Asn Lys Glu Arg Ser Val Ala Gln Lys Glu Ile
1               5                   10                  15

Trp Glu Leu Pro Asn Leu Asn Arg Trp Gln Ala Gly Ala Phe Ile Lys
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 682
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 682

Val Asp Asn Lys Phe Asn Lys Glu Lys Met Asp Ala Met Gly Glu Ile
1               5                   10                  15

Trp Asp Leu Pro Asn Leu Asn Arg Gly Gln Ala Ser Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 683
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 683
```

```
Val Asp Asn Lys Phe Asn Lys Glu Lys Arg Asn Ala Gln Val Glu Ile
1               5                   10                  15

Trp Thr Leu Pro Asn Leu Asn Ser Lys Gln Arg Ala Ala Phe Ile Lys
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 684
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 684

Val Asp Asn Lys Phe Asn Lys Glu Arg Arg Asp Ala Arg Phe Glu Ile
1               5                   10                  15

Trp Glu Leu Pro Asn Leu Asn Lys Tyr Gln Arg Ala Ala Phe Ile Ser
                20                  25                  30

Ser Leu Asp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 685
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 685

Val Asp Asn Lys Phe Asn Lys Glu Arg Ser Met Ala Arg Phe Glu Ile
1               5                   10                  15

Trp Glu Leu Pro Asn Leu Asn Arg Gly Gln Lys Ser Ala Phe Ile Ala
                20                  25                  30

Ser Leu Glu Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 686
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 686

Val Asp Asn Lys Phe Asn Lys Glu Trp His Gly Ala Ala Ser Glu Ile
1               5                   10                  15

Trp Glu Leu Pro Asn Leu Asn Lys Ser Gln Lys Ser Ala Phe Ile Lys
                20                  25                  30

Ser Leu Pro Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 687
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 687

Val Asp Asn Lys Phe Asn Lys Glu Trp Lys Gln Ala Ala Glu Glu Ile
1               5                   10                  15

Trp Asp Leu Pro Asn Leu Asn Arg Arg Gln Ala Gly Ala Phe Ile Thr
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 688
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 688

Val Asp Asn Lys Phe Asn Lys Glu Lys Val Gln Ala Ser Glu Glu Ile
1               5                   10                  15

Trp Asn Leu Pro Asn Leu Asn Arg Arg Gln Arg Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 689
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 689

Val Asp Asn Lys Phe Asn Lys Glu Arg Tyr Ser Ala Thr Val Glu Ile
1               5                   10                  15

Trp Asp Leu Pro Asn Leu Asn Thr Leu Gln Lys Ser Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 690
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 690

Val Asp Asn Lys Phe Asn Lys Glu Arg Tyr Ser Ala Tyr Tyr Glu Ile
1               5                   10                  15

```
Trp Gln Leu Pro Asn Leu Asn Arg Ile Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 691
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 691

Val Asp Asn Lys Phe Asn Lys Glu Arg Tyr Arg Ala Tyr Phe Glu Ile
1               5                   10                  15

Trp Gln Leu Pro Asn Leu Asn Arg Leu Gln Lys Ala Ala Phe Ile Ser
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 692
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 692

Val Asp Asn Lys Phe Asn Lys Glu Lys Tyr Lys Ala Tyr Gly Glu Ile
1               5                   10                  15

Trp Gln Leu Pro Asn Leu Asn Arg Val Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 693
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 693

Val Asp Asn Lys Phe Asn Lys Glu Arg Lys Gln Ala Thr Phe Glu Ile
1               5                   10                  15

Trp Glu Leu Pro Asn Leu Asn Gln Arg Gln Lys Ala Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 694
<211> LENGTH: 58
<212> TYPE: PRT
```

<213> ORGANISM: Artificial Sequence
<220> FEATURE:
<223> OTHER INFORMATION: Engineered polypeptide

<400> SEQUENCE: 694

Val Asp Asn Lys Phe Asn Lys Glu Trp Lys Ile Ala Ala Gly Glu Ile
1               5                   10                  15

Trp Gln Leu Pro Asn Leu Asn Arg His Gln Lys Gly Ala Phe Ile Ser
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 695
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 695

Val Asp Asn Lys Phe Asn Lys Glu Lys Tyr Lys Ala Tyr Val Glu Ile
1               5                   10                  15

Trp Gln Leu Pro Asn Leu Asn Arg Tyr Gln Arg Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 696
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 696

Val Asp Asn Lys Phe Asn Lys Glu Arg Lys Ala Ala Thr Phe Glu Ile
1               5                   10                  15

Trp Glu Leu Pro Asn Leu Asn Arg Ile Gln Lys Ala Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 697
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 697

Val Asp Asn Lys Phe Asn Lys Glu Lys Tyr Lys Ala Tyr Gly Glu Ile
1               5                   10                  15

Trp Gln Leu Pro Asn Leu Asn Arg Ile Gln Lys Ala Ala Phe Ile Ser
            20                  25                  30

Ser Leu Gln Asp Asp Pro Ser Gln Ser Ala Asn Leu Leu Ala Glu Ala

-continued

```
                35                  40                  45
Lys Lys Leu Asn Asp Ala Gln Ala Pro Lys
     50                  55

<210> SEQ ID NO 698
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 698

Val Asp Asn Lys Phe Asn Lys Glu Lys Arg Ile Ala Thr Trp Glu Ile
1               5                   10                  15

Trp Gln Leu Pro Asn Leu Asn Gln His Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 699
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 699

Val Asp Asn Lys Phe Asn Lys Glu Lys Tyr Lys Ala Tyr Val Glu Ile
1               5                   10                  15

Trp Gln Leu Pro Asn Leu Asn Arg Gly Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 700
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 700

Val Asp Asn Lys Phe Asn Lys Glu Arg Tyr Leu Ala Tyr Tyr Glu Ile
1               5                   10                  15

Trp Gln Leu Pro Asn Leu Asn Arg Thr Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
     50                  55

<210> SEQ ID NO 701
<211> LENGTH: 58
<212> TYPE: PRT
<213> ORGANISM: Artificial Sequence
<220> FEATURE:
<223> OTHER INFORMATION: Engineered polypeptide
```

-continued

<400> SEQUENCE: 701

Val Asp Asn Lys Phe Asn Lys Glu Arg Tyr Ile Ala Tyr Trp Glu Ile
1               5                   10                  15

Trp Gln Leu Pro Asn Leu Asn Arg Arg Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 702
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 702

Val Asp Asn Lys Phe Asn Lys Glu Lys Tyr Arg Ala Tyr Gly Glu Ile
1               5                   10                  15

Trp Gln Leu Pro Asn Leu Asn Arg Gly Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 703
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 703

Val Asp Asn Lys Phe Asn Lys Glu Lys Tyr Thr Ala Tyr Phe Glu Ile
1               5                   10                  15

Trp Gln Leu Pro Asn Leu Asn Val Arg Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 704
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 704

Val Asp Asn Lys Phe Asn Lys Glu Arg Tyr Ser Ala Tyr Tyr Glu Ile
1               5                   10                  15

Trp Gln Leu Pro Asn Leu Asn Val Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 705
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 705

Val Asp Asn Lys Phe Asn Lys Glu Lys Tyr Ala Ala Tyr Gly Glu Ile
1               5                   10                  15

Trp Gln Leu Pro Asn Leu Asn Arg Ser Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 706
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 706

Val Asp Asn Lys Phe Asn Lys Glu Arg Lys Arg Ala Thr Val Glu Ile
1               5                   10                  15

Trp Glu Leu Pro Asn Leu Asn Arg Leu Gln Arg Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 707
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 707

Val Asp Asn Lys Phe Asn Lys Glu Trp Lys Gln Ala Ser Phe Glu Ile
1               5                   10                  15

Trp Glu Leu Pro Asn Leu Asn Arg Leu Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 708
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 708

Val Asp Asn Lys Phe Asn Lys Glu Arg Lys His Ala Thr Val Glu Ile
1               5                   10                  15
```

Trp Glu Leu Pro Asn Leu Asn Arg Val Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 709
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 709

Val Asp Asn Lys Phe Asn Lys Glu Lys Tyr Lys Ala Tyr Val Glu Ile
1               5                   10                  15

Trp Gln Leu Pro Asn Leu Asn Gln Arg Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 710
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 710

Val Asp Asn Lys Phe Asn Lys Glu Lys Tyr Val Ala Tyr Gly Glu Ile
1               5                   10                  15

Trp Gln Leu Pro Asn Leu Asn Arg Thr Gln Lys Ala Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 711
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 711

Val Asp Asn Lys Phe Asn Lys Glu Arg Tyr Ile Ala Tyr Tyr Glu Ile
1               5                   10                  15

Trp Gln Leu Pro Asn Leu Asn Arg Tyr Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 712
<211> LENGTH: 58

```
<212> TYPE: PRT
<213> ORGANISM: Artificial Sequence
<220> FEATURE:
<223> OTHER INFORMATION: Engineered polypeptide

<400> SEQUENCE: 712

Val Asp Asn Lys Phe Asn Lys Glu Lys Tyr Asn Ala Tyr Gly Glu Ile
1               5                   10                  15
Trp Gln Leu Pro Asn Leu Asn Val Arg Gln Lys Ala Ala Phe Ile Ser
            20                  25                  30
Ser Leu Ala Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 713
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 713

Val Asp Asn Lys Phe Asn Lys Glu Arg Lys Ala Ala Thr Val Glu Ile
1               5                   10                  15
Trp Glu Leu Pro Asn Leu Asn Arg Val Gln Lys Ala Ala Phe Ile Lys
            20                  25                  30
Ser Leu Phe Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 714
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 714

Val Asp Asn Lys Phe Asn Lys Glu Arg Tyr Val Ala Tyr Tyr Glu Ile
1               5                   10                  15
Trp Glu Leu Pro Asn Leu Asn Gln Arg Gln Lys Ala Ala Phe Ile Gly
            20                  25                  30
Ser Leu Gln Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 715
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 715

Val Asp Asn Lys Phe Asn Lys Glu Arg Tyr Arg Ala Tyr Tyr Glu Ile
1               5                   10                  15
Trp Gln Leu Pro Asn Leu Asn Gln Arg Gln Lys Ala Ala Phe Ile Gly
            20                  25                  30
```

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 716
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 716

Val Asp Asn Lys Phe Asn Lys Glu Trp Lys Ser Ala Ala Phe Glu Ile
1               5                  10                  15

Trp Glu Leu Pro Asn Leu Asn Arg Leu Gln Lys Ala Ala Phe Ile Arg
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 717
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 717

Val Asp Asn Lys Phe Asn Lys Glu Arg Lys Gln Ala Thr Phe Glu Ile
1               5                  10                  15

Trp Glu Leu Pro Asn Leu Asn Arg His Gln Lys Gly Ala Phe Ile Ala
            20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 718
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 718

Val Asp Asn Lys Phe Asn Lys Glu Trp Lys Ile Ala Ala Gly Glu Ile
1               5                  10                  15

Trp Gln Leu Pro Asn Leu Asn Arg Arg Gln Lys Ala Ala Phe Ile Ala
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 719
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 719

Val Asp Asn Lys Phe Asn Lys Glu Arg Tyr Leu Ala Tyr Tyr Glu Ile
1               5                   10                  15

Trp Gln Leu Pro Asn Leu Asn Arg Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 720
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 720

Val Asp Asn Lys Phe Asn Lys Glu Arg Tyr His Ala Tyr Tyr Glu Ile
1               5                   10                  15

Trp Glu Leu Pro Asn Leu Asn Arg Leu Gln Lys Ala Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 721
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 721

Val Asp Asn Lys Phe Asn Lys Glu Lys Tyr Lys Ala Tyr Ala Glu Ile
1               5                   10                  15

Trp Gln Leu Pro Asn Leu Asn Arg Thr Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 722
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 722

Val Asp Asn Lys Phe Asn Lys Glu Arg Tyr Lys Ala Tyr Tyr Glu Ile
1               5                   10                  15

Trp Gln Leu Pro Asn Leu Asn Arg Gln Gln Lys Gly Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys

```
            50                  55

<210> SEQ ID NO 723
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 723

Val Asp Asn Lys Phe Asn Lys Glu Arg Lys Leu Ala Thr Phe Glu Ile
1               5                   10                  15

Trp Glu Leu Pro Asn Leu Asn Thr Ser Gln Lys Gly Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 724
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 724

Val Asp Asn Lys Phe Asn Lys Glu Arg Tyr Val Ala Tyr Tyr Glu Ile
1               5                   10                  15

Trp Gln Leu Pro Asn Leu Asn Val Gln Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 725
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 725

Val Asp Asn Lys Phe Asn Lys Glu Arg Ser Ile Ala Ser Val Glu Ile
1               5                   10                  15

Trp Glu Leu Pro Asn Leu Asn Gln Arg Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 726
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 726

Val Asp Asn Lys Phe Asn Lys Glu Arg Lys Gln Ala Ala Val Glu Ile
```

```
                1               5                  10                  15
Trp Glu Leu Pro Asn Leu Asn Val Arg Gln Lys Ala Ala Phe Ile Arg
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 727
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 727

Val Asp Asn Lys Phe Asn Lys Glu Lys Lys Ile Ala Ala Phe Glu Ile
1               5                  10                  15

Trp Glu Leu Pro Asn Leu Asn Gln Trp Gln Lys Ala Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 728
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 728

Val Asp Asn Lys Phe Asn Lys Glu Arg Lys Ile Ala Thr Val Glu Ile
1               5                  10                  15

Trp Glu Leu Pro Asn Leu Asn Arg Ile Gln Lys Gly Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 729
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 729

Val Asp Asn Lys Phe Asn Lys Glu Lys Tyr Arg Ala Ala Gly Glu Ile
1               5                  10                  15

Trp Glu Leu Pro Asn Leu Asn Val Leu Gln Lys Ala Ala Phe Ile Lys
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 730
```

```
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 730

Val Asp Asn Lys Phe Asn Lys Glu Arg Lys Ile Ala Ala Val Glu Ile
1               5                   10                  15

Trp Glu Leu Pro Asn Leu Asn Arg Tyr Gln Lys Ala Ala Phe Ile Lys
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 731
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 731

Val Asp Asn Lys Phe Asn Lys Glu Lys Arg Thr Ala Thr Trp Glu Ile
1               5                   10                  15

Trp Gln Leu Pro Asn Leu Asn Gln Arg Gln Arg Ala Ala Phe Ile Gly
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 732
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 732

Val Asp Asn Lys Phe Asn Lys Glu Arg Lys Thr Ala Thr Val Glu Ile
1               5                   10                  15

Trp Glu Leu Pro Asn Leu Asn Arg Arg Gln Lys Ala Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 733
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 733

Val Asp Asn Lys Phe Asn Lys Glu Arg Lys Gln Ala Ala Val Glu Ile
1               5                   10                  15

Trp Glu Leu Pro Asn Leu Asn Arg Ile Gln Lys Gly Ala Phe Ile Lys
                20                  25                  30
```

Ser Leu Trp Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 734
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 734

Val Asp Asn Lys Phe Asn Lys Glu Arg Tyr Ile Ala Tyr Gly Glu Ile
 1               5                  10                  15

Trp Gln Leu Pro Asn Leu Asn Arg Arg Gln Lys Ala Ala Phe Ile Gly
             20                  25                  30

Ser Leu Ser Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 735
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 735

Val Asp Asn Lys Phe Asn Lys Glu Arg Tyr Arg Ala Tyr Tyr Glu Ile
 1               5                  10                  15

Trp Gln Leu Pro Asn Leu Asn Arg Thr Gln Lys Val Ala Phe Ile Gly
             20                  25                  30

Ser Leu Gln Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 736
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 736

Val Asp Asn Lys Phe Asn Lys Glu Arg Arg Leu Ala Tyr Trp Glu Ile
 1               5                  10                  15

Trp Gln Leu Pro Asn Leu Asn Thr Thr Gln Lys Ala Ala Phe Ile Gly
             20                  25                  30

Ser Leu Gln Asp Asp Pro Ser Gln Ser Ala Asn Leu Leu Ala Glu Ala
         35                  40                  45

Lys Lys Leu Asn Asp Ala Gln Ala Pro Lys
 50                  55

<210> SEQ ID NO 737
<211> LENGTH: 58
<212> TYPE: PRT
<213> ORGANISM: Artificial Sequence
<220> FEATURE:

<223> OTHER INFORMATION: Engineered polypeptide

<400> SEQUENCE: 737

Val Asp Asn Lys Phe Asn Lys Glu Arg Arg Ala Tyr Tyr Glu Ile
1               5                   10                  15

Trp Gln Leu Pro Asn Leu Asn Arg Ile Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 738
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 738

Val Asp Asn Lys Phe Asn Lys Glu Arg Arg Leu Ala Tyr Tyr Glu Ile
1               5                   10                  15

Trp Glu Leu Pro Asn Leu Asn Val Ala Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 739
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 739

Val Asp Asn Lys Phe Asn Lys Glu Arg Tyr Leu Ala Tyr Tyr Glu Ile
1               5                   10                  15

Trp Glu Leu Pro Asn Leu Asn Val Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 740
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 740

Val Asp Asn Lys Phe Asn Lys Glu Arg Tyr Ala Ala Tyr Tyr Glu Ile
1               5                   10                  15

Trp Gln Leu Pro Asn Leu Asn Ser Arg Gln Lys Ala Ala Phe Ile Gly
            20                  25                  30

Ser Leu Ser Asp Asp Pro Ser Gln Ser Ala Asn Leu Leu Ala Glu Ala
        35                  40                  45

<210> SEQ ID NO 741
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 741

Val Asp Asn Lys Phe Asn Lys Glu Arg Tyr Leu Ala Tyr Tyr Glu Ile
1               5                   10                  15

Trp Gln Leu Pro Asn Leu Asn Gln Leu Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 742
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 742

Val Asp Asn Lys Phe Asn Lys Glu Arg Tyr His Ala Tyr Tyr Glu Ile
1               5                   10                  15

Trp Gln Leu Pro Asn Leu Asn Ser Trp Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 743
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 743

Val Asp Asn Lys Phe Asn Lys Glu Arg Tyr His Ala Tyr Tyr Glu Ile
1               5                   10                  15

Trp Gln Leu Pro Asn Leu Asn Ser Ala Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 744
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 744

Val Asp Asn Lys Phe Asn Lys Glu Arg Tyr Glu Ala Tyr Tyr Glu Ile
1               5                   10                  15

Trp Gln Leu Pro Asn Leu Asn Ser Val Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 745
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 745

Val Asp Asn Lys Phe Asn Lys Glu Arg Tyr His Ala Tyr Tyr Glu Ile
1               5                   10                  15

Trp Gln Leu Pro Asn Leu Asn Arg Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 746
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 746

Val Asp Asn Lys Phe Asn Lys Glu Arg Tyr Thr Ala Tyr Tyr Glu Ile
1               5                   10                  15

Trp Gln Leu Pro Asn Leu Asn Arg Ala Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 747
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 747

Val Asp Asn Lys Phe Asn Lys Glu Arg Tyr Ser Ala Tyr Tyr Glu Ile
1               5                   10                  15

Trp Gln Leu Pro Asn Leu Asn Arg Ala Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 748
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 748

Val Asp Asn Lys Phe Asn Lys Glu Arg Tyr Ser Ala Tyr Tyr Glu Ile
1               5                   10                  15

Trp Glu Leu Pro Asn Leu Asn Arg Ala Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 749
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 749

Val Asp Asn Lys Phe Asn Lys Glu Arg Tyr His Ala Tyr Tyr Glu Ile
1               5                   10                  15

Trp Gln Leu Pro Asn Leu Asn Arg Ala Gln Lys Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 750
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 750

Val Asp Asn Lys Phe Asn Lys Glu Arg Tyr Ser Ala Tyr Val Glu Ile
1               5                   10                  15

Trp Gln Leu Pro Asn Leu Asn Arg Gly Gln Lys Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 751
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 751

Val Asp Asn Lys Phe Asn Lys Glu Arg Tyr Ser Ala Tyr Phe Glu Ile
1               5                   10                  15

Trp Gln Leu Pro Asn Leu Asn Arg Leu Gln Lys Ala Ala Phe Ile Gly
```

```
                 20                  25                  30

Ser Leu Gln Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 752
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 752

Val Asp Asn Lys Phe Asn Lys Glu Arg Tyr Asn Ala Tyr Phe Glu Ile
1               5                  10                  15

Trp Gln Leu Pro Asn Leu Asn Arg Tyr Gln Lys Ser Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 753
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 753

Val Asp Asn Lys Phe Asn Lys Glu Arg Tyr Ala Ala Tyr Phe Glu Ile
1               5                  10                  15

Trp Gln Leu Pro Asn Leu Asn Val Ala Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 754
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 754

Val Asp Asn Lys Phe Asn Lys Glu Arg Tyr Gln Ala Tyr Phe Glu Ile
1               5                  10                  15

Trp Gln Leu Pro Asn Leu Asn Gln Trp Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 755
<211> LENGTH: 58
<212> TYPE: PRT
<213> ORGANISM: Artificial Sequence
```

```
<220> FEATURE:
<223> OTHER INFORMATION: Engineered polypeptide

<400> SEQUENCE: 755

Val Asp Asn Lys Phe Asn Lys Glu Arg Tyr Lys Ala Tyr Trp Glu Ile
1               5                   10                  15

Trp Gln Leu Pro Asn Leu Asn Gln Gly Gln Lys Ala Ala Phe Ile Gly
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 756
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 756

Val Asp Asn Lys Phe Asn Lys Glu Arg Tyr Ile Ala Tyr Gly Glu Ile
1               5                   10                  15

Trp Gln Leu Pro Asn Leu Asn Val Gly Gln Lys Ala Ala Phe Ile Gly
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 757
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 757

Val Asp Asn Lys Phe Asn Lys Glu Arg Tyr Arg Ala Tyr Val Glu Ile
1               5                   10                  15

Trp Gln Leu Pro Asn Leu Asn Arg Val Gln Lys Ala Ala Phe Ile Gly
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 758
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 758

Val Asp Asn Lys Phe Asn Lys Glu Arg Tyr Lys Ala Tyr Val Glu Ile
1               5                   10                  15

Trp Gln Leu Pro Asn Leu Asn Arg Thr Gln Lys Ala Ala Phe Ile Gly
                20                  25                  30

Ser Leu Gln Asp Asp Pro Ser Gln Ser Ala Asn Leu Leu Ala Glu Ala
            35                  40                  45
```

<210> SEQ ID NO 759
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 759

Val Asp Asn Lys Phe Asn Lys Glu Lys Tyr Glu Ala Tyr Gly Glu Ile
1               5                   10                  15
Trp Glu Leu Pro Asn Leu Asn Arg Ser Gln Lys Ala Ala Phe Ile Gly
            20                  25                  30
Ser Leu Glu Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 760
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 760

Val Asp Asn Lys Phe Asn Lys Glu Lys Tyr Gln Ala Tyr Gly Glu Ile
1               5                   10                  15
Trp Gln Leu Pro Asn Leu Asn Arg Ser Gln Lys Ala Ala Phe Ile Thr
            20                  25                  30
Ser Leu Glu Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 761
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 761

Val Asp Asn Lys Phe Asn Lys Glu Lys Tyr Ala Ala Tyr Gly Glu Ile
1               5                   10                  15
Trp Leu Leu Pro Asn Leu Asn Arg Ile Gln Lys Ala Ala Phe Ile Gly
            20                  25                  30
Ser Leu Gln Asp Asp Pro Ser Gln Ser Ala Asn Leu Leu Ala Glu Ala
        35                  40                  45
Lys Lys Leu Asn Asp Ala Gln Ala Pro Lys
    50                  55

<210> SEQ ID NO 762
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 762

Val Asp Asn Lys Phe Asn Lys Glu Lys Tyr Lys Ala Tyr Gly Glu Ile
1               5                   10                  15

Trp Glu Leu Pro Asn Leu Asn Arg Arg Gln Lys Val Ala Phe Ile Ser
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 763
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 763

Val Asp Asn Lys Phe Asn Lys Glu Lys Tyr Lys Ala Tyr Gly Glu Ile
1               5                   10                  15

Trp Glu Leu Pro Asn Leu Asn Arg Ser Gln Lys Ala Ala Phe Ile Ala
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 764
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 764

Val Asp Asn Lys Phe Asn Lys Glu Lys Tyr Lys Ala Tyr Gly Glu Ile
1               5                   10                  15

Trp Gln Leu Pro Asn Leu Asn Gln Arg Gln Lys Ala Ala Phe Ile Ala
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 765
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 765

Val Asp Asn Lys Phe Asn Lys Glu Lys Tyr Lys Ala Tyr Gly Glu Ile
1               5                   10                  15

Trp Gln Leu Pro Asn Leu Asn Arg Ser Gln Lys Ala Ala Phe Ile Ser
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

-continued

<210> SEQ ID NO 766
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 766

Val Asp Asn Lys Phe Asn Lys Glu Lys Tyr Lys Ala Tyr Gly Glu Ile
1               5                   10                  15

Trp Gln Leu Pro Asn Leu Asn Arg Arg Gln Lys Ala Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 767
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 767

Val Asp Asn Lys Phe Asn Lys Glu Lys Tyr Asn Ala Tyr Gly Glu Ile
1               5                   10                  15

Trp Gln Leu Pro Asn Leu Asn Arg Gly Gln Lys Ala Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 768
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 768

Val Asp Asn Lys Phe Asn Lys Glu Lys Tyr Val Ala Tyr Ala Glu Ile
1               5                   10                  15

Trp Gln Leu Pro Asn Leu Asn Arg Val Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 769
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 769

Val Asp Asn Lys Phe Asn Lys Glu Lys Tyr Gln Ala Tyr Gly Glu Ile
1               5                   10                  15

Trp Gln Leu Pro Asn Leu Asn Arg Val Gln Lys Ala Ala Phe Ile Gly
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 770
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 770

Val Asp Asn Lys Phe Asn Lys Glu Lys Tyr His Ala Tyr Gly Glu Ile
1               5                   10                  15

Trp Gln Leu Pro Asn Leu Asn Arg Ile Gln Lys Ala Ala Phe Ile Ala
            20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 771
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 771

Val Asp Asn Lys Phe Asn Lys Glu Lys Tyr Thr Ala Tyr Val Glu Ile
1               5                   10                  15

Trp Gln Leu Pro Asn Leu Asn Arg Tyr Gln Arg Ala Ala Phe Ile Ala
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 772
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 772

Val Asp Asn Lys Phe Asn Lys Glu Lys Tyr Lys Ala Tyr Val Glu Ile
1               5                   10                  15

Trp Gln Leu Pro Asn Leu Asn Arg Gly Gln Lys Ala Ala Phe Ile Gly
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 773
<211> LENGTH: 58
<212> TYPE: PRT

<213> ORGANISM: Artificial Sequence
<220> FEATURE:
<223> OTHER INFORMATION: Engineered polypeptide

<400> SEQUENCE: 773

Val Asp Asn Lys Phe Asn Lys Glu Lys Tyr Val Ala Tyr Val Glu Ile
1               5                   10                  15

Trp Gln Leu Pro Asn Leu Asn Arg Thr Gln Lys Ala Ala Phe Ile Ala
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 774
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 774

Val Asp Asn Lys Phe Asn Lys Glu Lys Tyr Ile Ala Tyr Val Glu Ile
1               5                   10                  15

Trp Gln Leu Pro Asn Leu Asn Arg Thr Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 775
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 775

Val Asp Asn Lys Phe Asn Lys Glu Lys Tyr Lys Ala Tyr Ala Glu Ile
1               5                   10                  15

Trp Gln Leu Pro Asn Leu Asn Arg Ala Gln Lys Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 776
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 776

Val Asp Asn Lys Phe Asn Lys Glu Lys Tyr Thr Ala Tyr Gly Glu Ile
1               5                   10                  15

Trp Gln Leu Pro Asn Leu Asn Val Arg Gln Lys Ala Ala Phe Ile Ser
            20                  25                  30

Ser Leu Ser Asp Asp Pro Ser Gln Ser Ala Asn Leu Leu Ala Glu Ala

<210> SEQ ID NO 777
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 777

Val Asp Asn Lys Phe Asn Lys Glu Lys Tyr Thr Ala Tyr Gly Glu Ile
1               5                   10                  15

Trp Gln Leu Pro Asn Leu Asn Gln Arg Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 778
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 778

Val Asp Asn Lys Phe Asn Lys Glu Lys Tyr Thr Ala Tyr Phe Glu Ile
1               5                   10                  15

Trp Gln Leu Pro Asn Leu Asn Gln Gly Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 779
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 779

Val Asp Asn Lys Phe Asn Lys Glu Lys Tyr Gln Ala Tyr Val Glu Ile
1               5                   10                  15

Trp Gln Leu Pro Asn Leu Asn Gln Arg Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 780
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 780

Val Asp Asn Lys Phe Asn Lys Glu Lys Tyr Ala Ala Tyr Val Glu Ile
1               5                   10                  15

Trp Gln Leu Pro Asn Leu Asn Gln Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 781
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 781

Val Asp Asn Lys Phe Asn Lys Glu Lys Tyr Val Ala Tyr Val Glu Ile
1               5                   10                  15

Trp Gln Leu Pro Asn Leu Asn Thr Ser Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 782
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 782

Val Asp Asn Lys Phe Asn Lys Glu Lys Tyr Gln Ala Tyr Ala Glu Ile
1               5                   10                  15

Trp Gln Leu Pro Asn Leu Asn Val Arg Gln Lys Ser Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 783
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 783

Val Asp Asn Lys Phe Asn Lys Glu Lys Tyr Gln Ala Tyr Tyr Glu Ile
1               5                   10                  15

Trp Glu Leu Pro Asn Leu Asn Val Gln Gln Lys Ser Ala Phe Ile Thr
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 784
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 784

Val Asp Asn Lys Phe Asn Lys Glu Lys Tyr His Ala Tyr Tyr Glu Ile
1               5                   10                  15

Trp Gln Leu Pro Asn Leu Asn Val His Gln Lys Ala Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 785
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 785

Val Asp Asn Lys Phe Asn Lys Glu Lys Tyr Gln Ala Tyr Tyr Glu Ile
1               5                   10                  15

Trp Gln Leu Pro Asn Leu Asn Val Ala Gln Lys Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 786
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 786

Val Asp Asn Lys Phe Asn Lys Glu Lys Tyr Thr Ala Tyr Tyr Glu Ile
1               5                   10                  15

Trp Gln Leu Pro Asn Leu Asn Arg Thr Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 787
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 787

Val Asp Asn Lys Phe Asn Lys Glu Arg Tyr Arg Ala Tyr Tyr Glu Ile
1               5                   10                  15

-continued

Trp Gln Leu Pro Asn Leu Asn Arg Gln Gln Lys Gly Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 788
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 788

Val Asp Asn Lys Phe Asn Lys Glu Lys Tyr Ala Tyr Tyr Glu Ile
1               5                   10                  15

Trp Gln Leu Pro Asn Leu Asn Arg Ser Gln Lys Gly Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 789
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 789

Val Asp Asn Lys Phe Asn Lys Glu Lys Tyr Ile Ala Tyr Tyr Glu Ile
1               5                   10                  15

Trp Gln Leu Pro Asn Leu Asn Arg Ser Gln Lys Gly Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 790
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 790

Val Asp Asn Lys Phe Asn Lys Glu Arg Tyr Lys Ala Tyr Tyr Glu Ile
1               5                   10                  15

Trp Gln Leu Pro Asn Leu Asn Arg Gln Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 791
<211> LENGTH: 58

```
<212> TYPE: PRT
<213> ORGANISM: Artificial Sequence
<220> FEATURE:
<223> OTHER INFORMATION: Engineered polypeptide

<400> SEQUENCE: 791

Val Asp Asn Lys Phe Asn Lys Glu Arg Tyr Leu Ala Tyr Tyr Glu Ile
1               5                   10                  15

Trp Gln Leu Pro Asn Leu Asn Gln Phe Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 792
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 792

Val Asp Asn Lys Phe Asn Lys Glu Arg Tyr Leu Ala Tyr Tyr Glu Ile
1               5                   10                  15

Trp Gln Leu Pro Asn Leu Asn Arg Glu Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 793
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 793

Val Asp Asn Lys Phe Asn Lys Glu Arg Tyr Val Ala Tyr Gly Glu Ile
1               5                   10                  15

Trp Gln Leu Pro Asn Leu Asn Arg Tyr Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 794
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 794

Val Asp Asn Lys Phe Asn Lys Glu Arg Tyr Ile Ala Tyr Tyr Glu Ile
1               5                   10                  15

Trp Gln Leu Pro Asn Leu Asn Arg Ala Gln Lys Ala Ala Phe Ile Ala
            20                  25                  30
```

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 795
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 795

Val Asp Asn Lys Phe Asn Lys Glu Arg Tyr Gln Ala Tyr Tyr Glu Ile
1               5                   10                  15

Trp Gln Leu Pro Asn Leu Asn Arg Ile Gln Lys Ala Ala Phe Ile Lys
            20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 796
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 796

Val Asp Asn Lys Phe Asn Lys Glu Arg Tyr Thr Ala Tyr Tyr Glu Ile
1               5                   10                  15

Trp Gln Leu Pro Asn Leu Asn Thr Gln Gln Lys Ala Ala Phe Ile Arg
            20                  25                  30

Ser Leu Glu Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 797
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 797

Val Asp Asn Lys Phe Asn Lys Glu Arg Tyr Gln Ala Tyr Tyr Glu Ile
1               5                   10                  15

Trp Gln Leu Pro Asn Leu Asn Thr Ile Gln Lys Ala Ala Phe Ile Arg
            20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 798
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 798

Val Asp Asn Lys Phe Asn Lys Glu Arg Tyr Ala Ala Tyr Ala Glu Ile
1               5                   10                  15

Trp Gln Leu Pro Asn Leu Asn Arg Trp Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 799
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 799

Val Asp Asn Lys Phe Asn Lys Glu Arg Tyr Arg Ala Tyr Ala Glu Ile
1               5                   10                  15

Trp Gln Leu Pro Asn Leu Asn Arg Trp Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 800
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 800

Val Asp Asn Lys Phe Asn Lys Glu Arg Tyr Arg Ala Tyr Ala Glu Ile
1               5                   10                  15

Trp Gln Leu Pro Asn Leu Asn Arg Ile Gln Lys Ala Ala Phe Ile Gly
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 801
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 801

Val Asp Asn Lys Phe Asn Lys Glu Arg Tyr His Ala Tyr Ala Glu Ile
1               5                   10                  15

Trp Gln Leu Pro Asn Leu Asn Arg Ile Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys 50                  55

<210> SEQ ID NO 802
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 802

Val Asp Asn Lys Phe Asn Lys Glu Arg Tyr Arg Ala Tyr Tyr Glu Ile
1               5                   10                  15

Trp Gln Leu Pro Asn Leu Asn Arg Tyr Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 803
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 803

Val Asp Asn Lys Phe Asn Lys Glu Arg Tyr Thr Ala Tyr Tyr Glu Ile
1               5                   10                  15

Trp Gln Leu Pro Asn Leu Asn Arg Val Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 804
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 804

Val Asp Asn Lys Phe Asn Lys Glu Arg Tyr His Ala Tyr Tyr Glu Ile
1               5                   10                  15

Trp Gln Leu Pro Asn Leu Asn Arg Thr Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 805
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 805

Val Asp Asn Lys Phe Asn Lys Glu Arg Tyr Val Ala Tyr Tyr Glu Ile

```
                1               5                   10                  15
Trp Gln Leu Pro Asn Leu Asn Arg Arg Gln Lys Ala Ala Phe Ile Ser
                20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 806
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 806

Val Asp Asn Lys Phe Asn Lys Glu Arg Tyr Leu Ala Tyr Phe Glu Ile
1               5                   10                  15

Trp Gln Leu Pro Asn Leu Asn Arg His Gln Lys Gly Ala Phe Ile Ala
                20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 807
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 807

Val Asp Asn Lys Phe Asn Lys Glu Arg Tyr Thr Ala Tyr Phe Glu Ile
1               5                   10                  15

Trp Gln Leu Pro Asn Leu Asn Arg Trp Gln Lys Gly Ala Phe Ile Ala
                20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 808
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 808

Val Asp Asn Lys Phe Asn Lys Glu Arg Tyr Ala Ala Tyr Phe Glu Ile
1               5                   10                  15

Trp Gln Leu Pro Asn Leu Asn Arg Leu Gln Lys Ala Ala Phe Ile Ser
                20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 809
```

```
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 809

Val Asp Asn Lys Phe Asn Lys Glu Arg Tyr Val Ala Tyr Phe Glu Ile
1               5                   10                  15

Trp Gln Leu Pro Asn Leu Asn Arg Ser Gln Lys Ala Ala Phe Ile Ser
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 810
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 810

Val Asp Asn Lys Phe Asn Lys Glu Arg Tyr Gly Ala Tyr Phe Glu Ile
1               5                   10                  15

Trp Gln Leu Pro Asn Leu Asn Arg Thr Gln Lys Ala Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 811
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 811

Val Asp Asn Lys Phe Asn Lys Glu Lys Tyr Ile Ala Tyr Trp Glu Ile
1               5                   10                  15

Trp Gln Leu Pro Asn Leu Asn Arg Glu Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 812
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 812

Val Asp Asn Lys Phe Asn Lys Glu Arg Tyr Ile Ala Tyr Ala Glu Ile
1               5                   10                  15

Trp Gln Leu Pro Asn Leu Asn Arg Arg Gln Lys Ala Ala Phe Ile Ala
            20                  25                  30
```

```
Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 813
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 813

Val Asp Asn Lys Phe Asn Lys Glu Arg Tyr Ile Ala Tyr Trp Glu Ile
1               5                   10                  15

Trp Gln Leu Pro Asn Leu Asn Gln Arg Gln Lys Ala Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 814
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 814

Val Asp Asn Lys Phe Asn Lys Glu Arg Tyr Ile Ala Tyr Trp Glu Ile
1               5                   10                  15

Trp Gln Leu Pro Asn Leu Asn Arg Leu Gln Lys Ser Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 815
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 815

Val Asp Asn Lys Phe Asn Lys Glu Arg Tyr His Ala Tyr Trp Glu Ile
1               5                   10                  15

Trp Gln Leu Pro Asn Leu Asn Arg Ala Gln Lys Ala Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 816
<211> LENGTH: 58
<212> TYPE: PRT
<213> ORGANISM: Artificial Sequence
<220> FEATURE:
```

<223> OTHER INFORMATION: Engineered polypeptide

<400> SEQUENCE: 816

Val Asp Asn Lys Phe Asn Lys Glu Arg Tyr Asn Ala Tyr Trp Glu Ile
1               5                   10                  15

Trp Gln Leu Pro Asn Leu Asn Arg Leu Gln Lys Ala Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 817
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 817

Val Asp Asn Lys Phe Asn Lys Glu Arg Tyr Thr Ala Tyr Gly Glu Ile
1               5                   10                  15

Trp Glu Leu Pro Asn Leu Asn Arg Val Gln Arg Ala Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 818
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 818

Val Asp Asn Lys Phe Asn Lys Glu Arg Tyr Thr Ala Tyr Gly Glu Ile
1               5                   10                  15

Trp Glu Leu Pro Asn Leu Asn Arg Leu Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 819
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 819

Val Asp Asn Lys Phe Asn Lys Glu Arg Tyr His Ala Tyr Gly Glu Ile
1               5                   10                  15

Trp Glu Leu Pro Asn Leu Asn Arg Arg Gln Lys Ala Ala Phe Ile Thr
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 820
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 820

Val Asp Asn Lys Phe Asn Lys Glu Arg Tyr Lys Ala Tyr Gly Glu Ile
1               5                   10                  15

Trp Gln Leu Pro Asn Leu Asn Arg Leu Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 821
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 821

Val Asp Asn Lys Phe Asn Lys Glu Arg Tyr Gln Ala Tyr Gly Glu Ile
1               5                   10                  15

Trp Gln Leu Pro Asn Leu Asn Arg Leu Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 822
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 822

Val Asp Asn Lys Phe Asn Lys Glu Arg Tyr Val Ala Tyr Gly Glu Ile
1               5                   10                  15

Trp Gln Leu Pro Asn Leu Asn Arg Leu Gln Lys Ala Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 823
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 823

Val Asp Asn Lys Phe Asn Lys Glu Arg Tyr Ile Ala Tyr Gly Glu Ile
1               5                   10                  15

Trp Glu Leu Pro Asn Leu Asn Arg Leu Gln Lys Ala Ala Phe Ile Gly
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 824
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 824

Val Asp Asn Lys Phe Asn Lys Glu Arg Tyr Gln Ala Tyr Gly Glu Ile
1               5                   10                  15

Trp Gln Leu Pro Asn Leu Asn Arg Arg Gln Lys Ala Ala Phe Ile Ser
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 825
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 825

Val Asp Asn Lys Phe Asn Lys Glu Arg Arg Gln Ala Tyr Phe Glu Ile
1               5                   10                  15

Trp Glu Leu Pro Asn Leu Asn Arg Tyr Gln Lys Ala Ala Phe Ile Ser
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 826
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 826

Val Asp Asn Lys Phe Asn Lys Glu Arg Tyr Arg Ala Tyr Val Glu Ile
1               5                   10                  15

Trp Glu Leu Pro Asn Leu Asn Arg Ile Gln Lys Val Ala Phe Ile Ala
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55

```
<210> SEQ ID NO 827
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 827

Val Asp Asn Lys Phe Asn Lys Glu Lys Tyr Thr Ala Tyr Gly Glu Ile
1               5                   10                  15

Trp Glu Leu Pro Asn Leu Asn Arg Ile Gln Lys Val Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 828
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 828

Val Asp Asn Lys Phe Asn Lys Glu Lys Tyr Ala Ala Tyr Val Glu Ile
1               5                   10                  15

Trp Glu Leu Pro Asn Leu Asn Arg Arg Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 829
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 829

Val Asp Asn Lys Phe Asn Lys Glu Arg Tyr Arg Ala Tyr Val Glu Ile
1               5                   10                  15

Trp Glu Leu Pro Asn Leu Asn Arg Trp Gln Lys Ala Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 830
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 830

Val Asp Asn Lys Phe Asn Lys Glu Arg Tyr Arg Ala Tyr Phe Glu Ile
1               5                   10                  15

Trp Glu Leu Pro Asn Leu Asn Arg Ala Gln Lys Ala Ala Phe Ile Ser
```

```
               20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 831
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 831

Val Asp Asn Lys Phe Asn Lys Glu Arg Tyr Gln Ala Tyr Phe Glu Ile
1               5                   10                  15

Trp Gln Leu Pro Asn Leu Asn Arg Leu Gln Ala Gly Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 832
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 832

Val Asp Asn Lys Phe Asn Lys Glu Lys Tyr Gln Ala Tyr Val Glu Ile
1               5                   10                  15

Trp Gln Leu Pro Asn Leu Asn Arg Leu Gln Lys Gly Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 833
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 833

Val Asp Asn Lys Phe Asn Lys Glu Lys Tyr Ala Ala Tyr Tyr Glu Ile
1               5                   10                  15

Trp Gln Leu Pro Asn Leu Asn Arg Ser Gln Lys Gly Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 834
<211> LENGTH: 58
<212> TYPE: PRT
<213> ORGANISM: Artificial Sequence
```

<220> FEATURE:
<223> OTHER INFORMATION: Engineered polypeptide

<400> SEQUENCE: 834

Val Asp Asn Lys Phe Asn Lys Glu Lys Tyr Gln Ala Tyr Tyr Glu Ile
1               5                   10                  15

Trp Glu Leu Pro Asn Leu Asn Arg Gly Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 835
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 835

Val Asp Asn Lys Phe Asn Lys Glu Lys Tyr Asn Ala Tyr Phe Glu Ile
1               5                   10                  15

Trp Gln Leu Pro Asn Leu Asn Arg Leu Gln Lys Ala Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 836
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 836

Val Asp Asn Lys Phe Asn Lys Glu Lys Tyr Ser Ala Tyr Phe Glu Ile
1               5                   10                  15

Trp Gln Leu Pro Asn Leu Asn Thr Ser Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 837
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 837

Val Asp Asn Lys Phe Asn Lys Glu Arg Tyr Asn Ala Tyr Phe Glu Ile
1               5                   10                  15

Trp Glu Leu Pro Asn Leu Asn Val Arg Gln Lys Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 838
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 838

Val Asp Asn Lys Phe Asn Lys Glu Lys Tyr Glu Ala Tyr Phe Glu Ile
1               5                   10                  15

Trp Glu Leu Pro Asn Leu Asn Ser Arg Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 839
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 839

Val Asp Asn Lys Phe Asn Lys Glu Arg Tyr Arg Ala Tyr Trp Glu Ile
1               5                   10                  15

Trp Glu Leu Pro Asn Leu Asn Gln Gln Gln Lys Val Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 840
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 840

Val Asp Asn Lys Phe Asn Lys Glu Arg Tyr Asn Ala Tyr Trp Glu Ile
1               5                   10                  15

Trp Glu Leu Pro Asn Leu Asn Gln Gly Gln Lys Val Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
        50                  55

<210> SEQ ID NO 841
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 841

-continued

Val Asp Asn Lys Phe Asn Lys Glu Arg Arg His Ala Tyr Gly Glu Ile
1               5                   10                  15

Trp Gln Leu Pro Asn Leu Asn Gln Arg Gln Lys Val Ala Phe Ile Ser
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 842
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 842

Val Asp Asn Lys Phe Asn Lys Glu Lys Tyr Val Ala Thr Trp Glu Ile
1               5                   10                  15

Trp Glu Leu Pro Asn Leu Asn Arg Ala Gln Lys Val Ala Phe Ile Gly
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 843
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 843

Val Asp Asn Lys Phe Asn Lys Glu Arg Arg Ile Ala Arg Trp Glu Ile
1               5                   10                  15

Trp Glu Leu Pro Asn Leu Asn Arg Leu Gln Lys Val Ala Phe Ile Gly
                20                  25                  30

Ser Leu Glu Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 844
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 844

Val Asp Asn Lys Phe Asn Lys Glu Lys Tyr Lys Ala Ala Gly Glu Ile
1               5                   10                  15

Trp Gln Leu Pro Asn Leu Asn Arg Gly Gln Lys Val Ala Phe Ile Gly
                20                  25                  30

Ser Leu Glu Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 845
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 845

Val Asp Asn Lys Phe Asn Lys Glu Lys Tyr Leu Ala Tyr Gly Glu Ile
1               5                   10                  15

Trp Gln Leu Pro Asn Leu Asn Arg His Gln Lys Val Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 846
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 846

Val Asp Asn Lys Phe Asn Lys Glu Lys Tyr Gln Ala Tyr Gly Glu Ile
1               5                   10                  15

Trp Gln Leu Pro Asn Leu Asn Arg Gln Gln Lys Val Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 847
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 847

Val Asp Asn Lys Phe Asn Lys Glu Lys Tyr Lys Ala Tyr Gly Glu Ile
1               5                   10                  15

Trp Gln Leu Pro Asn Leu Asn Arg Gln Gln Lys Val Ala Phe Ile Ile
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 848
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 848

Val Asp Asn Lys Phe Asn Lys Glu Lys Tyr Ala Ala Ala Tyr Glu Ile
1               5                   10                  15

```
Trp Gln Leu Pro Asn Leu Asn Gln Arg Gln Lys Gly Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 849
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 849

```
Val Asp Asn Lys Phe Asn Lys Glu Lys Tyr Ala Ala Ser Tyr Glu Ile
1               5                   10                  15

Trp Glu Leu Pro Asn Leu Asn Gln Arg Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 850
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 850

```
Val Asp Asn Lys Phe Asn Lys Glu Lys Tyr Leu Ala Ser Tyr Glu Ile
1               5                   10                  15

Trp Gln Leu Pro Asn Leu Asn Arg Arg Gln Lys Ala Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 851
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 851

```
Val Asp Asn Lys Phe Asn Lys Glu Lys Tyr Ser Ala Thr Phe Glu Ile
1               5                   10                  15

Trp Gln Leu Pro Asn Leu Asn Gln Arg Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 852
<211> LENGTH: 58
<212> TYPE: PRT

<213> ORGANISM: Artificial Sequence
<220> FEATURE:
<223> OTHER INFORMATION: Engineered polypeptide

<400> SEQUENCE: 852

Val Asp Asn Lys Phe Asn Lys Glu Lys Tyr Ala Ala Ser Phe Glu Ile
1               5                   10                  15

Trp Gln Leu Pro Asn Leu Asn Thr His Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 853
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 853

Val Asp Asn Lys Phe Asn Lys Glu Lys Tyr Lys Ala Ser Gly Glu Ile
1               5                   10                  15

Trp Gln Leu Pro Asn Leu Asn Arg Leu Gln Arg Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 854
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 854

Val Asp Asn Lys Phe Asn Lys Glu Lys Tyr Ser Ala Ser Gly Glu Ile
1               5                   10                  15

Trp Gln Leu Pro Asn Leu Asn Arg Thr Gln Lys Ala Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 855
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 855

Val Asp Asn Lys Phe Asn Lys Glu Lys Tyr His Ala Ala Gly Glu Ile
1               5                   10                  15

Trp Glu Leu Pro Asn Leu Asn Arg Leu Gln Lys Ala Ala Phe Ile Arg
            20                  25                  30

Ser Leu Trp Asp Asp Pro Ser Gln Ser Ala Asn Leu Leu Ala Glu Ala

<210> SEQ ID NO 856
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 856

Val Asp Asn Lys Phe Asn Lys Glu Lys Tyr Arg Ala Ala Gly Glu Ile
1               5                   10                  15

Trp Glu Leu Pro Asn Leu Asn Arg Gln Gln Lys Ala Ala Phe Ile Arg
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 857
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 857

Val Asp Asn Lys Phe Asn Lys Glu Lys Tyr Gln Ala Ser Gly Glu Ile
1               5                   10                  15

Trp Glu Leu Pro Asn Leu Asn Arg Leu Gln Lys Ala Ala Phe Ile Arg
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 858
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 858

Val Asp Asn Lys Phe Asn Lys Glu Lys Tyr Lys Ala Thr Gly Glu Ile
1               5                   10                  15

Trp Glu Leu Pro Asn Leu Asn Arg Ile Gln Lys Ala Ala Phe Ile Arg
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 859
<211> LENGTH: 58
<212> TYPE: PRT
<213> ORGANISM: Artificial Sequence
<220> FEATURE:
<223> OTHER INFORMATION: Engineered polypeptide -continued

<400> SEQUENCE: 859

Val Asp Asn Lys Phe Asn Lys Glu Lys Tyr Gln Ala Ser Phe Glu Ile
1               5                   10                  15

Trp Glu Leu Pro Asn Leu Asn Arg Ser Gln Lys Ala Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 860
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 860

Val Asp Asn Lys Phe Asn Lys Glu Arg Lys Val Ala Ala Val Glu Ile
1               5                   10                  15

Trp Gln Leu Pro Asn Leu Asn Arg Trp Gln Arg Gly Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 861
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 861

Val Asp Asn Lys Phe Asn Lys Glu Arg Lys Leu Ala Ala Val Glu Ile
1               5                   10                  15

Trp Glu Leu Pro Asn Leu Asn Gln Tyr Gln Arg Gly Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 862
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 862

Val Asp Asn Lys Phe Asn Lys Glu Arg Lys Lys Ala Ser Val Glu Ile
1               5                   10                  15

Trp Glu Leu Pro Asn Leu Asn Arg Tyr Gln Lys Gly Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 863
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 863

```
Val Asp Asn Lys Phe Asn Lys Glu Arg Lys His Ala Ala Trp Glu Ile
1               5                   10                  15

Trp Glu Leu Pro Asn Leu Asn Arg His Gln Lys Gly Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 864
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 864

```
Val Asp Asn Lys Phe Asn Lys Glu Arg Lys His Ala Ala Val Glu Ile
1               5                   10                  15

Trp Glu Leu Pro Asn Leu Asn Arg Trp Gln Lys Gly Ala Phe Ile Gly
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 865
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 865

```
Val Asp Asn Lys Phe Asn Lys Glu Lys Arg His Ala Ala Val Glu Ile
1               5                   10                  15

Trp Glu Leu Pro Asn Leu Asn Val Phe Gln Arg Gly Ala Phe Ile Ala
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 866
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 866

```
Val Asp Asn Lys Phe Asn Lys Glu Arg Lys His Ala Ala Val Glu Ile
1               5                   10                  15
```

Trp Glu Leu Pro Asn Leu Asn Arg Leu Gln Arg Gly Ala Phe Ile Ala
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 867
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 867

Val Asp Asn Lys Phe Asn Lys Glu Trp Lys Thr Ala Ala Val Glu Ile
1               5                   10                  15

Trp Glu Leu Pro Asn Leu Asn Arg Arg Gln Lys Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 868
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 868

Val Asp Asn Lys Phe Asn Lys Glu Arg Lys Val Ala Ala Phe Glu Ile
1               5                   10                  15

Trp Glu Leu Pro Asn Leu Asn Arg Gly Gln Lys Ala Ala Phe Ile Gly
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 869
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 869

Val Asp Asn Lys Phe Asn Lys Glu Lys Arg Asn Ala Ala Val Glu Ile
1               5                   10                  15

Trp Glu Leu Pro Asn Leu Asn Arg Arg Gln Arg Ala Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 870
<211> LENGTH: 58

```
<212> TYPE: PRT
<213> ORGANISM: Artificial Sequence
<220> FEATURE:
<223> OTHER INFORMATION: Engineered polypeptide

<400> SEQUENCE: 870

Val Asp Asn Lys Phe Asn Lys Glu Arg Arg Asn Ala Ala Val Glu Ile
1               5                   10                  15

Trp Glu Leu Pro Asn Leu Asn Arg His Gln Arg Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 871
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 871

Val Asp Asn Lys Phe Asn Lys Glu Lys Arg Gln Ala Ser Val Glu Ile
1               5                   10                  15

Trp Glu Leu Pro Asn Leu Asn Arg Ile Gln Lys Ala Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 872
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 872

Val Asp Asn Lys Phe Asn Lys Glu Lys Arg Arg Ala Ala Val Glu Ile
1               5                   10                  15

Trp Glu Leu Pro Asn Leu Asn Arg Ile Gln Lys Ser Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 873
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 873

Val Asp Asn Lys Phe Asn Lys Glu Lys Arg His Ala Ala Trp Glu Ile
1               5                   10                  15

Trp Glu Leu Pro Asn Leu Asn Arg Ala Gln Lys Ser Ala Phe Ile Lys
            20                  25                  30
```

-continued

Ser Leu Trp Asp Asp Pro Ser Gln Ser Ala Asn Leu Leu Ala Glu Ala
          35                      40                      45

Lys Lys Leu Asn Asp Ala Gln Ala Pro Lys
    50                  55

<210> SEQ ID NO 874
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 874

Val Asp Asn Lys Phe Asn Lys Glu Lys Arg Asn Ala Thr Val Glu Ile
1               5                   10                  15

Trp Glu Leu Pro Asn Leu Asn Arg Ile Gln Arg Ala Ala Phe Ile Ala
            20                  25                  30

Ser Leu Trp Asp Asp Pro Ser Gln Ser Ala Asn Leu Leu Ala Glu Ala
          35                      40                      45

Lys Lys Leu Asn Asp Ala Gln Ala Pro Lys
    50                  55

<210> SEQ ID NO 875
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 875

Val Asp Asn Lys Phe Asn Lys Glu Lys Arg Ala Ala Thr Val Glu Ile
1               5                   10                  15

Trp Glu Leu Pro Asn Leu Asn Arg Leu Gln Lys Gly Ala Phe Ile Ala
            20                  25                  30

Ser Leu Trp Asp Asp Pro Ser Gln Ser Ala Asn Leu Leu Ala Glu Ala
          35                      40                      45

Lys Lys Leu Asn Asp Ala Gln Ala Pro Lys
    50                  55

<210> SEQ ID NO 876
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 876

Val Asp Asn Lys Phe Asn Lys Glu Arg Arg Gly Ala Ala Val Glu Ile
1               5                   10                  15

Trp Glu Leu Pro Asn Leu Asn Arg Gln Gln Lys Ala Ala Phe Ile Ala
            20                  25                  30

Ser Leu Trp Asp Asp Pro Ser Gln Ser Ala Asn Leu Leu Ala Glu Ala
          35                      40                      45

Lys Lys Leu Asn Asp Ala Gln Ala Pro Lys
    50                  55

<210> SEQ ID NO 877
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 877

Val Asp Asn Lys Phe Asn Lys Glu Arg Arg Lys Ala Thr Val Glu Ile
1               5                   10                  15

Trp Glu Leu Pro Asn Leu Asn Arg Gln Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 878
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 878

Val Asp Asn Lys Phe Asn Lys Glu Lys Ser Thr Ala Ala Val Glu Ile
1               5                   10                  15

Trp Glu Leu Pro Asn Leu Asn Arg Ile Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 879
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 879

Val Asp Asn Lys Phe Asn Lys Glu Lys Ser Thr Ala Ala Val Glu Ile
1               5                   10                  15

Trp Glu Leu Pro Asn Leu Asn Arg Tyr Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 880
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 880

Val Asp Asn Lys Phe Asn Lys Glu Lys Ser His Ala Ala Val Glu Ile
1               5                   10                  15

Trp Glu Leu Pro Asn Leu Asn Arg Trp Gln Lys Ala Ala Phe Ile Lys
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys

```
                      50                  55

<210> SEQ ID NO 881
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 881

Val Asp Asn Lys Phe Asn Lys Glu Arg Ser Ser Ala Ala Val Glu Ile
1               5                   10                  15

Trp Glu Leu Pro Asn Leu Asn Arg Phe Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 882
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 882

Val Asp Asn Lys Phe Asn Lys Glu Lys Arg Ile Ala Ala Ala Glu Ile
1               5                   10                  15

Trp Glu Leu Pro Asn Leu Asn Arg Val Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 883
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 883

Val Asp Asn Lys Phe Asn Lys Glu Lys Arg His Ala Ala Gly Glu Ile
1               5                   10                  15

Trp Glu Leu Pro Asn Leu Asn Arg Ile Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 884
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 884

Val Asp Asn Lys Phe Asn Lys Glu Lys Arg Ile Ala Ala Val Glu Ile
```

```
                 1               5                  10                 15
Trp Glu Leu Pro Asn Leu Asn Arg Val Gln Lys Ala Ala Phe Ile Ala
                 20                 25                 30

Ser Leu Tyr Asp Asp Pro Ser Gln Ser Ala Asn Leu Leu Ala Glu Ala
             35                 40                 45

Lys Lys Leu Asn Asp Ala Gln Ala Pro Lys
     50                 55
```

<210> SEQ ID NO 885
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 885

```
Val Asp Asn Lys Phe Asn Lys Glu Lys Arg Ile Ala Ser Tyr Glu Ile
1               5                  10                 15

Trp Glu Leu Pro Asn Leu Asn Arg Arg Gln Arg Ala Ala Phe Ile Ala
                 20                 25                 30

Ser Leu Trp Asp Asp Pro Ser Gln Ser Ala Asn Leu Leu Ala Glu Ala
             35                 40                 45

Lys Lys Leu Asn Asp Ala Gln Ala Pro Lys
     50                 55
```

<210> SEQ ID NO 886
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 886

```
Val Asp Asn Lys Phe Asn Lys Glu Lys Arg Asn Ala Thr Phe Glu Ile
1               5                  10                 15

Trp Glu Leu Pro Asn Leu Asn Arg Ser Gln Lys Gly Ala Phe Ile Ser
                 20                 25                 30

Ser Leu Tyr Asp Asp Pro Ser Gln Ser Ala Asn Leu Leu Ala Glu Ala
             35                 40                 45

Lys Lys Leu Asn Asp Ala Gln Ala Pro Lys
     50                 55
```

<210> SEQ ID NO 887
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 887

```
Val Asp Asn Lys Phe Asn Lys Glu Arg Lys Val Ala Thr Phe Glu Ile
1               5                  10                 15

Trp Glu Leu Pro Asn Leu Asn Ser Arg Gln Lys Ala Ala Phe Ile Lys
                 20                 25                 30

Ser Leu Phe Asp Asp Pro Ser Gln Ser Ala Asn Leu Leu Ala Glu Ala
             35                 40                 45

Lys Lys Leu Asn Asp Ala Gln Ala Pro Lys
     50                 55
```

<210> SEQ ID NO 888

```
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 888

Val Asp Asn Lys Phe Asn Lys Glu Arg Lys Asn Ala Thr Phe Glu Ile
1               5                   10                  15

Trp Glu Leu Pro Asn Leu Asn Gln Arg Gln Lys Ser Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 889
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 889

Val Asp Asn Lys Phe Asn Lys Glu Arg Ser Ala Ala Thr Phe Glu Ile
1               5                   10                  15

Trp Glu Leu Pro Asn Leu Asn Gln Arg Gln Lys Ser Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 890
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 890

Val Asp Asn Lys Phe Asn Lys Glu Arg Lys His Ala Thr Phe Glu Ile
1               5                   10                  15

Trp Glu Leu Pro Asn Leu Asn Gln Leu Gln Lys Ser Ala Phe Ile Gly
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 891
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 891

Val Asp Asn Lys Phe Asn Lys Glu Arg Lys Gln Ala Thr Phe Glu Ile
1               5                   10                  15

Trp Glu Leu Pro Asn Leu Asn Gln Gln Gln Lys Gly Ala Phe Ile Ala
            20                  25                  30
```

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 892
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 892

Val Asp Asn Lys Phe Asn Lys Glu Arg Lys Arg Ala Thr Phe Glu Ile
1               5                   10                  15

Trp Glu Leu Pro Asn Leu Asn Arg Thr Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 893
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 893

Val Asp Asn Lys Phe Asn Lys Glu Arg Lys Thr Ala Thr Phe Glu Ile
1               5                   10                  15

Trp Glu Leu Pro Asn Leu Asn Arg Val Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 894
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 894

Val Asp Asn Lys Phe Asn Lys Glu Arg Lys Leu Ala Thr Trp Glu Ile
1               5                   10                  15

Trp Glu Leu Pro Asn Leu Asn Arg Ser Gln Lys Ala Ala Phe Ile Ile
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 895
<211> LENGTH: 58
<212> TYPE: PRT
<213> ORGANISM: Artificial Sequence
<220> FEATURE:

<223> OTHER INFORMATION: Engineered polypeptide

<400> SEQUENCE: 895

Val Asp Asn Lys Phe Asn Lys Glu Arg Lys Val Ala Ala Val Glu Ile
1               5                   10                  15

Trp Glu Leu Pro Asn Leu Asn Arg Ile Gln Lys Ala Ala Phe Ile Arg
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 896
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 896

Val Asp Asn Lys Phe Asn Lys Glu Arg Lys Glu Ala Ala Val Glu Ile
1               5                   10                  15

Trp Glu Leu Pro Asn Leu Asn Arg Leu Gln Lys Ala Ala Phe Ile Arg
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 897
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 897

Val Asp Asn Lys Phe Asn Lys Glu Arg Lys Arg Ala Ala Val Glu Ile
1               5                   10                  15

Trp Glu Leu Pro Asn Leu Asn Arg Gly Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 898
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 898

Val Asp Asn Lys Phe Asn Lys Glu Arg Lys Leu Ala Ala Val Glu Ile
1               5                   10                  15

Trp Glu Leu Pro Asn Leu Asn Arg Thr Gln Lys Ala Ala Phe Ile Lys
            20                  25                  30

Ser Leu Phe Asp Asp Pro Ser Gln Ser Ala Asn Leu Leu Ala Glu Ala
        35                  40                  45

```
Lys Lys Leu Asn Asp Ala Gln Ala Pro Lys
    50                  55

<210> SEQ ID NO 899
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 899

Val Asp Asn Lys Phe Asn Lys Glu Arg Lys Val Ala Ala Val Glu Ile
1               5                   10                  15

Trp Glu Leu Pro Asn Leu Asn Arg Val Gln Lys Ala Ala Phe Ile Lys
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 900
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 900

Val Asp Asn Lys Phe Asn Lys Glu Arg Lys Glu Ala Ala Val Glu Ile
1               5                   10                  15

Trp Glu Leu Pro Asn Leu Asn Arg Val Gln Lys Ala Ala Phe Ile Lys
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 901
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 901

Val Asp Asn Lys Phe Asn Lys Glu Arg Lys Ala Ala Thr Val Glu Ile
1               5                   10                  15

Trp Glu Leu Pro Asn Leu Asn Arg Arg Gln Lys Ala Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 902
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 902
```

-continued

Val Asp Asn Lys Phe Asn Lys Glu Lys Arg His Ala Ser Trp Glu Ile
1               5                   10                  15

Trp Glu Leu Pro Asn Leu Asn Gln Trp Gln Lys Ala Ala Phe Ile Arg
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 903
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 903

Val Asp Asn Lys Phe Asn Lys Glu Arg Lys Ser Ala Thr Trp Glu Ile
1               5                   10                  15

Trp Glu Leu Pro Asn Leu Asn Gln Leu Gln Lys Ala Ala Phe Ile Arg
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 904
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 904

Val Asp Asn Lys Phe Asn Lys Glu Lys Lys Ala Ala Val Glu Ile
1               5                   10                  15

Trp Glu Leu Pro Asn Leu Asn Gln Arg Gln Lys Ala Ala Phe Ile Gly
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 905
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 905

Val Asp Asn Lys Phe Asn Lys Glu Lys Lys Leu Ala Ser Phe Glu Ile
1               5                   10                  15

Trp Glu Leu Pro Asn Leu Asn Gln Arg Gln Lys Ala Ala Phe Ile Arg
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

```
<210> SEQ ID NO 906
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 906
```

Val Asp Asn Lys Phe Asn Lys Glu Arg Lys Val Ala Thr Val Glu Ile
1               5                   10                  15

Trp Glu Leu Pro Asn Leu Asn Arg Val Gln Ala Ala Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 907
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 907
```

Val Asp Asn Lys Phe Asn Lys Glu Arg Lys Thr Ala Thr Val Glu Ile
1               5                   10                  15

Trp Glu Leu Pro Asn Leu Asn Arg Ile Gln Lys Ala Ala Phe Ile Lys
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 908
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 908
```

Val Asp Asn Lys Phe Asn Lys Glu Arg Lys Ser Ala Thr Val Glu Ile
1               5                   10                  15

Trp Glu Leu Pro Asn Leu Asn Arg Val Gln Lys Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 909
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 909
```

Val Asp Asn Lys Phe Asn Lys Glu Arg Lys Val Ala Thr Val Glu Ile
1               5                   10                  15

Trp Glu Leu Pro Asn Leu Asn Arg Gly Gln Lys Ala Ala Phe Ile Ser

```
                20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 910
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 910

Val Asp Asn Lys Phe Asn Lys Glu Arg Lys Gln Ala Thr Val Glu Ile
1               5                   10                  15

Trp Glu Leu Pro Asn Leu Asn Arg Arg Gln Arg Ala Ala Phe Ile Ser
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 911
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 911

Val Asp Asn Lys Phe Asn Lys Glu Arg Lys Lys Ala Thr Val Glu Ile
1               5                   10                  15

Trp Glu Leu Pro Asn Leu Asn Arg Arg Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 912
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 912

Val Asp Asn Lys Phe Asn Lys Glu Arg Lys Val Ala Thr Val Glu Ile
1               5                   10                  15

Trp Glu Leu Pro Asn Leu Asn Arg Arg Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 913
<211> LENGTH: 58
<212> TYPE: PRT
<213> ORGANISM: Artificial Sequence
```

```
<220> FEATURE:
<223> OTHER INFORMATION: Engineered polypeptide

<400> SEQUENCE: 913

Val Asp Asn Lys Phe Asn Lys Glu Arg Lys Leu Ala Thr Val Glu Ile
1               5                   10                  15

Trp Glu Leu Pro Asn Leu Asn Arg Tyr Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 914
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 914

Val Asp Asn Lys Phe Asn Lys Glu Arg Lys Ala Ala Thr Val Glu Ile
1               5                   10                  15

Trp Glu Leu Pro Asn Leu Asn Arg Leu Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 915
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 915

Val Asp Asn Lys Phe Asn Lys Glu Arg Lys Ile Ala Thr Val Glu Ile
1               5                   10                  15

Trp Glu Leu Pro Asn Leu Asn Arg Val Gln Lys Ser Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 916
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 916

Val Asp Asn Lys Phe Asn Lys Glu Arg Lys Asn Ala Thr Val Glu Ile
1               5                   10                  15

Trp Glu Leu Pro Asn Leu Asn Arg Ala Gln Lys Ala Ala Phe Ile Ala
            20                  25                  30

Ser Leu Trp Asp Asp Pro Ser Gln Ser Ala Asn Leu Leu Ala Glu Ala
        35                  40                  45
```

```
Lys Lys Leu Asn Asp Ala Gln Ala Pro Lys
    50                  55
```

<210> SEQ ID NO 917
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 917

```
Val Asp Asn Lys Phe Asn Lys Glu Arg Lys Asn Ala Thr Val Glu Ile
1               5                  10                  15

Trp Glu Leu Pro Asn Leu Asn Arg Ser Gln Lys Ala Ala Phe Ile Gly
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 918
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 918

```
Val Asp Asn Lys Phe Asn Lys Glu Arg Lys Thr Ala Thr Val Glu Ile
1               5                  10                  15

Trp Glu Leu Pro Asn Leu Asn Arg Gly Gln Lys Ala Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 919
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 919

```
Val Asp Asn Lys Phe Asn Lys Glu Arg Lys His Ala Ala Val Glu Ile
1               5                  10                  15

Trp Glu Leu Pro Asn Leu Asn Arg Ile Gln Arg Ala Ala Phe Ile Ala
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 920
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 920

Val Asp Asn Lys Phe Asn Lys Glu Arg Lys Ile Ala Thr Val Glu Ile
1               5                   10                  15

Trp Glu Leu Pro Asn Leu Asn Arg Ile Gln Arg Ala Ala Phe Ile Ala
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 921
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 921

Val Asp Asn Lys Phe Asn Lys Glu Arg Lys Ile Ala Ala Val Glu Ile
1               5                   10                  15

Trp Glu Leu Pro Asn Leu Asn Arg Ile Gln Ala Ala Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 922
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 922

Val Asp Asn Lys Phe Asn Lys Glu Arg Lys Ser Ala Thr Val Glu Ile
1               5                   10                  15

Trp Glu Leu Pro Asn Leu Asn Arg Thr Gln Arg Ala Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 923
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 923

Val Asp Asn Lys Phe Asn Lys Glu Arg Lys Ser Ala Ala Val Glu Ile
1               5                   10                  15

Trp Glu Leu Pro Asn Leu Asn Arg Thr Gln Lys Ala Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
    50                  55

<210> SEQ ID NO 924
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 924

Val Asp Asn Lys Phe Asn Lys Glu Lys Ser Ala Thr Val Glu Ile
1               5                   10                  15

Trp Glu Leu Pro Asn Leu Asn Arg Ile Gln Lys Ala Ala Phe Ile Gly
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 925
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 925

Val Asp Asn Lys Phe Asn Lys Glu Lys Ser Ala Tyr Val Glu Ile
1               5                   10                  15

Trp Glu Leu Pro Asn Leu Asn Arg Tyr Gln Lys Ala Ala Phe Ile Lys
                20                  25                  30

Ser Leu Phe Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 926
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 926

Val Asp Asn Lys Phe Asn Lys Glu Arg Lys Ile Ala Thr Tyr Glu Ile
1               5                   10                  15

Trp Glu Leu Pro Asn Leu Asn Arg Gln Arg Gln Lys Ala Ala Phe Ile Ala
                20                  25                  30

Ser Leu Trp Asp Asp Pro Ser Gln Ser Ala Asn Leu Leu Ala Glu Ala
            35                  40                  45

Lys Lys Leu Asn Asp Ala Gln Ala Pro Lys
        50                  55

<210> SEQ ID NO 927
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 927

Val Asp Asn Lys Phe Asn Lys Glu Arg Ser Val Ala Thr Trp Glu Ile
1               5                   10                  15

-continued

```
Trp Gln Leu Pro Asn Leu Asn Gln Arg Gln Lys Ala Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 928
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 928

```
Val Asp Asn Lys Phe Asn Lys Glu Lys Arg Lys Ala Thr Gly Glu Ile
1               5                   10                  15

Trp Gln Leu Pro Asn Leu Asn Gln Arg Gln Lys Gly Ala Phe Ile Ala
            20                  25                  30

Ser Leu Trp Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 929
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 929

```
Val Asp Asn Lys Phe Asn Lys Glu Arg Lys Glu Ala Arg Phe Glu Ile
1               5                   10                  15

Trp Glu Leu Pro Asn Leu Asn Gln Arg Gln Ala Ala Ala Phe Ile Ser
            20                  25                  30

Ser Leu Phe Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 930
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 930

```
Val Asp Asn Lys Phe Asn Lys Glu Arg Lys Ala Ala Ser Trp Glu Ile
1               5                   10                  15

Trp Glu Leu Pro Asn Leu Asn Gln Arg Gln Lys Ala Ala Phe Ile Ser
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 931
<211> LENGTH: 58
<212> TYPE: PRT

```
<213> ORGANISM: Artificial Sequence
<220> FEATURE:
<223> OTHER INFORMATION: Engineered polypeptide

<400> SEQUENCE: 931

Val Asp Asn Lys Phe Asn Lys Glu Trp Lys His Ala Ala Gly Glu Ile
1               5                   10                  15

Trp Glu Leu Pro Asn Leu Asn Arg Ser Gln Lys Val Ala Phe Ile Ala
            20                  25                  30

Ser Leu Glu Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 932
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 932

Val Asp Asn Lys Phe Asn Lys Glu Trp Lys Arg Ala Ala Gly Glu Ile
1               5                   10                  15

Trp Glu Leu Pro Asn Leu Asn Arg Ala Gln Lys Val Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 933
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 933

Val Asp Asn Lys Phe Asn Lys Glu Trp Lys Ile Ala Ala Gly Glu Ile
1               5                   10                  15

Trp Glu Leu Pro Asn Leu Asn Gln Arg Gln Lys Val Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 934
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 934

Val Asp Asn Lys Phe Asn Lys Glu Trp Lys Thr Ala Ala Tyr Glu Ile
1               5                   10                  15

Trp Glu Leu Pro Asn Leu Asn Thr Tyr Gln Lys Val Ala Phe Ile Arg
            20                  25                  30

Ser Leu Gln Asp Asp Pro Ser Gln Ser Ala Asn Leu Leu Ala Glu Ala
```

```
<210> SEQ ID NO 935
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 935

Val Asp Asn Lys Phe Asn Lys Glu Trp Lys Val Ala Ala Gly Glu Ile
1               5                   10                  15

Trp Glu Leu Pro Asn Leu Asn Arg Thr Gln Lys Val Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 936
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 936

Val Asp Asn Lys Phe Asn Lys Glu Trp Lys Val Ala Ala Gly Glu Ile
1               5                   10                  15

Trp Glu Leu Pro Asn Leu Asn Arg Trp Gln Lys Val Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 937
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 937

Val Asp Asn Lys Phe Asn Lys Glu Trp Lys Gln Ala Ala Gly Glu Ile
1               5                   10                  15

Trp Glu Leu Pro Asn Leu Asn Arg Leu Gln Lys Val Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 938
<211> LENGTH: 58
<212> TYPE: PRT
<213> ORGANISM: Artificial Sequence
<220> FEATURE:
<223> OTHER INFORMATION: Engineered polypeptide
```

<400> SEQUENCE: 938

Val Asp Asn Lys Phe Asn Lys Glu Trp Lys Val Ala Ala Gly Glu Ile
1               5                   10                  15

Trp Glu Leu Pro Asn Leu Asn Val Trp Gln Lys Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 939
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 939

Val Asp Asn Lys Phe Asn Lys Glu Trp Lys Val Ala Ala Trp Glu Ile
1               5                   10                  15

Trp Glu Leu Pro Asn Leu Asn Arg Gly Gln Lys Val Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 940
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 940

Val Asp Asn Lys Phe Asn Lys Glu Trp Lys Arg Ala Ala Phe Glu Ile
1               5                   10                  15

Trp Glu Leu Pro Asn Leu Asn Gln Ala Gln Lys Val Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 941
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 941

Val Asp Asn Lys Phe Asn Lys Glu Trp Lys Lys Ala Ala Gly Glu Ile
1               5                   10                  15

Trp Leu Leu Pro Asn Leu Asn Arg Arg Gln Arg Gly Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 942
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 942

Val Asp Asn Lys Phe Asn Lys Glu Trp Lys Lys Ala Ala Gly Glu Ile
1               5                   10                  15

Trp Glu Leu Pro Asn Leu Asn Ser Arg Gln Lys Gly Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 943
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 943

Val Asp Asn Lys Phe Asn Lys Glu Trp Arg Gly Ala Ala Gly Glu Ile
1               5                   10                  15

Trp Glu Leu Pro Asn Leu Asn Arg Arg Gln Arg Ala Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 944
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 944

Val Asp Asn Lys Phe Asn Lys Glu Trp Lys Val Ala Ala Gly Glu Ile
1               5                   10                  15

Trp Gln Leu Pro Asn Leu Asn Arg Arg Gln Arg Ala Ala Phe Ile Ala
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 945
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 945

Val Asp Asn Lys Phe Asn Lys Glu Trp Lys Ile Ala Ala Val Glu Ile
1               5                   10                  15
```

-continued

Trp Glu Leu Pro Asn Leu Asn Thr Arg Gln Lys Gly Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 946
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 946

Val Asp Asn Lys Phe Asn Lys Glu Trp Lys Ile Ala Ala Phe Glu Ile
1               5                   10                  15

Trp Glu Leu Pro Asn Leu Asn Val Arg Gln Arg Ser Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 947
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 947

Val Asp Asn Lys Phe Asn Lys Glu Trp Lys Thr Ala Ala Tyr Glu Ile
1               5                   10                  15

Trp Glu Leu Pro Asn Leu Asn Gln Arg Gln Arg Gly Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 948
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 948

Val Asp Asn Lys Phe Asn Lys Glu Trp Lys Thr Ala Ala Gly Glu Ile
1               5                   10                  15

Trp Glu Leu Pro Asn Leu Asn Ser Arg Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 949
<211> LENGTH: 58

```
<212> TYPE: PRT
<213> ORGANISM: Artificial Sequence
<220> FEATURE:
<223> OTHER INFORMATION: Engineered polypeptide

<400> SEQUENCE: 949

Val Asp Asn Lys Phe Asn Lys Glu Trp Lys Thr Ala Ala Gly Glu Ile
1               5                   10                  15

Trp Glu Leu Pro Asn Leu Asn Val Gly Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 950
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 950

Val Asp Asn Lys Phe Asn Lys Glu Trp Lys His Ala Ala Gly Glu Ile
1               5                   10                  15

Trp Glu Leu Pro Asn Leu Asn Arg Thr Gln Lys Ala Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 951
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 951

Val Asp Asn Lys Phe Asn Lys Glu Trp Lys Arg Ala Ala Gly Glu Ile
1               5                   10                  15

Trp Glu Leu Pro Asn Leu Asn Arg Leu Gln Lys Ala Ala Phe Ile Arg
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 952
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 952

Val Asp Asn Lys Phe Asn Lys Glu Trp Lys Gln Ala Ala Gly Glu Ile
1               5                   10                  15

Trp Glu Leu Pro Asn Leu Asn Arg Gly Gln Lys Ala Ala Phe Ile Ser
            20                  25                  30
```

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 953
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 953

Val Asp Asn Lys Phe Asn Lys Glu Trp Lys Gln Ala Ala Gly Glu Ile
1               5                   10                  15

Trp Glu Leu Pro Asn Leu Asn Arg Gly Gln Lys Ala Ala Phe Ile Thr
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 954
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 954

Val Asp Asn Lys Phe Asn Lys Glu Trp Lys Glu Ala Ala Gly Glu Ile
1               5                   10                  15

Trp Glu Leu Pro Asn Leu Asn Arg Gly Gln Lys Ala Ala Phe Ile Lys
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 955
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 955

Val Asp Asn Lys Phe Asn Lys Glu Trp Lys Thr Ala Ala Gly Glu Ile
1               5                   10                  15

Trp Glu Leu Pro Asn Leu Asn Arg Arg Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 956
<211> LENGTH: 58
<212> TYPE: PRT
<213> ORGANISM: Artificial Sequence
<220> FEATURE:
<223> OTHER INFORMATION: Engineered polypeptide

```
<400> SEQUENCE: 956

Val Asp Asn Lys Phe Asn Lys Glu Trp Lys Arg Ala Ala Gly Glu Ile
1               5                   10                  15

Trp Glu Leu Pro Asn Leu Asn Arg Ala Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 957
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 957

Val Asp Asn Lys Phe Asn Lys Glu Trp Lys His Ala Ala Phe Glu Ile
1               5                   10                  15

Trp Glu Leu Pro Asn Leu Asn Val Arg Gln Lys Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 958
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 958

Val Asp Asn Lys Phe Asn Lys Glu Trp Lys Asn Ala Ala Phe Glu Ile
1               5                   10                  15

Trp Glu Leu Pro Asn Leu Asn Val Ser Gln Lys Ala Ala Phe Ile Arg
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 959
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 959

Val Asp Asn Lys Phe Asn Lys Glu Trp Lys Ala Ala Ala Tyr Glu Ile
1               5                   10                  15

Trp Glu Leu Pro Asn Leu Asn Val Trp Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
```

<210> SEQ ID NO 960
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 960

Val Asp Asn Lys Phe Asn Lys Glu Trp Lys Val Ala Ala Gly Glu Ile
1               5                   10                  15

Trp Glu Leu Pro Asn Leu Asn Arg Trp Gln Lys Gly Ala Phe Ile Thr
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 961
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 961

Val Asp Asn Lys Phe Asn Lys Glu Trp Lys Val Ala Ala Gly Glu Ile
1               5                   10                  15

Trp Glu Leu Pro Asn Leu Asn Arg Trp Gln Lys Ala Ala Phe Ile Ala
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 962
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 962

Val Asp Asn Lys Phe Asn Lys Glu Trp Lys Val Ala Ala Gly Glu Ile
1               5                   10                  15

Trp Glu Leu Pro Asn Leu Asn Arg Leu Gln Arg Ala Ala Phe Ile Lys
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 963
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 963

Val Asp Asn Lys Phe Asn Lys Glu Trp Lys Val Ala Ala Tyr Glu Ile

-continued

```
               1               5                  10                  15
Trp Glu Leu Pro Asn Leu Asn Arg Leu Gln Lys Ala Ala Phe Ile Ala
                20                  25                  30

Ser Leu Tyr Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 964
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 964

```
Val Asp Asn Lys Phe Asn Lys Glu Trp Lys Val Ala Ala Phe Glu Ile
1               5                  10                  15

Trp Glu Leu Pro Asn Leu Asn Arg Thr Gln Arg Ala Ala Phe Ile Ile
                20                  25                  30

Ser Leu Gln Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 965
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 965

```
Val Asp Asn Lys Phe Asn Lys Glu Trp Lys Thr Ala Ala Val Glu Ile
1               5                  10                  15

Trp Glu Leu Pro Asn Leu Asn Arg Leu Gln Lys Ala Ala Phe Ile Thr
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 966
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 966

```
Val Asp Asn Lys Phe Asn Lys Glu Trp Lys Thr Ala Ala Val Glu Ile
1               5                  10                  15

Trp Glu Leu Pro Asn Leu Asn Arg Leu Gln Lys Ala Ala Phe Ile Gly
                20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
        50                  55
```

<210> SEQ ID NO 967

```
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 967

Val Asp Asn Lys Phe Asn Lys Glu Trp Lys Thr Ala Ala Phe Glu Ile
1               5                   10                  15

Trp Glu Leu Pro Asn Leu Asn Arg Gly Gln Lys Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 968
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 968

Val Asp Asn Lys Phe Asn Lys Glu Trp Lys Arg Ala Ala Phe Glu Ile
1               5                   10                  15

Trp Glu Leu Pro Asn Leu Asn Arg Leu Gln Lys Ser Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 969
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 969

Val Asp Asn Lys Phe Asn Lys Glu Trp Lys Gln Ala Ala Phe Glu Ile
1               5                   10                  15

Trp Glu Leu Pro Asn Leu Asn Arg Tyr Gln Ala Ala Ala Phe Ile Gly
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 970
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 970

Val Asp Asn Lys Phe Asn Lys Glu Trp Lys His Ala Ala Phe Glu Ile
1               5                   10                  15

Trp Glu Leu Pro Asn Leu Asn Arg Arg Gln Ala Gly Ala Phe Ile Ala
            20                  25                  30
```

```
Ser Leu Gln Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 971
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 971

Val Asp Asn Lys Phe Asn Lys Glu Trp Lys Gln Ala Ser Gly Glu Ile
 1               5                  10                  15

Trp Glu Leu Pro Asn Leu Asn Val Arg Gln Lys Ala Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 972
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 972

Val Asp Asn Lys Phe Asn Lys Glu Trp Lys Gln Ala Ser Phe Glu Ile
 1               5                  10                  15

Trp Glu Leu Pro Asn Leu Asn Val Arg Gln Lys Ala Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 973
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 973

Val Asp Asn Lys Phe Asn Lys Glu Trp Lys Leu Ala Ala Gly Glu Ile
 1               5                  10                  15

Trp Glu Leu Pro Asn Leu Asn Val Arg Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
 50                  55

<210> SEQ ID NO 974
<211> LENGTH: 58
<212> TYPE: PRT
<213> ORGANISM: Artificial Sequence
<220> FEATURE:
```

```
<223> OTHER INFORMATION: Engineered polypeptide

<400> SEQUENCE: 974

Val Asp Asn Lys Phe Asn Lys Glu Trp Lys Ile Ala Ala Gly Glu Ile
1               5                   10                  15

Trp Glu Leu Pro Asn Leu Asn Val Arg Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 975
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 975

Val Asp Asn Lys Phe Asn Lys Glu Trp Lys His Ala Ala Gly Glu Ile
1               5                   10                  15

Trp Gln Leu Pro Asn Leu Asn Val Thr Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 976
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 976

Val Asp Asn Lys Phe Asn Lys Glu Trp Lys Ile Ala Ala Gly Glu Ile
1               5                   10                  15

Trp Glu Leu Pro Asn Leu Asn Arg Arg Gln Ala Ala Ala Phe Ile Val
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 977
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 977

Val Asp Asn Lys Phe Asn Lys Glu Trp Lys Ser Ala Ala Gly Glu Ile
1               5                   10                  15

Trp Glu Leu Pro Asn Leu Asn Arg Ala Gln Lys Ala Ala Phe Ile Ile
            20                  25                  30

Ser Leu Ser Asp Asp Pro Ser Gln Ser Ala Asn Leu Leu Ala Glu Ala
        35                  40                  45
```

Lys Lys Leu Asn Asp Ala Gln Ala Pro Lys
    50                  55

<210> SEQ ID NO 978
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 978

Val Asp Asn Lys Phe Asn Lys Glu Trp Lys His Ala Ala Val Glu Ile
1               5                   10                  15

Trp Gln Leu Pro Asn Leu Asn Arg Phe Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 979
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 979

Val Asp Asn Lys Phe Asn Lys Glu Trp Lys Gln Ala Ala Trp Glu Ile
1               5                   10                  15

Trp Gln Leu Pro Asn Leu Asn Thr Gly Gln Lys Ala Ala Phe Ile Arg
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 980
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 980

Val Asp Asn Lys Phe Asn Lys Glu Trp Lys Gln Ala Ser Trp Glu Ile
1               5                   10                  15

Trp Glu Leu Pro Asn Leu Asn Arg Gly Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 981
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 981

Val Asp Asn Lys Phe Asn Lys Glu Trp Lys Thr Ala Ser Tyr Glu Ile
1               5                   10                  15

Trp Gln Leu Pro Asn Leu Asn Arg Arg Gln Ala Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 982
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 982

Val Asp Asn Lys Phe Asn Lys Glu Trp Lys Asn Ala Ser Phe Glu Ile
1               5                   10                  15

Trp Leu Leu Pro Asn Leu Asn Arg Ile Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 983
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 983

Val Asp Asn Lys Phe Asn Lys Glu Trp Lys Asn Ala Ala Phe Glu Ile
1               5                   10                  15

Trp Leu Leu Pro Asn Leu Asn Gln Arg Gln Lys Ala Ala Phe Ile Ala
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 984
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 984

Val Asp Asn Lys Phe Asn Lys Glu Trp Arg Gly Ala Ala Phe Glu Ile
1               5                   10                  15

Trp Gln Leu Pro Asn Leu Asn Gln Arg Gln Lys Ala Ala Phe Ile Ala
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

```
<210> SEQ ID NO 985
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 985

Val Asp Asn Lys Phe Asn Lys Glu Trp Lys Val Ala Ser Trp Glu Ile
1               5                   10                  15

Trp Gln Leu Pro Asn Leu Asn Arg Gln Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 986
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 986

Val Asp Asn Lys Phe Asn Lys Glu Trp Lys Leu Ala Ser Trp Glu Ile
1               5                   10                  15

Trp Gln Leu Pro Asn Leu Asn Arg Trp Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 987
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 987

Val Asp Asn Lys Phe Asn Lys Glu Trp Lys Arg Ala Ser Val Glu Ile
1               5                   10                  15

Trp Glu Leu Pro Asn Leu Asn Arg Gln Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 988
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 988

Val Asp Asn Lys Phe Asn Lys Glu Trp Lys Arg Ala Ser Phe Glu Ile
1               5                   10                  15

Trp Gln Leu Pro Asn Leu Asn Arg Leu Gln Lys Ala Ala Phe Ile Ala
```

```
                 20                  25                  30

Ser Leu Ala Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 989
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 989

Val Asp Asn Lys Phe Asn Lys Glu Trp Lys Gly Ala Ala Gly Glu Ile
1               5                  10                  15

Trp Gln Leu Pro Asn Leu Asn Arg Arg Gln Lys Ala Ala Phe Ile Ser
             20                  25                  30

Ser Leu Tyr Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 990
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 990

Val Asp Asn Lys Phe Asn Lys Glu Trp Lys Val Ala Ala Phe Glu Ile
1               5                  10                  15

Trp Gln Leu Pro Asn Leu Asn Arg Ala Gln Lys Ala Ala Phe Ile Ser
             20                  25                  30

Ser Leu Ala Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 991
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 991

Val Asp Asn Lys Phe Asn Lys Glu Trp Lys His Ala Ala Gly Glu Ile
1               5                  10                  15

Trp Gln Leu Pro Asn Leu Asn Arg Ala Gln Lys Ala Ala Phe Ile Ser
             20                  25                  30

Ser Leu Ala Asp Asp Pro Ser Gln Ser Ala Asn Leu Leu Ala Glu Ala
         35                  40                  45

Lys Lys Leu Asn Asp Ala Gln Ala Pro Lys
     50                  55

<210> SEQ ID NO 992
<211> LENGTH: 58
<212> TYPE: PRT
<213> ORGANISM: Artificial Sequence
```

<220> FEATURE:
<223> OTHER INFORMATION: Engineered polypeptide

<400> SEQUENCE: 992

Val Asp Asn Lys Phe Asn Lys Glu Trp Lys Lys Ala Ala Tyr Glu Ile
1               5                   10                  15

Trp Gln Leu Pro Asn Leu Asn Arg Ala Gln Lys Ala Ala Phe Ile Ser
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 993
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 993

Val Asp Asn Lys Phe Asn Lys Glu Trp Lys Leu Ala Ala Tyr Glu Ile
1               5                   10                  15

Trp Gln Leu Pro Asn Leu Asn Arg His Gln Lys Ala Ala Phe Ile Ser
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 994
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 994

Val Asp Asn Lys Phe Asn Lys Glu Trp Lys Arg Ala Ala Phe Glu Ile
1               5                   10                  15

Trp Gln Leu Pro Asn Leu Asn Arg Ser Gln Lys Ala Ala Phe Ile Ser
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 995
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 995

Val Asp Asn Lys Phe Asn Lys Glu Trp Lys Thr Ala Ala Phe Glu Ile
1               5                   10                  15

Trp Gln Leu Pro Asn Leu Asn Arg Ser Gln Lys Ala Ala Phe Ile Ala
            20                  25                  30

Ser Leu Ala Asp Asp Pro Ser Gln Ser Ala Asn Leu Leu Ala Glu Ala
        35                  40                  45

```
Lys Lys Leu Asn Asp Ala Gln Ala Pro Lys
    50                  55
```

<210> SEQ ID NO 996
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 996

```
Val Asp Asn Lys Phe Asn Lys Glu Trp Lys Ile Ala Ala Phe Glu Ile
1               5                   10                  15

Trp Gln Leu Pro Asn Leu Asn Arg Ile Gln Lys Ala Ala Phe Ile Gly
            20                  25                  30

Ser Leu Ala Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 997
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 997

```
Val Asp Asn Lys Phe Asn Lys Glu Trp Lys Gln Ala Ala Phe Glu Ile
1               5                   10                  15

Trp Gln Leu Pro Asn Leu Asn Arg Ile Gln Lys Ala Ala Phe Ile Thr
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 998
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 998

```
Val Asp Asn Lys Phe Asn Lys Glu Trp Lys Gln Ala Ala Phe Glu Ile
1               5                   10                  15

Trp Gln Leu Pro Asn Leu Asn Arg Val Gln Lys Ala Ala Phe Ile Val
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 999
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 999

```
Val Asp Asn Lys Phe Asn Lys Glu Trp Lys Val Ala Ala Gly Glu Ile
1               5                   10                  15

Trp Gln Leu Pro Asn Leu Asn Arg Ile Gln Lys Ala Ala Phe Ile Gly
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 1000
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 1000

Val Asp Asn Lys Phe Asn Lys Glu Trp Lys Ile Ala Ala Phe Glu Ile
1               5                   10                  15

Trp Gln Leu Pro Asn Leu Asn Arg Trp Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 1001
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 1001

Val Asp Asn Lys Phe Asn Lys Glu Trp Lys Glu Ala Ala Gly Glu Ile
1               5                   10                  15

Trp Gln Leu Pro Asn Leu Asn Arg Tyr Gln Lys Ala Ala Phe Ile Ala
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 1002
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 1002

Val Asp Asn Lys Phe Asn Lys Glu Trp Lys Thr Ala Ser Phe Glu Ile
1               5                   10                  15

Trp Gln Leu Pro Asn Leu Asn Arg Tyr Gln Lys Ala Ala Phe Ile Ser
            20                  25                  30

Ser Leu Gln Asp Asp Pro Ser Gln Ser Ala Asn Leu Leu Ala Glu Ala
        35                  40                  45

Lys Lys Leu Asn Asp Ala Gln Ala Pro Lys
    50                  55
```

<210> SEQ ID NO 1003
<211> LENGTH: 51
<212> TYPE: PRT
<213> ORGANISM: Artificial Sequence
<220> FEATURE:
<223> OTHER INFORMATION: Engineered polypeptide

<400> SEQUENCE: 1003

```
Tyr Ala Lys Glu Met Arg Asn Ala Tyr Trp Glu Ile Ala Leu Leu Pro
1               5                   10                  15

Asn Leu Thr Asn Gln Gln Lys Arg Ala Phe Ile Arg Lys Leu Tyr Asp
            20                  25                  30

Asp Pro Ser Gln Ser Ser Glu Leu Leu Ser Glu Ala Lys Lys Leu Asn
        35                  40                  45

Asp Ser Gln
    50
```

<210> SEQ ID NO 1004
<211> LENGTH: 51
<212> TYPE: PRT
<213> ORGANISM: Artificial Sequence
<220> FEATURE:
<223> OTHER INFORMATION: Engineered polypeptide

<400> SEQUENCE: 1004

```
Tyr Ala Lys Glu Met Trp Ile Ala Trp Glu Glu Ile Arg Asn Leu Pro
1               5                   10                  15

Asn Leu Asn Gly Trp Gln Met Thr Ala Phe Ile Ala Lys Leu Leu Asp
            20                  25                  30

Asp Pro Ser Gln Ser Ser Glu Leu Leu Ser Glu Ala Lys Lys Leu Asn
        35                  40                  45

Asp Ser Gln
    50
```

<210> SEQ ID NO 1005
<211> LENGTH: 46
<212> TYPE: PRT
<213> ORGANISM: Artificial Sequence
<220> FEATURE:
<223> OTHER INFORMATION: Engineered polypeptide

<400> SEQUENCE: 1005

```
Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45
```

<210> SEQ ID NO 1006
<211> LENGTH: 58
<212> TYPE: PRT
<213> ORGANISM: Artificial Sequence
<220> FEATURE:
<223> OTHER INFORMATION: Engineered polypeptide

<400> SEQUENCE: 1006

```
Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30
```

Ser Leu Lys Asp Asp Pro Ser Gln Ser Ala Asn Leu Leu Ala Glu Ala
                35                  40                  45

Lys Lys Leu Asn Asp Ala Gln Ala Pro Lys
 50                  55

<210> SEQ ID NO 1007
<211> LENGTH: 643
<212> TYPE: PRT
<213> ORGANISM: Homo sapiens

<400> SEQUENCE: 1007

Ser Glu Val Gly Asn Ser Gln Ala Val Cys Pro Gly Thr Leu Asn Gly
 1               5                  10                  15

Leu Ser Val Thr Gly Asp Ala Glu Asn Gln Tyr Gln Thr Leu Tyr Lys
                20                  25                  30

Leu Tyr Glu Arg Cys Glu Val Val Met Gly Asn Leu Glu Ile Val Leu
            35                  40                  45

Thr Gly His Asn Ala Asp Leu Ser Phe Leu Gln Trp Ile Arg Glu Val
 50                  55                  60

Thr Gly Tyr Val Leu Val Ala Met Asn Glu Phe Ser Thr Leu Pro Leu
 65                  70                  75                  80

Pro Asn Leu Arg Val Val Arg Gly Thr Gln Val Tyr Asp Gly Lys Phe
                85                  90                  95

Ala Ile Phe Val Met Leu Asn Tyr Asn Thr Asn Ser Ser His Ala Leu
            100                 105                 110

Arg Gln Leu Arg Leu Thr Gln Leu Thr Glu Ile Leu Ser Gly Gly Val
        115                 120                 125

Tyr Ile Glu Lys Asn Asp Lys Leu Cys His Met Asp Thr Ile Asp Trp
130                 135                 140

Arg Asp Ile Val Arg Asp Arg Asp Ala Glu Ile Val Val Lys Asp Asn
145                 150                 155                 160

Gly Arg Ser Cys Pro Pro Cys His Glu Val Cys Lys Gly Arg Cys Trp
                165                 170                 175

Gly Pro Gly Ser Glu Asp Cys Gln Thr Leu Thr Lys Thr Ile Cys Ala
            180                 185                 190

Pro Gln Cys Asn Gly His Cys Phe Gly Pro Asn Pro Asn Gln Cys Cys
        195                 200                 205

His Asp Glu Cys Ala Gly Gly Cys Ser Gly Pro Gln Asp Thr Asp Cys
    210                 215                 220

Phe Ala Cys Arg His Phe Asn Asp Ser Gly Ala Cys Val Pro Arg Cys
225                 230                 235                 240

Pro Gln Pro Leu Val Tyr Asn Lys Leu Thr Phe Gln Leu Glu Pro Asn
                245                 250                 255

Pro His Thr Lys Tyr Gln Tyr Gly Gly Val Cys Val Ala Ser Cys Pro
            260                 265                 270

His Asn Phe Val Val Asp Gln Thr Ser Cys Val Arg Ala Cys Pro Pro
        275                 280                 285

Asp Lys Met Glu Val Asp Lys Asn Gly Leu Lys Met Cys Glu Pro Cys
    290                 295                 300

Gly Gly Leu Cys Pro Lys Ala Cys Glu Gly Thr Gly Ser Gly Ser Arg
305                 310                 315                 320

Phe Gln Thr Val Asp Ser Ser Asn Ile Asp Gly Phe Val Asn Cys Thr
                325                 330                 335

Lys Ile Leu Gly Asn Leu Asp Phe Leu Ile Thr Gly Leu Asn Gly Asp
            340                 345                 350

```
Pro Trp His Lys Ile Pro Ala Leu Asp Pro Glu Lys Leu Asn Val Phe
            355                 360                 365

Arg Thr Val Arg Glu Ile Thr Gly Tyr Leu Asn Ile Gln Ser Trp Pro
    370                 375                 380

Pro His Met His Asn Phe Ser Val Phe Ser Asn Leu Thr Thr Ile Gly
385                 390                 395                 400

Gly Arg Ser Leu Tyr Asn Arg Gly Phe Ser Leu Leu Ile Met Lys Asn
                405                 410                 415

Leu Asn Val Thr Ser Leu Gly Phe Arg Ser Leu Lys Glu Ile Ser Ala
            420                 425                 430

Gly Arg Ile Tyr Ile Ser Ala Asn Arg Gln Leu Cys Tyr His His Ser
            435                 440                 445

Leu Asn Trp Thr Lys Val Leu Arg Gly Pro Thr Glu Glu Arg Leu Asp
    450                 455                 460

Ile Lys His Asn Arg Pro Arg Asp Cys Val Ala Glu Gly Lys Val
465                 470                 475                 480

Cys Asp Pro Leu Cys Ser Ser Gly Gly Cys Trp Gly Pro Gly Pro Gly
                485                 490                 495

Gln Cys Leu Ser Cys Arg Asn Tyr Ser Arg Gly Gly Val Cys Val Thr
            500                 505                 510

His Cys Asn Phe Leu Asn Gly Glu Pro Arg Glu Phe Ala His Glu Ala
            515                 520                 525

Glu Cys Phe Ser Cys His Pro Glu Cys Gln Pro Met Gly Gly Thr Ala
    530                 535                 540

Thr Cys Asn Gly Ser Gly Ser Asp Thr Cys Ala Gln Cys Ala His Phe
545                 550                 555                 560

Arg Asp Gly Pro His Cys Val Ser Ser Cys Pro His Gly Val Leu Gly
                565                 570                 575

Ala Lys Gly Pro Ile Tyr Lys Tyr Pro Asp Val Gln Asn Glu Cys Arg
            580                 585                 590

Pro Cys His Glu Asn Cys Thr Gln Gly Cys Lys Gly Pro Glu Leu Gln
    595                 600                 605

Asp Cys Leu Gly Gln Thr Leu Val Leu Ile Gly Lys Thr His Leu Thr
    610                 615                 620

Met Ala Leu Thr Val Ile Ala Gly Leu Val Val Ile Phe Met Met Leu
625                 630                 635                 640

Gly Gly Thr

<210> SEQ ID NO 1008
<211> LENGTH: 631
<212> TYPE: PRT
<213> ORGANISM: Homo sapiens

<400> SEQUENCE: 1008

Ser Thr Gln Val Cys Thr Gly Thr Asp Met Lys Leu Arg Leu Pro Ala
1               5                   10                  15

Ser Pro Glu Thr His Leu Asp Met Leu Arg His Leu Tyr Gln Gly Cys
            20                  25                  30

Gln Val Val Gln Gly Asn Leu Glu Leu Thr Tyr Leu Pro Thr Asn Ala
            35                  40                  45

Ser Leu Ser Phe Leu Gln Asp Ile Gln Glu Val Gln Gly Tyr Val Leu
    50                  55                  60

Ile Ala His Asn Gln Val Arg Gln Val Pro Leu Gln Arg Leu Arg Ile
65              70                  75                  80
```

```
Val Arg Gly Thr Gln Leu Phe Glu Asp Asn Tyr Ala Leu Ala Val Leu
                85                  90                  95

Asp Asn Gly Asp Pro Leu Asn Asn Thr Thr Pro Val Thr Gly Ala Ser
            100                 105                 110

Pro Gly Gly Leu Arg Glu Leu Gln Leu Arg Ser Leu Thr Glu Ile Leu
            115                 120                 125

Lys Gly Gly Val Leu Ile Gln Arg Asn Pro Gln Leu Cys Tyr Gln Asp
    130                 135                 140

Thr Ile Leu Trp Lys Asp Ile Phe His Lys Asn Asn Gln Leu Ala Leu
145                 150                 155                 160

Thr Leu Ile Asp Thr Asn Arg Ser Arg Ala Cys His Pro Cys Ser Pro
                165                 170                 175

Met Cys Lys Gly Ser Arg Cys Trp Gly Glu Ser Ser Glu Asp Cys Gln
            180                 185                 190

Ser Leu Thr Arg Thr Val Cys Ala Gly Gly Cys Ala Arg Cys Lys Gly
            195                 200                 205

Pro Leu Pro Thr Asp Cys Cys His Glu Gln Cys Ala Ala Gly Cys Thr
    210                 215                 220

Gly Pro Lys His Ser Asp Cys Leu Ala Cys Leu His Phe Asn His Ser
225                 230                 235                 240

Gly Ile Cys Glu Leu His Cys Pro Ala Leu Val Thr Tyr Asn Thr Asp
                245                 250                 255

Thr Phe Glu Ser Met Pro Asn Pro Glu Gly Arg Tyr Thr Phe Gly Ala
            260                 265                 270

Ser Cys Val Thr Ala Cys Pro Tyr Asn Tyr Leu Ser Thr Asp Val Gly
            275                 280                 285

Ser Cys Thr Leu Val Cys Pro Leu His Asn Gln Glu Val Thr Ala Glu
    290                 295                 300

Asp Gly Thr Gln Arg Cys Glu Lys Cys Ser Lys Pro Cys Ala Arg Val
305                 310                 315                 320

Cys Tyr Gly Leu Gly Met Glu His Leu Arg Glu Val Arg Ala Val Thr
                325                 330                 335

Ser Ala Asn Ile Gln Glu Phe Ala Gly Cys Lys Lys Ile Phe Gly Ser
            340                 345                 350

Leu Ala Phe Leu Pro Glu Ser Phe Asp Gly Asp Pro Ala Ser Asn Thr
            355                 360                 365

Ala Pro Leu Gln Pro Glu Gln Leu Gln Val Phe Glu Thr Leu Glu Glu
    370                 375                 380

Ile Thr Gly Tyr Leu Tyr Ile Ser Ala Trp Pro Asp Ser Leu Pro Asp
385                 390                 395                 400

Leu Ser Val Phe Gln Asn Leu Gln Val Ile Arg Gly Arg Ile Leu His
                405                 410                 415

Asn Gly Ala Tyr Ser Leu Thr Leu Gln Gly Leu Gly Ile Ser Trp Leu
            420                 425                 430

Gly Leu Arg Ser Leu Arg Glu Leu Gly Ser Gly Leu Ala Leu Ile His
            435                 440                 445

His Asn Thr His Leu Cys Phe Val His Thr Val Pro Trp Asp Gln Leu
    450                 455                 460

Phe Arg Asn Pro His Gln Ala Leu Leu His Thr Ala Asn Arg Pro Glu
465                 470                 475                 480

Asp Glu Cys Val Gly Glu Gly Leu Ala Cys His Gln Leu Cys Ala Arg
                485                 490                 495
```

```
Gly His Cys Trp Gly Pro Gly Pro Thr Gln Cys Val Asn Cys Ser Gln
            500                 505                 510

Phe Leu Arg Gly Gln Glu Cys Val Glu Glu Cys Arg Val Leu Gln Gly
        515                 520                 525

Leu Pro Arg Glu Tyr Val Asn Ala Arg His Cys Leu Pro Cys His Pro
    530                 535                 540

Glu Cys Gln Pro Gln Asn Gly Ser Val Thr Cys Phe Gly Pro Glu Ala
545                 550                 555                 560

Asp Gln Cys Val Ala Cys Ala His Tyr Lys Asp Pro Pro Phe Cys Val
                565                 570                 575

Ala Arg Cys Pro Ser Gly Val Lys Pro Asp Leu Ser Tyr Met Pro Ile
            580                 585                 590

Trp Lys Phe Pro Asp Glu Glu Gly Ala Cys Gln Pro Cys Pro Ile Asn
        595                 600                 605

Cys Thr His Ser Cys Val Asp Leu Asp Asp Lys Gly Cys Pro Ala Glu
    610                 615                 620

Gln Arg Ala Ser Pro Leu Thr
625                 630

<210> SEQ ID NO 1009
<211> LENGTH: 626
<212> TYPE: PRT
<213> ORGANISM: Homo sapiens

<400> SEQUENCE: 1009

Gln Ser Val Cys Ala Gly Thr Glu Asn Lys Leu Ser Ser Leu Ser Asp
1               5                   10                  15

Leu Glu Gln Gln Tyr Arg Ala Leu Arg Lys Tyr Tyr Glu Asn Cys Glu
            20                  25                  30

Val Val Met Gly Asn Leu Glu Ile Thr Ser Ile Glu His Asn Arg Asp
        35                  40                  45

Leu Ser Phe Leu Arg Ser Val Arg Glu Val Thr Gly Tyr Val Leu Val
    50                  55                  60

Ala Leu Asn Gln Phe Arg Tyr Leu Pro Leu Glu Asn Leu Arg Ile Ile
65              70                  75                  80

Arg Gly Thr Lys Leu Tyr Glu Asp Arg Tyr Ala Leu Ala Ile Phe Leu
            85                  90                  95

Asn Tyr Arg Lys Asp Gly Asn Phe Gly Leu Gln Glu Leu Gly Leu Lys
        100                 105                 110

Asn Leu Thr Glu Ile Leu Asn Gly Gly Val Tyr Val Asp Gln Asn Lys
    115                 120                 125

Phe Leu Cys Tyr Ala Asp Thr Ile His Trp Gln Asp Ile Val Arg Asn
130                 135                 140

Pro Trp Pro Ser Asn Leu Thr Leu Val Ser Thr Asn Gly Ser Ser Gly
145                 150                 155                 160

Cys Gly Arg Cys His Lys Ser Cys Thr Gly Arg Cys Trp Gly Pro Thr
                165                 170                 175

Glu Asn His Cys Gln Thr Leu Thr Arg Thr Val Cys Ala Glu Gln Cys
            180                 185                 190

Asp Gly Arg Cys Tyr Gly Pro Tyr Val Ser Asp Cys Cys His Arg Glu
        195                 200                 205

Cys Ala Gly Gly Cys Ser Gly Pro Lys Asp Thr Asp Cys Phe Ala Cys
    210                 215                 220

Met Asn Phe Asn Asp Ser Gly Ala Cys Val Thr Gln Cys Pro Gln Thr
225                 230                 235                 240
```

Phe Val Tyr Asn Pro Thr Thr Phe Gln Leu Glu His Asn Phe Asn Ala
                245                 250                 255

Lys Tyr Thr Tyr Gly Ala Phe Cys Val Lys Lys Cys Pro His Asn Phe
                260                 265                 270

Val Val Asp Ser Ser Cys Val Arg Ala Cys Pro Ser Ser Lys Met
            275                 280                 285

Glu Val Glu Glu Asn Gly Ile Lys Met Cys Lys Pro Cys Thr Asp Ile
        290                 295                 300

Cys Pro Lys Ala Cys Asp Gly Ile Gly Thr Gly Ser Leu Met Ser Ala
305                 310                 315                 320

Gln Thr Val Asp Ser Ser Asn Ile Asp Lys Phe Ile Asn Cys Thr Lys
                325                 330                 335

Ile Asn Gly Asn Leu Ile Phe Leu Val Thr Gly Ile His Gly Asp Pro
                340                 345                 350

Tyr Asn Ala Ile Glu Ala Ile Asp Pro Glu Lys Leu Asn Val Phe Arg
            355                 360                 365

Thr Val Arg Glu Ile Thr Gly Phe Leu Asn Ile Gln Ser Trp Pro Pro
        370                 375                 380

Asn Met Thr Asp Phe Ser Val Phe Ser Asn Leu Val Thr Ile Gly Gly
385                 390                 395                 400

Arg Val Leu Tyr Ser Gly Leu Ser Leu Leu Ile Leu Lys Gln Gln Gly
                405                 410                 415

Ile Thr Ser Leu Gln Phe Gln Ser Leu Lys Glu Ile Ser Ala Gly Asn
                420                 425                 430

Ile Tyr Ile Thr Asp Asn Ser Asn Leu Cys Tyr Tyr His Thr Ile Asn
            435                 440                 445

Trp Thr Thr Leu Phe Ser Thr Ile Asn Gln Arg Ile Val Ile Arg Asp
        450                 455                 460

Asn Arg Lys Ala Glu Asn Cys Thr Ala Glu Gly Met Val Cys Asn His
465                 470                 475                 480

Leu Cys Ser Ser Asp Gly Cys Trp Gly Pro Gly Pro Asp Gln Cys Leu
                485                 490                 495

Ser Cys Arg Arg Phe Ser Arg Gly Arg Ile Cys Ile Glu Ser Cys Asn
            500                 505                 510

Leu Tyr Asp Gly Glu Phe Arg Glu Phe Glu Asn Gly Ser Ile Cys Val
        515                 520                 525

Glu Cys Asp Pro Gln Cys Glu Lys Met Glu Asp Gly Leu Leu Thr Cys
    530                 535                 540

His Gly Pro Gly Pro Asp Asn Cys Thr Lys Cys Ser His Phe Lys Asp
545                 550                 555                 560

Gly Pro Asn Cys Val Glu Lys Cys Pro Asp Gly Leu Gln Gly Ala Asn
                565                 570                 575

Ser Phe Ile Phe Lys Tyr Ala Asp Pro Asp Arg Glu Cys His Pro Cys
            580                 585                 590

His Pro Asn Cys Thr Gln Gly Cys Asn Gly Pro Thr Ser His Asp Cys
        595                 600                 605

Ile Tyr Tyr Pro Trp Thr Gly His Ser Thr Leu Pro Gln His Ala Arg
    610                 615                 620

Thr Pro
625

<210> SEQ ID NO 1010
<211> LENGTH: 29

```
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (2)..(2)
<223> OTHER INFORMATION: Xaa is selected from R, K, L, W and V
<220> FEATURE:
<221> NAME/KEY: MISC_FEATURE
<222> LOCATION: (3)..(3)
<223> OTHER INFORMATION: Xaa is selected from R, H, K, M, S, W, Y and V
<220> FEATURE:
<221> NAME/KEY: MISC_FEATURE
<222> LOCATION: (4)..(4)
<223> OTHER INFORMATION: Xaa is selected from A, R, N, D, Q, E, G, H, I,
      L, K, M, S, T, W and V
<220> FEATURE:
<221> NAME/KEY: MISC_FEATURE
<222> LOCATION: (6)..(6)
<223> OTHER INFORMATION: Xaa is selected from A, R, Q, M, S, T and Y
<220> FEATURE:
<221> NAME/KEY: MISC_FEATURE
<222> LOCATION: (7)..(7)
<223> OTHER INFORMATION: Xaa is selected from A, E, G, H, K, F, S, T, W,
      Y and V
<220> FEATURE:
<221> NAME/KEY: MISC_FEATURE
<222> LOCATION: (11)..(11)
<223> OTHER INFORMATION: Xaa is selected from A, N, D, Q, E, I, L and T
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from A, R, N, Q, K, P, S, T and
      V
<220> FEATURE:
<221> NAME/KEY: MISC_FEATURE
<222> LOCATION: (18)..(18)
<223> OTHER INFORMATION: Xaa is selected from A, R, N, E, F, D, Q, G, H,
      I, L, K, S, T, W, Y and V
<220> FEATURE:
<221> NAME/KEY: MISC_FEATURE
<222> LOCATION: (20)..(20)
<223> OTHER INFORMATION: Xaa is selected from A, R and K
<220> FEATURE:
<221> NAME/KEY: MISC_FEATURE
<222> LOCATION: (21)..(21)
<223> OTHER INFORMATION: Xaa is selected from A, R, N, G, H, S and V
<220> FEATURE:
<221> NAME/KEY: MISC_FEATURE
<222> LOCATION: (25)..(25)
<223> OTHER INFORMATION: Xaa is selected from A, R, E, G, I, K, S, T and
      V
<220> FEATURE:
<221> NAME/KEY: MISC_FEATURE
<222> LOCATION: (26)..(26)
<223> OTHER INFORMATION: Xaa is selected from S and K
<220> FEATURE:
<221> NAME/KEY: MISC_FEATURE
<222> LOCATION: (28)..(28)
<223> OTHER INFORMATION: Xaa is selected from A, D, Q, E, F, P, S, T, W
      and Y

<400> SEQUENCE: 1010

Glu Xaa Xaa Xaa Ala Xaa Xaa Glu Ile Trp Xaa Leu Pro Asn Leu Xaa
1               5                   10                  15

Xaa Xaa Gln Xaa Xaa Ala Phe Ile Xaa Xaa Leu Xaa Asp
            20                  25

<210> SEQ ID NO 1011
<211> LENGTH: 49
<212> TYPE: PRT
```

```
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (3)..(3)
<223> OTHER INFORMATION: Xaa is selected from R, K, L, W and V
<220> FEATURE:
<221> NAME/KEY: MISC_FEATURE
<222> LOCATION: (4)..(4)
<223> OTHER INFORMATION: Xaa is selected from R, H, K, M, S, W, Y and V
<220> FEATURE:
<221> NAME/KEY: MISC_FEATURE
<222> LOCATION: (5)..(5)
<223> OTHER INFORMATION: Xaa is selected from A, R, N, D, Q, E, G, H, I,
      L, K, M, S, T, W and V
<220> FEATURE:
<221> NAME/KEY: MISC_FEATURE
<222> LOCATION: (7)..(7)
<223> OTHER INFORMATION: Xaa is selected from A, R, Q, M, S, T and Y
<220> FEATURE:
<221> NAME/KEY: MISC_FEATURE
<222> LOCATION: (8)..(8)
<223> OTHER INFORMATION: Xaa is selected from A, E, G, H, K, F, S, T, W,
      Y and V
<220> FEATURE:
<221> NAME/KEY: MISC_FEATURE
<222> LOCATION: (12)..(12)
<223> OTHER INFORMATION: Xaa is selected from A, N, D, Q, E, I, L and T
<220> FEATURE:
<221> NAME/KEY: MISC_FEATURE
<222> LOCATION: (17)..(17)
<223> OTHER INFORMATION: Xaa is selected from N and T
<220> FEATURE:
<221> NAME/KEY: MISC_FEATURE
<222> LOCATION: (18)..(18)
<223> OTHER INFORMATION: Xaa is selected from A, R, N, Q, K, P, S, T and
      V
<220> FEATURE:
<221> NAME/KEY: MISC_FEATURE
<222> LOCATION: (19)..(19)
<223> OTHER INFORMATION: Xaa is selected from  A, R, N, E, F, D, Q, G,
      H, I, L, K, S, T, W, Y and V
<220> FEATURE:
<221> NAME/KEY: MISC_FEATURE
<222> LOCATION: (21)..(21)
<223> OTHER INFORMATION: Xaa is selected from  A, R and K
<220> FEATURE:
<221> NAME/KEY: MISC_FEATURE
<222> LOCATION: (22)..(22)
<223> OTHER INFORMATION: Xaa is selected from  A, R, N, G, H, S and V
<220> FEATURE:
<221> NAME/KEY: MISC_FEATURE
<222> LOCATION: (26)..(26)
<223> OTHER INFORMATION: Xaa is selected from  A, R, E, G, I, K, S, T
      and V
<220> FEATURE:
<221> NAME/KEY: MISC_FEATURE
<222> LOCATION: (27)..(27)
<223> OTHER INFORMATION: Xaa is selected from  S and K
<220> FEATURE:
<221> NAME/KEY: MISC_FEATURE
<222> LOCATION: (29)..(29)
<223> OTHER INFORMATION: Xaa is selected from  A, D, Q, E, F, P, S, T,
      W and Y
<220> FEATURE:
<221> NAME/KEY: MISC_FEATURE
<222> LOCATION: (36)..(36)
<223> OTHER INFORMATION: Xaa is selected from  A and S
<220> FEATURE:
<221> NAME/KEY: MISC_FEATURE
<222> LOCATION: (37)..(37)
<223> OTHER INFORMATION: Xaa is selected from  N and E
<220> FEATURE:
<221> NAME/KEY: MISC_FEATURE
<222> LOCATION: (40)..(40)
<223> OTHER INFORMATION: Xaa is selected from  A, S and C
<220> FEATURE:
<221> NAME/KEY: MISC_FEATURE
```

<222> LOCATION: (48)..(48)
<223> OTHER INFORMATION: Xaa is selected from A and S

<400> SEQUENCE: 1011

Lys Glu Xaa Xaa Xaa Ala Xaa Xaa Glu Ile Trp Xaa Leu Pro Asn Leu
1               5                   10                  15

Xaa Xaa Xaa Gln Xaa Xaa Ala Phe Ile Xaa Xaa Leu Xaa Asp Asp Pro
            20                  25                  30

Ser Gln Ser Xaa Xaa Leu Leu Xaa Glu Ala Lys Lys Leu Asn Asp Xaa
        35                  40                  45

Gln

<210> SEQ ID NO 1012
<211> LENGTH: 53
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (5)..(5)
<223> OTHER INFORMATION: Xaa is selected from R, K, L, W and V
<220> FEATURE:
<221> NAME/KEY: MISC_FEATURE
<222> LOCATION: (6)..(6)
<223> OTHER INFORMATION: Xaa is selected from R, H, K, M, S, W, Y and V
<220> FEATURE:
<221> NAME/KEY: MISC_FEATURE
<222> LOCATION: (7)..(7)
<223> OTHER INFORMATION: Xaa is selected from A, R, N, D, Q, E, G, H, I,
    L, K, M, S, T, W and V
<220> FEATURE:
<221> NAME/KEY: MISC_FEATURE
<222> LOCATION: (9)..(9)
<223> OTHER INFORMATION: Xaa is selected from A, R, Q, M, S, T and Y
<220> FEATURE:
<221> NAME/KEY: MISC_FEATURE
<222> LOCATION: (10)..(10)
<223> OTHER INFORMATION: Xaa is selected from A, E, G, H, K, F, S, T, W,
    Y and V
<220> FEATURE:
<221> NAME/KEY: MISC_FEATURE
<222> LOCATION: (14)..(14)
<223> OTHER INFORMATION: Xaa is selected from A, N, D, Q, E, I, L and T
<220> FEATURE:
<221> NAME/KEY: MISC_FEATURE
<222> LOCATION: (19)..(19)
<223> OTHER INFORMATION: Xaa is selected from N and T
<220> FEATURE:
<221> NAME/KEY: MISC_FEATURE
<222> LOCATION: (20)..(20)
<223> OTHER INFORMATION: Xaa is selected from A, R, N, Q, K, P, S, T and
    V
<220> FEATURE:
<221> NAME/KEY: MISC_FEATURE
<222> LOCATION: (21)..(21)
<223> OTHER INFORMATION: Xaa is selected from A, R, N, E, F, D, Q, G, H,
    I, L, K, S, T, W, Y and V
<220> FEATURE:
<221> NAME/KEY: MISC_FEATURE
<222> LOCATION: (23)..(23)
<223> OTHER INFORMATION: Xaa is selected from A, R and K
<220> FEATURE:
<221> NAME/KEY: MISC_FEATURE
<222> LOCATION: (24)..(24)
<223> OTHER INFORMATION: Xaa is selected from A, R, N, G, H, S and V
<220> FEATURE:
<221> NAME/KEY: MISC_FEATURE
<222> LOCATION: (28)..(28)
<223> OTHER INFORMATION: Xaa is selected from A, R, E, G, I, K, S, T and
    V
<220> FEATURE:
<221> NAME/KEY: MISC_FEATURE
<222> LOCATION: (29)..(29)

```
<223> OTHER INFORMATION: Xaa is selected from S and K
<220> FEATURE:
<221> NAME/KEY: MISC_FEATURE
<222> LOCATION: (31)..(31)
<223> OTHER INFORMATION: Xaa is selected from A, D, Q, E, F, P, S, T, W
      and Y
<220> FEATURE:
<221> NAME/KEY: MISC_FEATURE
<222> LOCATION: (42)..(42)
<223> OTHER INFORMATION: Xaa is selected from S and C

<400> SEQUENCE: 1012

Tyr Ala Lys Glu Xaa Xaa Xaa Ala Xaa Xaa Glu Ile Trp Xaa Leu Pro
1               5                   10                  15

Asn Leu Xaa Xaa Xaa Gln Xaa Xaa Ala Phe Ile Xaa Xaa Leu Xaa Asp
            20                  25                  30

Asp Pro Ser Gln Ser Ser Glu Leu Leu Xaa Glu Ala Lys Lys Leu Asn
        35                  40                  45

Asp Ser Gln Ala Pro
    50

<210> SEQ ID NO 1013
<211> LENGTH: 53
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (5)..(5)
<223> OTHER INFORMATION: Xaa is selected from R, K, L, W and V
<220> FEATURE:
<221> NAME/KEY: MISC_FEATURE
<222> LOCATION: (6)..(6)
<223> OTHER INFORMATION: Xaa is selected from R, H, K, M, S, W, Y and V
<220> FEATURE:
<221> NAME/KEY: MISC_FEATURE
<222> LOCATION: (7)..(7)
<223> OTHER INFORMATION: Xaa is selected from A, R, N, D, Q, E, G, H, I,
      L, K, M, S, T, W and V
<220> FEATURE:
<221> NAME/KEY: MISC_FEATURE
<222> LOCATION: (9)..(9)
<223> OTHER INFORMATION: Xaa is selected from A, R, Q, M, S, T and Y
<220> FEATURE:
<221> NAME/KEY: MISC_FEATURE
<222> LOCATION: (10)..(10)
<223> OTHER INFORMATION: Xaa is selected from A, E, G, H, K, F, S, T, W,
      Y and V
<220> FEATURE:
<221> NAME/KEY: MISC_FEATURE
<222> LOCATION: (14)..(14)
<223> OTHER INFORMATION: Xaa is selected from A, N, D, Q, E, I, L and T
<220> FEATURE:
<221> NAME/KEY: MISC_FEATURE
<222> LOCATION: (19)..(19)
<223> OTHER INFORMATION: Xaa is selected from N and T
<220> FEATURE:
<221> NAME/KEY: MISC_FEATURE
<222> LOCATION: (20)..(20)
<223> OTHER INFORMATION: Xaa is selected from A, R, N, Q, K, P, S, T and
      V
<220> FEATURE:
<221> NAME/KEY: MISC_FEATURE
<222> LOCATION: (21)..(21)
<223> OTHER INFORMATION: Xaa is selected from A, R, N, E, F, D, Q, G, H,
      I, L, K, S, T, W, Y and V
<220> FEATURE:
<221> NAME/KEY: MISC_FEATURE
<222> LOCATION: (23)..(23)
<223> OTHER INFORMATION: Xaa is selected from A, R and K;
<220> FEATURE:
<221> NAME/KEY: MISC_FEATURE
<222> LOCATION: (24)..(24)
```

```
<223> OTHER INFORMATION: Xaa is selected from A, R, N, G, H, S and V;
<220> FEATURE:
<221> NAME/KEY: MISC_FEATURE
<222> LOCATION: (28)..(28)
<223> OTHER INFORMATION: Xaa is selected from A, R, E, G, I, K, S, T and
      V
<220> FEATURE:
<221> NAME/KEY: MISC_FEATURE
<222> LOCATION: (29)..(29)
<223> OTHER INFORMATION: Xaa is selected from S and K
<220> FEATURE:
<221> NAME/KEY: MISC_FEATURE
<222> LOCATION: (31)..(31)
<223> OTHER INFORMATION: Xaa is selected from A, D, Q, E, F, P, S, T, W
      and Y
<220> FEATURE:
<221> NAME/KEY: MISC_FEATURE
<222> LOCATION: (42)..(42)
<223> OTHER INFORMATION: Xaa is selected from A and C

<400> SEQUENCE: 1013

Phe Asn Lys Glu Xaa Xaa Xaa Ala Xaa Xaa Glu Ile Trp Xaa Leu Pro
1               5                   10                  15

Asn Leu Xaa Xaa Xaa Gln Xaa Xaa Ala Phe Ile Xaa Xaa Leu Xaa Asp
            20                  25                  30

Asp Pro Ser Gln Ser Ala Asn Leu Leu Xaa Glu Ala Lys Lys Leu Asn
        35                  40                  45

Asp Ala Gln Ala Pro
    50

<210> SEQ ID NO 1014
<211> LENGTH: 24
<212> TYPE: DNA
<213> ORGANISM: Artificial Sequence
<220> FEATURE:
<223> OTHER INFORMATION: synthetic construct

<400> SEQUENCE: 1014
tgcttccggc tcgtatgttg tgtg                                          24

<210> SEQ ID NO 1015
<211> LENGTH: 21
<212> TYPE: DNA
<213> ORGANISM: Artificial Sequence
<220> FEATURE:
<223> OTHER INFORMATION: synthetic construct

<400> SEQUENCE: 1015
cggaaccaga gccaccaccg g                                             21

<210> SEQ ID NO 1016
<211> LENGTH: 21
<212> TYPE: DNA
<213> ORGANISM: Artificial Sequence
<220> FEATURE:
<223> OTHER INFORMATION: synthetic construct

<400> SEQUENCE: 1016
cggaaccaga gccaccaccg g                                             21

<210> SEQ ID NO 1017
<211> LENGTH: 4
<212> TYPE: PRT
<213> ORGANISM: Artificial Sequence
<220> FEATURE:
<223> OTHER INFORMATION: synthetic linker

<400> SEQUENCE: 1017
```

Gly Gly Gly Ser
1

<210> SEQ ID NO 1018
<211> LENGTH: 20
<212> TYPE: PRT
<213> ORGANISM: Artificial Sequence
<220> FEATURE:
<223> OTHER INFORMATION: synthetic linker construct

<400> SEQUENCE: 1018

Gly Gly Gly Gly Ser Gly Gly Gly Leu Val Gly Leu Gly Ser Gly
1               5                   10                  15

Gly Gly Gly Ser
            20

<210> SEQ ID NO 1019
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Individual Z variant

<400> SEQUENCE: 1019

His His His His His His Cys
1               5

<210> SEQ ID NO 1020
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01820 occur between
      position 6 and 7

<400> SEQUENCE: 1020

His His His His His His Cys
1               5

<210> SEQ ID NO 1021
<211> LENGTH: 16
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (8)..(9)
<223> OTHER INFORMATION: Individual Z variant
<220> FEATURE:
<221> NAME/KEY: MISC_FEATURE
<222> LOCATION: (12)..(13)
<223> OTHER INFORMATION: Albumin binding domain

<400> SEQUENCE: 1021

Ala Gln His Asp Glu Ala Leu Glu Val Asp Tyr Val Tyr Val Pro Gly
1               5                   10                  15

<210> SEQ ID NO 1022
<211> LENGTH: 7

```
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Two individual Z variants

<400> SEQUENCE: 1022

His His His His His His Cys
1               5

<210> SEQ ID NO 1023
<211> LENGTH: 15
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (12)..(13)
<223> OTHER INFORMATION: Two individual Z variants

<400> SEQUENCE: 1023

Met Gly Ser Ser His His His His His His Leu Gln Val Asp Cys
1               5                   10                  15

<210> SEQ ID NO 1024
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01748 occur between
      position 6 and 7

<400> SEQUENCE: 1024

His His His His His His Cys
1               5

<210> SEQ ID NO 1025
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01749 occur between
      position 6 and 7

<400> SEQUENCE: 1025

His His His His His His Cys
1               5

<210> SEQ ID NO 1026
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01751 occur between
      position 6 and 7
```

```
<400> SEQUENCE: 1026

His His His His His His Cys
1               5

<210> SEQ ID NO 1027
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01753 occur between
      position 6 and 7

<400> SEQUENCE: 1027

His His His His His His Cys
1               5

<210> SEQ ID NO 1028
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01815 occur between
      position 6 and 7

<400> SEQUENCE: 1028

His His His His His His Cys
1               5

<210> SEQ ID NO 1029
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01817 occur between
      position 6 and 7

<400> SEQUENCE: 1029

His His His His His His Cys
1               5

<210> SEQ ID NO 1030
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01828 occur between
      position 6 and 7

<400> SEQUENCE: 1030

His His His His His His Cys
1               5
```

```
<210> SEQ ID NO 1031
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01830 occur between
      position 6 and 7

<400> SEQUENCE: 1031

His His His His His His Cys
1               5

<210> SEQ ID NO 1032
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 02011 occur between 6
      and 7

<400> SEQUENCE: 1032

His His His His His His Cys
1               5

<210> SEQ ID NO 1033
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 01826 occur between
      position 6 and 7

<400> SEQUENCE: 1033

His His His His His His Cys
1               5

<210> SEQ ID NO 1034
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: 2 copies of Z variant 02009 occur between
      position 6 and 7

<400> SEQUENCE: 1034

His His His His His His Cys
1               5

<210> SEQ ID NO 1035
<211> LENGTH: 7
<212> TYPE: PRT
<213> ORGANISM: Artificial Sequence
<220> FEATURE:
<223> OTHER INFORMATION: Engineered Polypeptide
<220> FEATURE:
```

<221> NAME/KEY: MISC_FEATURE
<222> LOCATION: (6)..(7)
<223> OTHER INFORMATION: 2 copies of Z variant 02010 occur between
      position 6 and 7

<400> SEQUENCE: 1035

His His His His His His Cys
1               5

<210> SEQ ID NO 1036
<211> LENGTH: 110
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<223> OTHER INFORMATION: Randomized codons are illustrated as NNN

<400> SEQUENCE: 1036

Gly Ala Ala Asn Asn Asn Asn Asn Asn Asn Asn Gly Cys Gly Asn
1               5                   10                  15

Asn Asn Asn Asn Asn Gly Ala Gly Ala Thr Cys Thr Gly Gly Asn Asn
                20                  25                  30

Asn Thr Thr Ala Cys Cys Thr Ala Cys Thr Thr Ala Ala Ala Cys
            35                  40                  45

Asn Asn Asn Asn Asn Asn Cys Ala Ala Asn Asn Asn Asn Asn Gly
            50                  55                  60

Cys Cys Thr Thr Cys Ala Thr Cys Asn Asn Ala Gly Thr Thr Thr
65                  70                  75                  80

Ala Asn Asn Asn Gly Ala Thr Gly Ala Cys Cys Cys Ala Ala Gly Cys
                85                  90                  95

Cys Ala Ala Ala Gly Cys Gly Cys Thr Ala Ala Cys Thr Thr
                100                 105                 110

<210> SEQ ID NO 1037
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Individual Z variant 05416 occurs between
      position 6 and 7

<400> SEQUENCE: 1037

His His His His His His Cys
1               5

<210> SEQ ID NO 1038
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Individual Z variant 05417 occurs between
      position 6 and 7

<400> SEQUENCE: 1038

His His His His His His Cys
1               5

<210> SEQ ID NO 1039
<211> LENGTH: 7
<212> TYPE: PRT
<213> ORGANISM: Artificial Sequence
<220> FEATURE:
<223> OTHER INFORMATION: Engineered Polypeptide
<220> FEATURE:
<221> NAME/KEY: MISC_FEATURE
<222> LOCATION: (6)..(7)
<223> OTHER INFORMATION: Individual Z variant 01155 occurs between
      position 6 and 7

<400> SEQUENCE: 1039

His His His His His His Cys
1               5

<210> SEQ ID NO 1040
<211> LENGTH: 29
<212> TYPE: PRT
<213> ORGANISM: Artificial Sequence
<220> FEATURE:
<223> OTHER INFORMATION: Engineered polypeptide
<220> FEATURE:
<221> NAME/KEY: MISC_FEATURE
<222> LOCATION: (2)..(2)
<223> OTHER INFORMATION: Xaa is selected from K, R and W
<220> FEATURE:
<221> NAME/KEY: MISC_FEATURE
<222> LOCATION: (3)..(3)
<223> OTHER INFORMATION: Xaa is selected from K, R, and Y
<220> FEATURE:
<221> NAME/KEY: MISC_FEATURE
<222> LOCATION: (4)..(4)
<223> OTHER INFORMATION: Xaa is selected from A, D, E, G, H, I, K, L,
      M, N, Q, R, S, T, V and W
<220> FEATURE:
<221> NAME/KEY: MISC_FEATURE
<222> LOCATION: (7)..(7)
<223> OTHER INFORMATION: Xaa is selected from A, E, F, G, H, K, S, T,
      V, W and Y
<220> FEATURE:
<221> NAME/KEY: MISC_FEATURE
<222> LOCATION: (11)..(11)
<223> OTHER INFORMATION: Xaa is selected from E and Q
<220> FEATURE:
<221> NAME/KEY: MISC_FEATURE
<222> LOCATION: (16)..(16)
<223> OTHER INFORMATION: Xaa is selected from N and T
<220> FEATURE:
<221> NAME/KEY: MISC_FEATURE
<222> LOCATION: (17)..(17)
<223> OTHER INFORMATION: Xaa is selected from R, T and V
<220> FEATURE:
<221> NAME/KEY: MISC_FEATURE
<222> LOCATION: (18)..(18)
<223> OTHER INFORMATION: Xaa is selected from R, T and V
<220> FEATURE:
<221> NAME/KEY: MISC_FEATURE
<222> LOCATION: (20)..(20)
<223> OTHER INFORMATION: Xaa is selected from K and R
<220> FEATURE:
<221> NAME/KEY: MISC_FEATURE
<222> LOCATION: (21)..(21)
<223> OTHER INFORMATION: Xaa is selected from A and G
<220> FEATURE:
<221> NAME/KEY: MISC_FEATURE
<222> LOCATION: (25)..(25)
<223> OTHER INFORMATION: Xaa is selected from A, G, K, R and S
<220> FEATURE:
<221> NAME/KEY: MISC_FEATURE
<222> LOCATION: (26)..(26)
<223> OTHER INFORMATION: Xaa is selected from S and K
<220> FEATURE:
<221> NAME/KEY: MISC_FEATURE
<222> LOCATION: (28)..(28)

-continued

```
<223> OTHER INFORMATION: Xaa is selected from A, D, E, F, P, Q, S, T,
      W and Y

<400> SEQUENCE: 1040

Glu Xaa Xaa Xaa Ala Tyr Xaa Glu Ile Trp Xaa Leu Pro Asn Leu Xaa
1               5                   10                  15

Xaa Xaa Gln Xaa Xaa Ala Phe Ile Xaa Xaa Leu Xaa Asp
            20                  25
```